(12) United States Patent
Salvati et al.

(10) Patent No.: US 7,001,911 B2
(45) Date of Patent: Feb. 21, 2006

(54) FUSED CYCLIC MODULATORS OF NUCLEAR HORMONE RECEPTOR FUNCTION

(75) Inventors: Mark E. Salvati, Lawrenceville, NJ (US); James Aaron Balog, Lambertville, NJ (US); Weifang Shan, Princeton, NJ (US); Sören Giese, New Hope, PA (US); Lalgudi S. Harikrishnan, Princeton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 18 days.

(21) Appl. No.: 10/322,306

(22) Filed: Dec. 18, 2002

(65) Prior Publication Data

US 2004/0077606 A1 Apr. 22, 2004

Related U.S. Application Data

(63) Continuation-in-part of application No. 10/025,233, filed on Dec. 19, 2001, now abandoned, and a continuation-in-part of application No. 09/885,798, filed on Jun. 20, 2001, and a continuation-in-part of application No. 09/885,827, filed on Jun. 20, 2001.

(60) Provisional application No. 60/284,617, filed on Apr. 18, 2001, provisional application No. 60/284,438, filed on Apr. 18, 2001, and provisional application No. 60/214,392, filed on Jun. 28, 2000.

(51) Int. Cl.
| | |
|---|---|
| C07D 471/08 | (2006.01) |
| C07D 471/18 | (2006.01) |
| C07D 487/08 | (2006.01) |
| A61K 31/439 | (2006.01) |
| A61P 35/00 | (2006.01) |

(52) U.S. Cl. ............... 514/292; 546/23; 546/86; 544/183; 544/337; 544/348; 548/453; 548/531; 548/536

(58) Field of Classification Search .......... 546/23, 546/86; 514/292
See application file for complete search history.

(56) References Cited

U.S. PATENT DOCUMENTS

| | | | |
|---|---|---|---|
| 3,261,845 A | 7/1966 | Bockstahler | |
| 3,343,940 A | 9/1967 | Popoff et al. | |
| 3,428,538 A | 2/1969 | Scheiner | |
| 3,821,232 A | 6/1974 | Redmore | |
| 3,906,102 A | 9/1975 | Tottori et al. | |
| 3,923,490 A | 12/1975 | Redmore | |
| 3,925,554 A | 12/1975 | Tottori et al. | |
| 3,965,264 A | 6/1976 | Redmore | |
| 3,997,293 A | 12/1976 | Redmore | |
| 3,998,833 A | 12/1976 | Redmore | |
| 4,089,650 A | 5/1978 | Redmore | |
| 4,092,413 A | 5/1978 | Arth et al. | |
| 4,097,578 A | 6/1978 | Perronnet | |

(Continued)

FOREIGN PATENT DOCUMENTS

| | | |
|---|---|---|
| AU | A-16993-83 | 1/1984 |
| CN | 1050877 | 4/1991 |
| DE | 2365677 | 11/1975 |
| DE | 3227055 A1 | 7/1982 |
| EP | 0001813 A1 | 10/1978 |
| EP | 0051020 A1 | 5/1982 |
| EP | 0082402 B1 | 6/1982 |
| EP | 0091596 A2 | 3/1983 |
| EP | 0253503 B1 | 6/1987 |
| EP | 0277476 A2 | 1/1988 |
| EP | 0436426 A1 | 12/1990 |

(Continued)

OTHER PUBLICATIONS

Kucharczyk et al., J. Med. Chem., vol. 36, pp. 1654–1661, 1993.
Ben–Ishai et al., Tetrahedron, vol. 27, pp. 3119–3127, 1971.
Krow et al, Tetrahedron, vol. 30, p. 2977–2981 (1974).
Kucharczyk et al., J. Med. Chem., vol. 36, p. 1645–1661 (1993).

(Continued)

Primary Examiner—Mark L. Berch
Assistant Examiner—Kahsay Habte
(74) Attorney, Agent, or Firm—Suzanne E. Babajko; Anastasia P. Winslow

(57) ABSTRACT

The invention pertains to fused cyclic compounds having the formula, (I)

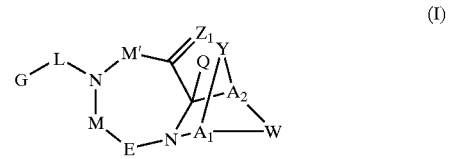

wherein G is an optionally substituted aryl or heterocyclo, L is an optional linker, M is a bond, O, $CR^7R^{7'}$ or $NR^{10}$, and M' is a bond or $NR^{10}$, with the proviso that at least one of M or M' must be a bond; E is $C=Z_2$, $CR^7CR^{7'}$, $SO_2$, $P=OR^2$, or $P=OOR^2$; $Z_1$ is O, S, NH, or $NR^6$; $Z_2$ is O, S, NH, or $NR^6$; $A_1$ is $CR^7$ or N; $A_2$ is $CR^7$ or N; Y is J—J'—J" where J is $(CR^7R^{7'})n$ and n=0–3, J' is a bond or O, S, S=O, $SO_2$, NH, $NR^6$, C=O, OC=O, $NR^1C=O$, $CR^7R^{7'}$, $C=CR^8R^{8'}$, $R^2P=O$, $OPOOR^2$, $OPO_2$, $OSO_2$, C=N, NHNH, $NHNR^6$, $NR^6NH$, N=N, cycloalkyl or substituted cycloalkyl, cycloalkenyl or substituted cycloalkenyl, heterocyclo or substituted heterocyclo or aryl or substituted aryl, and J" is $(CR^7R^{7'})n$ and n=0–3; W is $CR^7R^{7'}$—$CR^7R^{7'}$, $CR^8=CR^{8'}$, $CR^7R^{7'}$—C=O, $NR^9$—$CR^7R^{7'}$, N=$CR^8$, N=N, $NR^9$—$NR^{9'}$, cycloalkyl or substituted cycloalkyl, cycloalkenyl or substituted cycloalkenyl, heterocyclo or substituted heterocyclo, or aryl or substituted aryl; and O, $R^2$, $R^6$, $R^7$, $R^{7'}$, $R^8$, $R^{8'}$, $R^9$, $R^{9'}$, and $R^{10}$ are as defined in the specification, to methods of using such compounds in the treatment of nuclear hormone receptor-associated conditions such as cancer and immune disorders, and to pharmaceutical compositions containing such compounds.

21 Claims, No Drawings

U.S. PATENT DOCUMENTS

| | | |
|---|---|---|
| 4,191,775 A | 3/1980 | Glen |
| 4,234,736 A | 11/1980 | Bernauer et al. |
| 4,239,776 A | 12/1980 | Glen et al. |
| 4,397,857 A | 8/1983 | Vincent et al. |
| 4,472,382 A | 9/1984 | Labrie et al. |
| 4,473,393 A | 9/1984 | Nagpal |
| 4,476,184 A | 10/1984 | Lubowitz et al. |
| 4,507,303 A | 3/1985 | Ishizumi et al. |
| 4,533,737 A | 8/1985 | Ryang |
| 4,536,559 A | 8/1985 | Lubowitz et al. |
| 4,543,355 A | 9/1985 | Ishizumi et al. |
| 4,562,255 A | 12/1985 | Freed et al. |
| 4,584,364 A | 4/1986 | Lubowitz et al. |
| 4,598,072 A | 7/1986 | Schweikert et al. |
| 4,656,235 A | 4/1987 | Tesoro et al. |
| 4,659,695 A | 4/1987 | Labrie |
| 4,666,885 A | 5/1987 | Labrie |
| 4,673,748 A | 6/1987 | Rock et al. |
| 4,739,075 A | 4/1988 | Odagiri et al. |
| 4,753,957 A | 6/1988 | Chan |
| 4,760,053 A | 7/1988 | Labrie |
| 4,775,660 A | 10/1988 | Labrie et al. |
| 4,775,661 A | 10/1988 | Labrie |
| 4,851,495 A | 7/1989 | Sheppard et al. |
| 4,873,256 A | 10/1989 | Coussediere et al. |
| 4,892,578 A | 1/1990 | Chang et al. |
| 4,944,791 A | 7/1990 | Schroder et al. |
| 4,980,481 A | 12/1990 | Lubowitz et al. |
| 5,084,472 A | 1/1992 | Moguilewsky et al. |
| 5,093,500 A | 3/1992 | Wang |
| 5,098,888 A | 3/1992 | Vincent et al. |
| 5,104,967 A | 4/1992 | Sheppard et al. |
| 5,112,939 A | 5/1992 | Lubowitz et al. |
| 5,114,612 A | 5/1992 | Benicewicz et al. |
| 5,116,935 A | 5/1992 | Lubowitz et al. |
| 5,151,487 A | 9/1992 | Lubowitz et al. |
| 5,155,206 A | 10/1992 | Lubowitz et al. |
| 5,210,213 A | 5/1993 | Sheppard et al. |
| 5,239,046 A | 8/1993 | Lubowitz et al. |
| 5,367,083 A | 11/1994 | Sheppard et al. |
| 5,403,666 A | 4/1995 | Lubowitz et al. |
| 5,434,176 A | 7/1995 | Claussner et al. |
| 5,446,120 A | 8/1995 | Lubowitz et al. |
| 5,455,115 A | 10/1995 | Lubowitz et al. |
| 5,463,076 A | 10/1995 | Sheppard et al. |
| 5,482,921 A | 1/1996 | Secking et al. |
| 5,512,676 A | 4/1996 | Sheppard et al. |
| 5,516,876 A | 5/1996 | Lubowitz et al. |
| 5,530,089 A | 6/1996 | Sheppard et al. |
| 5,532,372 A | 7/1996 | Saji et al. |
| 5,550,107 A | 8/1996 | Labrie |
| 5,556,983 A | 9/1996 | Claussner et al. |
| 5,573,854 A | 11/1996 | Sheppard et al. |
| 5,587,105 A | 12/1996 | Sheppard et al. |
| 5,589,497 A | 12/1996 | Claussner et al. |
| 5,594,089 A | 1/1997 | Lubowitz et al. |
| 5,595,985 A | 1/1997 | Labrie |
| 5,610,317 A | 3/1997 | Lubowitz et al. |
| 5,627,201 A | 5/1997 | Gaillard-Kelley et al. |
| 5,643,855 A | 7/1997 | Kilama |
| 5,645,925 A | 7/1997 | Sheppard et al. |
| 5,693,741 A | 12/1997 | Sheppard et al. |
| 5,714,566 A | 2/1998 | Lubowitz et al. |
| 5,750,553 A | 5/1998 | Claussner et al. |
| 5,780,583 A | 7/1998 | Lubowitz et al. |
| 5,817,649 A | 10/1998 | Labrie |
| 5,817,744 A | 10/1998 | Sheppard et al. |
| RE35,956 E | 11/1998 | Gaillard-Kelley et al. |
| 5,929,146 A | 7/1999 | Amos et al. |
| 6,017,924 A | 1/2000 | Edwards et al. |
| 6,020,327 A | 2/2000 | Messenger |
| 6,054,487 A | 4/2000 | Sekut et al. |
| 6,071,957 A | 6/2000 | Miller et al. |
| 6,124,460 A | 9/2000 | Tomiyama et al. |
| 6,162,444 A | 12/2000 | Dubois |
| 6,200,573 B1 | 3/2001 | Locke |
| 6,242,611 B1 | 6/2001 | Claussner et al. |
| 6,670,386 B2 | 12/2003 | Sun et al. |
| 2001/0012839 A1 | 8/2001 | Miller et al. |
| 2001/0020002 A1 | 9/2001 | Lederman et al. |
| 2002/0173445 A1 | 11/2002 | Salvati et al. |
| 2003/0181728 A1 | 9/2003 | Salvati et al. |
| 2004/0019063 A1 | 1/2004 | Sun et al. |
| 2004/0077606 A1 | 4/2004 | Salvati et al. |
| 2004/0087548 A1 | 5/2004 | Salvati et al. |
| 2004/0181064 A1 | 9/2004 | Sun et al. |

FOREIGN PATENT DOCUMENTS

| | | |
|---|---|---|
| EP | 0494819 A1 | 1/1992 |
| EP | 0406119 B1 | 1/1994 |
| EP | 0678507 | 10/1995 |
| EP | 1008457 A1 | 6/2000 |
| FR | 2075751 | 1/1971 |
| FR | 2329276 | 11/1975 |
| GB | 2133066 B | 10/1986 |
| GB | 2290296 | 12/1995 |
| GB | 1039020 | 4/2001 |
| JP | 51088631 | 8/1976 |
| JP | 53-86035 | 7/1978 |
| JP | 64-6258 | 2/1989 |
| JP | 1-125381 | 5/1989 |
| JP | 7-144477 | 6/1995 |
| WO | WO98/32439 | 7/1978 |
| WO | WO98/ 29495 | 7/1988 |
| WO | WO95/18794 | 7/1995 |
| WO | WO96/19458 | 6/1996 |
| WO | WO97/49709 | 12/1997 |
| WO | WO98/16830 | 4/1998 |
| WO | WO 98/39303 | 9/1998 |
| WO | WO98/49555 | 11/1998 |
| WO | WO99/27365 | 6/1999 |
| WO | WO99/32463 | 7/1999 |
| WO | WO02/00653 | 1/2000 |
| WO | WO00/06525 | 2/2000 |
| WO | WO00/37430 | 6/2000 |
| WO | WO01/07052 | 2/2001 |
| WO | WO01/16108 | 3/2001 |
| WO | WO01/16133 | 3/2001 |
| WO | WO01/19831 | 3/2001 |
| WO | WO01/30781 | 5/2001 |
| WO | WO02/00617 | 1/2002 |
| WO | WO01/16139 | 3/2002 |
| WO | WO02/24702 | 3/2002 |

OTHER PUBLICATIONS

Ben–Ishai et al., Tetrahedron, vol. 27, p. 3319–3127 (1971).

Vincent et al., Tetrahedron Letters, vol. 33, No. 48, p. 7369–7372 (1992).

Goldstein et al., Tetrahedron Letters, vol. 31, p. 2631–2634 (1969).

Evnin et al., J. Org. Che., vol. 35, No. 9, p. 3097–3106 (1970).

Kobayashi et al., Bull. Chem. Soc. Jpn., vol. 67, No. 11, p. 3082–3087 (1994).

Kobayashi et al., Bull. Chem. Soc. Jpn., vol. 65, p. 61–65 (1992).

Pons et al., Eur. J. Org. Chem., p. 853–859 (1998).

Pons et al., Pept. Proc. Am. Pept. Symp., 15th p. 176–177 (1999).

Reyniers et al., Bull. Soc. Chim. Belg. vol. 94(6), pp. 413–419 (1985).
Anteunis et al., Tetrahedron Lett., vol. 22(32), p. 3101–3104 (1981).
Mauger et al., J. Chem. Soc., Perkin Trans. 1, vol. 17, p. 2146–2148 (1972).
Mauger, J. Chem. Soc. d, vol. 1, p. 39–40 (1971).
Lee et al., Tetrahedron Lett., vol. 37(34), p. 6053–6056 (1996).
Verbruggen et al., Acta Crystallogr., Sect. C: Cryst. Struct. Commun., vol. C49(6), p. 1113–1116 (1993).
Shalati et al., Journal of Polymer Science: Polm. Chem. Ed., vol. 22(1), p. 107–120 (1984).
Van Poucke et al., Bull. Soc. Chim. Belg., vol. 91(3), p. 213–218 (1982).
Schrooten et al., Bull. Soc. Chim. Belg., vol. 89(8), p. 615–628 (1980).
Hausler et al., Chem. Ber. vol. 107(9), p. 2804–2815 (1974).
Vicar et al., Collect. Czech. Chem. Commun. vol. 38(7), p. 1940–1956 (1973).
Vicar et al., Collect. Czech. Chem. Commun. vol. 37(12), p. 4060–4071 (1972).
Kovtunenko et al., Ukr. Khim. Zh. (Russ. Ed), vol. 58(11), p. 1035–1040 (1992).
Kovtunenko et al., Ukr. Khim. Zh. (Russ. Ed), vol. 58(7), p. 588–592 (1992).
Kreher et al., Chem. Ber., vol. 125(1), p. 183–189 (1992).
Kovtunenko et al., Ukr. Khim. Zh. (Russ. Ed), vol. 57(1), p. 71–77 (1991).
Kovtunenko et al., Khim. Geterotsikl. Soedin., vol. (2), p. 190–202 (1990).
Kreher et al., Chem. Ber., vol. 123(2), p. 381–390 (1990).
Kreher et al., Chem.-Ztg., vol. 112(11), p. 335–342 (1988).
Kovtunenko et al., Ukr. Khim. Zh. (Russ. ed.), vol. 55(1), p. 64–69 (1989).
Kovtunenko et al., Ukr. Khim. Zh. (Russ. ed.), vol. 54(11), p. 1186–1190 (1988).
Kovtunenko et al., Ukr. Khim. Zh., vol. 54(2), p. 186–190 (1988).
Kreher et al., Chem.-Ztg., vol. 111(12), p. 349–356 (1987).
Kreher et al., Chem. Ber., vol. 121(5), p. 927–934 (1988).
Kreher at al., Chem.-Ztg., vol. 110(10), p. 363–367 (1986).
Kovtunenko et al., Khim. Geterotsikl. Soedin., vol. 20(9), p. 1200–1205 (1984).
Kreher et al., Angew. Chem., vol. 96(7), p. 507–508 (1984).
Kovtunenko et al., Ukr. Khim. Zh., vol. 49(12), p. 1287–1293 (1983).
Kreher et al., Angew. Chem., vol. 94(8), p. 634–635 (1982).
Munoz et al., Biotechnol. Bioeng., vol. 71(1), p. 78–84 (2000).
Chen et al., Tetrahedron Lett., vol. 40(18), p. 3491–3494 (1999).
Srivastav et al., Natl. Acad. Sci. Lett., vol. 19(1&2), p. 16–18 (1996).
Tosunyan et al., Khim. Geterotsikl. Soedin., vol. (11), p. 1465–1471 (1992).
Kirby et al., J. Chem. Res., Synop., vol. (9), p. 273 (1985).
Krow et al., J. Heterocycl. Chem., vol. 22(1), p. 131–135 (1985).
Krow et al., J. Org. Chem., vol. 47(11), p. 1989–1993 (1982).
Knaus et al., J. Heterocycl. Chem., vol. 13(3), p. 481–486 (1976).
Lyle et al., J. Org. Chem., vol. 39(25), p. 3708–3711 (1974).
Lin et al., Journal of the Chinese Chemical Society, vol. 48, p. 49–53 (2001).
Kirby et al., J. Chem. Res. Miniprint, vol. 9, p. 3089–3097 (1985).
Xu, Trends in Pharmacological Science, vol. 2 (10), p. 271–272 (1981).
Li et al., J. Pharm. Biomed. Anal. vol. 7(12), p. 1635–1639 (1989).
Cheng et al., Huaxue Shiji, vol. 15(1), p. 1–4 (1993).
Liu et al., Yaoxue Xuebao, vol. 18(10), p. 752–759 (1983).
Bockstahler et al., J. Med. Chem., vol. 11(3), p. 603–606 (1968).
Srivastava et al., Natl. Acad. Sci. Lett., vol. 15(2), p. 41–44 (1992).
Joshi et al., Indian J. Chem., Sect. B, vol. 22B(2), p. 131–135 (1983).
Fisera et al., Chem. Pap., vol. 49(4), p. 186–191 (1995).
Fang et al., Huaxue Tongbao, vol. (1), p. 27–30 (1994).
Wijnberg et al., Tetrahedron, vol. 38, p. 209–217 (1982).
Grogan et al., J. Med. Chem., vol. 6, p. 802–805 (1963).
Gringauz et al., J. Med. Chem., vol. 11, p. 611–612 (1968).
Chem. Abstr., vol. 65 p. 15325h (1966).
Dominianni, J. Med. Chem., vol. 14, No. 2, pp. 175 (1971).
Chem. Abstr., vol. 57, p. 16561f (1962).
Jolivet, Ann. Chim., vol. 5, p. 1165–1217 (1960).
Maruyama et al., J. Org. Chem., vol. 46, p. 27–34 (1981).
Chem. Abstr., vol. 68, p. 39458j (1964).
Kwart, J. Amer. Chem. Soc., vol. 74 p. 3094–3097 (1952).
Berson et al., J. Amer. Chem. Soc., vol. 76, p. 4060–4067 (1954).
Yur'ev et al., J. Gen. Chem. (Engl. Transl.), vol. 30, p. 869–872 (1960).
Jolivet, C.R. Hebd. Seances Acad. Sci., vol. 243, p. 2085–2086 (1956).
Lin et al., Biorganic Chemistry, vol. 28, p. 266–272 (2000).
Mel'nikow, Zh. Obshch. Khim., vol. 26, p. 227–232 (1956).
Mel'nikow, Zh. Obshch. Khim., vol. 29, p. 968,970 (1956).
CA 54:1480g.
CA 65:15326c.
Warrener et al., Tetrahedron Lett., vol. 36(42), p. 7753–7756 (1995).
Qimin et al., J. Pharm. Biomed. Anal., vol. 7(12), p. 1635–1639 (1989).
Maruyama et al., J. Org. Chem., vol. 46(1), p. 27–34 (1981).
Zawadowski et al., Rocz. Chem., vol. 51(3), p. 557–560 (1977).
Liu et al., Eur. J. Canada, vol. 31A, (6), p. 953–963 (1995).
Lin, Journal of Natural Toxins, vol. 4 (2), p. 147–153 (1995).
Walter et al., Biochemica et Biophysica Acta, 1155, p. 207–0226 (1993).
Walter, J. Pharm. Sci., vol. 78 (1), p. 66–67 (1989).
Yin et al., Chem. Chinese Chemical Society, No. 1, p. 27–30 (1994).
Bockstahler et al., J. Med. Chem., vol. 11 (3), p. 603–606 (1968).
Dominianni et al., J. Med. Chem., vol. 14 (2), p. 175 (1971).
Zhou et al., Acta Pharm. Sinica, vol. 18 (10), p. 725–729 (1983).
Wang, J. Ethnopharm., vol. 26, p. 147–162 (1989).
Honkanen, FEBS Letters, vol. 330 (3), p. 283–286 (1993).
Waller, Toxicol. Appl. Pharmacol., vol. 137 (2), p. 219–227 (1996).
Search Report "A" (Scifinder Jun. 23, 2000).

Search Report "B" (Scifinder Jun. 5, 2001).
Search Report "C" (Scifinder, Jun. 20, 2001).
Search Report "D" (Scifinder, Jun. 20, 2001).
Search Report "E" (Scifinder, Jun. 20, 2001).
Search Report "F" (Scifinder, Aug. 16, 2000).
Search Report "G" (Scifinder, Aug. 22, 2000).
Search Report "H" (Scifinder, Sep. 12, 2000).
Search Report "I".
Search Report "J".
Search Report "K" (Scifinder, Sep. 11, 2000).
Search Report "L" (Scifinder, Sep. 11, 2000).
Search Report "M" (Scifinder, Sep. 11, 2000).
Search Report "N" (Scifinder, Sep. 11, 2000).
Search Report "O" (Scifinder, Sep. 11, 2000).
Search Report "P" (Scifinder, Sep. 11, 2000).
Search Report "Q" (Scifinder, Sep. 11, 2000).
Search Report "R" (Scifinder, Sep. 11, 2000).
Search Report "S" (Scifinder, Sep. 11, 2000).
Search Report "T" (Scifinder, Sep. 11, 2000).
Search Report "U" (Scifinder, Sep. 11, 2000).
Search Report "V" (Scifinder, Sep. 11, 2000).
Search Report "W".
Search Report "X".
Search Report "Y" (Scifinder, Sep. 11, 2000).
Search Report "Z".
Search Report "AA".
Search Report "BB" (Scifinder, Sep. 11, 2000).
Tanaka et al., Tetrahedron, Elsevier Science Publishers, Amsterdam, NL, vol. 54 (34), p. 10029–10042 (1998).
Rosen et al., J. Med. Chem., vol. 31 (8), p 1598–1611 (1988).
Remuzon et al., Journal of Medicinal Chemistry, American Chemical Society, vol. 35, (15), p. 2898–2909, 1992.
Evans, American Association for the Advancement of Science, vol. 240, No. 4854, p. 889–895 (1988).
Denison, J. Biol. Chem., vol. 270 (31), p. 18175–18178 (1995).
Furr, Eur. Urol., vol. 29 (Suppl. 2), 83–95 (1996).
Negro–Vilar, Journal of Clinical Endocrinology & Metabolism, vol. 84, No. 10, 3459–3462 (1999).
Reid et al., Investigational New Drugs, vol. 17, 271–284 (1999).
Avolos et al., Tetra. Ltrs., vol. 39, 9301–9304 (1998).
Rul et al., ACTA Pharmaceutica Sinica, vol. 10, 783–786 (1981).
Tsuchiya et al., Tetra., vol. 29, No. 18, 2747–2751 (1973).

FUSED CYCLIC MODULATORS OF NUCLEAR HORMONE RECEPTOR FUNCTION

This application claims priority from and is a continuation-in-part of U.S. application Ser. No. 10/025,233 filed Dec. 19, 2001 now abandoned and from U.S. Application Ser. No. 60/214,392, filed Jun. 28, 2000, from U.S. Application Ser. No. 60/284,617, filed Apr. 18, 2001, and from U.S. application Ser. No. 60/284,438, filed Apr. 18, 2001, which provisional applications are incorporated herein by reference in their entirety, and further claims priority from and is a continuation-in-part of U.S. application Ser. No. 09/885,798, filed Jun. 20, 2001, and U.S. application Ser. No. 09/885,827, filed Jun. 20, 2001, which applications are incorporated herein by reference in their entirety.

FIELD OF THE INVENTION

The present invention relates to fused cyclic compounds, to methods of using such compounds in the treatment of nuclear hormone receptor-associated conditions such as cancer, and to pharmaceutical compositions containing such compounds.

BACKGROUND OF THE INVENTION

Nuclear hormone receptors (NHR's) constitute a large super-family of ligand-dependent and sequence-specific transcription factors. Members of this family influence transcription either directly, through specific binding to the promoter target genes (Evans, in Science 240: 889–895 (1988)), or indirectly, via protein-protein interactions with other transcription factors (Jonat et al., Cell 62: 1189–1204 (1990), Schuele et al., Cell 62: 1217–1226 (1990), and Yang-Yen et al., Cell 62: 1205–1215 (1990)). The nuclear hormone receptor super-family (also known in the art as the "asteroid/thyroid hormone receptor super-family") includes receptors for a variety of hydrophobic ligands, including cortisol, aldosterone, estrogen, progesterone, testosterone, vitamine D3, thyroid hormone and retinoic acid (Evans, 1988, supra). In addition to these conventional nuclear hormone receptors, the super-family contains a number of proteins that have no known ligands, termed orphan nuclear hormone receptors (Mangelsdorf et al., Cell 83: 835–839 (1995), O'Malley et al., Mol. Endocrinol. 10: 1293 (1996), Enmark et al., Mol. Endocrinol. 10, 1293–1307 (1996) and Giguere, Endocrin. Rev. 20, 689–725 (1999)). The conventional nuclear hormone receptors are generally transactivators in the presence of ligand, and can either be active repressors or transcriptionally inert in the absence of ligand. Some of the orphan receptors behave as if they are transcriptionally inert in the absence of ligand. Others, however, behave as either constitutive activators or repressors. These orphan nuclear hormone receptors are either under the control of ubiquitous ligands that have not been identified, or do not need to bind ligand to exert these activities.

In common with other transcription factors, the nuclear hormone receptors have a modular structure, being comprised of three distinct domains: an N-terminal domain of variable size containing a transcriptional activation function AF-1, a highly conserved DNA binding domain and a moderately conserved ligand-binding domain. The ligand-binding domain is not only responsible for binding the specific ligand but also contains a transcriptional activation function called AF-2 and a dimerisation domain (Wurtz et al., Nature Struc. Biol. 3, 87–94 (1996), Parker et al., Nature Struc. Biol. 3, 113–115 (1996) and Kumar et al., Steroids 64, 310–319 (1999)). Although the overall protein sequence of these receptors can vary significantly, all share both a common structural arrangement indicative of divergence from an ancestral archetype, and substantial homology (especially, sequence identity) at the ligand-binding domain.

The steroid binding nuclear hormone receptors (SB-NHR's) comprise a sub-family of nuclear hormone receptors. These receptors are related in that they share a stronger sequence homology to one another, particularly in the ligand binding domain (LBD), than to the other members of the NHR super-family (Evans, 1988, supra) and they all utilize steroid based ligands. Some examples of this sub-family of NHR's are the androgen receptor (AR), the estrogen receptor (ER), the progesterone receptor (PR), the glucocorticoid receptor (GR), the mineralocorticoid receptor (MR), the aldosterone receptor (ALDR) and the steroid and xenobiotic receptor (SXR) (Evans et al., WO 99/35246). Based on the strong sequence homology in the LBD, several orphan receptors may also be members of the SB-NHR sub-family.

Consistent with the high sequence homology found in the LBD for each of the SB-NHR's, the natural ligands for each is derived from a common steroid core. Examples of some of the steroid based ligands utilized by members of the SB-NHR's include cortisol, aldosterone, estrogen, progesterone, testosterone and dihydrotestosterone. Specificity of a particular steroid based ligand for one SB-NHR versus another is obtained by differential substitution about the steroid core. High affinity binding to a particular SB-NHR, coupled with high level specificity for that particular SB-NHR, can be achieved with only minor structural changes about the steroid core (e.g., Waller et al., Toxicol. Appl. Pharmacol. 137, 219–227 (1996) and Mekenyan et al., Environ. Sci. Technol. 31, 3702–3711 (1997), binding affinity for progesterone towards the androgen receptor as compared to testosterone).

Numerous synthetically derived steroidal and non-steroidal agonists and antagonists have been described for the members of the SB-NHR family. Many of these agonist and antagonist ligands are used clinically in man to treat a variety of medical conditions. RU486 is an example of a synthetic agonist of the PR, which is utilized as a birth control agent (Vegeto et al., Cell 69: 703–713 (1992)), and Flutamide is an example of an antagonist of the AR, which is utilized for the treatment of prostate cancer (Neri et al, Endo. 91, 427–437 (1972)). Tamoxifen is an example of a tissues specific modulator of the ER function, that is used in the treatment of breast cancer (Smigel J. Natl. Cancer Inst. 90, 647–648 (1998)). Tamoxifen can function as an antagonist of the ER in breast tissue while acting as an agonist of the ER in bone (Grese et al., Proc. Natl. Acad. Sci. USA 94, 14105–14110 (1997)). Because of the tissue selective effects seen for Tamoxifen, this agent and agents like it are referred to as "partial-agonist" or partial-antagonist. In addition to synthetically derived non-endogenous ligands, non-endogenous ligands for NHR's can be obtained from food sources (Regal et al., Proc. Soc. Exp. Biol. Med. 223, 372–378 (2000) and Hempstock et al., J. Med. Food 2, 267–269 (1999)). The flavanoid phytoestrogens are an example of an unnatural ligand for SB-NHR's that are readily obtained from a food source such as soy (Quella et al., J. Clin. Oncol. 18, 1068–1074 (2000) and Banz et al., J. Med. Food 2, 271–273 (1999)). The ability to modulate the transcriptional activity of individual NHR by the addition of a small molecule ligand, makes them ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's or through directed approaches using the available crystal structures of a variety of NHR ligand binding domains (Bourguet et al., *Nature* 375, 377–382 (1995), Brzozowski, et al., *Nature* 389, 753–758 (1997), Shiau et al., *Cell* 95, 927–937 (1998) and Tanenbaum et al., *Proc. Natl. Acad. Sci. USA* 95, 5998–6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHR in *J. Med. Chem.*, 41, 623 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

The compounds of the present invention comprise a core which serves as a steroid mimic, and are useful as modulators of the function of steroid binding nuclear hormone receptors, as well as other NHR as described following.

SUMMARY OF THE INVENTION

The present invention provides fused cyclic compounds of the following formula I and pharmaceutically acceptable salts, solvates, prodrugs and stereoisomers thereof, which compounds are especially useful as modulators of nuclear hormone receptor function:

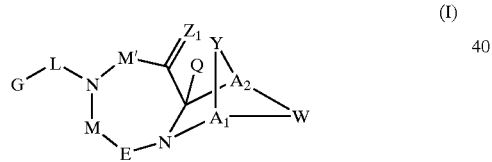

(I)

As used in formula I, and throughout the specification, the symbols have the following meanings unless otherwise indicated, and are, for each occurrence, independently selected:

G is an aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1OC=O$, $R^1C=O$, $R^1C=S$, $R^1HNC=O$, $R^1R^2NC=O$, $HOCR^3R^{3'}$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1'}$, $(R^1O)(R^{1'}O)P=O$, $(R^1)(R^{1'})P=O$, or $(R^{1'})(NHR^1)P=O$;

E is $C=Z_2$, $CR^7R^{7'}$ (e.g., $CHR^7$), $SO_2$, $P=OR^2$, or $P=OOR^2$;

$Z_1$ is O, S, NH, or $NR^6$;

$Z_2$ is O, S, NH, or $NR^6$;

$A_1$ is $CR^7$ or N;

$A_2$ is $CR^7$ or N;

Y is J—J'—J" where J is $(CR^7R^{7'})n$ and n=0–3, J' is a bond or O, S, S=O, $SO_2$, NH, $NR^6$, C=O, OC=O, $NR^1C=O$, $CR^7R^{7'}$, $C=CR^8R^{8'}$, $R^2P=O$, $OPOOR^2$, $OPO_2$, $OSO_2$, C=N, NHNH, $NHNR^6$, $NR^6NH$, N=N, cycloalkyl or substituted cycloalkyl, cycloalkenyl or substituted cycloalkenyl, heterocyclo or substituted heterocyclo or aryl or substituted aryl, and J" is $(CR^7R^{7'})n$ and n=0–3, where Y is not a bond (i.e., if J' is a bond, then in at least one of J or J" (each defined as $(CR^7R^{7'})n$), n is not zero);

W is $CR^7R^{7'}$—$CR^7R^{7'}$, $CR^8=CR^{8'}$, $CR^7R^{7'}$—C=O, $NR^9$—$CR^7R^{7'}$, N=$CR^8$, N=N, $NR^9$—$NR^{9'}$, cycloalkyl or substituted cycloalkyl, cycloalkenyl or substituted cycloalkenyl, heterocyclo or substituted heterocyclo, or aryl or substituted aryl;

Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

M is a bond, O, $CR^7R^{7'}$ or $NR^{10}$, and M' is a bond or $NR^{10}$, with the proviso that at least one of M or M' must be a bond;

L is a bond, $(CR^7R^{7'})n$, NH, $NR^5$ or $N(CR^7R^{7'})n$, where n=0–3;

$R^1$ and $R^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl;

$R^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^3$ and $R^{3'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, hydroxylamine, hydroxamide, alkoxy or substituted alkoxy, amino, $NR^1R^2$, thiol, alkylthio or substituted alkylthio;

$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C=O$, $R^1NHC=O$, $SO_2OR^1$, or $SO_2NR^1R^{1'}$;

$R^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C=O$, $R^1NHC=O$, $SO_2R^1$, $SO_2OR^1$, or $SO_2NR^1R^{1'}$;

$R^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C=O$, $R^1NHC=O$, $SO_2R^1$, $SO_2OR^1$, or $SO_2NR^1R^{1'}$;

$R^7$ and $R^{7'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, $OR^1$, nitro, hydroxylamine, hydroxylamide, amino, $NHR^4$, $NR^2R^5$, $NOR^1$, thiol, alkylthio or substituted alkylthio, $R^1C=O$, $R^1(C=O)O$, $R^1OC=O$, $R^1NHC=O$, $SO_2R^1$, $SOR^1$, $PO_3R^1R^{1'}$, $R^1R^{1'}NC=O$, $C=OSR^1$, $SO_2R^1$, $SO_2OR^1$, or $SO_2NR^1R^{1'}$;

$R^8$ and $R^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, $OR^1$, amino, $NHR^4$, $NR^2R^5$, $NOR^1$, alkylthio or substituted alkylthio, $C=OSR^1$, $R^1OC=O$, $R^1C=O$, $R^1NHC=O$, $R^1R^{1'}NC=O$, $SO_2OR^1$, $S=OR^1$, $SO_2R^1$, $PO_3R^1R^{1'}$, or $SO_2NR^1R^{1'}$;

$R^9$ and $R^{9'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted cycloalkenylalkyl, heterocycloalkyl or substituted arylalkyl, CN, OH, $OR^1$, $R^1C=O$, $R^1OC=O$, $R^1NHC=O$, $SO_2R^1$, $SO_2OR^1$, or $SO_2NR^1R^{1'}$; and $R^{10}$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C=O$, $R^1OC=O$, $R^1R^{1'}NC=O$, $SO_2R^1$, $SO_2OR^1$, or $SO_2NR^1R^{1'}$.

The compounds of formula I and salts thereof, comprising a core which can serve as a steroid mimic (and which do not require the presence of a steroid-type (e.g., cyclopentanoperhydrophenanthrene analog) structure), are novel except that:

where E is C=O, M and M' are both a bond, $Z_1$ is O, Q is H and $A_1$ and $A_2$ are CH: (i) G—L— is not phenyl, 4-chlorophenyl or benzyl when W is —CH=CH— and Y is —$CH_2$—$CH_2$—; (ii) G—L— is not phenyl when W is —CH=CH— or —$CH_2$—$CH_2$— and Y is —$CH_2$—; (iii) G—L— is not phenyl, 4-methoxyphenyl, 4-chlorophenyl, or certain (optionally substituted aryl)-($C_1$-$C_3$)-alkyl- groups (e.g., benzyl), when W and Y are —$CH_2$—$CH_2$—; and (iv) G—L— is not 4-chlorophenyl or benzyl when W and Y are phenylene;

where E is C=O, M and M' are both a bond, $Z_1$ is O, and $A_1$ and $A_2$ are CH: (i) G—L— is not benzyl when Q is —$CO_2CH_3$, W is —CH=CH— and Y is —$CH_2$— or —$CH_2$—$CH_2$—; and (ii) G—L— is not phenyl when Q is methyl, W is —CH=CH— and Y is —$CH_2$—;

where E is C=S, M and M' are both a bond, $Z_1$ is O, Q is H, $A_1$ and $A_2$ are CH, W is —CH=CH— and Y is —$CH_2$— or —$CH_2$—$CH_2$—, G—L— is not phenyl; and where E is C=O, M and M' are both a bond, $Z_1$ is O, Q is H, Y is —$CH_2$—$CH_2$—, and W is —CH=CH— or —$CH_2$—$CH_2$—, G—L— is not 4-chlorophenyl (i) when $A_1$ and $A_2$ are C—$CH_3$; and (ii) when $A_1$ is C-isopropyl and $A_2$ is C—$CH_3$.

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include but are not limited to one or more of the following groups: halo (e.g., a single halo substituent or multiple halo substitutents forming, in the latter case, groups such as a perfluoroalkyl group or an alkyl group bearing $Cl_3$ or $CF_3$), alkoxy, alkylthio, hydroxy, carboxy (i.e., —COOH), alkoxycarbonyl, alkylcarbonyloxy, amino (i.e., —$NH_2$), carbamoyl or substituted carbomoyl, carbamate or substituted carbamate, urea or substituted urea, amidinyl or substituted amidinyl, thiol (—SH), aryl, heterocycle, cycloalkyl, heterocycloalkyl, —S-aryl, —S-heterocycle, —S=O-aryl, —S=O-heterocycle, —$S(O)_2$-aryl, —$S(O)_2$-heterocycle, —$NHS(O)_2$-aryl, —$NHS(O)_2$-heterocycle, —$NHS(O)_2NH$- aryl, —NHS(O)₂NH-heterocycle, —P(O)₂-aryl, —P(O)₂-heterocycle, —NHP(O)₂-aryl, —NHP(O)₂-heterocycle, —NHP(O)₂NH-aryl, —NHP(O)₂NH-heterocycle, —O-aryl, —O-heterocycle, —NH-aryl, —NH-heterocycle, —NHC=O-aryl, —NHC=O-heterocycle, —OC=O-aryl, —OC=O-heterocycle, —NHC=ONH-aryl, —NHC=ONH-heterocycle, —OC=OO-aryl, —OC=OO-heterocycle, —OC=ONH-aryl, —OC=ONH-heterocycle, —NHC=OO-aryl, —NHC=OO-heterocycle, —C=ONH-aryl, —C=ONH-heterocycle, —C=OO-aryl, —C=OO-heterocycle, —N(alkyl)S(O)₂-aryl, —N(alkyl)S(O)₂-heterocycle, —N(alkyl)S(O)₂NH-aryl, N(alkyl)S(O)₂NH-heterocycle, —N(alkyl)P(O)₂-aryl, —N(alkyl)P(O)₂-heterocycle, —N(alkyl)P(O)₂NH-aryl, N(alkyl)P(O)₂NH-heterocycle, —N(alkyl)-aryl, —N(alkyl)-heterocycle, —N(alkyl)C=O-aryl, —N(alkyl)C=O-heterocycle, —N(alkyl)C=ONH-aryl, —N(alkyl)C=ONH-heterocycle, —OC=ON(alkyl)-aryl, —OC=ON(alkyl)-heterocycle, —N(alkyl)C=OO-aryl, —N(alkyl)C=OO-heterocycle, —C=ON(alkyl)-aryl, —C=ON(alkyl)-heterocycle, —NHS(O)₂N(alkyl)-aryl, NHS(O)₂N(alkyl)-heterocycle, NHP(O)₂N(alkyl)-aryl, NHP(O)₂N(alkyl)-heterocycle, —NHC=ON(alkyl)-aryl, —NHC=ON(alkyl)-heterocycle, —N(alkyl)S(O)₂N(alkyl)-aryl, —N(alkyl)S(O)₂N(alkyl)-heterocycle, —N(alkyl)P(O)₂N(alkyl)-aryl, —N(alkyl)P(O)₂N(alkyl)-heterocycle, —N(alkyl)C=ON(alkyl)-aryl, and —N(alkyl)C=ON(alkyl)-heterocycle, as well as by OR$^{13}$ where R$^{13}$ is defined below in Scheme XV. In the aforementioned exemplary substitutents, groups such as "aryl" and "heterocycle" can themselves be optionally substituted.

The term "alkenyl" refers to a straight or branched chain hydrocarbon radical containing from 2 to 12 carbon atoms and at least one carbon-carbon double bond. Exemplary such groups includes ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkenyl or substituted cycloalkenyl.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkyl or substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "alkoxycarbonyl" refers to an alkoxy group bonded through a carbonyl group.

The term "alkylcarbonyl" refers to an alkyl group bonded through a carbonyl group. The term "alkylcarbonyloxy" refers to an alkylcarbonyl group bonded through an oxygen linkage.

The terms "arylalkyl", "substituted arylalkyl," "cycloalkylalkyl," "substituted cycloalkylalkyl," "cycloalkenylalkyl", "substituted cycloalkenylalkyl", "heterocycloalkyl" and "substituted heterocycloalkyl" refer to aryl, cycloalkyl, cycloalkenyl and heterocyclo groups bonded through an alkyl group, substituted on the aryl, cycloalkyl, cycloalkenyl or heterocyclo and/or the alkyl group where indicated as "substituted."

The term "aryl" refers to cyclic, aromatic hydrocarbon groups which have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl-S(O)$_m$— (m=0, 1 or 2), alkyl or substituted alkyl, as well as those groups recited above as exemplary alkyl substituents and as previously mentioned as preferred aryl substituents in the definition for G. Exemplary substituents also include fused cyclic substituents, such as heterocyclo or cycloalkenyl, or substituted heterocyclo or cycloalkenyl, groups.

"Carbamoyl" refers to the group —CONH— which is bonded on one end to the remainder of the molecule and on the other to hydrogen or an organic moiety (such as alkyl, substituted alkyl, aryl, substituted aryl, heterocycle, alkylcarbonyl, hydroxyl and substituted nitrogen). "Carbamate" refers to the group —O—CO—NH— which is bonded on one end to the remainder of the molecule and on the other to hydrogen or an organic moiety (such as those listed above). "Urea" refers to the group —NH—CO—NH— which is bonded on one end to the remainder of the molecule and on the other to hydrogen or an organic moiety (such as those listed above). "Amidinyl" refers to the group —C(=NH)(NH₂). "Substituted carbamoyl," "substituted carbamate," "substituted urea" and "substituted amidinyl" refer to carbamoyl, carbamate, urea or amidinyl groups as described above in which one more of the hydrogen groups are replaced by an organic moiety (such as those listed above).

The terms "heterocycle", heterocyclic and "heterocyclo" refer to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-]pyridiny or furo 2,3-pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle," "substituted heterocyclic," and "substituted heterocyclo" (such as "substituted heteroaryl") refer to heterocycle, heterocyclic or heterocyclo groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl-S(O)$_m$— (m=0, 1 or 2), alkyl or substituted alkyl, as well as those groups recited above as exemplary alkyl substituents, and as previously mentioned as preferred heterocyclo substituents in the definition for G.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine or iodine.

The terms "hydroxylamine" and "hydroxylamide" refer to the groups OH—NH— and OH—NH—CO—, respectively.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis,* Wiley, N. Y. (1991).

When a term such as "(CRR)n" is used, it denotes an optionally substituted alkyl chain existing between the two fragments to which it is bonded, the length of which chain is defined by the range described for the term n. An example of this is n=0–3, implying from zero to three (CRR) units existing between the two fragments, which are attached to the primary and terminal (CRR) units. In the situation where the term n is set to zero (n=0) then a bond exists between the two fragments attached to (CRR).

Unless otherwise indicated, any heteroatom with unsatisfied valences is assumed to have hydrogen atoms sufficient to satisfy the valences.

Divalent groups, such as those in the definition of W (e.g., NR$^9$—CR$^7$R$^{7'}$), may be bonded in either direction to the remainder of the molecule (e.g,

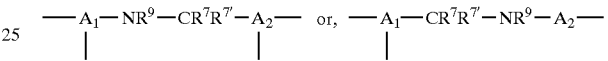

for the aforementioned group within the definition of W).

Carboxylate anion refers to a negatively charged group —COO$^-$.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

Throughout the specifications, groups and substituents thereof may be chosen to provide stable moieties and compounds.

Methods of Preparation

The compounds of the present invention may be prepared by methods such as those illustrated in the following Schemes I to XV. Solvents, temperatures, pressures, and other reaction conditions may readily be selected by one of ordinary skill in the art. Starting materials are commercially available or readily prepared by one of ordinary skill in the art or prepared by methods illustrated in FIGS. 1 to 3. Combinatorial techniques may be employed in the preparation of compounds, for example, where the intermediates possess groups suitable for these techniques. See the following for alternative methods which may be employed in the preparation of compounds of the present invention: Tetrahedron, 27, 3119 (1971); Tetrahedron, 30, 2977 (1974); Tetrahedron. Let, 31, 2631 (1969); J. Org. Chem., 35, 3097 (1970); Bull. Chem. Soc. Jpn., 67, 3082 (1994); Bull. Chem. Soc. Jpn., 65, 61 (1992); European Patent (EP) No. 406119; U.S. Pat. No. 4,397,857; Pons et al., Eur. J. Org. Chem., 853–859 (1998); Kucharczyk et al., J. Med. Chem., 1654–1661 (1993); and German Patent (DE) Document No. 3227055.

All documents cited in the present specification, such as those cited in this "Methods of Preparation" as well as other sections herein, are incorporated herein by reference in their entirety. Such documents are not admitted as prior art.

Scheme I

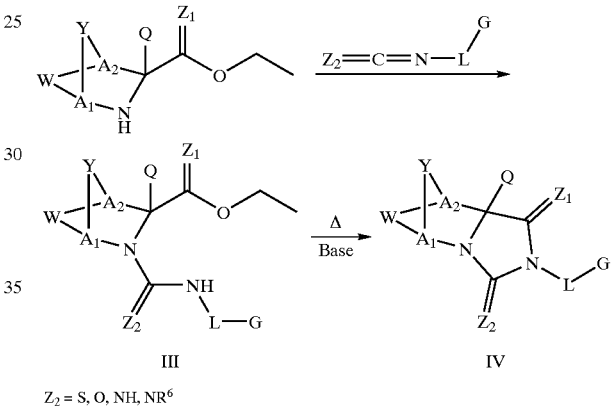

$Z_2$ = S, O, NH, $NR^6$

As illustrated in Scheme I, compounds of formula I can be obtained from azabicyclo-3-ethylcarboxylate intermediates of formula II. Intermediates of formula II can be prepared, for example, from the synthetic approaches described in Bull. Chem. Soc. Jpn., 65, 61 (1992), Tetrahedron Let. 31, 2603 (1990), Chem. Commun. 597 (1999), Tetrahedron Lett. 38, 4021, (1997), Tetrahedron Lett. 40, 7929 (1999), Synlett. 1, 29 (1991), J. Chem. Soc., Chem. Commun. 1601 (1988), J. Org. Chem. 31, 1059 (1966), Synthesis 10, 925 (1990), Tetrahedron Lett. 40, 8447 (1999), U.S. Pat. No. 4,775,668 and EP No. 266576 and the references therein, by one of ordinary skill in the art (incorporated herein by reference in their entirety). In addition to a racemic mixture of a compound of formula II, individual antipodes can be synthesized, for example, in accordance with procedures set forth in the above documents. Exemplary methods for preparing compounds of the formula II are described further below in FIGS. 1 to 3.

Treatment of II with an intermediate of formula $Z_2$=C=N—L—G, yields an intermediate of formula III. The intermediates of formula $Z_2$=C=N—L—G can be obtained, for example, from commercially available isocyanates, thioisocyanates and carbodiimides or can be readily prepared by one skilled in the art. An intermediate of formula III can be heated with or without the presence of a base, such as DBU or triethylamine, to yield a compound of formula IV, which is compound of formula I where M' and M are each a bond and E is C=$Z_2$. The individual optical isomers of a compound of Formula IV (also known as antipodes) can be obtained, for example, by use of the corresponding individual antipodes of a compound of formula II or by separation of the racemic mixture by standard techniques. The individual α or β (endo or exo) isomers of a compound of formula IV can be obtained, for example, by separation of a resulting mixture by standard techniques.

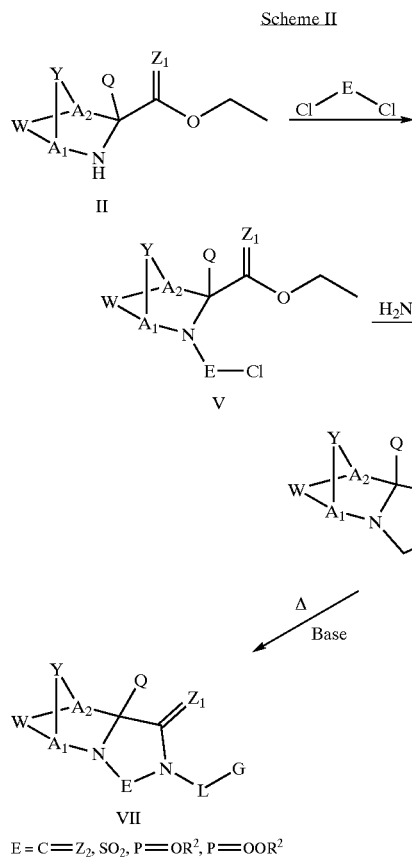

Scheme II

E = C=$Z_2$, $SO_2$, P=$OR^2$, P=$OOR^2$ obtained, for example, by use of the corresponding individual antipodes of a compound of formula II or by separation of the racemic mixture by standard techniques. The individual α or β isomers of a compound of formula VII can be obtained, for example, by separation of a resulting mixture by standard techniques.

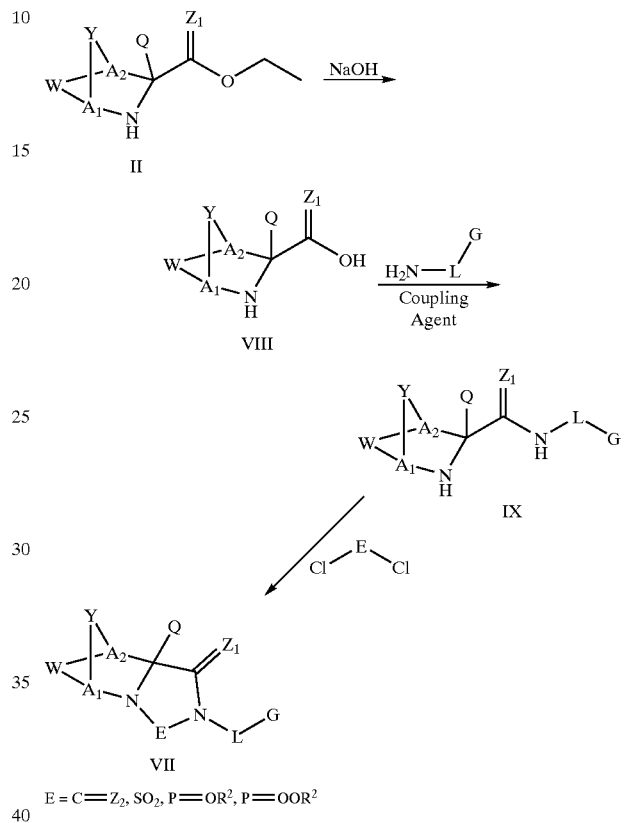

Scheme III

E = C=$Z_2$, $SO_2$, P=$OR^2$, P=$OOR^2$

Scheme II describes a method for preparing compounds of formula I wherein an intermediate of formula II is treated with a phosgene like reagent of formula Cl—E—Cl in the presence of a base, such as $NaHCO_3$, to yield an intermediate of formula V. The phosgene like intermediates of formula Cl—E—Cl can be obtained from commercially available sources or can readily be prepared by one skilled in the art. Phosgene equivalents such as carbonyldiimidazoles may alternatively be employed in this step, and elsewhere in these Schemes as appropriate, in place of Cl—E—Cl. The intermediate of formula V can be reacted with an amine of formula $H_2N$—L—G in the presence of a base, such as diisopropylamine or triethylamine, with or without a coupling reagent, such as DMAP, to give an intermediate of formula VI. The amine intermediates of formula $H_2N$—L—G can be obtained from commercially available sources or can readily be prepared by one skilled in the art. The intermediate of formula VI can be converted to a compound of formula VII by heating with or without the presence of a base, such as DBU or triethylamine. A compound of formula VII is a compound of formula I where M and M' are each a bond and E is C=$Z_2$, $SO_2$, P=$OR^2$ or P=$OOR^2$. The individual antipodes of a compound of formula VII can be obtained, for example, by use of the corresponding individual antipodes of a compound of formula II or by separation of the racemic mixture by standard techniques. The individual α or β isomers of a compound of formula VII can be obtained, for example, by separation of a resulting mixture by standard techniques.

Scheme III describes a method for preparing compounds of formula I wherein an intermediate of formula II is saponified to an acid of formula VIII by treatment with a base, such as sodium hydroxide. The acid can then by coupled to an amine of formula $H_2N$—L—G via a variety of coupling reagents, for example, as described in The Practice of Peptide Synthesis, Springer-Verlag, $2^{nd}$ Ed., Bodanszy, Miklos, 1993 (incorporated herein by reference in its entirety), to yield an amide intermediate of formula IX. The intermediate of formula IX can be heated, with or without the presence of a base such as triethylamine, with a phosgene like reagent of formula Cl—E—Cl, to yield a compound of formula VII, which is a compound of formula I where M and M' are each a bond and E is C=$Z_2$, $SO_2$, P=$OR^2$ or P=$OOR^2$. The individual antipodes of a compound of formula VII can be obtained, for example, by use of the corresponding individual antipodes of a compound of formula II or by separation of the racemic mixture by standard techniques. The individual α or β isomers of a compound of formula VII can be obtained, for example, by separation of a resulting mixture by standard techniques.

Scheme IV

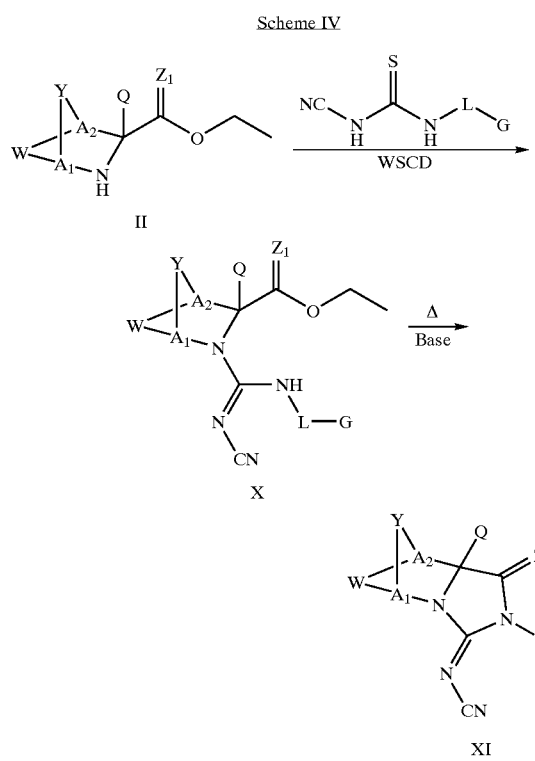

As shown in Scheme IV, a route to compounds of formula I in which E is C=$Z_2$ and $Z_2$=N—CN, involves treatment of an intermediate of formula II with a substituted cyanothiourea of formula NC—NH—C(S)—NH—L—G, in the presence of a water soluble coupling reagent (WSCD), such as 1-(3-dimethylaminopropyl)-3-ethylcarbodiimide hydrochloride, as described in *Tetrahedron. Let.* 30, 7313 (1989) (incorporated herein by reference in its entirety), to yield an intermediate of formula X. The substituted cyanothioureas of formula NC—NH—C(S)—NH—L—G can be obtained from commercially available sources or can readily be prepared by one skilled in the art. An intermediate of formula X can be heated with or without the presence of a base, such as DBU, to yield a compound of formula XI, which is a compound of formula I where, in addition to E being C=N—CN, M and M' are each a bond. The individual antipodes of a compound of formula XI can be obtained, for example, by use of the corresponding individual antipodes of a compound of formula II or by separation of the racemic mixture by standard techniques. The individual α or β isomers of a compound of formula XI can be obtained, for example, by separation of a resulting mixture by standard techniques.

Scheme V

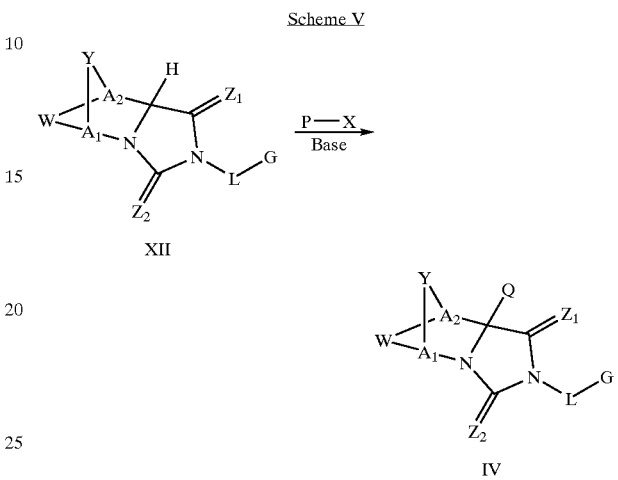

As illustrated in Scheme V, a compound of formula XII, which is a compound of formula I in which Q=H, can be converted to a compound of formula I where Q is equal to substituents as defined herein other than H, by treatment with a base such as LDA and an alkyl halide such as methyl iodide, preferably in a solvent such as tetrahydrofuran at low temperatures (e.g., −78° C.) to yield a compound of formula IV, which is a compound of formula I where M' and M are each a bond and E is C=$Z_2$. The individual antipodes of a compound of formula IV can be obtained, for example, by use of the corresponding individual antipodes of a compound of formula XII or by separation of the racemic mixture by standard techniques. The individual α or β isomers of a compound of formula IV can be obtained, for example, by use of the corresponding individual endo or exo isomers of a compound of formula XII or by separation of a resulting mixture by standard techniques. Compounds of the formula XII may be obtained, for example, by employing the procedure of Scheme I wherein Q=H.

Scheme VI

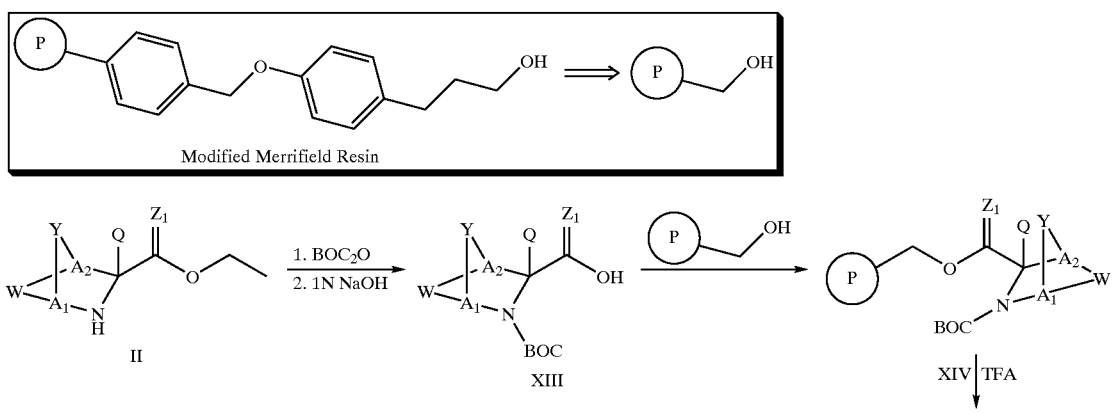

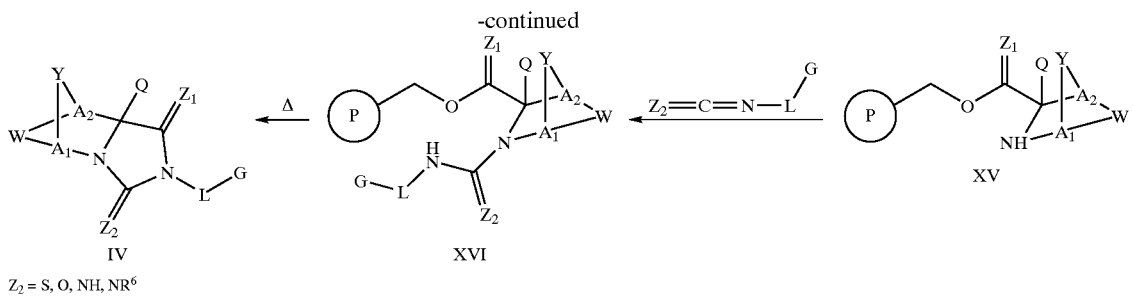

$Z_2 = S, O, NH, NR^6$

As shown in Scheme VI, compounds of formula I can be synthesized by means of a solid support route. As such, the above synthetic route allows for the synthesis of combinatorial libraries of compounds of formula I via, for example, standard procedures of automated solid phase synthesis. Treatment of a compound of formula II with a protecting agent such as di-tertbutylcarbonate, followed by hydrolysis of the ester group by treatment with a base, such as sodium hydroxide, yields an intermediate of formula XIII. The intermediate of formula XIII can be attached to a solid support, such as a modified Merrifield resin, by treatment with a coupling reagent such as 2,6-dichloro-benzoyl chloride in the presence of pyridine and DMF, to yield a solid support intermediate of formula XIV. Removal of the protecting group can be achieved by treatment with an acid, such as trifluoroacetic acid in DMF with sonication, to yield a compound of formula XV, which can be reacted with an intermediate of formula $Z_2$=C=N—L—G, to yield an intermediate of formula XVI. The final product, IV, can be formed and liberated from the solid support by heating the intermediate of formula XVI with or without a base, such as DBU. A compound of formula IV is a compound of formula I where M' and M are each a bond and E is C=$Z_2$. The individual antipodes of a compound of formula IV can be obtained, for example, by use of the corresponding individual antipodes of a compound of formula II or by separation of the racemic mixture by standard techniques. The individual α or β isomers of a compound of formula IV can be obtained, for example, by separation of a resulting mixture by standard techniques.

Scheme VII

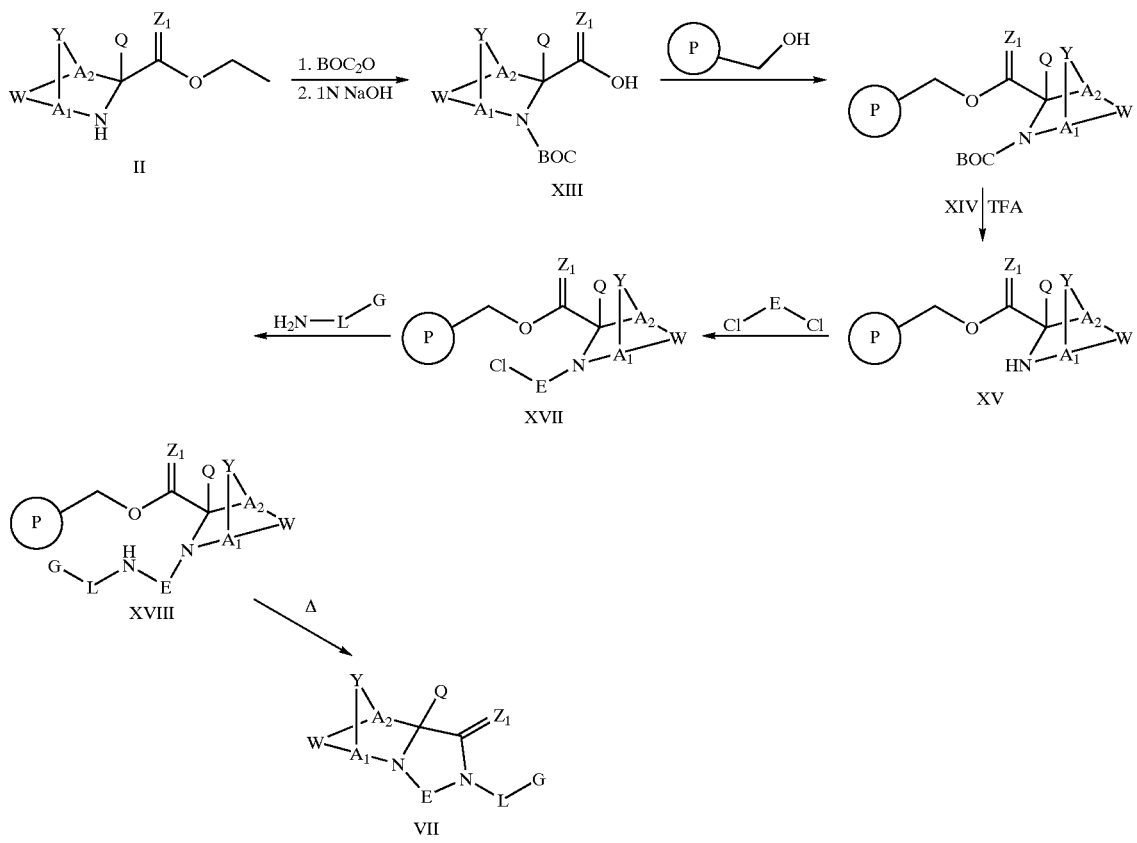

$E = C=Z_2, SO_2, P=OR^2, P=OOR^2$

Scheme VII shows an alternate approach to the synthesis of compounds of formula I on solid support. As described for Scheme VI, an intermediate of formula XV can readily be synthesized. The intermediate of formula XV can be treated, with or without the presence of a base such as triethylamine or NaHCO$_3$, with a phosgene like reagent of formula Cl—E—Cl, to yield an intermediate of formula XVII. The intermediate of formula XVII can be reacted with an amine of formula H$_2$N—L—G in the presence of a base, such as diisopropylamine, with or without a coupling reagent, such as 4-dimethylamino pyridine, to give an intermediate of formula XVIII. The final product VII can be formed and liberated from the solid support by heating the intermediate of formula XVIII with or without a base, such as DBU. A compound of formula VII is a compound of formula I where M and M' are each a bond and E is C=Z$_2$, SO$_2$, P=OR$^2$ or P=OOR$^2$. The individual antipodes of a compound of formula VII can be obtained, for example, by use of the corresponding individual antipodes of a compound of formula II or by separation of the racemic mixture by standard techniques. The individual α or β isomers of a compound of formula VII can be obtained, for example, by separation of a resulting mixture by standard techniques.

a base, such as triethylamine, to yield a compound of formula XXIII, which is a compound of formula I where M is a bond, M' is NR$^{10}$ and E is C=Z$_2$, SO$_2$, P=OR$^2$ or P=OOR$^2$. The individual antipodes of a compound of formula XXIII can be obtained, for example, by use of the corresponding individual antipodes of a compound of formula II or by separation of the racemic mixture by standard techniques. The individual α or β isomers of a compound of formula XXIII can be obtained, for example, by separation of a resulting mixture by standard techniques.

Scheme IX

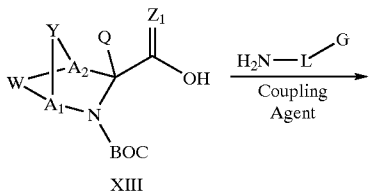

Scheme VIII

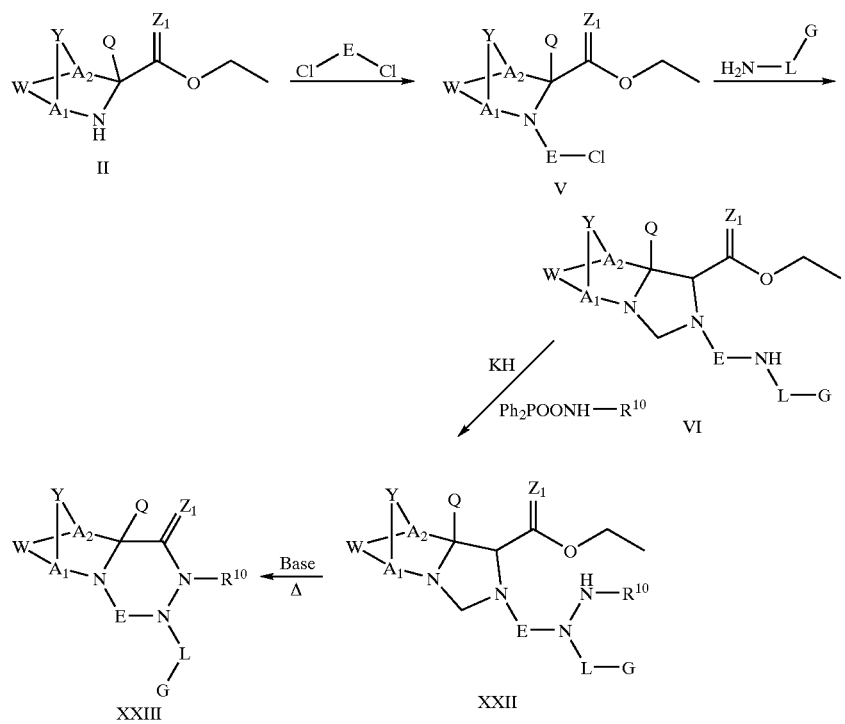

E = C=Z$_2$, SO$_2$, P=OR$^2$, P=OOR$^2$

As described in Scheme II, an intermediate of formula VI can be readily synthesized. As shown in Scheme VIII, treatment of an intermediate of formula VI with a substituted O-diphenylphosphinylhydroxylamine of formula Ph$_2$POONH—R$^{10}$, and potassium hydride as described in *Synthesis*, 7, 592 (1982) and *Tetrahedron Let.*, 29, 1777 (1988) (both incorporated herein by reference in their entirety), yields an intermediate of formula XXII. The intermediate of formula XXII can be heated with or without -continued

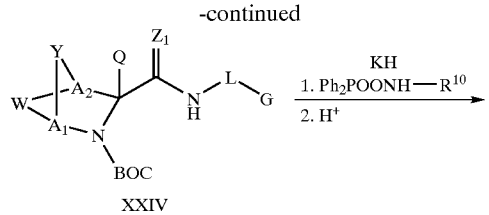

-continued

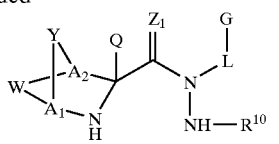

XXV

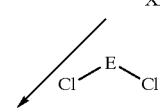

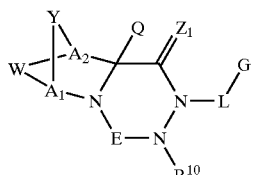

XXVI

-continued

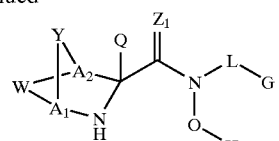

XXVII

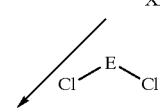

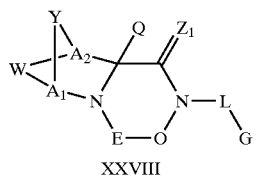

XXVIII

As described in Scheme VI, an intermediate of formula XIII can be readily synthesized. As shown in Scheme IX, the acid intermediate of formula XIII can be coupled to an amine of formula $H_2N-L-G$ via use of a variety of coupling reagents, as described in Scheme III, to yield an amide intermediate of formula XXIV. Treatment of the intermediate of formula XXIV with potassium hydride and a substituted O-diphenylphosphinylhydroxylamine of formula $Ph_2POONH-R^{10}$, as described in Scheme VIII, followed by removal of the BOC protecting group by treatment with an acid, such as trifluoroacetic acid, yields an intermediate of formula XXV. The intermediate of formula XXV can be treated with a phosgene like reagent of formula Cl—E—Cl, to yield an intermediate which can be heated with or without a base, such as triethylamine, to yield a compound of formula XXVI, which is a compound of formula I where M' is a bond, M is $NR^{10}$ and E is C=$Z_2$, $SO_2$, P=$OR^2$ or P=$OOR^2$. The individual antipodes of a compound of formula XXVI can be obtained, for example, by use of the corresponding individual antipodes of a compound of formula XIII or by separation of the racemic mixture by standard techniques. The individual α or β isomers of a compound of formula XXVI can be obtained, for example, by separation of a resulting mixture by standard techniques.

Scheme X

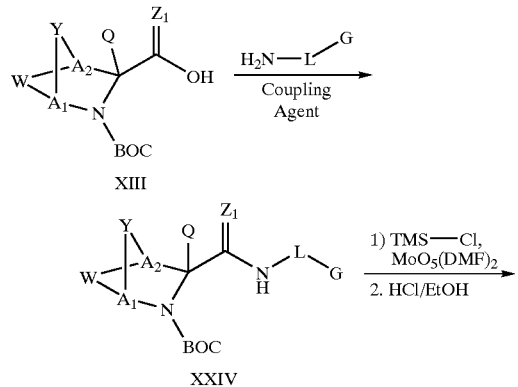

As described in Scheme IX, an intermediate of formula XXIV can be readily synthesized. As shown in Scheme X, treatment of an intermediate of formula XXIV with agents suitable for forming a hydroxylamide moiety, such as TMS—Cl followed by $MoO_5(DMF)_2$ as described in *J. Org. Chem.*, 54, 5852 (1989) and *J. Org. Chem.*, 59, 8065 (1994) (both incorporated herein by reference in their entirety), and for deprotection of a BOC group, such as ethanol saturated with HCl gas, results in the generation of a hydroxylamide intermediate of formula XXVII. The intermediate of formula XXVII can be treated with a phosgene like reagent of formula Cl—E—Cl, to yield a compound of formula XXVIII, which is a compound of formula I where M is O, M' is a bond, and E is C=$Z_2$, $SO_2$, P=$OR^2$ or P=$OOR^2$. The individual antipodes of a compound of formula XXVIII can be obtained, for example, by use of the corresponding individual antipodes of a compound of formula XIII or by separation of the racemic mixture by standard techniques. The individual α or β isomers of a compound of formula XXVIII can be obtained, for example, by separation of a resulting mixture by standard techniques.

Scheme XI

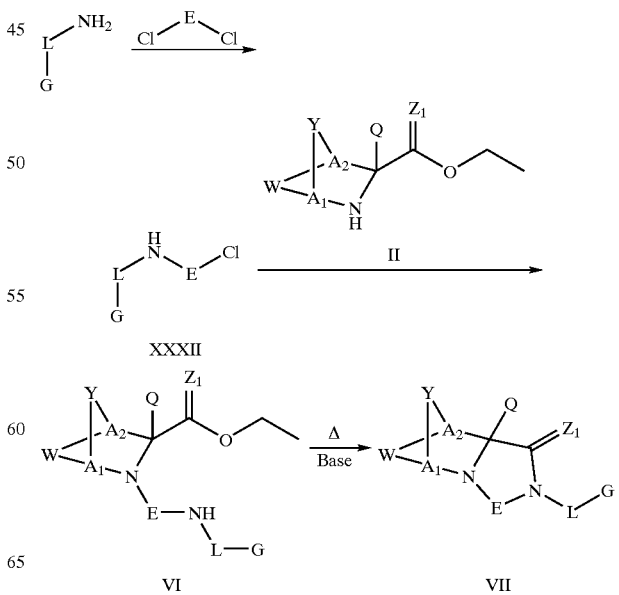

E=C=Z$_2$, SO$_2$, P=OR$^2$, P=OOR$^2$

As shown in Scheme XI, treatment of an intermediate of formula H$_2$N—L—G with a phosgene like reagent of formula Cl—E—Cl as described in *Oppi. Briefs* 17, 235 (1985), results in an intermediate of formula XXXII. The intermediate of formula XXXII can be reacted with an intermediate of formula II to yield an intermediate of formula VI. As described in Scheme II, an intermediate of formula VI can readily be converted to an intermediate of formula VII, which is a compound of formula I where M and M' are each a bond and E is C=Z$_2$, SO$_2$, P=OR$^2$ or P=OOR$^2$. The individual antipodes of a compound of formula VII can be obtained, for example, by use of the corresponding individual antipodes of a compound of formula II or by separation of the racemic mixture by standard techniques. The individual α or β isomers of a compound of formula VII can be obtained, for example, by use of the corresponding individual endo or exo isomers of a compound of formula II or by separation of a resulting mixture by standard techniques.

Scheme XII

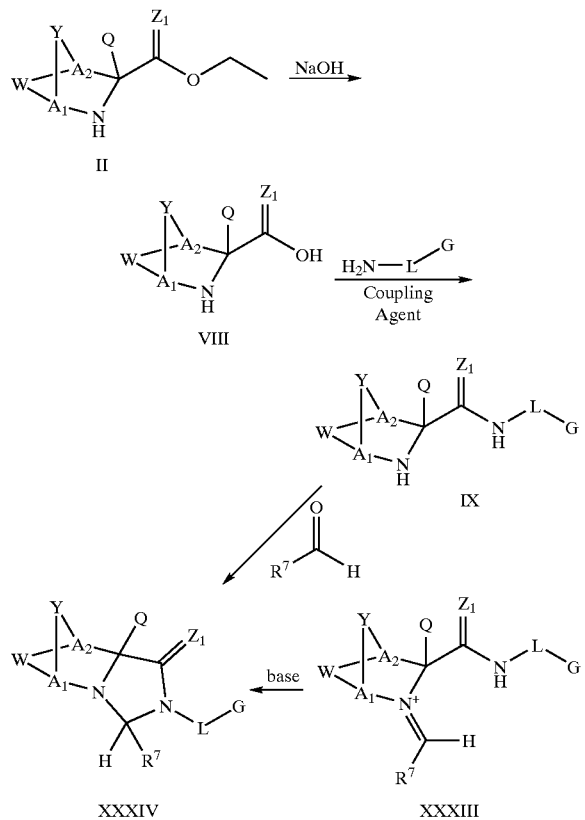

As described in Scheme III, a compound of formula IX can readily be made by the process described. As illustrated in Scheme XII, treatment of a compound of formula IX, with an aldehyde reagent of formula R$^7$CHO, which can be obtained from commercial sources or readily synthesized by one skilled in the art, yields an imine intermediate of formula XXXIII. Treatment of the intermediate of formula XXXIII, with a base such as DBU, results in a compound of formula XXXIV, which is a compound of formula I where M and M' are each a bond and E is CHR$^7$. The individual antipodes of a compound of formula XXXIV can be obtained, for example, by use of the corresponding individual antipodes of a compound of formula II or by separation of the racemic mixture by standard techniques. The individual α or β isomers of a compound of formula XXXIV can be obtained by separation of a resulting mixture by standard techniques.

Scheme XIII

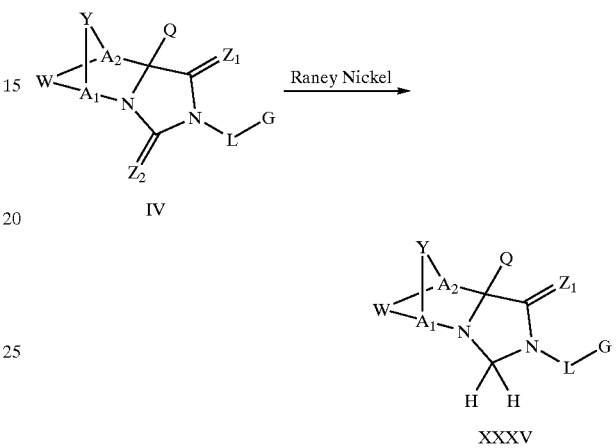

Z$_2$ = S

As described in Scheme I a compound of formula IV, where Z$_2$=S, can readily be made by the process described. As illustrated in Scheme XIII, treatment of a compound of formula IV, where Z$_2$=S, with an agent capable of reductively eliminating sulfur, such as Raney nickel, yields a compound of formula XXXV, which is a compound of formula I, where M and M' are each a bond and E is CH$_2$. The individual antipodes of a compound of formula XXXV can be obtained, for example, by use of the corresponding individual antipodes of a compound of formula II or by separation of the racemic mixture by standard techniques. The individual α or β isomers of a compound of formula XXXV can be obtained by separation of a resulting mixture by standard techniques.

Scheme XIV

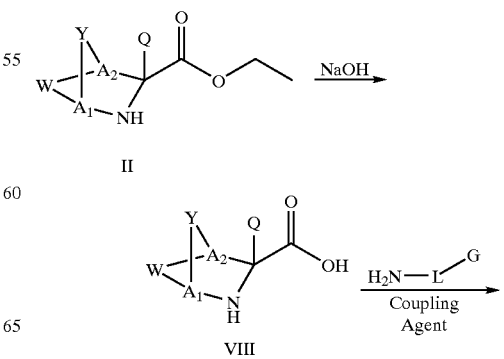

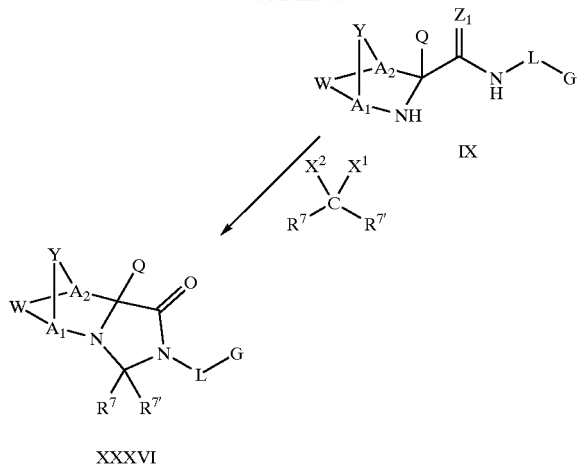

XXXVI

Scheme XIV describes a method for preparing compounds of formula I wherein an intermediate of formula II (where $Z_1$ is O) is saponified to an acid of formula VIII by treatment with a base, such as sodium hydroxide. The acid can then by coupled to an amine of formula $H_2N$—L—G via a variety of coupling reagents, for example, as described in The Practice of Peptide Synthesis, Springer-Verlag, $2^{nd}$ Ed., Bodanszy, Miklos, 1993 (incorporated herein by reference in its entirety), to yield an amide intermediate of formula IX. The intermediate of formula IX can be treated with a reagent of formula $R^7R^{7'}$—C—$X^1X^2$ (where $X^1$ and $X^2$ are independently F, Br, Cl, or I, or $X^1$ and $X^2$ are taken together along with the carbon to which they are attached to form C=O), to yield a compound of formula XXXVI, which is a compound of formula I where $Z_1$ is O, M and M' are bonds and E is $CR^7R^{7'}$ (such as where one of $R^7$ and $R^{7'}$ is H, $C_{1-4}$alkyl or $C_{1-4}$haloalkyl and the other is $R^1OC$=O).

When the intermediate of formula $R^7R^{7'}$—C—$X^1X^2$ is a ketone ($X^1$ and $X^2$ are taken together with the attached carbon to form C=O), amines of formula IX can be condensed with these intermediate carbonyl compounds, for example, in the presence of sodium hydroxide in water at a temperature between 0° C. and 25° C. using the procedures described by D. A. Johnson et. al., *J. Org. Chem.* 31, 897 (1966) and Uozumi et. al., *Tetrahedron Letters,* 42 407–410 (2001). (See Scheme XII above for when the intermediate of formula $R^7R^{7'}$—C—$X^1X^2$ is an aldehyde). When the intermediate of formula $R^7R^{7'}$—C—$X^1X^2$ is a dihalide ($X^1$ and $X^2$ are halogens), the condensation can be conducted, for example, in the presence of a base by heating the mixture of IX and $R^7R^{7'}$—C—$X^1X^2$ in an inert solvent. Preferred dihalides of formula $R^7R^{7'}$—C—$X^1X^2$ are ethyl bromofluoroacetate and ethyl bromodifluoroacetate. Examples of suitable bases include alkali salts of carbonate, such as potassium, sodium and lithium, and hydride bases such as sodium hydride. Examples of inert solvents include ethers such as diethyl ether, tetrahydrofuran and dioxane; esters such as ethyl acetate; amides such as dimethylformamide; and acetonitrile. Although the cyclization of compounds of formula IX and $R^7R^{7'}$—C—$X^1X^2$ can proceed at room temperature, the reaction is preferably performed by heating above room temperature. Dihalides, aldehydes and ketones of formula $R^7R^{7'}$—C—$X^1X^2$ can be prepared by known methods and many are commercially available. For example, see March, J. *Advanced Organic Chemistry;* $3^{rd}$ ed., John Wiley: New York, 1985. Other synthetic routes which can be employed for the conversion of compounds of formula IX to compounds of formula XXXVI are analogous to those found in WO-9414817, U.S. Pat. No. 5,643,855, WO-0107440, WO-9910313, WO-9910312 and JP-46016990 and the references therein. The individual optical isomers of a compound of formula XXXVI (also known as antipodes) can be obtained, for example, by use of the corresponding individual antipodes of a compound of formula II or by separation of the racemic mixture by standard techniques. The individual α or β isomers of a compound of formula XXXVI can be isolated from the resulting mixture, for example, by standard techniques.

Scheme XV

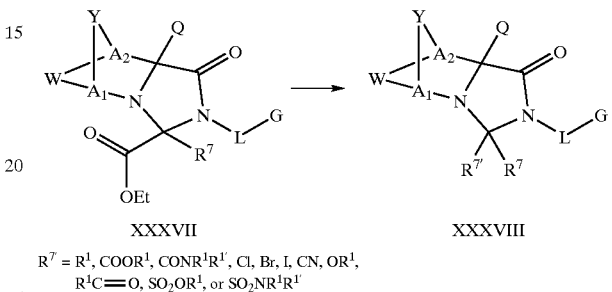

XXXVII      XXXVIII $R^7 = R^1$, $COOR^1$, $CONR^1R^{1'}$, Cl, Br, I, CN, $OR^1$,
$R^1C$=O, $SO_2OR^1$, or $SO_2NR^1R^{1'}$

As shown in Scheme XV, compounds of formula I where $Z_1$ is O, M and M' are bonds and E is $CR^7R^{7'}$ can be prepared by transforming the imidazolinones of formula XXVII. The ester of formula XXXVII is hydrolyzed, for example, with sodium hydroxide in a solvent such as methanol or ethanol at about 0° C. to 50° C. to provide the corresponding carboxylic acid. The acid can be converted to the corresponding ester ($R^{7'}$=$COOR^1$) or amide ($R^{7'}$=$CONR^1R^1$) of formula XXXVIII by treatment with thionyl chloride or oxalyl chloride to form the acid chloride followed by treatment with the appropriate alcohol $R^1$—OH or amine H—$NR^1R^{1'}$, respectively.

Treatment of the acid chloride with ammonia produces the unsubstituted amide, $R^{7'}$=$CONH_2$, which can be dehydrated such as by conventional methods to form the nitrile, $R^{7'}$=CN.

Alternatively, esterification of the carboxlic acid can be achieved by reacting the acid with an appropriate alkyl halide in the presence of a base such as potassium carbonate in an inert solvent such as dimethylformamide, for example, at about 0° C. to 60° C. to give the ester of formula XXXVIII ($R^{7'}$=$COOR^1$).

The amide of compound XXXVIII ($R^{7'}$=$CONR^1R^{1'}$), can also be obtained by 1,3-dicyclohexylcarbodiimide (DCC) coupling between the carboxylic acid and the appropriate amine H—$NR^1R^{1'}$. The DCC coupling procedure is described by Bodanszky, M. and Bodanszky, A; in *Practice of Peptide Synthesis,* Vol. 21; Springer-Verlag, New York: (1984).

Reduction of the carboxylic acid or ester with a reducing agent such as aluminum hydride in solvent such as tetrahydrofuran, for example, at 0° C. to 80° C. produces the corresponding alcohol, a compound of formula XXXVIII wherein $R^{7'}$=$CH_2OH$.

Treatment of the alcohol with an $R^{13}$-halide (where $R^{13}$ is alkyl (e.g., $C_1$–$C_6$ alkyl) or substituted alkyl; alkenyl (e.g., $C_1$–$C_6$ alkenyl) or substituted alkenyl; cycloalkyl (e.g., $C_3$–$C_6$-cycloalkyl) or substituted cycloalkyl; heterocycloalkyl or substituted heterocycloalkyl; aryl or substituted aryl (e.g., substituted by alkyl and additional substituents); heterocyclo or substituted heterocyclo (e.g., heteroaryl or substituted heteroaryl, such as heteroaryl substituted by alkyl and additional substituents), in the presence of a base such as potassium carbonate, in an inert solvent such as acetonitrile, produces compounds of formula XXXVIII, wherein $R^{7'}=CH_2OR^{13}$.

Other $R^{7'}$ substitutions are also obtainable from the $CO_2Et$ group of the compounds of formula XXXVII using functional group transformations, such as those known by one skilled in the art.

Scheme XVI

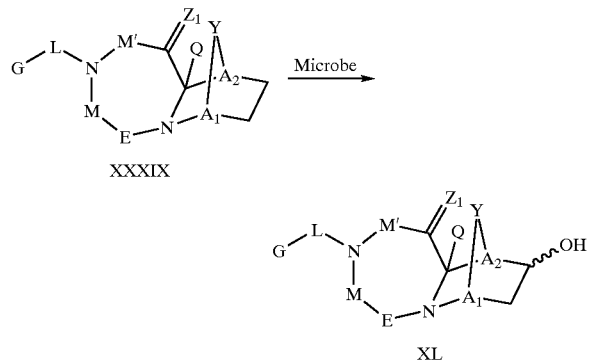

XXXIX

XL

Scheme XVI describes another approach to incorporating additional substitution onto a compound of formula I. As illustrated in Scheme XVI, a compound of formula XXXIX, which can be prepared in accordance with the above Schemes, can be incubated in the presence of a suitable enzyme or microorganism resulting in the formation of a hydroxylated analog of formula XL. Such a process can be employed to yield regiospecific as well as enantiospecific incorporation of a hydroxyl group into a molecule of formula XXXIX by a specific microorganism or by a series of different microorganisms. Such microorganisms can, for example, be bacterial, yeast or fungal in nature and can be obtained from distributors such as ATCC or identified for use in this method such as by methods known to one skilled in the art. Compound XL is a compound of formula I where Y is as described above and $A_1$ and $A_2$ are preferably $CR^7$.

Scheme XVII

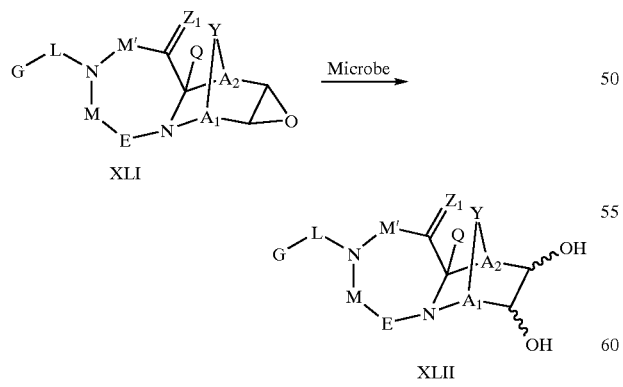

XLI

XLII

Scheme XVII describes another approach to incorporating additional substitution onto a compound of formula I. As illustrated in Scheme XVII, a compound of formula XLI, which can be prepared in accordance with the above Schemes, can be incubated in the presence of a suitable enzyme or microorganism resulting in the formation of a diol analog of formula XLII. Such a process can be employed to yield regiospecific as well as enantiospecific transformation of a compound of formula XLI to a 1-2 diol of formula XLII by a specific microorganism or by a series of different microorganisms. Such microorganisms can, for example, be bacterial, yeast or fungal in nature and can,be obtained from distributors such as ATCC or identified for use in this method such as by methods known to one skilled in the art. Compound XLII is a compound of formula I where Y is as described above and $A_1$ and $A_2$ are preferably $CR^7$.

The present invention also provides the methods of Schemes XVI and XVII.

Thus, in one embodiment, the present invention provides a method for preparation of a compound of the following formula XL, or salt thereof:

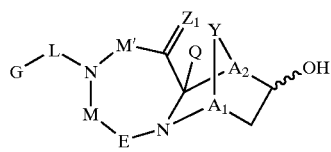

XL where the symbols are as defined herein, comprising the steps of contacting a compound of the following formula XXXIX, or salt thereof:

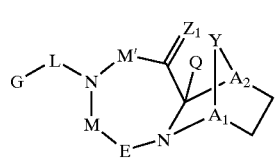

XXXIX where the symbols are as defined above;

with an enzyme or microorganism capable of catalyzing the hydroxylation of said compound XXXIX to form said compound XL, and effecting said hydroxylation.

In another preferred embodiment, the present invention provides a method for preparation of a compound of the following formula XLII, or salt thereof:

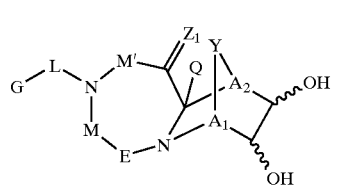

XLII where the symbols are as defined herein, comprising the steps of contacting a compound of the following formula XLI, or salt thereof:

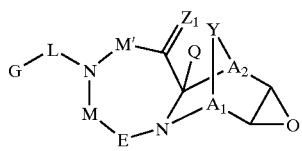

XLI where the symbols are as defined above;
with an enzyme or microorganism capable of catalyzing the opening of the epoxide ring of compound XLI to form the diol of said compound XLII, and effecting said ring opening and diol formation.

All stereoconfigurations of the unspecified chiral centers of the compounds of the formulae XXXIX, XL, XLI, and XLII are contemplated in the methods of the present invention, either alone (that is, substantially free of other stereoisomers) or in admixture with other stereoisomeric forms. Conversion of one isomer selectively (e.g., hydroxylation of the exo isomer preferentially to hydroxylation of the endo isomer) when contacting an isomeric mixture is a preferred embodiment of the invention. Conversion to one isomer selectively (e.g., hydroxylation on the exo face "exo isomer" preferentially to the endo face "endo isomer" or regioselective opening of an epoxide to form only one of two possible regioisomers of a trans diol) is a preferred embodiment of the invention. Hydroxylation of an achiral intermediate to form a single optical isomer of the hydroxylated product is also a preferred embodiment of the invention. Resolution of a recemic mixture of an intermediate by selective hydroxylation, or epoxide ring opening and diol formation, to generate one of the two possible optical isomers is also a preferred embodiment of the invention. The term "resolution" as used herein denotes partial, as well as, preferably, complete resolution.

The terms "enzymatic process" or "enzymatic method", as used herein, denote a process or method of the present invention employing an enzyme or microorganism. The term "hydroxylation", as used herein, denotes the addition of a hydroxyl group to a methylene group as described above. Hydroxylation can be achieved, for example, by contact with molecular oxygen according to the methods of the present invention. Diol formation can be achieved, for example, by contact with water according to the methods of the present invention. Use of "an enzyme or microorganism" in the present methods includes use of two or more, as well as a single, enzyme or microorganism.

The enzyme or microorganism employed in the present invention can be any enzyme or microorganism capable of catalyzing the enzymatic conversions described herein. The enyzmatic or microbial materials, regardless of origin or purity, can be employed in the free state or immobilized on a support such as by physical adsorption or entrapment. Microorganisms or enzymes suitable for use in the present invention can be selected by screening for the desired activity, for example, by contacting a candidate microorganism or enzyme with a starting compound XXXIX or XLI or salt thereof, and noting conversion to the corresponding compound XL or XLII or salt thereof. The enzyme may, for example, be in the form of animal or plant enzymes or mixtures thereof, cells of microorganisms, crushed cells, extracts of cells, or of synthetic origin.

Exemplary microorganisms include those within the genera: *Streptomyces* or *Amycolatopsis*. Particularly preferred microorganisms are those within the species *Streptomyces griseus*, especially *Streptomyces griseus* ATCC 10137, and *Amycolatopsis orientalis* such as ATCC 14930, ATCC 21425, ATCC 35165, ATCC 39444, ATCC 43333, ATCC 43490, ATCC 53550, ATCC 53630, and especially ATCC 43491. The term "ATCC" as used herein refers to the accession number of the American Type Culture Collection, 10801 University Blvd., Manassas Va. 20110-2209, the depository for the organism referred to. It should be understood that mutants of these organisms are also contemplated by the present invention, for use in the methods described herein, such as those modified by the use of chemical, physical (for example, X-rays) or biological means (for example, by molecular biology techniques).

Preferred enzymes include those derived from microorganisms, particularly those microorganisms described above. Enzymes may be isolated, for example, by extraction and purification methods such as by methods known to those of ordinary skill in the art. An enzyme may, for example, be used in its free state or in immobilized form. One embodiment of the invention is that where an enzyme is adsorbed onto a suitable carrier, e.g., diatomaceous earth (porous Celite Hyflo Supercel), microporous polypropylene (Enka Accurel® polypropylene powder), or a nonionic polymeric adsorbent such as Amberlite® XAD-2 (polystyrene) or XAD-7 (polyacrylate) from Rohm and Haas Co. When employed to immobilize an enzyme, a carrier may control the enzyme particle size and prevent aggregation of the enzyme particles when used in an organic solvent. Immobilization can be accomplished, for example, by precipitating an aqueous solution of the enzyme with cold acetone in the presence of the Celite Hyflo Supercel followed by vacuum drying, or in the case of a nonionic polymeric adsorbent, incubating enzyme solutions with adsorbent on a shaker, removing excess solution and drying enzyme-adsorbent resins under vacuum. While it is desirable to use the least amount of enzyme possible, the amount of enzyme required will vary depending upon the specific activity of the enzyme used.

Hydroxylation as described above can occur in vivo. For example, liver enzyme can selectively, relative to the endo isomer, hydroxylate the exo isomer of a compound of the present invention. In conducting the methods of the present invention outside the body, liver microsomal hydroxylase can be employed as the enzyme for catalysis.

These processes may also be carried out using microbial cells containing an enzyme having the ability to catalyze the conversions. When using a microorganism to perform the conversion, these procedures are conveniently carried out by adding the cells and the starting material to the desired reaction medium.

Where microorganisms are employed, the cells may be used in the form of intact wet cells or dried cells such as lyophilized, spray-dried or heat-dried cells, or in the form of treated cell material such as ruptured cells or cell extracts. Cell extracts immobilized on Celite® or Accurel® polypropylene as described earlier may also be employed. The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic methods of the present invention may be carried out subsequent to the fermentation of the microorganism (two-stage fermentation and conversion), or concurrently therewith, that is, in the latter case, by in situ fermentation and conversion (single-stage fermentation and conversion).

Growth of the microorganisms can be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources can include sugars such as maltose, lactose, glucose, fructose, glycerol, sorbitol, sucrose, starch, mannitol, propylene glycol, and the like; organic acids such as sodium acetate, sodium citrate, and the like; and alcohols such as ethanol, propanol and the like.

Nitrogen sources can include N—Z amine A, corn steep liquor, soy bean meal, beef extracts, yeast extracts, molasses, baker's yeast, tryptone, nutrisoy, peptone, yeastamin, amino acids such as sodium glutamate and the like, sodium nitrate, ammonium sulfate and the like.

Trace elements can include magnesium, manganese, calcium, cobalt, nickel, iron, sodium and potassium salts. Phosphates may also be added in trace or, preferably, greater than trace amounts.

The medium employed can include more than one carbon or nitrogen source or other nutrient.

Preferred media for growth include aqueous media.

The agitation and aeration of the reaction mixture affects the amount of oxygen available during the conversion process when conducted, for example, in shake-flask cultures or fermentor tanks during growth of microorganisms.

Incubation of the reaction medium is preferably at a temperature between about 4 and about 60° C. The reaction time can be appropriately varied depending upon the amount of enzyme used and its specific activity. Reaction times may be reduced by increasing the reaction temperature and/or increasing the amount of enzyme added to the reaction solution.

It is also preferred to employ an aqueous liquid as the reaction medium, although an organic liquid, or a miscible or immiscible (biphasic) organic/aqueous liquid mixture, may also be employed. The amount of enzyme or microorganism employed relative to the starting material is selected to allow catalysis of the enzymatic conversions of the present invention.

Solvents for the organic phase of a biphasic solvent system may be any organic solvent immiscible in water, such as toluene, cyclohexane, xylene, trichlorotrifluoroethane and the like. The aqueous phase is conveniently of water preferably deionized water, or a suitable aqueous buffer solution, especially a phosphate buffer solution. The biphasic solvent system preferably comprises between about 10 to 90 percent by volume of organic phase and between about 90 to 10 percent by volume of aqueous phase, and most preferably contains at or about 20 percent by volume of organic phase and at or about 80 percent by volume of the aqueous phase.

An exemplary embodiment of such processes starts with preparation of an aqueous solution of the enzyme(s) or microbes to be used. For example, the preferred enzyme(s) or microbes can be added to a suitable amount of an aqueous solvent, such as phosphate buffer or the like. This mixture is preferably adjusted to and maintained at a desired pH.

The compounds XL and XLII produced by the processes of the present invention can be isolated and purified, for example, by methods such as extraction, distillation, crystallization, and column chromatography.

Other compounds of the formula I, such as compounds where M is $CR^7R^{7'}$ or compounds where one of M or M' is other than a bond and E is $CHR^7$, can be readily prepared by one of ordinary skill in the art, for example, by methods analogous to those described herein.

Compounds of formula I can also be made, wherever appropriate, by methods described in U.S. application Ser. No. 10/025,116, filed concurrently herewith by Mark Salvati et al., entitled "Fused Heterocyclic Succinimide Compounds and Analogs Thereof, Modulators of Nuclear Hormone Receptor Function", incorporated herein by reference in its entirety, such as by microbial/enzymatic conversion and/or separation methods as described therein.

Exemplary methods for the preparation of compounds of the formula II (employed in the above Schemes) are illustrated in the following FIGS. 1 to 3.

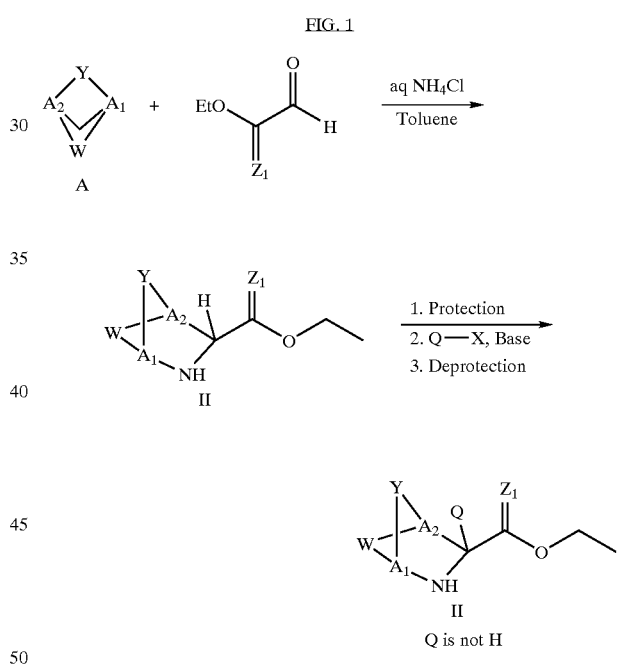

FIG. 1

As shown in FIG. 1, an ethyl glyoxylate derivative can be treated with saturated aq. $NH_4Cl$ and the appropriate diene of formula A to give the compound of formula II, where Q=H. Such a cyclization can be enhanced by the addition of metal salts, such as but not limited to Ytterbium (III) trifluoromethanesulfonate, as described in the documents cited previously. An intermediate of formula II can be made where Q≠H, by protection of the secondary nitrogen with a protection group such as a BOC, followed by treatment with reactive intermediates of formula Q—X, where X represents a leaving group or X is an electrophilic center which can react to ultimately make up the definition of Q as described earlier, in the presence of base, such as LDA, or a coupling agent as is readily known by one skilled in the art, followed by deprotection of the BOC group with an acid such as saturated ethanolic HCl.

FIG. 2

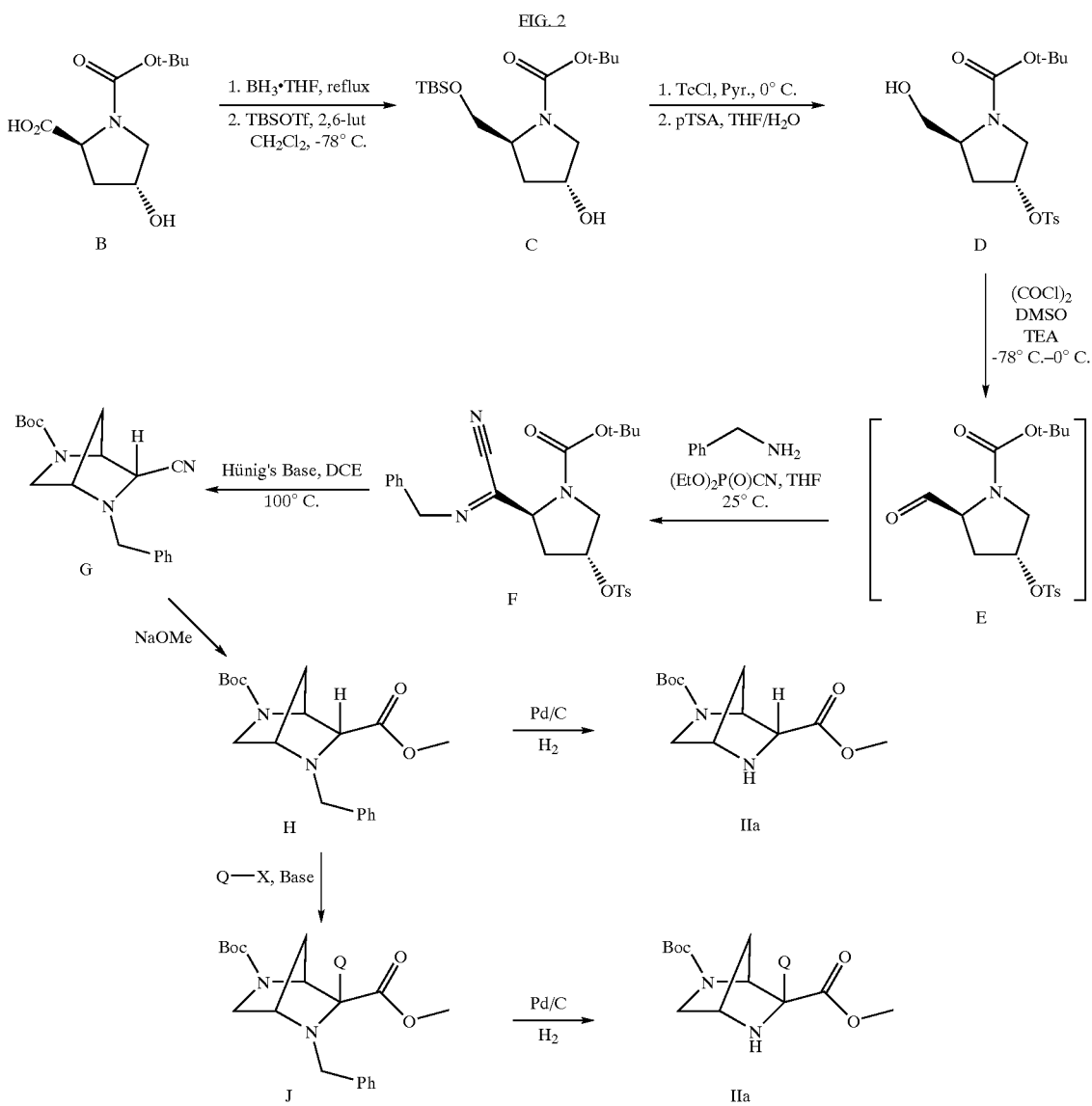

As shown in FIG. 2 (with preferred conditions indicated therein), the commercially available chiral (pure D or L) intermediate N-(tert-butoxycarbonyl)-L-4-hydroxyproline, B, can be treated with a reducing agent, such as $BH_3 \cdot THF$, to yield a primary alcohol, which can then be selectively protected with an agent such as TBSOTf, in the presence of base (e.g., 2,6-lutidine), to yield the intermediate alcohol C. The secondary alcohol of C can then be differentially protected by treatment with an agent such as TsCl, in the presence of a base (e.g., pyridine), followed by deprotection of the primary alcohol (which can be achieved by treatment with an acid, such as para-toluenesulphonic acid), to yield intermediate alcohol D. The resulting alcohol D can be oxidized, such as under standard Swern conditions, to yield the corresponding aldehyde intermediate E. The aldehyde intermediate E can be directly treated with benzylamine and diethyl cyanophosphonate to give intermediate F. Treatment of intermediate F with a base, such as Hüning's base, with heating, yields the bicyclic intermediate G. Treatment of G with a base, such as sodium methoxide, converts the nitrile intermediate G directly to the ester intermediate H. Treatment of intermediate H with an agent to remove the benzyl group, such as palladium on charcoal with hydrogen gas, results in the formation of an intermediate of Formula IIa where Q=Hydrogen. Alternatively, the intermediate of formula H can be treated with reactive intermediates of formula Q—X, where X represents a leaving group or X is an electrophilic center which can react to ultimately make up the definition of Q as described earlier, in the presence of base, such as LDA, or a coupling agent as is readily known by one skilled in the art, which, after treatment with an agent such as palladium on charcoal, yields an intermediate of formula IIa where Q≠H. The various intermediates of FIG. 2 can be purified, for example, by silica purification, or can, for example, be simply carried forward in situ to the next step (e.g., converting D to F without isolating E).

The method of FIG. 2 is novel, as are intermediates prepared therein, all of which form part of the present invention.

Thus, for example, the following method is novel as are the individual steps and intermediates produced therein (e.g., E, F, G, H, J and IIa): a method for the preparation of a compound of the following formula IIa:

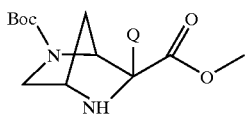
IIa where
BOC is t-butoxycarbonyl; and
Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo or substituted heterocyclo halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;
comprising the steps of
(i) treating a compound of the following formula B:

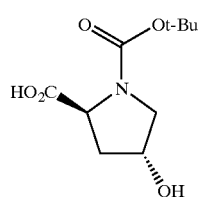
B with a reducing agent to reduce the carboxylic acid group to hydroxymethyl, followed by protection of said hydroxy to yield a compound of the following formula C:

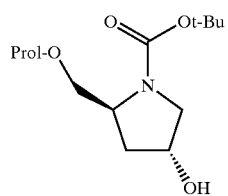
C where Pro1 is a hydroxyl protecting group;
(ii) protecting the unprotected hydroxyl group of the compound of formula C, followed by deprotection of Pro1-O— to form hydroxyl, yielding a compound of the following formula D:

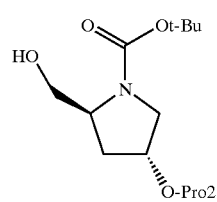
D where Pro2 is a protecting group;
(iii) oxidizing the hydroxymethyl group of D, yielding an aldehyde of the following formula E:

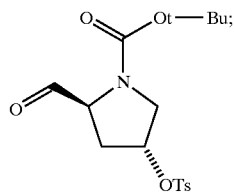
E (iii) treating E with benzylamine and diethyl cyanophosphonate, yielding a compound of the following formula F:

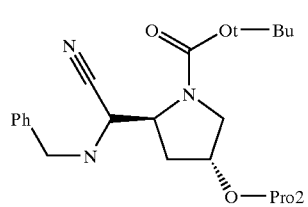
F (iv) treating said compound of the formula F with a base with heating to yield a compound of the following formula G:

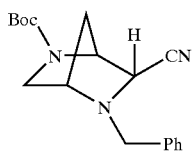
G (v) treating said compound of the formula G with a base to convert the nitrile group to methoxycarbonyl yielding a compound of the following formula H:

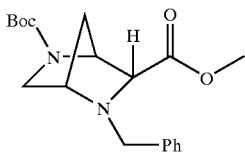
H and (vi) removing the benzyl group of said compound of the formula H to form said compound of the formula IIa, wherein, optionally, said compound of the formula H is contacted with a compound Q—X, where X is a leaving group or X is an electrophilic center which can react to form a group Q, prior to said removal to form compounds of the formula IIa where Q is other than hydrogen.

The method of FIG. 2 is especially useful for the preparation of unnatural amino acids IIa which can be employed, by methods analogous to those using compounds of the formula II, in the preparation of the present compounds of formula I.

FIG. 3

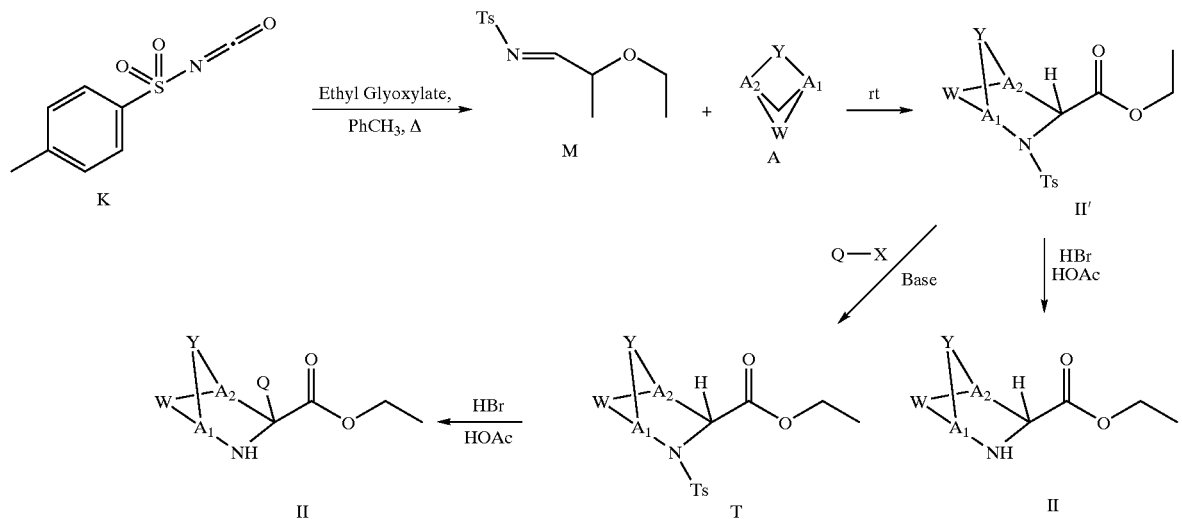

As shown in FIG. 3 (with preferred conditions indicated therein), the activated imine intermediate M can be generated by the reactions of an activated sulfonyl isocyanate, such as p-toluenesulfonyl isocyanate, with ethyl glyoxylate and heating. Imine M can undergo cyclization with an appropriate diene intermediate of formula A to give an intermediate of formula II'. Such a cyclization can be enhanced by the addition of metal salts, such as but not limited to Ytterbium (III) trifluoromethanesulfonate, as described in the references cited previously. The tosyl protecting group can be removed from intermediate II' by a number of reagents, such as those known to one skilled in the art, such as hydrogen bromide in acetic acid, to yield an intermediate of formula II. The intermediate of formula II' can be treated with reactive intermediates of formula Q—X, where X represents a leaving group or X is an electrophilic center which can react to ultimately make up the definition of Q as described earlier, in the presence of base, such as LDA, or a coupling agent as is readily known by one skilled in the art, to yield the intermediate of formula T. The tosyl protecting group can be removed from intermediate T by a number of reagents known to one skilled in the art, such as hydrogen bromide in acetic acid, to yield an intermediate of formula II, where Q≠H.

Preferred Compounds

A preferred subgenus of the compounds of the present invention includes compounds of the formula I or salts thereof wherein one or more, preferably all, of the following substituents are as defined below:

G is an aryl (especially, phenyl or naphthyl) or heterocyclo (e.g., heteroaryl) group, where said group is mono- or polycyclic, and which is optionally substituted at one or more positions, preferably with hydrogen, $C_{1-6}$ alkyl, alkyl substituted with one or more halogens (e.g., perfluoroalkyl), heterocyclo, alkyl substituted with hydroxy, allyl or substituted allyl, alkynyl, Cl, F, Br, I, CN, $R^1OC=O$, $R^1C=O$, $R^1HNC=O$, $R^1R^2NC=O$, $HOCR^3R^{3'}$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1'}$, $(R^1O)(R^{1'}O)P=O$, $(R^1)(R^{1'})P=O$, or $(R^1)(NHR^1)P=O$;

E is $C=Z_2$, $CHR^7$, $SO_2$, $P=OR^2$, or $P=OOR^2$;

$Z_1$ is O, S, or $NR^6$;

$Z_2$ is O, S, or $NR^6$;

$A_1$ is $CR^7$ (especially, CH);

$A_2$ is $CR^7$ (especially, CH);

Y is J—J'—J" where J is $(CR^7R^{7'})n$ and n=0–2, J' is a bond or NH, $NR^6$, C=O, cycloalkyl (especially, cyclopropyl or cyclobutyl), or cycloalkenyl (especially, cyclobutenyl or cyclopentenyl), and J" is $(CR^7R^{7'})n$ and n=1–2, where Y is not a bond;

W is $CR^7R^{7'}$—$CR^7R^{7'}$, $CR^8=CR^{8'}$, $CR^7R^{7'}$—C=O, $NR^9$—$CR^7R^{7'}$, cycloalkyl (especially, cyclopropyl or cyclobutyl) or cycloalkenyl (especially, cyclobutenyl or cyclopentenyl);

Q is H, $C_{1-6}$ alkyl, alkyl substituted with one or more halogens (e.g., perfluoroalkyl), $C_{1-6}$ alkyl substituted with hydroxy, alkenyl (e.g., allyl), alkynyl, Cl, F, Br, I, arylalkyl (e.g. benzyl) or substituted arylalkyl, CN, $R^1OC=O$, $R^4C=O$, $R^5R^6NC=O$, $HOCR^7R^{7'}$, $R^1OCH_2$, $R^1O$, $NH_2$, or $NR^4R^5$;

M is a bond or $NR^{10}$, and M' is a bond or $NR^{10}$, with the proviso that at least one of M or M' must be a bond;

L is a bond, $(CR^7R^{7'})n$, NH, or $NR^5$ where n=0–1;

$R^1$ and $R^{1'}$ are each independently H, alkyl, perfluoroalkyl, cycloalkyl, heterocyclo, cycloalkylalkyl, or heterocycloalkyl;

$R^2$ is alkyl, perfluoroalkyl, cycloalkyl, heterocyclo, cycloalkylalkyl, or heterocycloalkyl;

$R^3$ and $R^{3'}$ are each independently H, alkyl, perfluoroalkyl, cycloalkyl, heterocyclo, cycloalkylalkyl, heterocycloalkyl, Cl, F, Br, I, CN, alkoxy, amino, $NR^1R^2$, thiol, or alkylthio;

$R^4$ is H, alkyl, cycloalkyl, heterocyclo, cycloalkylalkyl, heterocycloalkyl, $R^1C=O$, $R^1NHC=O$, $SO_2OR^1$, or $SO_2NR^1R^{1'}$;

$R^5$ is alkyl, cycloalkyl, heterocyclo, cycloalkylalkyl, heterocycloalkyl, $R^1C=O$, $R^1NHC=O$, $SO_2OR^1$, or $SO_2NR^1R^{1'}$;

$R^6$ is alkyl or substituted alkyl, cycloalkyl or substituted cycloalkyl, heterocyclo or substituted heterocyclo, cycloalkylalkyl or substituted cycloalkylalkyl, heterocycloalkyl or substituted heterocycloalkyl, aryl or substituted aryl, arylalkyl or substituted arylalkyl, CN, OH, OR$^1$, R$^1$C=O, R$^1$NHC=O, SO$_2$OR$^1$, or SO$_2$NR$^1$R$^{1'}$;

R$^7$ and R$^{7'}$ are each independently H, alkyl, perfluoroalkyl, cycloalkyl, heterocyclo, cycloalkylalkyl, heterocycloalkyl, aryl, arylalkyl, Cl, F, Br, I, CN, OR$^1$, nitro, hydroxylamine, hydroxylamide, amino, NHR$^4$, NR$^2$R$^5$, NOR$^1$, thiol, alkylthio, R$^1$C=O, R$^1$NHC=O, SO$_2$OR$^1$, or SO$_2$NR$^1$R$^{1'}$;

R$^8$ and R$^{8'}$ are each independently H, alkyl or substituted alkyl, cycloalkyl or substituted cycloalkyl, heterocyclo or substituted heterocyclo, cycloalkylalkyl or substituted cycloalkyalkyl, heterocycloalkyl or substituted heterocycloalkyl, aryl or substituted aryl, arylalkyl or substituted arylalkyl, halo, CN, OR$^1$, amino, NHR$^4$, NR$^2$R$^5$, NOR$^1$, alkylthio or substituted alkylthio, R$^1$C=O, R$^1$NHC=O, SO$_2$OR$^1$, or SO$_2$NR$^1$R$^{1'}$;

R$^9$ and R$^{9'}$ are each independently H, alkyl, alkenyl, cycloalkyl, heterocyclo, cycloalkylalkyl, heterocycloalkyl, aryl, arylalkyl, CN, OH, OR$^1$, R$^1$C=O, R$^1$OC=O, R$^1$NHC=O, SO$_2$R$^1$, SO$_2$OR$^1$, or SO$_2$NR$^1$R$^{1'}$; and R$^{10}$ is H, alkyl, cycloalkyl, heterocyclo, cycloalkylalkyl, heterocycloalkyl, aryl, arylalkyl, CN, OH, OR$^1$, R$^1$C=O, R$^1$OC=O, R$^1$R$^{1'}$NC=O, SO$_2$OR$^1$, or SO$_2$NR$^1$R$^{1'}$.

A more preferred subgenus of the compounds of the invention includes compounds of the formula I or salts thereof wherein one or more, preferably all, of the following substituents are as defined below:

G is an aryl or heteroaryl group, where said group is mono- or polycyclic, and which is optionally substituted at one or more positions with hydrogen, C$_1$–C$_3$ alkyl, allyl or substituted allyl, alkynyl, Cl, F, Br, I, CN, R$^1$C=O, R$^1$HNC=O, R$^1$R$^2$NC=O, haloalkyl (especially, perfluoroalkyl), C$_1$–C$_3$ hydroxyalkyl, HOCR$^3$R$^{3'}$, nitro, R$^1$OCH$_2$, R$^1$O, NR$^4$R$^5$, or SR$^1$;

E is C=Z$_2$, CHR$^7$ or SO$_2$;

Z$_1$ is O, S, or NCN;

Z$_2$ is O, S, or NCN;

A$_1$ is CR$^7$ (especially, CH);

A$_2$ is CR$^7$ (especially, CH);

Y is J, cyclopropyl, or cyclobutyl, where J=(CR$^7$R$^{7'}$)n and n=1–3;

W is CR$^7$R$^{7'}$—CR$^7$R$^{7'}$, CR$^8$=CR$^{8'}$, CR$^7$R$^{7'}$—C=O, cyclopropyl, or cyclobutyl;

Q is hydrogen, C$_1$–C$_4$ alkyl, alkynyl, Cl, F, Br, I, CN, R$^1$OC=O, R$^4$C=O, R$^5$R$^6$NC=O, haloalkyl (especially, perfluoroalkyl), C$_1$–C$_6$ hydroxyalkyl, HOCR$^7$R$^{7'}$, R$^1$OCH$_2$, R$^1$O, NH$_2$ or NR$^4$R$^5$;

M is a bond and M' is a bond;

L is a bond, (CR$^7$R$^{7'}$)n, NH, or NR$^5$, where n=0–1;

R$^1$ and R$^{1'}$ are each independently H, alkyl, cycloalkyl, heterocycloalkyl, or perfluoroalkyl;

R$^2$ is alkyl, cycloalkyl, heterocycloalkyl, or perfluoroalkyl;

R$^3$ and R$^{3'}$ are each independently H, alkyl, perfluoroalkyl, Cl, F, Br, I, CN, alkoxy, amino, NR$^1$R$^2$, thiol, or alkylthio;

R$^4$ is H, alkyl, cycloalkyl, heterocycloalkyl, R$^1$C=O, R$^1$NHC=O, SO$_2$OR$^1$, or SO$_2$NR$^1$R$^{1'}$;

R$^5$ is alkyl, cycloalkyl, heterocycloalkyl, R$^1$C=O, R$^1$NHC=O, SO$_2$OR$^1$, or SO$_2$NR$^1$R$^{1'}$;

R$^7$ and R$^{7'}$ are each independently H, alkyl, arylalkyl, heteroaryl, perfluoroalkyl, heteroarylalkyl, Cl, F, Br, I, CN, OR$^1$, amino, NHR$^4$, NR$^2$R$^5$, NOR$^1$, thiol, alkylthio, R$^1$C=O, R$^1$NHC=O, SO$_2$OR$^1$, or SO$_2$NR$^1$R$^{1'}$; and R$^{10}$ is H, alkyl, cycloalkyl, heterocycloalkyl (especially, heteroarylalkyl), aryl, heteroaryl (such as heteroarylium), arylalkyl, CN, R$^1$C=O, R$^1$R$^{1'}$NC=O, SO$_2$OR$^1$, or SO$_2$NR$^1$R$^{1'}$.

Another more preferred subgenus of the compounds of the invention includes compounds of the formula I or salts thereof wherein one or more, preferably all, of the following substituents are as defined below:

G is an aryl or heteroaryl group, where said group is mono- or polycyclic, and which is optionally substituted at one or more positions with hydrogen, C$_1$–C$_3$ alkyl, allyl or substituted allyl, alkynyl, Cl, F, Br, I, CN, R$^1$C=O, R$^1$HNC=O, haloalkyl (especially, perfluoroalkyl), C$_1$–C$_3$ hydroxyalkyl, HOCR$^3$R$^{3'}$, nitro, R$^1$OCH$_2$, R$^1$O, NR$^4$R$^5$, or SR$^1$;

E is C=Z$_2$;

Z$_1$ is O;

Z$_2$ is O or NCN;

A$_1$ is CR$^7$ (especially, CH);

A$_2$ is CR$^7$ (especially, CH);

Y is J, where J=(CR$^7$R$^{7'}$)n and n=1–3;

W is CR$^7$R$^{7'}$—CR$^7$R$^{7'}$, CR$^8$=CR$^{8'}$, or CR$^7$R$^{7'}$—C=O;

Q is hydrogen, C$_1$–C$_4$ alkyl, alkynyl, Cl, F, Br, I, CN, R$^4$C=O, R$^5$R$^6$NC=O, haloalkyl (especially, perfluoroalkyl), C$_1$–C$_6$ hydroxyalkyl, HOCR$^7$R$^{7'}$, R$^1$OCH$_2$, R$^1$O, NH$_2$ or NR$^4$R$^5$;

M is a bond and M' is a bond;

L is a bond;

R$^1$ and R$^{1'}$ are each independently H, alkyl, or perfluoroalkyl;

R$^2$ is alkyl, or perfluoroalkyl;

R$^3$ and R$^{3'}$ are each independently H, alkyl, perfluoroalkyl, Cl, F, Br, I, CN, alkoxy, amino, NR$^1$R$^2$, thiol, or alkylthio;

R$^4$ is H, alkyl, R$^1$C=O, R$^1$NHC=O, or SO$_2$NR$^1$R$^{1'}$;

R$^5$ is alkyl, R$^1$C=O, R$^1$NHC=O, or SO$_2$NR$^1$R$^{1'}$;

R$^7$ and R$^{7'}$ are each independently H, alkyl, arylalkyl, heteroaryl, perfluoroalkyl, heteroarylalkyl, Cl, F, Br, I, CN, OR$^1$, amino, NHR$^4$, NR$^2$R$^5$, NOR$^1$, R$^1$C=O, R$^1$NHC=O, or SO$_2$NR$^1$R$^{1'}$; and R$^{10}$ is H, alkyl, aryl, heteroaryl, arylalkyl, heteroarylalkyl, CN, R$^1$C=O, R$^1$R$^{1'}$NC=O, or SO$_2$NR$^1$R$^{1'}$.

A particularly preferred subgenus of the compounds of the invention includes compounds of the formula I or salts thereof wherein one or more, preferably all, of the substituents are as defined below:

G is an aryl (especially, phenyl or naphthyl) or heterocyclo (especially benzo-fused heterocyclic groups such as indole, benzothiophene, benzothiazole, benzothiadiazole, benzisoxazole, benzoxadiazole, oxidobenzothiophene, benzofuran or benzopyran) group, where said group is mono- or polycyclic, and which is optionally substituted at one or more positions, such as 1 to 5 positions (preferably 1 to 2 positions), with substituents selected from one or more of hydrogen, NH$_2$, alkyl (especially having 1 to 4 carbons) or substituted alkyl (especially having 1 to 4 carbons and substituted with halo, such as the substituted alkyl group CF$_3$), halo (especially F, Cl, Br or I), heterocyclo (such as tetrazole or oxazole), CN, nitro, SR$^1$ or R$^1$O (especially where R$^1$ is alkyl);

E is C=Z$_2$ or CHR$^7$ (especially where R$^7$ is hydrogen);

Z$_1$ is O or S;

Z$_2$ is O, S, or NR$^6$ (especially where R$^6$ is CN or phenyl);

A$_1$ is CR$^7$ (especially where R$^7$ is hydrogen);

A$_2$ is CR$^7$ (especially where R$^7$ is hydrogen);

Y is (CR$^7$R$^{7'}$)n and n=1–2 (especially where R$^7$ and R$^{7'}$ are hydrogen);

W is CR$^7$R$^{7'}$—CR$^7$R$^{7'}$, CR$^8$=CR$^{8'}$, or NR$^9$—CR$^7$R$^{7'}$ (especially where R$^7$, R$^{7'}$, R$^8$ and R$^{8'}$ are hydrogen and R$^9$ is as defined in this preferred subgenus);

Q is H, alkyl (especially having 1 to 4 carbons), alkenyl (especially having 1 to 4 carbon atoms), arylalkyl (especially benzyl) or substituted arylalkyl (especially substituted benzyl, such as halo-substituted benzyl);

M is a bond or NH (especially a bond), and M' is a bond;

L is a bond;

R$^1$ and R$^{1'}$ are each independently alkyl (especially having 1 to 4 carbons) or substituted alkyl (especially having 1 to 4 carbons and substituted with halo), heterocyclo (such as imidazole or isoxazole) or substituted heterocyclo (such as imidazole substituted with methyl), aryl (especially phenyl) or substituted aryl (especially phenyl substituted with one or more of halo, nitro, halo-substituted alkyl such as CF$_3$, or alkyl having 1 to 4 carbons), arylalkyl (especially benzyl or phenethyl) or substituted arylalkyl (especially substituted benzyl such as halo- and/or nitro-substituted benzyl); and R$^9$ and R$^{9'}$ are each independently H, alkyl (especially having 1 to 4 carbons), alkenyl (especially having 1 to 4 carbons), arylalkyl (especially benzyl), R$^1$C=O, R$^1$OC=O, R$^1$NHC=O, or SO$_2$R$^1$ (especially where each R$^1$ is independently as defined in this preferred subgenus).

In this particularly preferred subgenus, G—L— can be, for example, selected from optionally substituted phenyl, optionally substituted naphthyl and optionally substituted fused bicyclic heterocyclic groups such as optionally substituted benzo-fused heterocyclic groups (e.g., bonded to the remainder of the molecule through the benzene portion), especially such groups wherein the heterocyclic ring bonded to benzene has 5 members exemplified by benzoxazole, benzothiazole, benzothiadiazole, benzoxadiazole or benzothiophene, for example:

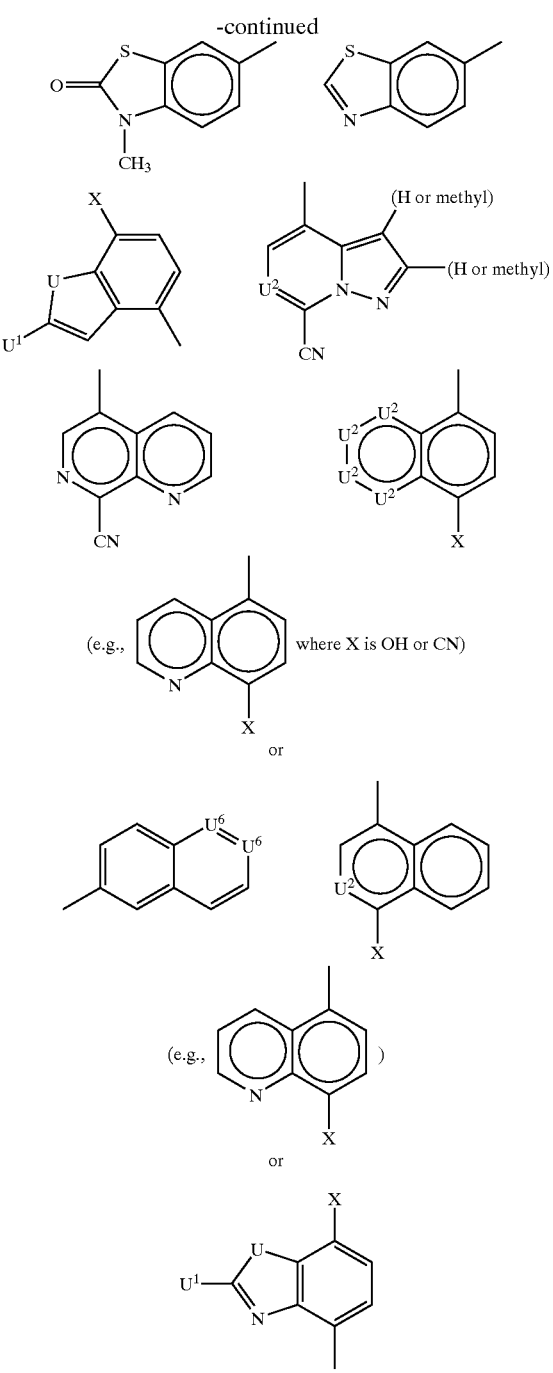

where
X=halo (especially F, Cl), OH, CN, NO$_2$ or

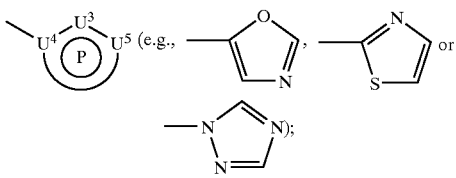

X'=halo (especially Cl, F, or I), CH$_3$, CF$_3$, CN or OCH$_3$;

U is O or S (where S can optionally be oxygenated, e.g., to SO);

$U^1$ is $CH_3$ or $CF_3$;

each $U^2$ is independently N, CH or CF;

$U^3$ is N, O or S;

$U^4$ and $U^5$, together with the atoms to which they are bonded, form an optionally substituted 5-membered heterocyclic ring which can be partially unsaturated or aromatic and which contains 1 to 3 ring heteroatoms;

each $U^6$ is independently CH or N; and

denotes optional double bond(s) within the ring formed by $U^3$, $U^4$ and $U^5$.

Especially preferred are compounds of the formula I having the following structure, or salts thereof:

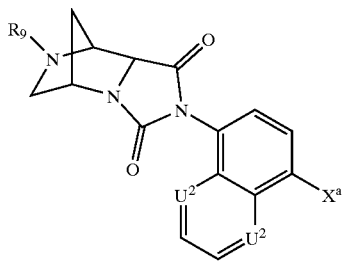

where $R^9$ and $U^2$ are as defined above, such as optionally substituted arylcarbonyl or optionally substituted aryloxycarbonyl, and $X^a$ is an aryl substituent, such as nitro.

Also especially preferred are compounds of the formula I having the following structure or salts thereof:

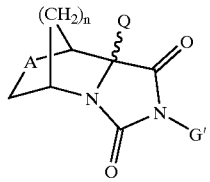

where n is 1 or 2;

Q is H, methyl or ethyl;

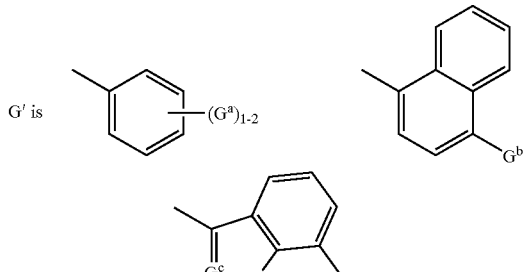

each $G^a$ is independently CN, $NO_2$, $CF_3$, Cl, Br, F, $OCH_3$, $SCH_3$, I, $CH_3$, $C(O)-CH_3$ or

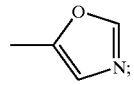

$G^b$ is CN, H, F, Br, $NO_2$ or

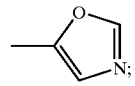

$G^c$ is CH or N;

$G^d$ is S or O;

$G^e$ is H or F;

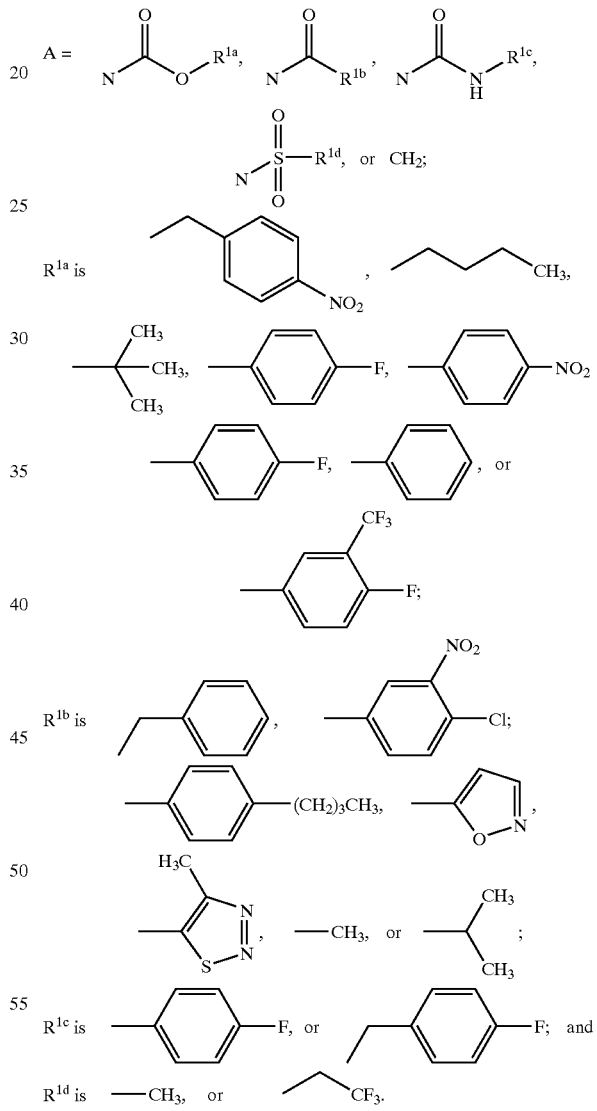

Use and Utility

The compounds of the present invention modulate the function of nuclear hormone receptors (NHR), and include compounds which are, for example, agonists, partial agonists, antagonists or partial antagonists of the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHR, the Orphan receptors or other NHR. Selective modulation of one such NHR relative to others within the NHR family is preferred. "Modulation" includes, for example, activation (e.g., agonist activity such as selective androgen receptor agonist activity) or inhibition (e.g., antagonist activity).

The present compounds are thus useful in the treatment of NHR-associated conditions. A "NHR-associated condition", as used herein, denotes a condition or disorder which can be treated by modulating the function of a NHR in a subject, wherein treatment comprises prevention (e.g., prophylatic treatment), partial alleviation or cure of the condition or disorder. Modulation may occur locally, for example, within certain tissues of the subject, or more extensively throughout a subject being treated for such a condition disorder.

The compounds of the present invention are useful for the treatment of a variety of conditions and disorders including, but not limited to, those described following:

Compounds of formula I can be applied as agonists, partial agonists, antagonists, or partial antagonists of the estrogen receptor, preferably selectively to that receptor, in an array of medical conditions which involve modulation of the estrogen receptor pathway. Applications of said compounds include but are not limited to: osteoporosis, hot flushes, vaginal dryness, prostate cancer, breast cancer, endometrial cancer, cancers expressing the estrogen receptor such as the aforementioned cancers and others, contraception, pregnancy termination, menopause, amennoreahea, and dysmennoreahea.

Compounds of formula I can be applied as agonists, partial agonists, antagonists or partial antagonists of the progesterone receptor, preferably selectively to that receptor, in an array of medical conditions which involve modulation of the progesterone receptor pathway. Applications of said compounds include but are not limited to: breast cancer, other cancers containing the progesterone receptor, endometriosis, cachexia, contraception, menopause, cyclesynchrony, meniginoma, dysmennoreahea, fibroids, pregnancy termination, labor induction and osteoporosis.

Compounds of formula I can be applied as agonists, partial agonists, antagonists or partial antagonists of the glucocorticoid receptor, preferably selectively to that receptor, in an array of medical conditions which involve modulation of the glucocorticoid receptor pathway. Applications of said compounds include but are not limited to: inflammatory diseases, autoimmune diseases, prostate cancer, breast cancer, Alzheimer's disease, psychotic disorders, drug dependence, non-insulin dependent Diabetes Mellitus, and as dopamine receptor blocking agents or otherwise as agents for the treatment of dopamine receptor mediated disorders.

Compounds of formula I can be applied as agonists, partial agonists, antagonists or partial antagonists of the mineralocorticoid receptor, preferably selectively to that receptor, in an array of medical conditions which involve modulation of the mineralocorticoid receptor pathway. Applications of said compounds include but are not limited to: drug withdrawal syndrome and inflammatory diseases.

Compounds of formula I can be applied as agonists, partial agonists, antagonists or partial antagonists of the aldosterone receptor, preferably selectively to that receptor, in an array of medical conditions which involve modulation of the aldosterone receptor pathway. One application of said compounds includes but is not limited to: congestive heart failure.

Compounds of formula I can be applied as agonists, partial agonists, antagonists or partial antagonists of the androgen receptor, preferably selectively to that receptor, in an array of medical conditions which involve modulation of the androgen receptor pathway. Applications of said compounds include but are not limited to: hirsutism, acne, seborrhea, Alzheimer's disease, androgenic alopecia, hypogonadism, hyperpilosity, benign prostate hypertrophia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers modulation of VCAM expression and applications therein for the treatment of heart disease, inflammation and immune modulations, modulation of VEGF expression and the applications therein for use as antiangiogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients. For example, pan AR modulation is contemplated, with prostate selective AR modulation ("SARM") being particularly preferred, such as for the treatment of early stage prostate cancers.

Compounds of formula I can be applied as (preferably, selective) antagonists of the mutated androgen receptor found in many tumor lines. Examples of such mutants are those found in representative prostate tumor cell lines such as LNCap, (T877A mutation, Biophys. Acta, 187, 1052 (1990)), PCa2b, (L701H & T877A mutations, J. Urol., 162, 2192 (1999)) and CWR22, (H874Y mutation, Mol. Endo., 11, 450 (1997)). Applications of said compounds include but are not limited to: adenomas and neoplasies of the prostate, breast cancer and endometrial cancer.

Compounds of formula I can be applied as agonists, partial agonists, antagonists or partial antagonists of the steroid and xenobiotic receptor, preferably selectively to that receptor, in an array of medical conditions which involve modulation of the steroid and xenobiotic receptor pathway. Applications of said compounds include but are not limited to: treatment of disregulation of cholesterol homeostasis, attenuation of metabolism of pharmaceutical agents by co-administration of an agent (compound of the present invention) which modulates the P450 regulator effects of SXR.

Along with the aforementioned NHR, there also exist a number of NHR for which the activating or deactivating ligands may not be characterized. These proteins are classified as NHR due to strong sequence homology to other NHR, and are known as the Orphan receptors. Because the Orphan receptors demonstrate strong sequence homology to other NHR, compounds of formula I include those which serve as modulators of the function of the Orphan NHR. Orphan receptors which are modulated by NHR modulators such as compounds within the scope of formula I are exemplified, but not limited to, those listed in Table 1. Exemplary therapeutic applications of modulators of said Orphan receptors are also listed in Table 1, but are not limited to the examples therein.

TABLE 1

Exemplary Orphan nuclear hormone receptors, form (M = monomeric, D = heterodimeric, H = homodimeric), tissue expression and target therapeutic applications. (CNS = central nervous system)

| Receptor | Form | Tissue Expression | Target Therapeutic Application |
|---|---|---|---|
| NURR1 | M/D | Dopaminergic Neurons | Parkinson's Disease |
| RZRβ | M | Brain (Pituitary), Muscle | Sleep Disorders |
| RORα | M | Cerebellum, Purkinje Cells | Arthritis, Cerebellar Ataxia |
| NOR-1 | M | Brain, Muscle, Heart, Adrenal, Thymus | CNS Disorders, Cancer |
| NGFI-Bβ | M/D | Brain | CNS Disorders |
| COUP-Tfα | H | Brain | CNS Disorders |
| COUP-TFβ | H | Brain | CNS Disorders |
| COUP-TFγχ | H | Brain | CNS Disorders |
| Nur77 | H | Brain, Thymus, Adrenals | CNS Disorders |
| Rev-ErbAα | H | Muscle, Brain (Ubiquitous) | Obesity |
| HNF4α | H | Liver, Kidney, Intestine | Diabetes |
| SF-1 | M | Gonads, Pituitary | Metabolic Disorders |
| LXRα,β | D | Kidney (Ubiquitous) | Metabolic Disorders |
| GCNF | M/H | Testes, Ovary | Infertility |
| ERRα,β | M | Placenta, Bone | Infertility, Osteoporosis |
| FXR | D | Liver, Kidney | Metabolic Disorders |
| CARα | H | Liver, Kidney | Metabolic Disorders |
| PXR | H | Liver, Intestine | Metabolic Disorders |
| COUP-TF2 (ARP1) | D | Testis | Oncology/angiogenesis |
| RORbeta | M | CNS, retina, pineal gland | Metabolic Disorders |

The present invention thus provides methods for the treatment of NHR-associated conditions, comprising the step of administering to a subject in need thereof at least one compound of formula I in an amount effective therefor. Other therapeutic agents such as those described below may be employed with the inventive compounds in the present methods (for example, separately, or formulated together as a fixed dose). In the methods of the present invention, such other therapeutic agent(s) can be administered prior to, simultaneously with or following the administration of the compound(s) of the present invention.

The present invention also provides pharmaceutical compositions comprising at least one of the compounds of the formula I capable of treating a NHR-associated condition in an amount effective therefor, and a pharmaceutically acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the compounds of the present invention are, without limitation as to their mechanism of action, useful in treating any of the conditions or disorders listed or described herein such as inflammatory diseases or cancers, or other proliferate diseases, and in compositions for treating such conditions or disorders. Such conditions and disorders include, without limitation, any of those described previously, as well as those described following such as: maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic malagia; treatment of acute fatigue syndrome and muscle loss following elective surgery (e.g., post-surgical rehabilitation); acceleration of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; conteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength; and the conditions, diseases, and maladies collectively referenced to as "Syndrome X" or Metabolic Syndrome as detailed in Johannsson *J. Clin. Endocrinol. Metab.*, 82, 727–34 (1997).

The present compounds have therapeutic utility in the modulation of immune cell activation/proliferation, e.g., as competitive inhibitors of intercellular ligand/receptor binding reactions involving CAMs (Cellular Adhesion Molecules) and Leukointegrins. For example, the present compounds modulate LFA-ICAM 1, and are particularly useful as LFA-ICAM 1 antagonists, and in the treatment of all conditions associated with LFA-ICAM 1 such as immunological disorders. Preferred utilities for the present compounds include, but are not limited to: inflammatory conditions such as those resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The present compounds can be used in treating asthma or as an adjunct to minimize toxicity with cytokine therapy in the treatment of cancers. The present compounds can be employed in the treatment of all diseases currently treatable through steroid therapy. The present compounds may be employed for the treatment of these and other disorders alone or with other immunosuppressive or antiinflammatory agents. In accordance with the invention, a compound of the formula I can be administered prior to the onset of inflammation (so as to suppress an anticipated inflammation) or after the initiation of inflammation. When provided prophylactically, the immunosuppressive compound(s) are preferably provided in advance of any inflammatory response or symptom (for example, prior to, at, or shortly after the time of an organ or tissue transplant but in advance of any symptoms or organ rejection). The prophylactic administration of a compound of the formula I prevents or attenuates any subsequent inflammatory response (such as, for example, rejection of a transplanted organ or tissue, etc.) Administration of a compound of the formula I attenuates any actual inflammation (such as, for example, the rejection of a transplanted organ or tissue).

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 1 to 100 (for example, 15) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

As mentioned above, the compounds of the present invention can be employed alone or in combination with each other and/or other suitable therapeutic agents useful in the treatment of NHR-associated conditions, e.g., an antibiotic or other pharmaceutically active material.

For example, the compounds of the present invention can be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention can also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY4447 11 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003–1008 (1999) and Hamann, L. G. et al., *J. Med. Chem.*, 42, 210–212 (1999).

A further use of the compounds of this invention is in combination with progesterone receptor agonists ("PRA"), such as levonorgestrel, medroxyprogesterone acetate (MPA).

The compounds of the present invention can be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e.g,. acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, steroidal or non-steroidal progesterone receptor agonists, RANK ligand antagonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®) integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI- 1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epothilones, cisplatin and carboplatin.

Compounds of the present invention can further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

In addition, compounds of the present invention can be used in combination with therapeutic agents used in the treatment of sexual dysfunction, including but not limited to PDE5 inhibitors, such as sildenafil or IC-351; with an antiresorptive agent, hormone replacement therapies, vitamin D analogues, calcitonins, elemental calcium and calcium supplements, cathepsin K inhibitors, MMP inhibitors, vitronectin receptor antagonists, Src $SH_2$ antagonists, vacular —H$^+$— ATPase inhibitors, progesterone receptor agonists, ipriflavone, fluoride, RANK antagonists, PTH and its analogues and fragments, Tibolone, HMG-CoA reductase inhibitors, SERM's, p38 inhibitors, prostanoids, 17-beta hydroxysteroid dehydrogenase inhibitors and Src kinase inhibitors.

Compounds of the present invention can be used in combination with male contraceptives, such as nonoxynol 9 or therapeutic agents for the treatment of hair loss, such as minoxidil and finasteride or chemotherapeutic agents, such as with LHRH agonists.

For their preferred anticancer or antiangiogenic use, the compounds of the present invention can be administered either alone or in combination with other anti-cancer and cytotoxic agents and treatments useful in the treatment of cancer or other proliferative diseases, for example, where the second drug has the same or different mechanism of action than the present compounds of formula I. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; EGFR inhibitors such as small molecule EGFR inhibitors, EGFR antibodies such as C225 (Erbitux); antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The combinations of the present invention can also be formulated or co-administered with other therapeutic agents that are selected for their particular usefulness in administering therapies associated with the aforementioned conditions. For example, the compounds of the invention may be formulated with agents to prevent nausea, hypersensitivity and gastric irritation, such as antiemetics, and $H_1$ and $H_2$ antihistaminics.

As it pertains to the treatment of cancer, the compounds of this invention are most preferably used alone or in combination with anti-cancer treatments such as radiation therapy and/or with cytostatic and/or cytotoxic agents, such as, but not limited to, DNA interactive agents, such as cisplatin or doxorubicin; inhibitors of farnesyl protein transferase, such as those described in U.S. Pat. No. 6,011,029; topoisomerase II inhibitors, such as etoposide; topoisomerase I inhibitors, such as CPT-11 or topotecan; tubulin stabilizing agents, such as paclitaxel, docetaxel, other taxanes, or epothilones; hormonal agents, such as tamoxifen; thymidilate synthase inhibitors, such as 5-fluorouracil; antimetabolites, such as methoxtrexate; antiangiogenic agents, such as angiostatin, ZD6474, ZD6126 and comberstatin A2; kinase inhibitors, such as her2 specific antibodies, Iressa and CDK inhibitors; histone deacetylase inhibitors, such as CI-994 and MS-27-275. Such compounds may also be combined with agents which suppress the production of circulating testosterone such as LHRH agonists or antagonists or with surgical castration. Exemplary combination therapies (e.g., for the treatment of prostate cancer) for use with a compound of the present invention include an LHRH modulator or prednisone.

The present invention also contemplates kits, for example, for the treatment of prostate cancer, comprising a first container (such as a vial) containing a pharmaceutical formulation comprising a compound of the present invention, said compound optionally in a pharmaceutically acceptable carrier, and a second container (such as a vial) containing a pharmaceutical formulation comprising one or more agents (such as an LHRH modulator) to be used in combination with said compound of the present invention, said agent(s) optionally in a pharmaceutically acceptable carrier.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists (which inhibit the function T/DHT derived from the conversion of circulating androgen precursors to T/DHT by the prostate tissue). The compounds of the present invention can be employed as AR antagonists in complete ablation therapy, alone or in combination with other AR antagonists such as Flutamide, Casodex, Nilutamide, or Cyproterone acetate.

The present invention provides compounds which can be used to treat patients suffering from prostate cancer resistant to androgen receptor antagonists which are not within formula I of the invention (or salts thereof), such as bicalutimide. The invention thus further contemplates a method of treating prostate cancer resistant to an androgen receptor antagonist other than those of formula I or salts thereof, comprising the step of administering to a patient in need thereof a compound capable of reducing the growth rate of the tumor mass of said cancer in an amount effective therefor. The term "reducing the growth rate of said tumor mass" denotes reduction in the growth rate (including, of course, stabilization or reduction in size) of said tumor mass upon treatment relative to the growth rate upon treatment with said androgen receptor antagonist other than those of formula I or salts thereof. Compounds of the formula I and pharmaceutically acceptable salts thereof of the present invention are preferred such compounds.

The present invention also contemplates use of an antiestrogen and/or aromatase inhibitor in combination with a compound of the present invention, for example, to assist in mitigating side effects associated with antiandrogen therapy such as gynecomastia. Exemplary antiestrogen and/or aromatase inhibitors include anastrozole (Arimidex), tamoxifen citrate (Nolvadex), exemestane (Aromasin), toremifene citrate (Fareston), letrozole (Femara), raloxifene hydrochloride (Evista), Faslodex, or 923 (Wyeth Ayerst).

The compounds of the present invention can be employed adjuvant to surgery.

Another application of the present compounds is in combination with antibody therapy such as but not limited to antibody therapy against PSCA. An additional application is in concert with vaccine/immune modulating agents for the treatment of cancer.

Compounds of the present invention can be employed in accordance with the methods described in U.S. Provisional Patent Application Serial No. 60/284,438, entitled "Selective Androgen Receptor Modulators and Methods for Their Identification, Design and Use" filed Apr. 18, 2001 by Mark E. Salvati et al,. which Provisional Patent Application is incorporated herein by reference in its entirety (including, but not limited to, reference to all specific compounds within formula I of the present invention), and U.S. patent application Ser. No. 09/885,827, entitled "Selective Androgen Receptor Modulators and Methods for their Indentification, Design and Use" filed Jun. 20, 2001 by Mark E. Salvati et al., which patent application is incorporated herein by reference in its entirety (including, but not limited to, reference to all specific compounds within formula I of the present invention).

The above other therapeutic agents, when employed in combination with the compounds of the present invention, can be used, for example, in those amounts indicated in the Physicians' Desk Reference (PDR) or as otherwise determined by one of ordinary skill in the art.

The following assays can be employed in ascertaining the activity of a compound as a NHR modulator. Various compounds of the present invention were determined to have AR modulator activity utilizing the transactivation assay, and standard AR binding assays as described following. At the concentration tested, certain compounds within formula I showed poor or no in vivo activity in the assay employed (e.g., compounds of Example 97).

Transactivation Assays
AR Specific Assay

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind III site at position 5831 of the human prostate specific antigen promoter (Accession # U37672), Schuur, et al., *J. Biol. Chem.*, 271 (12): 7043–51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions −5322 and −3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA 453 cells were collected in media containing 10% charcoal stripped FBS. Each cell suspension was distributed into two Gene Pulser Cuvetts (Bio-Rad) which then received 8 µg of the reporter construct, and electoporated using a Bio-Rad Gene Pulser at 210 volts and 960 µFaraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from 10-10 to 10-5 M (sample). Duplicates were used for each sample. The compound dilutions were performed on a Biomek 2000 laboratory workstation. After 48 hours, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

% Inhibition=100×(1−[average control−average blank/average sample−average blank ])

Data was plotted and the concentration of compound that inhibited 50% of the normalized SEAP was quantified ($IC_{50}$).
For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., Cell, 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 hours, either a saturation analysis to determine the $K_d$ for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM-0.2% CA-FBS) containing [$^3$H]-DHT (in concentrations ranging from 0.1 nM to 16 nM) in the absence (total binding) or presence (non-specific binding) of a 500-fold molar excess of unlabeled DHT were added to the cells. After 4 hours at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding, was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45–99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M were added to the cells. Two replicates were used for each sample. After 4 hours at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified ($IC_{50}$) after log-logit transformation. The $K_1$ values were determined by application of the Cheng-Prusoff equation to the $IC_{50}$ values, where:

$$K_I = \frac{IC_{50}}{(1 + (^3H - DHT)/K_d \text{ for } ^3H - DHT)}.$$

After correcting for non-specific binding, $IC_{50}$ values were determined. The $IC_{50}$ is defined as the concentration of competing ligand needed to reduce specific binding by 50%. The $K_d$'s for [$^3$H]-DHT for MDA 453 and LNCaP were 0.7 and 0.2 nM respectively.

Human Prostate Cell Proliferation Assay

Compounds of the present invention were tested ("test compounds") on the proliferation of human prostate cancer cell lines. For that, MDA PCa2b cells, a cell line derived from the metastasis of a patient that failed castration, Navone et al., *Clin. Cancer Res.*, 3, 2493–500 (1997), were incubated with or without the test compounds for 72 hours and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 hours, the cells were treated in the absence (blank) or presence of 1 nM DHT (control) or with test compounds (sample) of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi. of [$^3$H]-Thymidine (Amersham) was added per well and incubated for another 24 h followed by tripsinization, harvesting of the cells onto GF/B filters. Micro-scint PS were added to the filters before counting them on a Beckman TopCount.

The % Inhibition was calculated as:

$$\% \text{ Inhibition} = 100 \times (1 - [\text{average}_{control} - \text{average}_{blank}]/\text{average}_{sample} - \text{average}_{blank}])$$

Data was plotted and the concentration of compound that inhibited 50% of the [$^3$H]-Thymidine incorporation was quantified ($IC_{50}$).

C2C12 Mouse Myoblast Transactivation Assay

Two functional transactivation assays were developed to assess the efficacy of androgen agonists in a muscle cell background using a luciferase reporter. The first assay (ARTA Stable 1) uses a cell line, Stable 1 (clone #72), which stably expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which stably expresses both rAR and the enhancer/luciferase reporter.

The enhancer/reporter construct used in this system is pGL3/2XDR-1/luciferase. 2XDR-1 was reported to be an AR specific response element in CV-1 cells, Brown et. al. *The Journal of Biological Chemisty* 272, 8227–8235, (1997). It was developed by random mutagenesis of an AR/GR consensus enhancer sequence.

ARTA Stable 1

1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1X MEM Na Pyruvate (Gibco BRL, Cat. No.: 11360-070), 0.5X Antibiotic-Antimycotic, and 800 μg/ml Geneticin (Gibco BRL, Cat. No.: 10131-035).
2. 48 hours later, cells are transfected with pGL3/2XDR-1/luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 μl/well Opti-MEMem media (Gibco BRL, Cat. No.: 31985-070). To this, 0.5 μl/well Plus reagent is added. This mixture is incubated for 15 minutes at room temperature. In a separate vessel, 0.385 μl/well LipofectAMINE reagent is diluted with 5 μl/well Opti-MEM. The DNA mixture is then combined with the LipofectAMINE mixture and incubated for an additional 15 minutes at room temperature. During this time, the media from the cells is removed and replaced with 60 μl/well of Opti-MEM. To this is added 10 μl/well of the DNA/LipofectAMINE transfection mixture. The cells are incubated for 4 hours.
3. The transfection mixture is removed from the cells and replaced with 90 μl of media as in #1 above.
4. 10 μl/well of appropriate drug dilution is placed in each well.
5. 24 hours later, the Steady-Glo™ Luciferase Assay System is used to detect activity according to the manufacturer's instructions (Promega, Cat. No.: E2520).

ARTA Stable 2

1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1× MEM Na Pyruvate (Gibco BRL, Cat. No.: 11360-070), 0.5× Antibiotic-Antimycotic, 800 μg/ml Geneticin (Gibco BRL, Cat. No.: 10131-035) and 800 μg/ml Hygromycin β (Gibco BRL, Cat. No.: 10687-010).
2. 48 hours later, the media on the cells is removed and replaced with 90 μl fresh. 10 μl/well of appropriate drug dilution is placed in each well.
3. 24 hours later, the Steady-Glo™ Luciferase Assay System is used to detect activity according to the manufacturer's instructions (Promega, Cat. No.: E2520).

See U.S. patent application Ser. No. 09/885,831, entitled "Cell Lines and Cell-Based Assays for Identification of Androgen Receptor Modulators" filed Jun. 20, 2001 by Jacek Ostrowski et al., which Patent Application is incorporated herein by reference in its entirety.

Proliferation Assays

Murine Breast Cell Proliferation Assay

The ability of compounds of the present invention ("test compounds") to modulate the function of the AR was determined by testing said compounds in a proliferation assay using the androgen responsive murine breast cell line derived from the Shionogi tumor, Hiraoka et al., *Cancer Res.*, 47, 6560–6564 (1987). Stable AR dependent clones of the parental Shionogi line were established by passing tumor fragments under the general procedures originally described in Tetuo, et. al., *Cancer Research* 25, 1168–1175 (1965). From the above procedure, one stable line, SC114, was isolated, characterized and utilized for the testing of example compounds. SC114 cells were incubated with or without the test compounds for 72 hours and the amount of [$^3$H]-thymidine incorporated into DNA was quantified as a surrogate endpoint to assess the number of cells and therefore the proliferation rate as described in Suzuki et. al., *J. Steroid Biochem. Mol. Biol.* 37, 559–567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1;1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates were used for each sample. The compound dilutions were performed on a Biomek 2000 laboratory work station. Seventy two hours later 0.44 uCi of [$^3$H]-Thymidine (Amersham) was added per well and incubated for another 2 hr followed by tripsinization, and harvesting of the cells onto GF/B filters. Micro-scint PS were added to the filters before counting them on a Beckman TopCount. For the antagonist mode, the % Inhibition was calculated as:

% Inhibition=100×(1−[average$_{sample}$−average$_{blank}$/average$_{control}$−average$_{blank}$])

Data was plotted and the concentration of compound that inhibited 50% of the [$^3$H]-Thymidine incorporation was quantified (IC$_{50}$).

For the agonist mode % Control was referred as the effect of the tested compound compared to the maximal effect observed with the natural hormone, in this case DHT, and was calculated as:

% Control=100×(average$_{sample}$−average$_{blank}$)/(average$_{control}$−average$_{blank}$)

Data was plotted and the concentration of compound that inhibited 50% of the [$^3$H]-Thymidine incorporation was quantified (EC$_{50}$).

In Vitro Assay to Measure GR Induced AP-1 Transrepression

The AP-1 assay is a cell based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/Streptomycin with 0.5 mg/ml geneticin. Cells are plated the day before the assay at approximately 40000 cells/well. On assay day, the media is removed by aspiration and 20 μl assay buffer (RPMI without phenol red+10% FCS (charcoal-treated)+Pen/Strep) is added to each well. At this point either 20 μl assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 minutes at 37° C., followed by stimulation of the cells with 10 ng/ml PMA. The plates are then incubated for 7 hrs at 37° C. after which 40 μl luciferase substrate reagent is added to each well. Activity is measured by analysis in a luminometer as compared to control experiments treated with buffer or dexamethasome. Activity is designated as % inhibition of the reporter system as compared to the buffer control with 10 ng/ml PMA alone. The control, dexamethasone, at a concentration of ≦10 μM typically suppresses activity by 65%. Test compounds which demonstrate an inhibition of PMA induction of 50% or greater at a concentration of test compound of ≦10 μM are deemed active.

Wet Prostate Weight Assay AR Antagonist Assay

The activity of compounds of the present invention as AR antagonists was investigated in an immature male rat model, a standard, recognized test of antiandrogen activity of a given compound, as described in L. G. Hershberger et al., *Proc. Soc. Expt. Biol. Med.*, 83, 175 (1953); P. C. Walsh and R. F. Gittes, "Inhibition of extratesticular stimuli to prostate growth in the castrated rat by antiandrogens", *Endocrinology*, 86, 624 (1970); and B. J. Furr et al., "ICI 176,334: A novel non-steroid, peripherally selective antiandrogen", *J. Endocrinol.*, 113, R7–9 (1987), the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. Clin. Invest. Med., 16, 475–492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "*The Physiology of Reproduction*" ed. By E. Knobil and J. D. Neill, 1, 1435–1487 (1994). Since the male sex organs are the tissues most responsive to modulation of the androgen activity, this model is used to determine the androgen dependent growth of the sex accessory organs in immature castrated rats.

Male immature rats (19–20 days old Sprague-Dawley, Harlan Sprague-Dawely) were castrated under metofane ansestesia. Five days after surgery these castrated rats (60–70 g, 23–25 day-old) were dosed for 3 days. Animals were dosed sub-cutaneously (s.c.) 1 mg/kg with Testosterone Proprionate (TP) in arachis oil vehicle and anti-androgen test compounds (compounds of the present invention) were dosed orally by gavage (p.o.) in dissolved/suspensions of 80% PEG 400 and 20% Tween 80 (PEGTW). Animals were dosed (v/w) at 0.5 ml of vehicle/100 g body weight. Experimental groups were as follows:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 3-day treatment, the animals were sacrificed, and the ventral prostate weighed. To compare data from different experiments, the sexual organs weights were first standardized as mg per 100 g of body weight, and the increase in organ weight induced by TP was considered as the maximum increase (100%). ANOVA followed by one-tailed Student or Fischer's exact test was used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188–191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight was 4 to 5-fold when dosing 3 mg/rat/day of testosterone (T) or 1 mg/rat/day of testosterone propionate (TP) for 3 days. The EC$_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

In this immature castrated rat model, a known AR antagonist (Casodex) was also administered simultaneously with 0.1 mg of TP ($ED_{80}$), inhibiting the testosterone-mediated increase in the weights of the VP and SV in a dose dependent manner. The antagonist effects were similar when dosing orally or subcutaneously. Compounds of the invention also exhibited AR antagonist activity by suppressing the testosterone-mediated increase in the weights of VP and SV.

Levator Ani & Wet Prostate Weight Assay AR Agonist Assay

The activity of compounds of the present invention as AR agonists was investigated in an immature male rat model, a recognized test of anabolic effects in muscle and sustaining effects in sex organs for a given compound, as described in L. G. Hershberger et al., *Proc. Soc. Expt. Biol. Med.*, 83, 175 (1953); B. L. Beyler et al, "Methods for evaluating anabolic and catabolic agents in laboratory animals", *J. Amer. Med. Women's Ass.*, 23, 708 (1968); H. Fukuda et al., "Investigations of the levator ani muscle as an anabolic steroid assay", *Nago Dai. Yak. Ken. Nem.* 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized. M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll.—Soc. Ital. Biol. Sper.* 42, 1596 (1966); Z. Gori et al., "Testosterone hypertrophy of levator ani muscle of castrated rats. II. Electron-microscopic observations" *Boll.—Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200–250 g, 6–8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7–14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Super-anova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188–191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10–30-fold higher potency than free T.

MDA PCa2b Human Prostate Zenograft Assay

In Vivo Antitumor Testing: MDA-PCa-2b human prostate tumors were maintained in Balb/c nu/nu nude mice. Tumors were propagated as subcutaneous transplants in adult male nude mice (4–6 weeks old) using tumor fragments obtained from donor mice. Tumor passage occurred every 5–6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100–200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2–Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight=(length×width2)÷2

Tumor response end-point was expressed in terms of tumor growth inhibition (%T/C), defined as the ratio of median tumor weights of the treated tumors (T) to that of the control group (C).

To estimate tumor cell kill, the tumor volume doubling time was first calculated with the formula:

TVDT=Median time (days) for control tumors to reach target size−Median time (days) for control tumors to reach half the target size s And, Log cell kill=$(T-C) \div (3.32 \times TVDT)$ Statistical evaluations of data were performed using Gehan's generalized Wilcoxon test.

Dunning Prostate Tumor

Dunning R3327H prostate tumor is a spontaneously derived, well differentiated androgen responsive adenocarcinoma of the prostate (Smolev J K, Heston W D, Scott W W, and Coffey D S, *Cancer Treat Rep.* 61, 273–287 (1977)). The growth of the R3327H subline has been selected for its highly androgen-dependent and reproducible growth in intact male rats. Therefore, this model and other sublines of this tumor have been widely used to evaluate in vivo antitumor activities of antiandrogens such as flutamide and bacilutamide/Casodex (Maucher A., and von Angerer, *J. Cancer Res. Clin. Oncol.,* 119, 669–674 (1993), Furr B. J. A. *Euro. URL.* 18 (suppl. 3), 2–9 (1990), Shain S. A. and Huot R I. *J. Steriod Biochem.* 31, 711–718 (1988)).

At the beginning of the study, the Dunning tumor pieces (about 4×4 mm) are transplanted subcutaneously to the flank of mature male Copenhagen rats (6–7 weeks old, Harlan-Sprague Dawley, Indianapolis, Md.). About 6 weeks after the implantation, the animals with tumors of measurable size (about 80–120 mm$^2$) are randomized into treatment groups (8–10 rats/group) and the treatments are initiated. One group of the rats are castrated to serve as the negative control of tumor growth. Animals are treated daily with compounds of the current invention, standard antiandrogens such as bacilutamide or vehicle (control) for an average of 10 to 14 weeks. Test compounds are dissolved in a vehicle of (2.5 ml/kg of body weight) 10% polyethylene glycol and 0.05% Tween-80 in 1% carboxymethyl cellulose, PEG/CMC, (Sigma, St Louis, Mo.). Typical therapeutic experiments would include three groups of three escalating doses for each standard or test compound (in a range of 300–3 mg/kg).

Tumors in the vehicle (control) group reach a size of 1500 to 2500 mm$^3$, whereas the castrated animal group typically shows tumor stasis over the 14 weeks of observation. Animals treated orally with 20 mg/kg of bicalutamide or flutamide would be expected to show a 40% reduction in tumor volumes compared to control after 14 weeks of treatment. The size of tumors are measured weekly by vernier caliper (Froboz, Switzerland), taking perpendicular measurements of length and width. Tumor volumes are measured in mm$^3$ using the formula: Length×Width×Height=Volume. Statistical differences between treatment groups and control are evaluated using multiple ANOVA analysis followed by one tail non-parametric Student t test.

Mature Rat Prostate Weight Assay

The activity of compounds of the present invention were investigated in a mature male rat model, which is a variation of the Levator ani & wet prostate weight assay described above. The above in vivo assays are recognized assays for determining the anabolic effects in muscle and sustaining effects in sex organs for a given compound, as described in L. G. Hershberger et al., 83 *Proc. Soc. Expt. Biol. Med.,* 175 (1953); B. L. Beyler et al, "Methods for evaluating anabolic and catabolic agents in laboratory animals", 23 *J. Amer. Med. Women's Ass.,* 708 (1968); H. Fukuda et al., "Investigations of the levator ani muscle as an anabolic steroid assay", 14 *Nago Dai. Yak. Ken. Nem.* 84 (1966) the disclosures of which are herein incorporated by reference. The basis of this assay lies in the well-defined action of androgenic agents on the maintenance and growth of muscle tissues and sexual accessory organs in animals and man.

The male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et. al. 16 *Clin. Invest. Med.,* 475–492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues, M. C. Luke and D. S. Coffey, "The Physiology of Reproduction" ed. By E. Knobil and J. D. Neill, 1, 1435–1487 (1994). Since the male sex organs and the levator ani are the tissues most responsive to modulation of the androgen activity, this model is used to determine the activity of compounds that modulate the androgen receptor pathway in mature rats.

Along with its mitogenic activity on tissues such as prostate, seminal vesicle and muscle, testosterone also serves as a negative regulator for its own biosynthesis. Testosterone production in the Leydig cells of the testis is controlled by the level of circulating LH released from the pituitary gland. LH levels are themselves controlled by the level of LHRH produced in the hypothalmic region. Testosterone levels in the blood serve to inhibit the secretion of LHRH and subsequently reduce levels of LH and ultimately the levels of circulating testosterone levels. By measuring blood levels of LH as they are effected by compounds of the present invention ("test compounds"), it is possible to determine the level of agonist or antagonist activity of said compounds at the hypothalamic axis of this endocrine cycle.

Matched sets of Harlan Sprague-Dawely rats (40–42 days old, 180–220 g), were dosed orally by gavage (p.o.) with the test compounds in dissolved/suspensions of 80% PEG 400 and 20% Tween 20 (PEGTW) for 14 days. Two control groups, one intact and one castrated were dose orally only with the PEGTW vehicle. Animals were dosed (v/w) at 0.5 ml of vehicle /100 g body weight. Experimental groups were as follows:

1. Intact vehicle (p.o., PEGTW, QD)
2. Control vehicle (p.o., PEGTW, QD)
3. Bicalutamide (Casodex, a recognized antiandrogen, as a reference compound) or a compound of the present invention, p.o. in PEGTW QD. (in a range of doses). At the end of the 14-day treatment, the animals were sacrificed, and the ventral prostate, the seminal vesicles, and the levator ani were removed surgically and weighed. To compare data from different experiments, the organs weights were first standardized as mg per 100 g of body weight, and expressed as a percentage of the value of the respective organ in the intact group.

Rat luteinizing hormone (rLH) is quantitatively determined with the Biotrak [125 I] kit (Amersham Pharmacia Biotek), following the manufacturer directions. The assay is based on the competition by the LH present in the serum of the binding of [$^{125}$I] rLH to an Amerlex-M bead/antibody suspension. The radioactivity that remains after incubation with the serum and subsequent washes is extrapolated into a standard curve to obtain a reading in ng/ml.

The gain and loss of sexual organ and levator ani weight reflect the changes of the cell number (DNA content) and cell mass (protein content), depending upon the serum androgen concentration, see Y. Okuda et al., *J. Urol.,* 145, 188–191 (1991), the disclosure of which in herein incorporated by reference. Therefore, measurement of organ wet weight is sufficient to indicate the bioactivity of androgens and androgen antagonist. In the mature rats assay, active agonist agents will have no effect or will increase the weight of one or more of the androgen responsive organs (levator ani, prostate, seminal vessicle) and will have no effect or a suppressive effect on LH secretion. Compounds with antagonist activity will decrease the weight of one or more of the androgen responsive organs (levator ani, prostate, seminal vesicle) and will have no effect or a reduced suppressive effect on LH secretion.

CWR22 Human Prostate Zenograft Assay

In Vivo Antitumor Testing: CWR22 human prostate tumors were maintained in Balb/c nu/nu nude mice. Tumors were propagated as subcutaneous transplants in adult male nude mice (4–6 weeks old) using tumor fragments obtained from donor mice. Tumor passage occurred every 5–6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100–200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight= (length×width2)÷2.

Tumor response end-point was expressed in terms of tumor growth inhibition (%T/C), defined as the ratio of median tumor weights of the treated tumors (T) to that of the control group (C).

To estimate tumor cell kill, the tumor volume doubling time was first calculated with the formula:

*TVDT*=Median time (days) for control tumors to reach target size−Median time (days) for control tumors to reach half the target size And, Log cell kill=(T−C)÷(3.32×*TVDT*)

Statistical evaluations of data were performed using Gehan's generalized Wilcoxon test.

The following Examples illustrate embodiments of the present invention, and are not intended to limit the scope of the claims.

Abbreviations

The Following Abbreviations are used herein

DBU=1,8-diazabicyclo[5.4.0]undec-7-ene
4-DMAP=4-dimethylaminopyridine
ee=enantiomeric excess
DMF=dimethylformamide
Et=ethyl
EtOAc=ethyl acetate
LDA=lithium diisopropylamide
Hünig's Base=N,N-diisopropylethylamine
Me=methyl
RT=retention time
TFA=trifluoroacetic acid
THF=tetrahydrofuran
TLC=thin layer chromatography
TMS=trimethylsilyl
pTSA=para-toluenesulfonic acid
Δ=heat
t-Bu=tert-butyl
Ph=phenyl
PhCH₃=toluene
Pd/C=palladium on activated charcoal
TsCl=tosyl chloride
TBSOTf=tert-butyldimethylsilyl trifluoromethane sulfonate
TBS=tert-butyldimethylsilane
MeI=methyl iodide
(BOC)₂O=di-tert-butyl dicarbonate
TEA=triethylamine
n-BuLi=n-butyllithium
rt=room temperature
LC=liquid chromatography
EtOH=ethanol
DCE=dichloroethane
DMSO=dimethylsulfoxide
Ra—Ni=Raney Nickel
MS=molecular sieves
MS(ES)=Electro-Spray Mass Spectrometry
h=hours
Ac=acetyl
DEAD=diethyl azodicarboxylate
DPPA=diphenylphosphoryl azide

EXAMPLE 1

(5α,8 α,8aα)-8,8a-Dihydro-2-[3-(trifluoromethyl) phenyl]-5,8-methanoimidazo[1,5-a]pyridine-1,3(2H, 5H)-dione (1B)

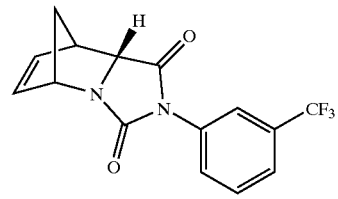

A. endo/exo-2-[[[3-(Trifluoromethyl)phenyl]amino] carbonyl]-2-azabicyclo[2.2.1]hept-5-ene-3-carboxylic acid ethyl ester (1A)

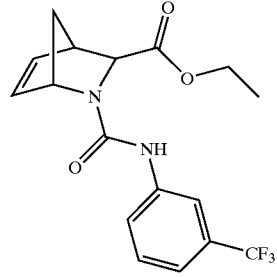

2-Azabicyclo[2.2.1.]hept-5-ene-3-carboxylic acid, ethyl ester (0.253 g, 0.15 mmol) was dissolved in toluene and 3-(trifluoromethylphenyl)isocyanate (0.311 g, 0.166 mmol) was added. The reaction was heated at 70° C. for 3 h and then cooled to −20° C. for 12 h. The compound 1A precipitated upon cooling, was filtered and rinsed with cold toluene.

Upon drying in vacuo 0.097 g of 1A was recovered and taken on into the next step with no further purification.

B. (5α,8 α,8aα)-8,8a-Dihydro-2-[3-(trifluoromethyl)phenyl]-5,8-methanoimidazo[1,5-a]pyridine-1,3-(2H,5H)-dione (1B)

The intermediate Compound 1A (0.150 g, mmol) was dissolved in toluene (5 mL) and DBU (0.1 mL) was added. The reaction was heated at 80° C. for 1.5 h and then the toluene was removed in vacuo. The resulting residue was purified by flash chromatography on $SiO_2$ eluting with 10%–30% acetone in hexanes to give 0.76 g of Compound 1B as a white solid. HPLC: 92% at 2.93 min (retention time) (YMC S5 ODS column 4.6×50 mm eluting with 10–90% aqueous methanol over 4 minutes containing 0.1% TFA, 4 mL/min, monitoring at 220 nm) MS (ES): m/z 309.09 $[M+H]^+$.

EXAMPLE 2

(5α,8 α,8aα)-8,8a-Dihydro-2-[3-(trifluoromethyl)phenyl]-5,8-methanoimidazo[1,5-a]pyridine-1,3(2H,5H)-dione (2C) (Alternative Procedure for Preparation of 1B)

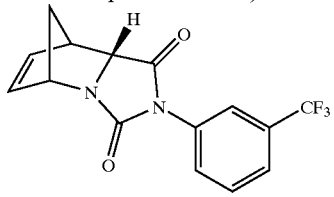

A. endo/exo-2-(Chlorocarbonyl)-2-azabicyclo[2.2.1]hept-5-ene-3-carboxylic acid, ethyl ester, (2A)

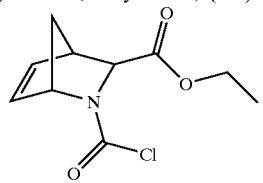

To a suspension of $NaHCO_3$ (2.5 g, 30 mmol) in $CH_2Cl_2$ at 25° C. was added phosgene (20% solution, 5.9 g, 12 mmol). 2-Azabicyclo[2.2.1.]hept-5-ene-3-carboxylic acid, ethyl ester (0.5 g, 3.0 mmol) was added and the reaction stirred at 25° C. for 2 h. The bicarbonate was then filtered off and rinsed with $CH_2Cl_2$. The product was purified by flash chromatography on $SiO_2$ eluting with 1%–2% MeOH in $CH_2Cl_2$ to give 0.367 g of intermediate Compound 2A as a yellow oil.

B. endo/exo-2-[[[3-(Trifluoromethyl)phenyl]amino]carbonyl]-2-azabicyclo[2.2.1]hept-5-ene-3-carboxylic acid ethyl ester (2B)

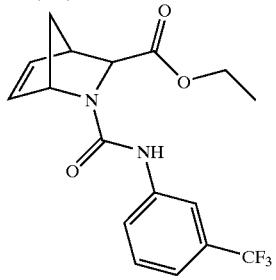

Intermediate Compound 2A (0.100 g, 0.44 mmol) and 3-trifluoro-methylaniline (0.075 mL, 0.44 mmol) were dissolved in 5.0 ml of toluene. Catalytic 4-DMAP and diisopropylamine (0.3 mL, 2.1 mmol) were then added. The reaction was heated at 50° C. for 14 h. The volatile organics were then removed and the residue was purified by flash chromatography on silica gel eluting with 0.5%–1.0% methanol/$CH_2Cl_2$ to give 0.39 g of intermediate Compound 2B as a pale yellow oil.

C. (5α,8 α,8aα)-8,8a-Dihydro-2-[3-(trifluoromethyl)phenyl]-5,8-methanoimidazo[1,5-a]pyridine-1,3(2H,5H)-dione (2C)

The title compound was prepared as described in Example 1, step B.

EXAMPLE 3

(5α,8 α,8aα)-8,8a-Dihydro-2-[1-naphthalenyl]-5,8-methanoimidazo[1,5-a]pyridine-1,3(2H,5H)-dione (3B)

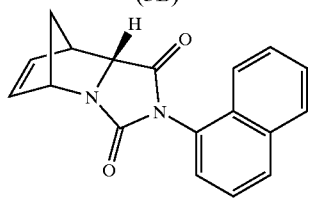

A. endo/exo-2-[(1-Naphthalenylamino)carbonyl]-2-azabicyclo[2.2.1]hept-5-ene-3-carboxylic acid ethyl ester (3A)

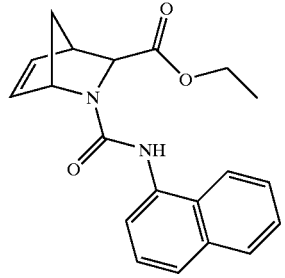

1-Naphthylamine (0.20 g, 1.39 mmol) was added to a solution of triphosgene (0.136 g, 0.46 mmol) in dichloroethane at 25° C. The solution was heated at 70° C. for 30 min and then cooled to 25° C. Triethylamine (0.58 mL, 4.17 mmol) was then added and the reaction was heated to 70° C. After 2h, the reaction was cooled to 25° C. and 2-azabicyclo[2.2.1.]hept-5-ene-3-carboxylic acid, ethyl ester (0.209 g, 1.25 mmol) was added. The reaction was stirred at 25° C. for 14 h. The volatile organics were then removed in vacuo and the resulting residue was purified by flash chromatography on $SiO_2$ eluting with (4:1–1:1) ethyl acetate/hexanes to give 0.190 g of intermediate Compound 3A as a white solid.

B. (5α,8 α,8aα)-8,8a-Dihydro-2-[1-naphthalenyl]-5,8-methanoimidazo[1,5-a]pyridine-1,3(2H,5H)-dione (3B)

Intermediate Compound 3A (0.150 g) was dissolved in toluene (5 mL) and DBU (0.1 mL) was added. The reaction was heated at 80° C. for 1.5 h and then the toluene was removed in vacuo. The resulting residue was purified by flash chromatography on $SiO_2$ eluting with 10%–30% acetone in hexanes to give 0.76 g of Compound 3B as a white solid. HPLC: 95% at 3.067 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 291.2 $[M+H]^+$.

EXAMPLE 4

(5α,8 α,8aα)-2,3,8,8a-Tetrahydro-2-[3-(trifluoromethyl)phenyl]-3-thioxo-5,8-methanoimidazo[1,5-a]pyridine-1,3(2H,5H)-one (4B)

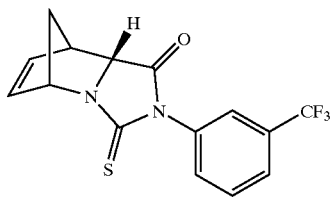

A. endo/exo-2-[[[3-(Trifluoromethyl)phenyl]amino]thioxomethyl]-2-azabicyclo[2.2.1]hept-5-ene-3-carboxylic acid, ethyl ester (4A)

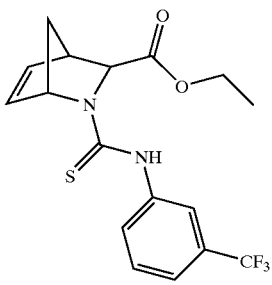

To a solution of 2-azabicyclo[2.2.1.]hept-5-ene-3-carboxylic acid, ethyl ester (0.253 g, 1.5 mmol) in toluene (7.0 mL) was added 3-(trifluoromethylphenyl) isothiocyanate (0.339 g, 1.66 mmol). After 14 h at 25° C., the reaction was diluted with EtOAc and washed with 1N NaOH (2×10 mL). The organic layer was dried over anhydrous sodium sulfate and the crude material was purified by silica gel chromatography using a gradient of 0 to 20% acetone in hexane to yield 188 mg (34%) of intermediate compound 4B.

B. (5α,8 α,8aα)-2,3,8,8a-Tetrahydro-2-[3-(trifluoromethyl)phenyl]-3-thioxo-5,8-methanoimidazo[1,5-a]pyridin-1(5H)-one (4B)

The intermediate compound 4A (180 mg, 0.5 mmol) was dissolved in anhydrous toluene (5 mL) and DBU (0.042 mL) was added. The reaction was heated at 80° C. for 1.5 h and then cooled to 25° C. The volatiles were removed in vacuo and the resulting residue was purified by flash chromatography on SiO$_2$ eluting with a gradient of 0 to 20% acetone/hexane giving pure compound 4B (67 mg) as a yellow oil. HPLC: 66.9% at 2.980 min (retention time) (YMC S5 ODS column 4.6×50 mm eluting with 10–90% aqueous methanol over 4 minutes containing 0.1% TFA, 4 mL/min, monitoring at 220 nm) MS (ES): m/z 343.07 [M+H]$^+$.

EXAMPLE 5

(5α,8α,8aα)-8,8a-Dihydro-8a-methyl-2-[3-(trifluoromethyl)phenyl]-5,8-methanoimidazo[1,5-a]pyridine-1,3(2H,5H)-dione (5)

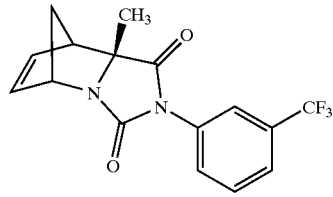

Intermediate Compound 1B (0.020 g, 0.06 mmol, from Example 1) was dissolved in anhydrous THF (2.0 mL) and cooled to −78° C. LDA (2.0 M soln in THF, 0.195 mL) was then slowly added. After 1 h, MeI (0.008 mL, 0.12 mmol) was added and the reaction was slowly warmed to 25° C. The reaction was then quenched with water and extracted with CH$_2$Cl$_2$ (3×10 mL). The combined organic layers were dried over anhydrous sodium sulfate and concentrated in vacuo to give pure compound 5 (0.008 g) as a white solid. HPLC: 100% at 3.620 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 323.0 [M+H]$^+$.

EXAMPLE 6

(5α,8α,8aα)-2,3,8,8a-Tetrahydro-8a-methyl-3-thioxo-2-[3-(trifluoromethyl)phenyl]-5,8-methanoimidazo[1,5-a]pyridin-1(5H)-one (6)

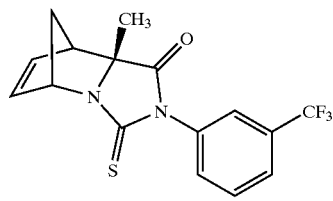

To a solution of Compound 4B (0.056 g, 0.173 mmol, Example 4) in THF at −78° C. was added lithium diisopropylamine (2.0 M soln in THF, 0.173 mL). After 2 h, MeI (0.022 mL, 0.35 mmol) was added and the reaction was warmed to 25° C. over 2 h. H$_2$O was then added and the mixture extracted with CH$_2$Cl$_2$ (3×30 mL). The combined organic layers were dried over anhydrous sodium sulfate. The crude product was purified by flash chromatography on SiO$_2$ eluting with 10% acetone in hexanes to give 0.034 g of Compound 6 as white solid. HPLC: 90% at 4.023 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 339.0 [M+H]$^+$.

EXAMPLE 7

(5α,8α,8aα) & (5α,8α,8aβ)-2-(3,5-Dichlorophenyl) tetrahydro-5,8-methanoimidazo[1,5-a]pyridine-1,3 (2H,5H)-dione (7Bi & 7Bii, Respectively)

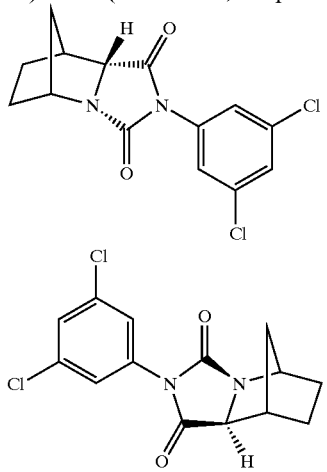

A. endo/exo-2-[[[3,5-Dichlorophenyl]amino]carbonyl]-2-azabicyclo[2.2.1]hept-5-ene-3-carboxylic acid ethyl ester (7A)

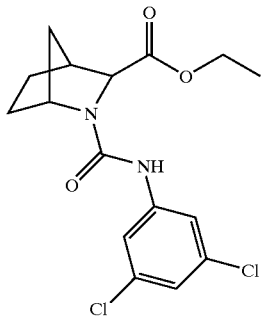

To a solution of 3,5-dichlorophenylisocyanate (3.01 g, 16 mmol) in toluene (100 mL) was added 2-azabicyclo[2.2.1.]heptane-3-carboxylic acid, ethyl ester (2.70 g, 16.0 mmol) in toluene and the reaction stirred at 25° C. for 14 h. A white solid formed after 14 h and diethyl ether was added to precipitate more product. The reaction was then filtered and rinsed with cold diethyl ether. The crude urea intermediate, 2.81 g of a white solid, was isolated by filtration, dried and taken on directly to the next step.

B. (5α,8α,8aα) & (5α,8α,8aβ)-2-(3,5-Dichlorophenyl) tetrahydro-5,8-methanoimidazo[1,5-a]pyridine-1,3(2H, 5H)-dione (7Bi & 7Bii)

Compound 7A (0.025 g, 0.070 mmol) was added to a suspension of freshly activated 4 Å MS (0.050 g) in toluene (2.0 mL). DBU (0.42 mL, 2.96 mmol) was then added followed by heating to 80° C. for 2 h. The mixture was then cooled to 25° C. and filtered through celite rinsing with methylene chloride. The organics were washed with 1 N HCl and then dried over anhydrous sodium sulfate. Crude NMR showed a mixture of Compound 7Bi and Compound 7Bii, in a ratio of 2:1.5, respectively. The diastereomers were separated by preparative TLC on $SiO_2$ eluting with methylene chloride. This gave 0.006 g of Compound 17Bi as a white solid and 0.008 g of Compound 17Bii as a white solid. 17Bi: HPLC: 100% at 3.383 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 312.1 [M+H]$^+$. 17Bii: HPLC: 99% at 3.497 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 311.2 [M+H]$^+$.

EXAMPLE 8

Tetrahydro-2-[3-(trifluoromethyl)phenyl]-5,8-ethanoimidazo[1,5-a]pyridine-1,3(2H,5H)-dione (8B)

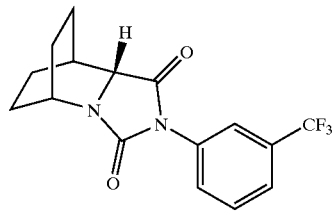

A. 2-[[[3-(Trifluoromethyl)phenyl]amino]carbonyl]-2-azabicyclo[2.2.2.]octane-3-carboxylic acid, ethyl ester (8A)

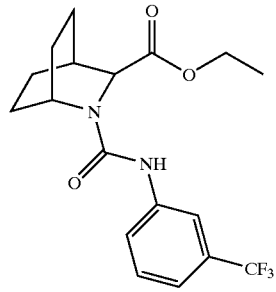

To a solution of 2-azabicyclo[2.2.2.]octane-3-carboxylic acid, ethyl ester (50 mg, 0.27 mmol) in anhydrous toluene (10 mL) was added 3-(trifluomethylphenyl)isocyanate (55.5 mg, 0.3 mmol). The reaction was stirred at 25° C. overnight, and then concentrated in vacuo and purified by preparative TLC on silica gel eluting with 30% acetone in hexanes to provide 37 mg (37%) of intermediate Compound 8A.

B. Tetrahydro-2-[3-(trifluoromethyl)phenyl]-5,8-ethanoimidazo[1,5-a]pyridine-1,3(2H,5H)-dione (8B)

To a solution of intermediate Compound 8A (37 mg, 0.1 mmol) in anhydrous toluene (10 mL) was added DBU (20 μL, 0.11 mmol). The solution was heated at 80° C. for 2 hours. The solvent was removed by rotary evaporation and the crude material was purified by preparative TLC on silica gel eluting with 30% acetone in hexanes to provide 16 mg (49%) of Compound 8B as a white solid. HPLC: 99% at 3.433 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 325.2 [M+H]$^+$.

EXAMPLE 9

(5α,8α,8aα) & (5α,8α,8aβ)-Tetrahydro-2-[3-(trifluoromethyl)phenyl]-5,8-methanoimidazo[1,5-a]pyridine-1,3(2H,5H)-dione (9Fi & 9Fii, Respectively) Solid Support Synthesis Route

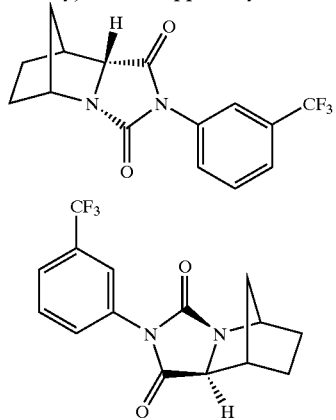

A. Formation of Modified Merrifield Resin (9A)

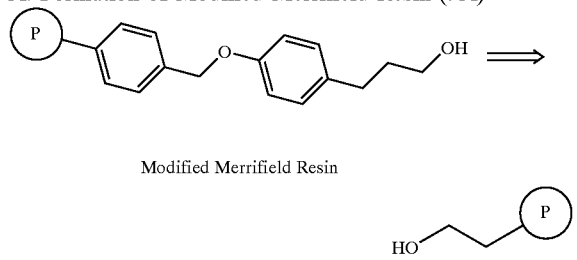

Modified Merrifield Resin

To a suspension of NaH (60% in mineral oil, 0.353 g, 8.84 mmol) in DMF at 0° C. was slowly added 3-(4-hydroxyphenyl)-1-propanol (1.3 g, 8.55 mmol), and then warmed to 25° C. and stirred for 1 h. Merrifield resin (5 g, 0.57 mmol/g) was washed sequentially with methylene chloride, DMF and then suspended in 20 mL of DMF. To the resin was added the preformed alkoxide over a 5 minute period. The reaction was then heated at 80° C. for 13 h. After cooling to 25° C., the reaction was filtered and rinsed sequentially with DMF (3×50 mL), hexanes (2×50 mL), methylene chloride (3×50 mL), methanol (2×50 mL), methylene chloride (3×50 mL) and dried under vacuum to give a white resin (4.6 g). Solid phase proton NMR demonstrated incorporation of the 3-(4-hydroxyphenyl)-1-propanol linker, to form Resin 9A.

B. endo/exo-2-Azabicyclo[2.2.1]heptane-2,3-dicarboxylic acid 2-(1,1-dimethylethyl)ester (9B)

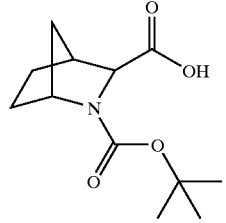

2-Azabicyclo[2.2.1]heptane-3-carboxylic acid, ethyl ester (10.0 g, 59.0 mmol) was dissolved in a mixture of dioxane (120 mL), water (60 mL) and 1 N NaOH (66 mL). (BOC)$_2$O (14.4 g, 218.25 mmol) was then added and the mixture was stirred at rt for 14 h. The volatile organics were removed in vacuo and additional water (200 mL) was then added and the mixture was extracted with CH$_2$Cl$_2$ (2×200 mL). The aqueous layer was then adjusted to pH=4–5 with the addition of 5% KHSO$_4$. The mixture was then extracted with CH$_2$Cl$_2$ (3×100 mL). The combined organic layers were concentrated to give crude intermediate Compound 9B as a white solid (8.5 g). This material was taken on without purification.

C. endo/exo-2-Azabicyclo[2.2.1]heptane-2,3-dicarboxylic acid, 2-(1,1-dimethylethyl) 3-(Modified Merrifield Resin) ester (9C)

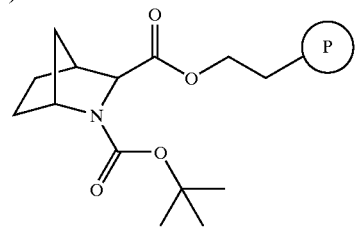

To Resin 9A was added DMF (15 mL) followed by shaking for 15 minutes. Compound 9B (0.275 g, 1.14 mmol) was then added in DMF followed by pyridine (0.152 mL, 1.88 mmol). 2,6-Dichlorobenzoyl chloride (0.163 mL, 1.14 mmol) was added and the reaction was shaken for 1 day. Identical amounts of acid, pyridine and chloride were then added followed by shaking for 2 days. The reaction was then filtered and rinsed sequentially with DMF (3×20 mL), methanol (3×20 mL), methylene chloride (6×20 mL) and dried in vacuo to give Resin 9C as a white powder.

D. endo/exo-2-Azabicyclo[2.2.1.]heptane-3-carboxylic acid, Modified Merrifield Resin ester (9D)

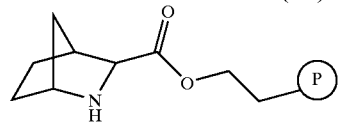

The Resin 9C (1 g) was suspended in 50% TFA/DMF (30 mL) and sonicated at 60° C. for 18 h. The reaction was then filtered and washed with DMF (5×20 mL), methanol (2×20 mL), methylene chloride (2×20 mL) and dried under vacuum to give 0.7 g of Resin 9D as a white powder.

E. endo/exo-2-[[[3-(Trifluoromethyl)phenyl]amino]carbonyl]-2-azabicyclo[2.2.1]heptane-3-carboxylic acid, Modified Merrifield Resin ester, (9E)

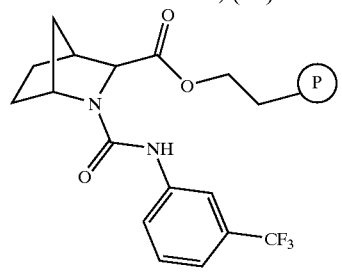

The Resin 9D (0.50 g) was suspended in CH$_2$Cl$_2$ (10 mL) and 3-(trifluoromethylphenyl)isocyanate (0.5 mL, 1.25 mmol) was added and the reaction was shaken for 24 h. The resin was filtered and washed with CH$_2$Cl$_2$ (8×20 mL) and dried in vacuo to give Resin 9E as a yellow solid.

79

F. (5α,8α,8aα) & (5α,8α,8aβ)-Tetrahydro-2-[3-(trifluoromethyl)phenyl]-5,8-methanoimidazo[1,5-a]pyridine-1,3(2H,5H)-dione (9Fi & 9Fii)

To Resin 9E was added dry toluene (10 mL) and 0.25 g of activated 4 Å MS. DBU (0.25 mL) was then added and the reaction was heated to 80° C. for 1.5 h. The reaction was filtered and rinsed with CH₂Cl₂ and the organics were washed once with 1 N HCl followed by drying over anhydrous sodium sulfate. The resulting process yielded 24 mg (26% yield from loading of Merrifield resin) of a 4 to 1 mixture of Compounds 9Fi & 9Fii, respectively. Separation of Compounds 9Fi & 9Fii was achieved by preparative HPLC (0%–100% aqueous methanol over 20 minutes, YMC ODSA reverse phase column, 20×100 mm) to yield 0.005 g of Compound 9Fi as a white solid and 0.019 g of Compound 9Fii as a white solid. See Example 11 and 12 for characterization.

EXAMPLE 10

(5α,8α,8aα) & (5α,8α,8aβ)-Tetrahydro-2-(2-naphthalenyl)-5,8-methanoimidazo[1,5-a]pyridine-1,3(2H,5H)-dione (10Ci & 10Cii, Respectively)

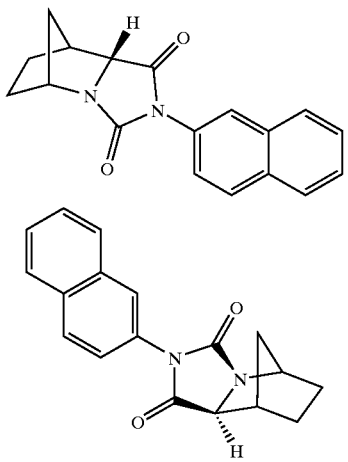

A. endo/exo-2-(Chlorocarbonyl)-2-azabicyclo[2.2.1]heptane-3-carboxylic acid Modified Merrifield Resin ester (10A)

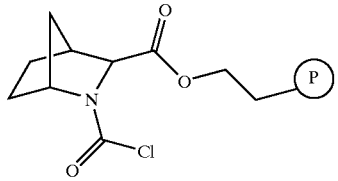

The Resin 9D (0.50 g, synthesized as described in Example 9) was suspended in CH₂Cl₂ (10 mL) and phosgene (20% in toluene, 4.5 g) and NaHCO₃ (1.5 g) were added. The resin was shaken for 22 h at 22° C. and then filtered rinsing with CH₂Cl₂ (5×50 mL). The resin was then dried in vacuo to give Resin 10A as a yellow resin.

80

B. endo/exo-2-[(2-Naphthalenylamino)carbonyl]-2-azabicyclo[2.2.1]heptane-3-carboxylic acid Modified Merrifield Resin ester (10B)

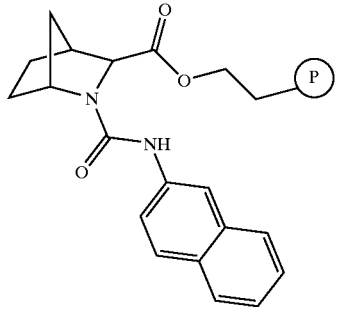

The Resin 10A (0.70 g) was suspended in CH₂Cl₂ (15 mL) and 2-naphthal amine (0.58 g, 4.0 mmol) was added. Hünig's base (0.88 mL) and catalytic 4-DMAP were added and the mixture was shaken at 70° C. for 20 h. After cooling to 22° C., the resin was filtered and washed with CH₂Cl₂ (8×20 mL) and dried in vacuo to give Resin 10B as a yellow solid.

C. (5α,8α,8aα) & (5α,8α,8aβ)-Tetrahydro-2-(2-naphthalenyl)-5,8-methanoimidazo[1,5-a]pyridine-1,3(2H,5H)-dione (10Ci & 10Cii)

To the Resin 10B (0.70 g) was added dry toluene (10 mL) and 0.25 g of activated 4 Å MS. DBU (0.65 mL, 4.0 mmol) was then added and the reaction was heated to 80° C. for 2.0 h. The reaction was filtered and rinsed with CH₂Cl₂ and the organics were washed twice with 1 N HCl (30 mL) followed by drying over anhydrous sodium sulfate. The resulting process yielded 13 mg (11% yield) of a 1.5 to 1 mixture of Compound 10Ci and 10Cii, respectively. Separation of the mixture was achieved by flash chromatography on SiO₂ eluting with 1% MeOH in CH₂Cl₂ to yield 6 mg of 10Ci as a white solid and 4 mg of Compound 10Cii as a white solid. 10Ci: HPLC: 99% at 2.94 minutes (YMC S5 ODS column, 4.6×50 mm; 10–90% MeOH/H₂O gradient, +0.1% TFA; 4 mL/min, 220 nM detection) MS (ES): m/z 293.0 [M+H]⁺. 10Cii: HPLC: 99% at 3.09 minutes (YMC S5 ODS column, 4.6×50 mm; 10–90% MeOH/H₂O gradient, +0.1% TFA; 4 mL/min, 220 nM detection) MS (ES): m/z 293.0 [M+H]⁺.

EXAMPLE 11

(5α,8α,8aβ)-Tetrahydro-2-[3-(trifluoromethyl)phenyl]-5,8-methanoimidazo[1.5-a]pyridine-1,3(2H,5H)-dione (11)

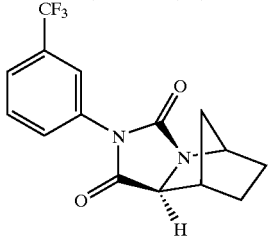

To a suspension of freshly activated 4 Å MS (1.5 g) in toluene (15 mL) was added 2-azabicyclo[2.2.1.]heptane-3-carboxylic acid, ethyl ester (0.50 g, 2.96 mmol) in toluene. After 15 min, 3-(trifluoromethyl)-phenylisocyanate (0.41 mL, 2.96 mmol) was added and the reaction stirred at 25° C. for 14 h. DBU (0.42 mL, 2.96 mmol) was then added followed by heating to 80° C. for 2 h. The mixture was then cooled to 25° C. and filtered through celite rinsing with methylene chloride. The organics were taken to dryness and allowed to stand neat in the remaining DBU at 35° C. for 5 h. The crude mixture was purified by silica gel chromatography to yield 735 mg (80.1% yield) of Compound 11 as a white solid. HPLC: 98% at 3.117 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 311.1 [M+H]$^+$.

EXAMPLE 12

(5α,8α,8aα) & (5α,8α,8aβ)-Tetrahydro-2-[3-(trifluoromethyl)phenyl]-5,8-methanoimidazo[1,5-a]pyridine-1,3(2H,5H)-dione (12i & 12ii, Respectively)

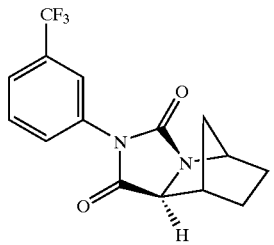

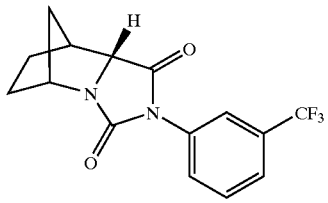

LDA was prepared by treating diisopropyl amine (0.091 mL, 0.650 mmol) in THF at −78° C. with n-BuLi (1.6 M in hexanes, 0.304 mL). After 20 min, Compound 11 (0.100 g, 0.325 mmol) was slowly added to the LDA in THF. The reaction was slowly warmed to −20° C. and held for 15 min. The reaction was then cooled to −78° C. and quenched by the addition of sat NH$_4$Cl. The solution was then extracted with CH$_2$Cl$_2$ (3×30 mL) and the organics were dried over anhydrous sodium sulfate. The crude material was purified by preparative TLC on SiO$_2$ eluting with CH$_2$Cl$_2$ to give a 1:3 mixture of Compound 12i (Compound 11) & 12ii (0.091 g, 91%) as a white solid. 12ii: HPLC: 98% at 2.987 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 311.1 [M+H]$^+$.

EXAMPLE 13

(5α,8α,8aα) & (5α,8α,8aβ)-[[2-(3,4-Dichlorophenyl)octahydro-1-oxo-5,8-methanoimidazo[1,5-a]pyridin-3-ylidene]amino] (13Bi & 13Bii, Respectively)

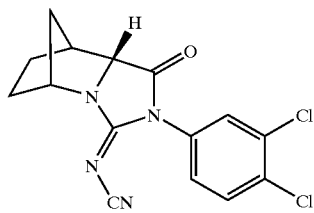

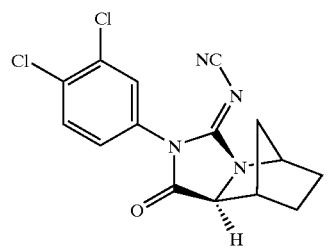

A. endo/exo-2-[(Cyanoimino)[(3,4-dichlorophenyl)amino]methyl]-2-azabicyclo[2.2.1]heptane-3-carboxylic acid ethyl ester (13A)

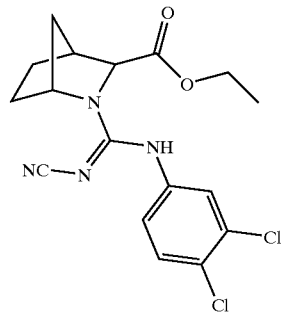

2-Azabicyclo[2.2.1.]heptane-3-carboxylic acid, ethyl ester (169 mg, 1.0 mmol, 1 eq) was combined in dimethylformamide with N-cyano-N'-(3,4-dichlorophenyl)-thiourea (246 mg, 1.0 mmol, 1 eq) and 1-[3-(dimethylamino)propyl]-3-ethylcarbodiimide hydrochloride (288 mg, 1.5 mmol, 1.5 eq). The mixture was stirred at ambient temperature overnight. The reaction was quenched with 1M aqueous citric acid and extracted with CH$_2$Cl$_2$. The combined organic extracts were dried and concentrated in vacuo. The crude material was purified by flash chromatography on silica gel eluting with 30% acetone in hexanes to provide 192 mg (50.4%) of Compound 13A as a white semi-solid. HPLC: 100% at 3.260 minutes (YMC Combiscreen ODS-A S5 column eluting with 10–90% aqueous methanol over a 4 minute gradient.) MS (ES): m/z 381. [M+H]$^+$.

B. (5α,8α,8aα) & (5α,8α,8aβ)-[[2-(3,4-Dichlorophenyl) octahydro-1-oxo-5,8-methanoimidazo[1,5-a]pyridin-3-ylidene]amino] (13Bi & 13Bii)

Compound 13A (180 mg, 0.47 mmol, 1 eq) was combined in anhydrous toluene with DBU (72 mg, 0.47 mmol, 1 eq). The solution was heated at 60° C. for 1 h. TLC (SiO$_2$ plate, 1% CH$_3$OH in CH$_2$Cl$_2$) showed no starting material remaining, while LC monitoring indicated a peak with the same retention time as the starting material. The reaction was quenched with saturated aqueous NH$_4$Cl and extracted with CH$_2$Cl$_2$. The combined organic extracts were dried and concentrated in vacuo. The crude material was purified by flash chromatography on silica gel eluting with 0.5% CH$_3$OH in CH$_2$Cl$_2$ to provide two isomers. Compound 13Bi was obtained in 52% yield (82 mg) as white semi-solid. HPLC: 100% at 3.297 minutes (YMC Combiscreen ODS-A S5 column eluting with 10–90% aqueous methanol over a 4 minute gradient.) MS(ES): 335.08 [M$^{+}$]. Compound 13Bii was obtained in 25% yield (40 mg) as white solid. HPLC: 100% at 3.323 minutes (YMC Combiscreen ODS-A S5 column eluting with 10–90% aqueous methanol over a 4 minute gradient.) MS (ES): m/z 335.06 [M]$^{+-}$ & 337.07 [M+2H]$^{+}$.

EXAMPLE 14

(5α,8α,8aα)-8a-[(4-Bromophenyl)methyl]-2-(3,5-Dichlorophenyl)tetrahydro-5,8-methanoimidazo[1,5-a]pyridine-1,3(2H,5H)-dione (14)

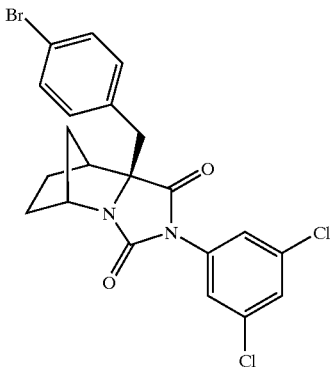

Compound 7Bi (0.217 g, 0.701 mmol, prepared as described in Example 7) was added to freshly prepared LDA (1.227 mmol n-BuLi, 1.402 mmol diisopropylamine) in THF at −78° C. After addition, the reaction was slowly warmed to −20° C. and kept at that temperature for 20 minutes. The mixture was then cooled to −78° C. and 4-bromobenzyl bromide (0.175 g, 0.701 mmol) was added in THF. The reaction was then warmed to 0° C. and after 2 h, quenched by the addition of saturated aq. NH$_4$Cl. The solution was then extracted with CH$_2$Cl$_2$ (2×30 mL) and dried over anhydrous sodium sulfate. The resulting material was purified by preparative silica gel TLC eluting with CH$_2$Cl$_2$ to give Compound 14 (0.083 g) as a clear oil. HPLC: 98% at 4.160 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 481.1 [M+H]$^{+}$

EXAMPLE 15

(5α,8α,8aα)-Hexahydro-2-(2-naphthaleny)-3-(phenylimino)-5,8-methanoimidazo[1,5-a]pyridine-1(5H)-one (15B)

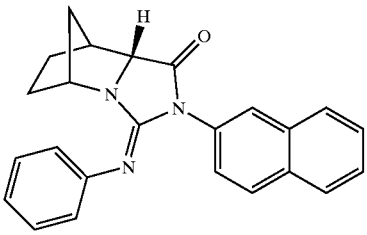

A. N-(2-Naphthalenyl)-2-azabicyclo[2.2.1.]heptane-3-carboxamide (15A)

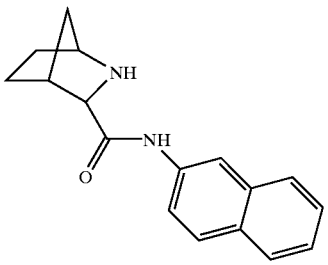

The intermediate Compound 9B (1.00 g, 4.15 mmol, as prepared in Example 9) was dissolved in CH$_2$Cl$_2$ (8.0 mL) and TEA (2.31 mL, 16.6 mmol) and 2,6-dichlorobenzoyl chloride (0.549 mL, 4.15 mmol) were added. The mixture was stirred for 14 h and 2-aminonaphthal (0.593 g, 4.15 mmol) was added in CH$_2$Cl$_2$ followed by addition of 4-DMAP (0.010 g). After 3 h, the reaction was diluted with CH$_2$Cl$_2$ and washed once with 1N HCT (40 mL), once with sat aq NaHCO$_3$ (40 mL) and dried over anhydrous sodium sulfate. The crude intermediate (1.00 g, 2.73 mmol) was dissolved in CH$_2$Cl$_2$ (2.0 mL) and treated with TFA (2.0 mL) at 20° C. After 3 h, the reaction was quenched with saturated aq. NaHCO$_3$ and extracted with CH$_2$Cl$_2$ (3×30 mL) and dried over anhydrous sodium sulfate. The crude reaction was purified by preparative reverse phase HPLC to give 0.770 g of Compound 15A as a white solid.

B. (5α,8α,8aα)-Hexahydro-2-(2-naphthaleny)-3-(phenylimino)-5,8-methanoimidazo[1,5-a]pyridine-1(5H)-one (15B)

The intermediate Compound 15A (0.050 g, 0.188 mmol) was dissolved in dichloroethane (2.0 mL) and the phenyl isocyanide dichloride (0.026 mL, 0.188 mmol), 4-DMAP (0.010 g) and DBU (0.084 mL, 0.564 mmol) were added and the reaction was heated to 90° C. in a sealed tube. After 14 h, the reaction was cooled to room temperature and concentrated in vacuo. The residue was purified by preparative TLC on SiO$_2$ eluting with CH$_2$Cl$_2$/acetone (9: 1) to give 0.063 g of Compound 15B as a tan oil. HPLC: 93% at 3.590 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 368.37 [M+H]$^{+}$

EXAMPLE 16

Hexahydro-2-[3-(trifluoromethyl)phenyl]-5,8-methanoimidazo[1,5-a]pyridine-1(5H)-one (16)

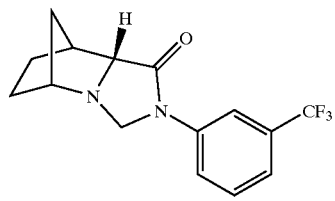

Compound 4B (0.020 g, 0.062 mmol, as described in Example 4) was dissolved in absolute EtOH (2.0 mL) and Ra—Ni (excess) was added. After 3 h at 25° C., the reaction was filtered thru celite rinsing with EtOH. The crude material was purified by preparative TLC eluting with 30% acetone in hexanes, yielding 0.6 mg of Compound 16 as a white solid. HPLC: 100% at 2.437 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 297.3 [M+H]$^+$.

Alternative Preparation of Compound 16

A. (5α,8α,8aα)-Hexahydro-3-thioxo-2-[3-(trifluoromethyl)phenyl]-5,8-methanoimidazo[1,5-a]pyridin-1(5H)-one (16A)

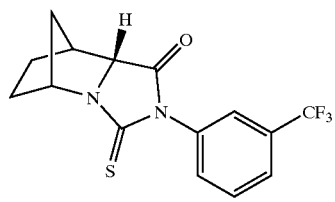

2-Azabicyclo[2.2.1.]hept-5-ene-3-carboxylic acid, ethyl ester (0.250 g, 0.15 mmol) was dissolved in toluene and 3-(trifluoromethylphenyl)isothiocyanate (0.334 g, 0.166 mmol) was added. The reaction was stirred at 25° C. for 14 h and then 1N NaOH (4 mL) was added. After half hour, the aqueous layer was extracted with dichloromethane (3×25 mL). The combined organic layers were washed with brine (50 mL) and dried over Na$_2$SO$_4$ and then the solvent was removed in vacuo. The resulting residue was purified by flash chromatography on SiO$_2$ eluting with 10%–30% acetone in hexanes to give 0.378 g of compound 16A as a yellow solid.

B. Hexahydro-2-[3-trifluoromethyl)phenyl]-5,8-methanoimidazo[1,5-a]pyridine-1(5H)-one (16b or 16)

Compound 16A (0.020 g, 0.062 mmol) was dissolved in ethanol (2 mL) and Ra—Ni (~0.020 g) was added. After 3 h, the reaction mixture was filtered through celite, concentrated, and the resulting residue purified by preparative TLC on silica eluting with 30% acetone in hexanes to give 0.8 mg of 16B as a white solid. HPLC: 99% at 2.437 min (retention time) (YMC S5 ODS column 4.6×50 mm eluting with 10–90% aqueous methanol over 4 minutes containing 0.1% TFA, 4 mL/min, monitoring at 220 nm) MS (ES): m/z 297.3 [M+H]$^+$.

EXAMPLE 17

[5R-(5α,8α,8aα)] & [5R-(5α,8α,8aβ)]-Tetrahydro-2-(4-nitro-1-naphthalenyl)-5,8-methanoimidazo[1,5-a]pyridine-1,3(2H,5H)-dione (17i & 17ii, Respectively)

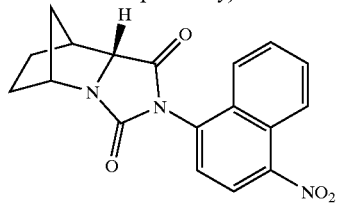

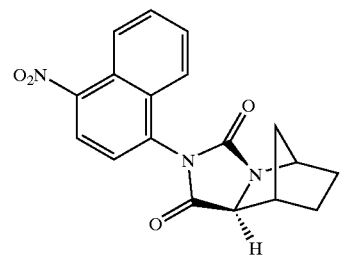

R-2-Azabicyclo[2.2.1.]heptane-3-carboxylic acid, ethyl ester (0.169 g, 1.0 mmol) was dissolved in toluene (10 mL) with freshly activated 4 Å MS (0.200 g). To this was added a solution of 4-nitro-1-naphthyl isocyanate (0.210 g, 1.0 mmol), prepared analogously to the procedure described in Example 3 step A) in 5 ml of toluene. After 15 h, the reaction was complete by LC, and DBU (0.224 mL, 1.5 mmol) was added and the reaction was heated at 80° C. for 1.5 h. After cooling to rt, the reaction was filtered and then poured into 1 N HCl and extracted with CH$_2$Cl$_2$ (2×30 mL). The organics were dried over anhydrous sodium sulfate and then concentrated. The crude mixture was determined to be a 1:2 ratio of Compound 17i and 17ii, respectively. The reaction mixture was separated by flash chromatography on silica gel eluting with CH$_2$Cl$_2$/acetone (1% acetone) to give Compound 17i: HPLC: 98% at 2.923 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 338.1 [M+H]$^+$ and Compound 17ii: HPLC: 96% at 2.753 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 338.1 [M+H]$^+$. Both were determined to be 94% ee by chiral HPLC analysis.

EXAMPLE 18

(6α,9α,9aα)-Tetrahydro-2-[3-(trifluoromethyl)phenyl]-6,9-methano-2H-pyrido[1,2-d][1,2,4]triazine-1,4(3H,9aH)-dione (18D)

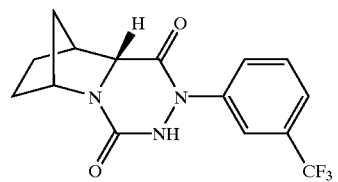

A. 3-[[[3-(Trifluoromethyl)phenyl]amino]carbonyl]-2-azabicyclo[2.2.1]heptane-2-carboxylic acid 1,1-dimethylethyl ester (18A)

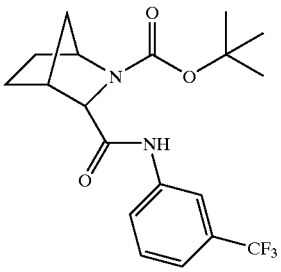

Intermediate Compound 9B (964 mg, 4 mmol, 1 eq, Example 9) was dissolved in 20 mL of tetrahydrofuran and 1-methyl-2-pyrrolidinone (487 μL, 4 mmol, 1 eq) was added followed by methyl chloroformate (309 μL, 4 mmol, 1 eq). The mixture was stirred at rt for 15 min. 3-(Trifluoromethyl)aniline (499 μL, 4 mmol, 1 eq) was then added, and the reaction was stirred at rt for 72 h. The reaction was quenched by addition of water and 0.1 M aqueous citric acid. The mixture was extracted with $CH_2Cl_2$. The combined organic extracts were dried, concentrated in vacuo, and purified by flash chromatography on silica gel eluting with 0.3% methanol in $CH_2Cl_2$ to provide 640 mg (41.6%) of intermediate Compound 18A.

B. 3-[[1-[3-(Trifluoromethyl)phenyl]hydrazino]carbonyl]-2-azabicyclo[2.2.1]heptane-2-carboxylic acid 1,1-dimethylethyl ester (18B)

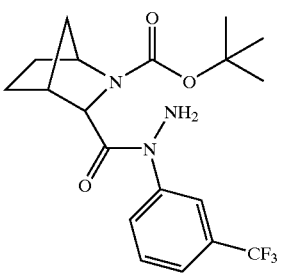

Compound 18A (308 mg, 0.8 mmol, 1 eq) was dissolved in 15 mL of tetrahydrofuran. Sodium hydride (60% in oil, 38 mg, 0.96 mmol, 1.2 eq) was added, and the mixture was stirred at rt for 15 min. O-Diphenylphosphinylhydroxylamine (224 mg, 0.96 mmol, 1.2 eq) was then added, and the reaction was stirred at rt for 1 h. LC analysis indicated that the starting material had been consumed. Water was added, and the reaction was extracted with $CH_2Cl_2$. The combined organic extracts were dried and concentrated in vacuo to provide Compound 18B as a semi-solid in quantitative yield. The compound was used without further purification. LC: R.T.=3.39 min (retention time) (YMC Combiscreen ODS-A S5 column eluting with 10–90% aqueous methanol over a 4 minute gradient.)

C. 2-Azabicyclo[2.2.1]heptane-3-carboxylic acid 1-[3-(trifluoromethyl)-phenyl]hydrazide (18C)

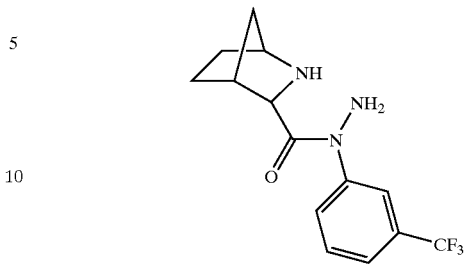

Compound 18B (136 mg, 0.34 mmol, 1 eq) was dissolved in 5 mL of $CH_2Cl_2$. Trifluoroacetic acid (2 mL) was added, and the mixture was stirred at rt for 1 h. LC analysis showed complete conversion to Compound 18C. The crude material was concentrated in vacuo and taken on to the next step.

D. (6α,9α,9aα)-Tetrahydro-2-[3-(trifluoromethyl)phenyl]-6,9-methano-2H-pyrido[1,2-d][1,2,4]triazine-1,4(3H,9aH)-dione (18D)

Compound 18C was dissolved in 10 mL of $CH_2Cl_2$, and Hünig's base (10 eq) was added to bring the pH to 10. The mixture was cooled to 10° C. Triphosgene (approx. 1.5 eq) was dissolved in $CH_2Cl_2$ and added dropwise to the reaction mixture. The reaction was stirred at 0° C. and then allowed to stir at rt overnight. LC analysis indicated that the starting material had been consumed. The mixture was washed with saturated aqueous $NH_4Cl$ followed by saturated aqueous NaCl. The $CH_2Cl_2$ layer was dried, concentrated in vacuo and purified by flash chromatography on silica gel eluting with 2% methanol in $CH_2Cl_2$. The material was purified further by preparative LC to provide 15 mg (14%) of Compound 18D as a light yellow solid. HPLC: 100% at 2.523 min (retention time) (YMC Combiscreen ODS-A S5 column eluting with 10–90% aqueous methanol over a 4 minute gradient.) MS (APCI): m/z 326.2 $[M+H]^+$

EXAMPLE 19

(5α,8α,8aα) & (5α,8α,8aβ)-8,8a-Dihydro-2-(1H-indol-3-yl)-5,8-methanoimidazo[1,5-a]pyridine-1,3(2H,5H)-dione (19Bi & 19Bii, Respectively)

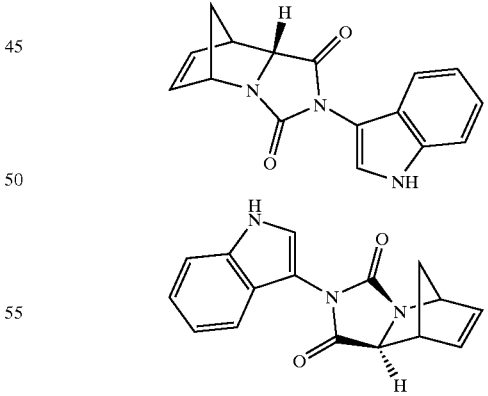

A. 3-Isocyanatoindole (19A)

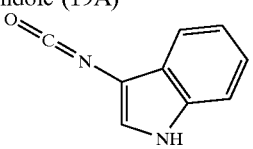

To a solution of indole-3-carboxylic acid (1 g, 6.20 mmol, 1 eq) in 30 mL of tetrahydrofuran was added triethylamine (0.86 mL, 6.20 mmol, 1 eq) and diphenylphosphoryl azide (1.3 mL, 6.20 mmol, 1 eq). The reaction was stirred at rt overnight. The mixture was concentrated in vacuo and purified by flash chromatography on silica gel eluting with 25% ethyl acetate in hexanes to provide a quantitative yield of the intermediate azide. The azide was heated at 100° C. in 60 mL of toluene for 5 h. Concentration in vacuo gave complete conversion to Compound 19A which was used directly in the next step.

B. (5α,8α,8aα) and (5α,8α,8aβ)-8,8a-Dihydro-2-(1H-indol-3-yl)-5,8-methanoimidazo[1,5-a]pyridine-1,3(2H,5H)-dione (19Bi & 19Bii)

To Compound 19A (6.20 mmol, 1 eq) in 50 mL of toluene at rt under Ar was added a solution of 2-azabicyclo[2.2.1.]heptane-3-carboxylic acid, ethyl ester (1.03 g, 6.20 mmol, 1 eq) in 10 mL of toluene with 4 Å MS. TLC analysis after several hours indicated that the starting material had been consumed. DBU (0.93 mL, 6.20 mmol, 1 eq) was added and the reaction was warmed at 80° C. for 3 h. The mixture was cooled, filtered, and purified by flash chromatography on silica gel eluting with 50% acetone in hexanes to provide 120 mg (7%) of Compound 19Bi as yellowish tan crystals. An additional 495 mg (29%) of material was a 4:1 mixture of 19Bi & 19Bii, respectively. HPLC: 94% at 2.17 min (retention time) (YMC S5 ODS column 4.6×50 mm eluting with 10–90% aqueous methanol over 4 minutes containing 0.2% phosphoric acid, 4 mL/min, monitoring at 220 nm). MS (APCI): m/z 279.8 [M+H]+

EXAMPLE 20

(5α,8α,8aα)-2-(Benzo[b]thiophene-3-yl)-8,8a-dihydro-5,8-methanoimidazo[1,5-a]pyridine-1,3(2H,5H)-dione (20B)

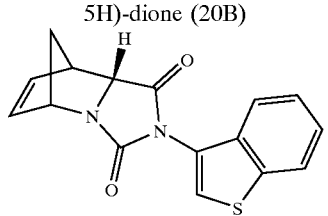

A. 3-Aminobenzothiophene (20A)

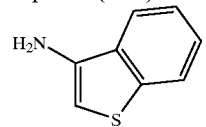

To a solution of 3-amino-benzo[b]thiophene-2-carboxylic acid, methyl ester (1 g, 4.83 mmol, 1 eq) in 1-methyl-2-pyrrolidinone (8 mL) was added piperazine (2.08 g, 24.13 mmol, 5 eq). The reaction was stirred at 130° C. overnight. Ice was added, and the mixture was extracted with ethyl acetate. The organic extracts were washed twice with water, dried, and concentrated in vacuo. The crude material was purified by flash chromatography on silica gel eluting with 40% ethyl acetate in hexanes to provide 600 mg (83%) of Compound 20A as a yellow oil.

B. (5α,8α,8aα)-2-(Benzo[b]thiophene-3-yl)-8,8a-dihydro-5,8-methanoimidazo[1,5-a]pyridine-1,3(2H,5H)-dione (20B)

Compound 20A (480 mg, 3.22 mmol, 1 eq) was added to a mixture of phosgene (20% in toluene, 6.38 g, 12.88 mmol, 4 eq) and NaHCO₃ (2.7 g, 32.2 mmol, 10 eq) in CH₂Cl₂ (50 mL). The resulting mixture was stirred at rt under N₂ for 10 min, filtered to remove NaHCO₃ and concentrated in vacuo without heating. To the resulting isocyanate was added 2-azabicyclo[2.2.1.]hept-5-ene-3-carboxylic acid, ethyl ester (599 mg, 3.54 mmol, 1.1 eq) in 25 mL of toluene with 4 Å MS. The reaction was stirred at rt overnight. DBU (0.48 mL, 3.22 mmol, 1 eq) was added and the reaction was warmed at 76° C. for 2 hr. The mixture was cooled, filtered through celite, and poured into saturated aqueous NH₄Cl solution. The mixture was extracted with CH₂Cl₂. The organic extracts were concentrated in vacuo and purified by flash chromatography on silica gel eluting with 0.6% methanol in CH₂Cl₂ to provide 480 mg (50.4%) of Compound 20B as a light yellow solid. HPLC: 99% at 2.57 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 297.1 [M+H]+.

EXAMPLE 21

(5α,8α,8aα) & (5α,8α,8aβ)-2-(1,2-Benzisoxazol-3-yl)tetrahydro-5,8-methanoimidazo[1,5-a]pyridine-1,3(2H,5H)-dione (21Bi & 21Bii, Respectively)

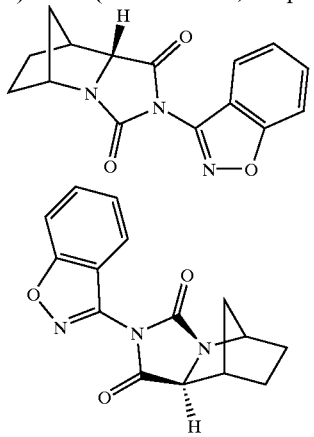

A. endo/exo-2-[(1,2-Benzisoxazol-3-ylamino)-2-azabicyclo[2.2.2]octane-3-carboxylic acid ethyl ester (21A)

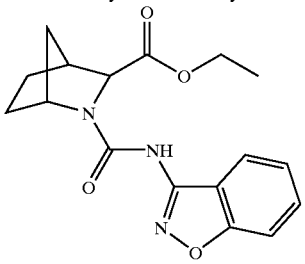

1,2-Benzisoxazol-3-amine (134 mg, 1 mmol, 1 eq) was added to phosgene (20% in toluene, 0.5 mL, 1 mmol, 1 eq) in 5 mL of ethyl acetate at −5° C. The reaction was allowed to warm to rt and then heated at reflux for 40 min. The mixture was cooled to rt and 2-azabicyclo[2.2.1.]heptane-3-carboxylic acid, ethyl ester (422 mg, 2.5 mmol, 2.5 eq) was added. The reaction was stirred at reflux for 2 h. The mixture was poured into water and extracted with CH₂Cl₂. The organic extracts were concentrated in vacuo and purified by flash chromatography on silica gel eluting with CH₂Cl₂ to provide 148 mg (45.0%) of Compound 21A as a light yellow solid.

B. (5α,8α,8aα) & (5α,8α,8aβ)-2-(1,2-Benzisoxazol-3-yl) tetrahydro-5,8-methanoimidazo[1,5-a]pyridine-1,3(2H,5H)-dione (21Bi & 21Bii)

Intermediate Compound 21A (140 mg, 0.42 mmol, 1 eq) was dissolved in toluene with 4 Å MS. DBU (65 mg, 0.42 mmol, 1 eq) was added and the reaction was stirred at 80° C. for 1 h. The mixture was quenched with 5% aqueous HCl and extracted with CH$_2$Cl$_2$. The organic extracts were dried, concentrated in vacuo, and purified by flash chromatography on silica gel eluting with CH$_2$Cl$_2$ to provide 16 mg (13.4%) of Compound 21Bi and 47 mg (39.5%) of Compound 21Bii. Compound 21Bi: HPLC: 93% at 2.367 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 284.12 [M+H]$^+$. Compound 21Bii: HPLC: 95% at 2.517 min (retention time) (YMC S5 ODS column 4.6×50 mm eluting with 10–90% aqueous methanol over 4 minutes containing 0.2% phosphoric acid, 4 mL/min, monitoring at 220 nm) MS (ES): m/z 284.13 [M+H]$^+$.

EXAMPLES 22 TO 88

Using the procedures described herein or by modification of the procedures described herein readily available to one of ordinary skill in the art, the following additional compounds of Table 2 were prepared. Those of the following compounds which were prepared enantiomerically pure are so indicated in the structure box by the nomenclature (R) or (S). Those compounds not so indicated were racemic mixtures which can readily be separated by one of ordinary skill in the art or prepared enantiomerically pure by the procedures described herein.

TABLE 2

| Ex. No. | Compound Structure | Compound Name | Retention Time Min. | Procedure of Example |
|---|---|---|---|---|
| 22. | 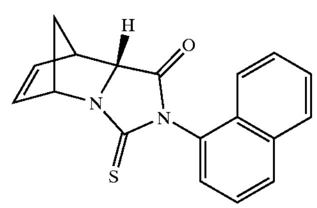 | (5α,8α,8aα)-2,3,8,8a-Tetrahydro-2-(1-naphthalenyl)-3-thioxo-5,8-methanoimidazo[1,5-a]pyridin-1(5H)-one | 3.093 LC | 1 |
| 23. | 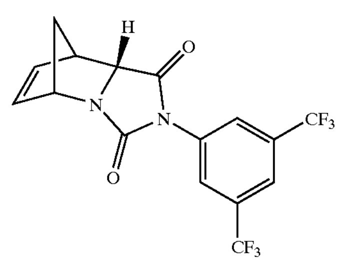 | (5α,8α,8aα)-2-[3,5-Bis(trifluoromethyl)phenyl]-8,8a-dihydro-5,8-methanoimidazo[1,5-a]pyridin-1,3(2H,5H)-one | 2.930 LC | 1 |
| 24. | 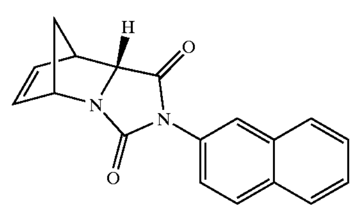 | (5α,8α,8aα)-8,8a-Dihydro-2-(2-naphthalenyl)-5,8-methanoimidazo[1,5-a]pyridine-1,3(2H,5H)-dione | 3.360 LC | 3 |
| 25. | 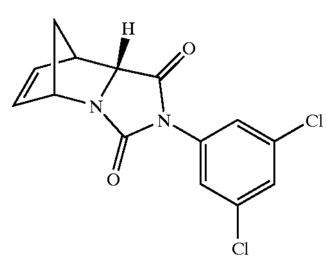 | (5α,8α,8aα)-2-(3,5-Dichlorophenyl)-8,8a-dihydro-5,8-methanoimidazo[1,5-a]pyridine-1,3(2H,5H)-dione | 3.823 LC | 1 |

TABLE 2-continued

| Ex. No. | Compound Structure | Compound Name | Retention Time Min. | Procedure of Example |
|---|---|---|---|---|
| 26. | 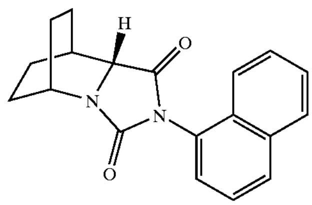 | Tetrahydro-2-(1-naphthalenyl)-5,8-ethanoimidazo[1,5-a]pyridine-1,3(2H,5H)-dione | 3.433 LC | 8 |
| 27. | 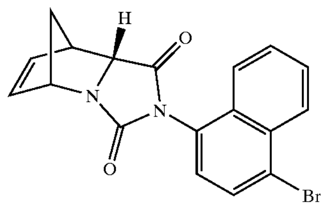 | (5α,8α,8aα)-2-(4-Bromo-1-naphthalenyl)-8,8a-dihydro-5,8-methanoimidazo[1,5-a]pyridine-1,3(2H,5H)-dione | 3.767 LC | 1 |
| 28. | 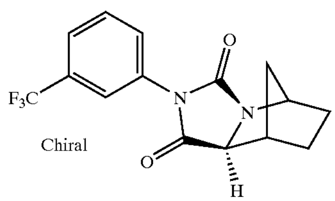 | [5R-(5α,8α,8aβ)]-Tetrahydro-2-[3-(trifluoromethyl)phenyl]-5,8-methanoimidazo[1,5-a]pyridine-1,3(2H,5H)-dione | 3.117 LC | 7 |
| 29. | 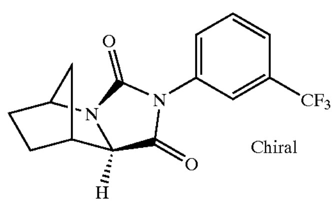 | [5S-(5α,8α,8aβ)]-Tetrahydro-2-[3-(trifluoromethyl)phenyl]-5,8-methanoimidazo[1,5-a]pyridine-1,3(2H,5H)-dione | 3.117 LC | 7 |
| 30. | 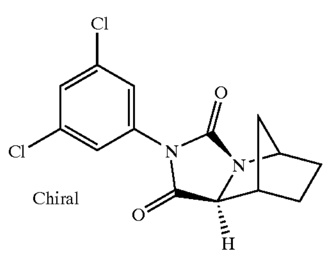 | [5R-(5α,8α,8aβ)]-2-(3,5-Dichlorophenyl)tetrahydro-5,8-methano-imidazo[1,5-a]pyridine-1,3(2H,5H)-dione | 4.017 LC | 17 |
| 31. | 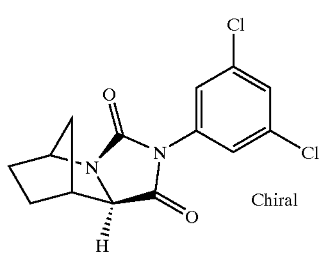 | [5S-(5α,8α,8aβ)]-2-(3,5-Dichlorophenyl)tetrahydro-5,8-methano-imidazo[1,5-a]pyridine-1,3(2H,5H)-dione | 4.017 LC | 17 |

TABLE 2-continued

| Ex. No. | Compound Structure | Compound Name | Retention Time Min. | Procedure of Example |
|---|---|---|---|---|
| 32. | 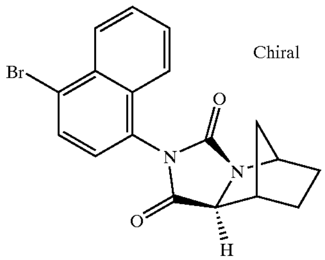 | [5R-(5α,8α,8aβ)]-2-(4-Bromo-1-naphthalenyl)tetrahydro-5,8-methanoimidazo[1,5-a]pyridine-1,3(2H,5H)-dione | 3.847 LC | 17 |
| 33. | 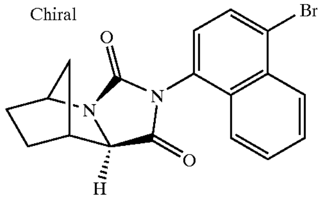 | [5S-(5α,8α,8aβ)]-2-(4-Bromo-1-naphthalenyl)tetrahydro-5,8-methanoimidazo[1,5-a]pyridine-1,3(2H,5H)-dione | 3.807 LC | 17 |
| 34. | 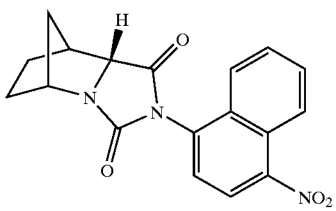 | (5α,8α,8aα)-Tetrahydro-2-(4-nitro-1-naphthalenyl)-5,8-methanoimidazo[1,5-a]pyridine-1,3(2H,5H)-dione | 2.840 LC | 11 |
| 35. | 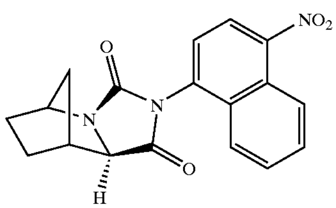 | (5α,8α,8aβ)-Tetrahydro-2-(4-nitro-1-naphthalenyl)-5,8-methanoimidazo[1,5-a]pyridine-1,3(2H,5H)-dione | 2.980 LC | 11 |
| 36. | 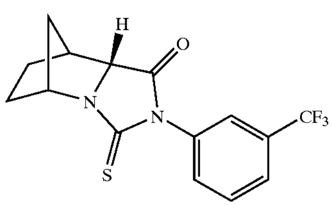 | (5α,8α,8aα)-Hexahydro-3-thioxo-2-[3-(trifluoromethyl)phenyl]-5,8-methanoimidazo[1,5-a]pyridine-1(5H)-one | 3.360 LC | 11 |
| 37. | 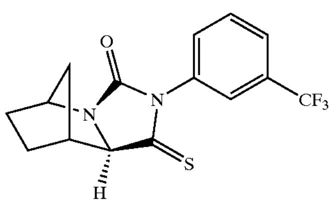 | (5α,8α,8aβ)-Hexahydro-3-thioxo-2-[3-(trifluoromethyl)phenyl]-5,8-methanoimidazo[1,5-a]pyridine-1(5H)-one | 3.443 LC | 11 |
| 38. | 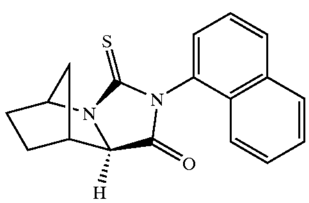 | (5α,8α,8aβ)-Hexahydro-2-(1-naphthaleny)-3-thioxo-5,8-methanoimidazo[1,5-a]pyridine-1(5H)-one | 3.487 LC | 11 |

TABLE 2-continued

| Ex. No. | Compound Structure | Compound Name | Retention Time Min. | Procedure of Example |
|---|---|---|---|---|
| 39. | 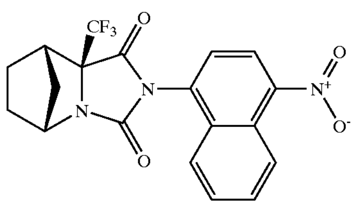 | (5α,8α,8aα)-Tetrahydro-8a-methyl-2-(4-nitro-1-naphthalenyl)-5,8-methano-imidazo[1,5-a]pyridine-1,3(2H,5H)-dione | 3.060 LC | 6 |
| 40. | 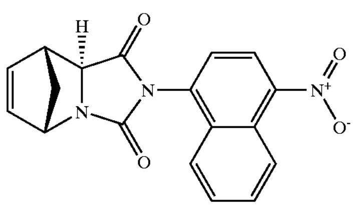 | (5α,8α,8aβ)-8,8a-Dihydro-2-(4-nitro-1-naphthalenyl)-5,8-methanoimidazo[1,5-a]pyridine-1,3(2H,5H)-dione | 2.880 LC | 1 |
| 41. | 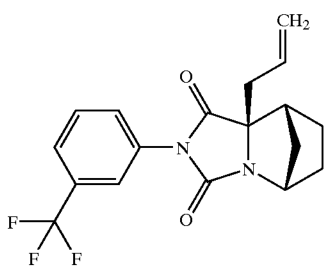 | (5α,8α,8aα)-Tetrahydro-8a-(2-propenyl)-2-[3-(trifluoromethyl)-phenyl]-5,8-methanoimidazo[1,5-a]pyridine-1,3(2H,5H)-dione | 3.390 LC | 5 |
| 42. | 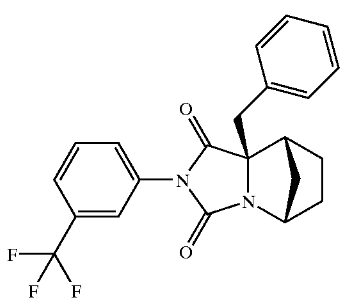 | (5α,8α,8aα)-Tetrahydro-8a-(phenylmethyl)-2-[3-(trifluoro-methyl)phenyl]-5,8-methano-imidazo[1,5-a]pyridine-1,3(2H,5H)-dione | 3.490 LC | 5 |
| 43. | 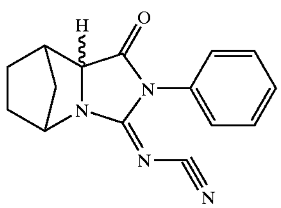 | [(Octahydro-1-oxo-2-phenyl-5,8-methanoimidazo[1,5-a]pyridin-3-ylidene)amino]carbonitrile | 2.357 LC | 13 |
| 44. | 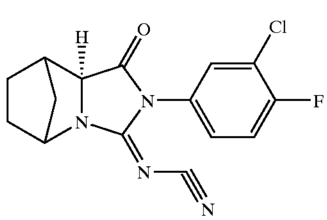 | (5α,8α,8aβ)-[[2-(3-Chloro-4-fluorophenyl)octahydro-1-oxo-5,8-methanoimidazo[1,5-a]pyridin-3-ylidene]amino]carbonitrile | 2.830 LCMS | 13 |

TABLE 2-continued

| Ex. No. | Compound Structure | Compound Name | Retention Time Min. | Procedure of Example |
|---|---|---|---|---|
| 45. | 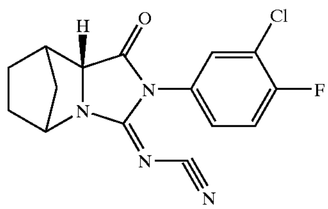 | (5α,8α,8aα)-[[2-(3-Chloro-4-fluorophenyl)octahydro-1-oxo-5,8-methanoimidazo[1,5-a]pyridin-3-ylidene]amino]carbonitrile | 2.833 LCMS | 13 |
| 46. | 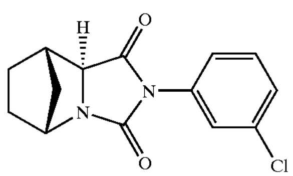 | (5α,8α,8aβ)-2-(3-Chlorophenyl)-tetrahydro-5,8-methanoimidazo[1,5-a]pyridine-1,3(2H,5H)-dione | 2.910 LC | 11 |
| 47. | 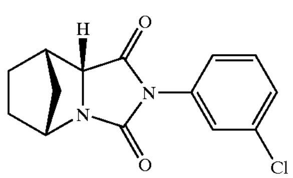 | (5α,8α,8aα)-2-(3-Chlorophenyl)-tetrahydro-5,8-methanoimidazo[1,5-a]pyridine-1,3(2H,5H)-dione | 2.470 LC | 11 |
| 48. | 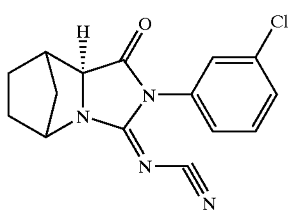 | (5α,8α,8aβ)-[[2-(3-Chlorophenyl)octahydro-1-oxo-5,8-methanoimidazo[1,5-a]pyridin-3-ylidene]-amino]carbonitrile | 2.727 LCMS | 13 |
| 49. | 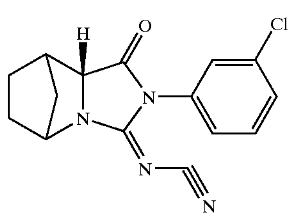 | (5α,8α,8aα)-[[2-(3-Chlorophenyl)octahydro-1-oxo-5,8-methanoimidazo[1,5-a]pyridin-3-ylidene]-amino]carbonitrile | 2.727 LCMS | 13 |
| 50. | 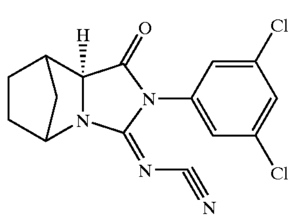 | (5α,8α,8aβ)-[[2-(3,5-Dichlorophenyl)octahydro-1-oxo-5,8-methanoimidazo[1,5-a]pyridin-3-ylidene]-amino]carbonitrile | 3.337 LCMS | 13 |
| 51. | 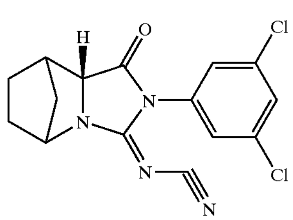 | (5α,8α,8aα)-[[2-(3,5-Dichlorophenyl)octahydro-1-oxo-5,8-methanoimidazo[1,5-a]pyridin-3-ylidene]-amino]carbonitrile | 3.413 LCMS | 13 |

TABLE 2-continued

| Ex. No. | Compound Structure | Compound Name | Retention Time Min. | Procedure of Example |
|---|---|---|---|---|
| 52. | 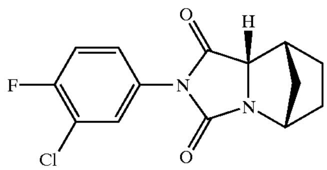 | (5α,8α,8aα)-2-(3-Chloro-4-fluorophenyl)tetrahydro-5,8-methanoimidazo[1,5-a]pyridine-1,3(2H,5H)-dione | 2.863 LC | 7 |
| 53. | 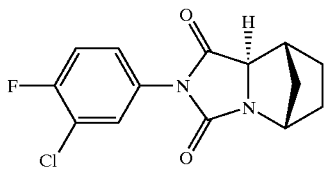 | (5α,8α,8aβ)-2-(3-Chloro-4-fluorophenyl)tetrahydro-5,8-methanoimidazo[1,5-a]pyridine-1,3(2H,5H)-dione | 3.007 LC | 7 |
| 54. | 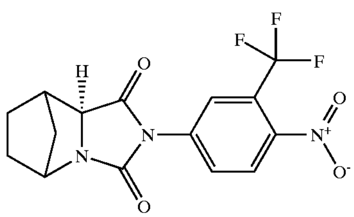 | (5α,8α,8aβ)-Tetrahydro-2-[4-nitro-3-(trifluoromethyl)phenyl]-5,8-methanoimidazo[1,5-a]pyridine-1,3(2H,5H)-dione | 3.167 LCMS | 7 |
| 55. | 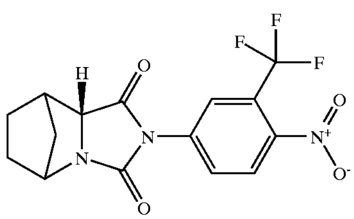 | (5α,8α,8aα)-Tetrahydro-2-[4-nitro-3-(trifluoromethyl)phenyl]-5,8-methanoimidazo[1,5-a]pyridine-1,3(2H,5H)-dione | 3.047 LCMS | 7 |
| 56. | 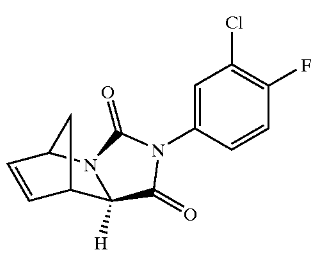 | (5α,8α,8aβ)-2-(3-Chloro-4-fluorophenyl)-8,8a-dihydro-5,8-methanoimidazo[1,5-a]pyridine-1,3(2H,5H)-dione | 2.920 LC | 7 |
| 57. | 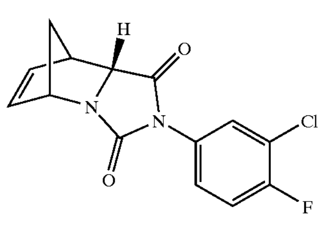 | (5α,8α,aα)-2-(3-Chloro-4-fluorophenyl)-8,8a-dihydro-5,8-methanoimidazo[1,5-a]pyridine-1,3(2H,5H)-dione | 2.783 LC | 7 |
| 58. | 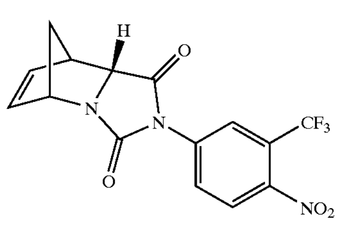 | (5α,8α,8aα)-8,8a-Dihydro-8a-methyl-2-[4-nitro-3-(trifluoromethyl)phenyl]-5,8-methanoimidazo[1,5-a]pyridine-1,3(2H,5H)-dione | 3.020 LC | 20 |

TABLE 2-continued

| Ex. No. | Compound Structure | Compound Name | Retention Time Min. | Procedure of Example |
|---|---|---|---|---|
| 59. | 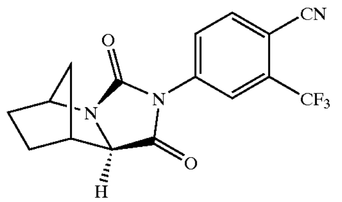 | (5α,8α,8aβ)-4-(Octahydro-1,3-dioxo-5,8-methanoimidazo[1,5-a]pyridin-2-yl)-2-(trifluoromethyl)benzonitrile | 3.107 LC | 7 |
| 60. | 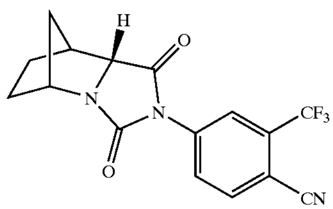 | (5α,8α,8aα)-4-(Octahydro-1,3-dioxo-5,8-methanoimidazo[1,5-a]pyridin-2-yl)-2-(trifluoromethyl)benzonitrile | 3.030 LC | 7 |
| 61. | 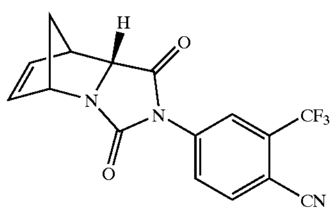 | (5α,8α,8aα)-4-(1,2,3,5,8,8a-Hexahydro-1,3-dioxo-5,8-methanoimidazo[1,5-a]pyridin-2-yl)-2-(trifluoromethyl)benzonitrile | 2.870 LC | 20 |
| 62. | 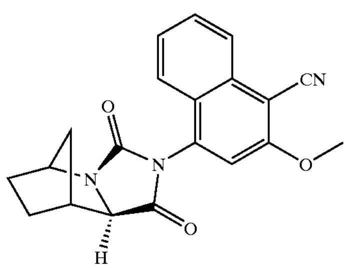 | (5α,8α,8aβ)-2-Methoxy-4-(octahydro-1,3-dioxo-5,8-methanoimidazo[1,5-a]pyridin-2-yl)-1-naphthalenecarbonitrile | 3.087 LC | 7 |
| 63. | 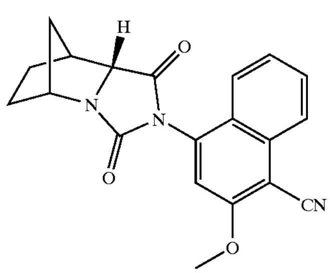 | (5α,8α,8aα)-2-Methoxy-4-(octahydro-1,3-dioxo-5,8-methanoimidazo[1,5-a]pyridin-2-yl)-1-naphthalenecarbonitrile | 2.827 LC | 7 |
| 64. | 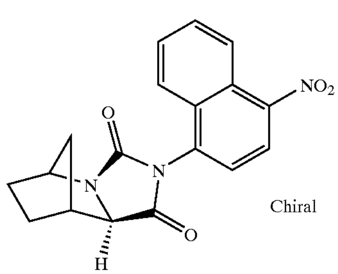 | [5S-(5α,8α,8aβ)]-Tetrahydro-2-(4-nitro-1-naphthalenyl)-5,8-methanoimidazo[1,5-a]pyridine-1,3(2H,5H)-dione | 2.980 LC | 17 |

TABLE 2-continued

| Ex. No. | Compound Structure | Compound Name | Retention Time Min. | Procedure of Example |
|---|---|---|---|---|
| 65. | 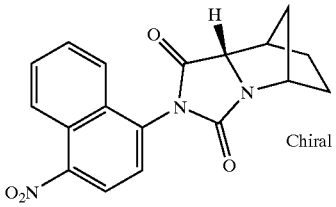 | [5S-(5α,8α,8aα)]-Tetrahydro-2-(4-nitro-1-naphthalenyl)-5,8-methanoimidazo[15-a]pyridine-1,3(2H,5H)-dione | 2.850 LC | 17 |
| 66. | 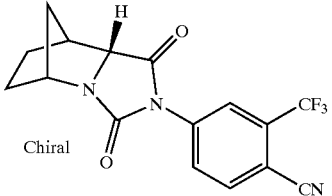 | [5R-(5α,8α,8aα)]-4-(Octahydro-1,3-dioxo-5,8-methanoimidazo[1,5-a]pyridin-2-yl)-2-(trifluoromethyl)benzonitrile | 2.920 LC | 17 |
| 67. | 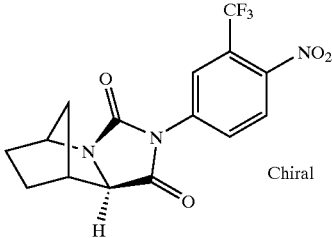 | [5S-(5α,8α,8aβ)]-Tetrahydro-2-[4-nitro-3-(trifluoromethyl)phenyl]-5,8-methanoimidazo[1,5-a]pyridine-1,3(2H,5H)-dione | 3.250 LC | 17 |
| 68. | 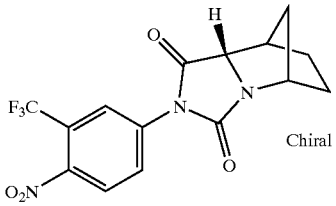 | [5S-(5α,8α,8aα)]-Tetrahydro-2-[4-nitro-3-(trifluoromethyl)phenyl]-5,8-methanoimidazo[1,5-a]pyridine-1,3(2H,5H)-dione | 3.120 LC | 17 |
| 69. | 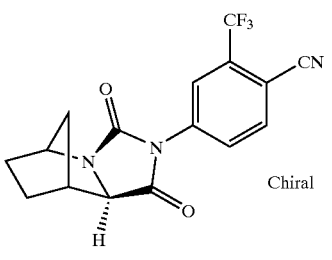 | [5S-(5α,8α,8aβ)]-4-(Octahydro-1,3-dioxo-5,8-methanoimidazo[1,5-a]pyridin-2-yl)-2-(trifluoromethyl)benzonitrile | 3.050 LC | 17 |
| 70. | 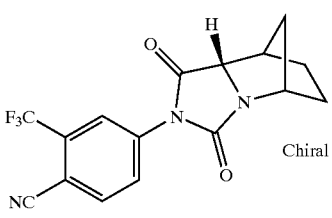 | [5S-(5α,8α,8aα)]-4-(Octahydro-1,3-dioxo-5,8-methanoimidazo[1,5-a]pyridin-2-yl)-2-(trifluoromethyl)benzonitrile | 2.940 LC | 17 |

TABLE 2-continued

| Ex. No. | Compound Structure | Compound Name | Retention Time Min. | Procedure of Example |
|---|---|---|---|---|
| 71. | 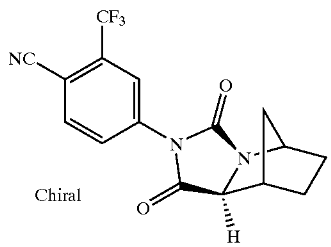 | [5R-(5α,8α,8aβ)]-4-(Octahydro-1,3-dioxo-5,8-methanoimidazo[1,5-a]pyridin-2-yl)-2-(trifluoromethyl)benzonitrile | 3.043 LC | 17 |
| 72. | 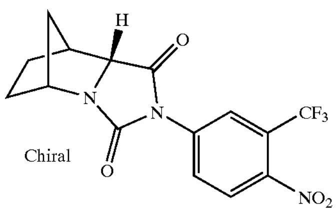 | [5R-(5α,8α,aα)]-Tetrahydro-2-[4-nitro-3-(trifluoromethyl)phenyl]-5,8-methanoimidazo[1,5-a]pyridine-1,3(2H,5H)-dione | 3.110 LC | 17 |
| 73. | 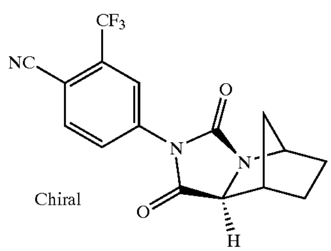 | [5R-(5α,8α,8aβ)]-Tetrahydro-2-[4-nitro-3-(trifluoromethyl)phenyl]-5,8-methanoimidazo[1,5-a]pyridine-1,3(2H,5H)-dione | 3.213 LC | 17 |
| 74. | 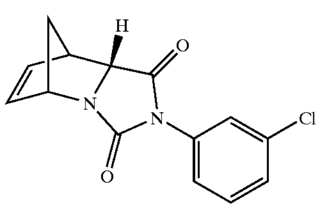 | (5α,8α,8aα)-2-(3-Chlorophenyl)-8,8a-dihydro-5,8-methanoimidazo[1,5-a]pyridine-1,3(2H,5H)-dione | 2.650 LC | 17 |
| 75. | 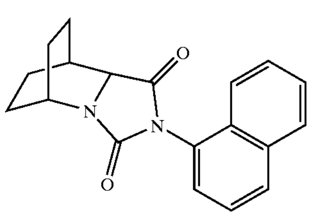 | Tetrahydro-2-(1-naphthalenyl)-5,8-ethanoimidazo[1,5-a]pyridine-1,3(2H,5H)-dione | 3.060 LC | 8 |
| 76. | 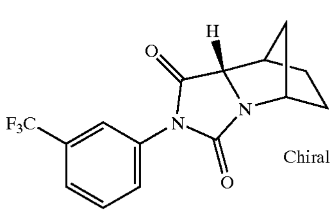 | [5S-(5α,8α,8aα)]-Tetrahydro-2-[3-(trifluoromethyl)phenyl]-5,8-methanoimidazo[1,5-a]pyridine-1,3(2H,5H)-dione | 2.943 LC | 7 |

TABLE 2-continued

| Ex. No. | Compound Structure | Compound Name | Retention Time Min. | Procedure of Example |
|---|---|---|---|---|
| 77. | 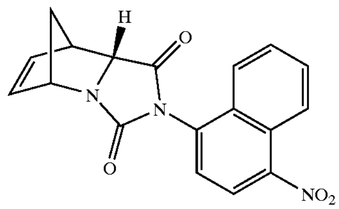 | (5α,8α,8aα)-8,8a-Dihydro-2-(4-nitro-1-naphthalenyl)-5,8-methanoimidazo[1,5-a]pyridine-1,3(2H,5H)-dione | 2.750 LC | 7 |
| 78. | 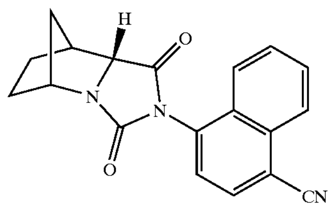 | (5α,8α,8aα)-4-(Octahydro-1,3-dioxo-5,8-methanoimidazo[1,5-a]pyridin-2-yl)-1-naphthalenecarbonitrile | 2.63 LC | 17 |
| 79. | 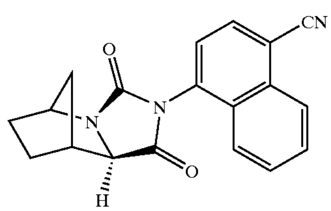 | (5α,8α,8aβ)-4-(Octahydro-1,3-dioxo-5,8-methanoimidazo[1,5-a]pyridin-2-yl)-1-naphthalenecarbonitrile | 2.77 LC | 17 |
| 80. | 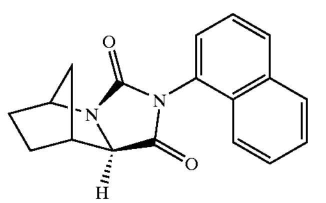 | (5α,8α,8aβ)-Tetrahydro-2-(1-naphthalenyl)-5,8-methano-imidazo[1,5-a]pyridine-1,3(2H,5H)-dione | 2.73 LC | 17 |
| 81. | 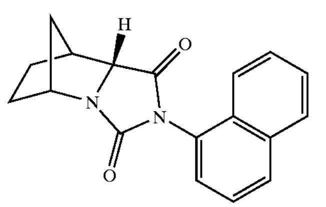 | (5α,8α,8aα)-Tetrahydro-2-(1-naphthalenyl)-5,8-methanoimidazo[1,5-a]pyridine-1,3(2H,5H)-dione | 2.58 LC | 17 |
| 82. | 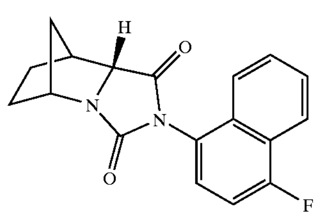 | (5α,8α,8aα)-2-(4-Fluoro-1-naphthalenyl)tetrahydro-5,8-methanoimidazo[1,5-a]pyridine-1,3(2H,5H)-dione | 2.80 LC | 17 |
| 83. | 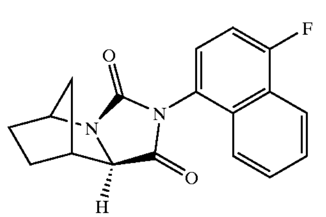 | (5α,8α,8aβ)-2-(4-Fluoro-1-naphthalenyl)tetrahydro-5,8-methanoimidazo[1,5-a]pyridine-1,3(2H,5H)-dione | 2.81 LCMS | 17 |

TABLE 2-continued

| Ex. No. | Compound Structure | Compound Name | Retention Time Min. | Procedure of Example |
|---|---|---|---|---|
| 84. | 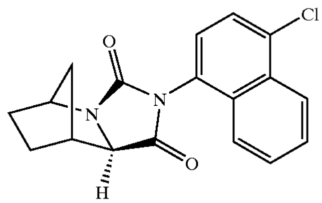 | (5α,8α,8aβ)-2-(4-Chloro-1-naphthalenyl)tetrahydro-5,8-methanoimidazo[15-a]pyridine-1,3(2H,5H)-dione | 3.18 LC | 17 |
| 85. | 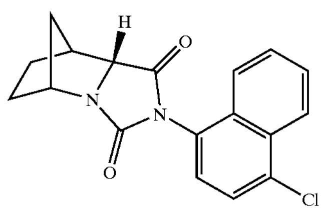 | (5α,8α,8aα)-2-(4-Chloro-1-naphthalenyl)tetrahydro-5,8-methanoimidazo[15-a]pyridine-1,3(2H,5H)-dione | 3.09 LC | 17 |
| 86. | 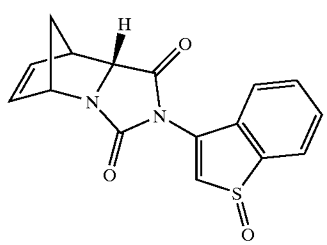 | (5α,8α,8aα)-8,8a-Dihydro-2-(1-oxidobenzo[b]thiophen-3-yl)-5,8-methanoimidazo[1,5-a]pyridine-1,3(2H,5H)-dione | 2.900 LC | 17 |
| 87. | 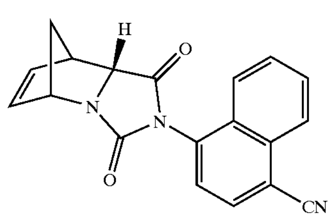 | (5α,8α,8aα)-4-(1,2,3,5,8,8a-Hexahydro-1,3-dioxo-5,8-methanoimidazo[1,5-a]pyridin-2-yl)-1-naphthalenecarbonitrile | 2.57 LC | 17 |
| 88. | 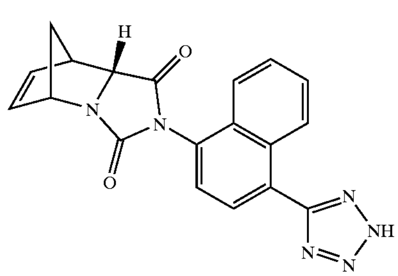 | (5α,8α,8aα)-Tetrahydro-2-[4-(1H-tetrazol-5-yl)-1-naphthalenyl]-5,8-methanoimidazo[1,5-a]pyridine-1,3(2H,5H)-dione | 2.52 LCMS | 17 |

The chromatography techniques used to determine the compound retention of Table 2 are as follows:
LC = YMC S5 ODS column 4.6 × 50 mm eluting with 10–90% MeOH/H$_2$O over 4 minutes containing 0.2% phosphoric acid, 4 mL/min, monitoring at 220 nm
LCMS = YMC S5 ODS column, 4.6 × 50 mm eluting with 10–90% MeOH/H$_2$O over 4 minutes containing 0.1% TFA; 4 mL/min, monitoring at 220 nm

EXAMPLE 89

(1S-exo)-2,5-Diazabicyclo[2.2.1]heptane-2,6-dicarboxylic acid, 2-(1,1-dimethylethyl) 6-methyl ester & (1S-endo)-2,5-Diazabicyclo[2.2.1]heptane-2,6-dicarboxylic acid, 2-(1,1-dimethylethyl) 6-methyl ester

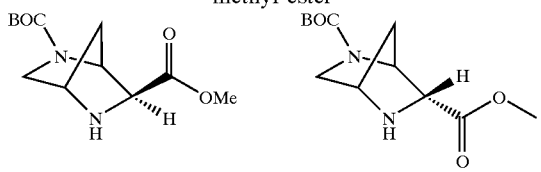

This example illustrates a preferred method for obtaining a compound of formula IIa, which compound is useful as an intermediate in the preparation of compounds of formula I (see, for example, FIG. 2 herein).

A (2S-trans)-4-Hydroxy-2-[[[(1,1-dimethylethyl)dimethylsilyl]oxy]methyl]-1-pyrrolidinecarboxylic acid, 1,1-dimethylethyl ester (89A)

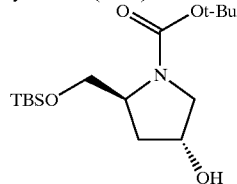

N-(tert-butoxycarbonyl)-L-4-hydroxyproline (10.0 g, 43.3 mmol) was dissolved in THF and cooled to 0° C. Borane/THF (1.0 M solution, 86.6 mL) was then added over a 15 min period. The reaction was then warmed to 25° C. followed by heating to reflux for 16 h. The reaction flask was then removed from the heat source and anhydrous methanol (35 mL) was added slowly. After cooling to 25° C., the solvent was removed in vacuo and the resulting crude diol intermediate was taken on directly. The crude diol (1.81 g, 8.34 mmol) was dissolved in methylene chloride (50 mL), 2,6-lutidine (1.46 mL, 12.51 mmol) was added and the mixture was cooled to −78° C. tert-Butyl dimethylsilyltrifluoro-methansulfonate (1.92 mL, 8.34 mmol) was then added. After 2 h, the mixture was poured into 1 N HCl (100 mL), extracted with methylene chloride (2×100 mL) and the organics were dried over anhydrous sodium sulfate. The resulting crude alcohol was purified by flash chromatography on SiO$_2$ eluting with acetone in chloroform (0–5–10% acetone) to give 1.011 g (37% for 2-steps) of the Compound 89A as a clear oil.

B. (2S-trans)-2-Hydroxymethyl-4-[[(4-methylphenyl)sulfonyl]oxy]-1-pyrrolidinecarboxylic acid, 1,1-dimethylethyl ester (89B)

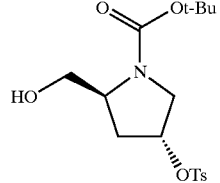

Intermediate Compound 89A (3.41 g, 10.3 mmol) was dissolved in anhydrous pyridine (30.0 mL) and cooled to 0° C. p-Toluenesulfonylchloride (5.89 g, 30.9 mmol) was then added in portions over a 10 minute period. The flask was then placed in a refrigerator at 4° C. for 48 h. The resulting solution was poured into 1 N HCl (300 mL), extracted with methylene chloride (3×200 mL) and the organics were dried over anhydrous sodium sulfate. The crude tosylate intermediate was dissolved in THF (50 mL), to which was added H$_2$O (0.5 mL) followed by pTSA-H$_2$O (1.03 mmol). Once the reaction was complete as determined by TLC, the mixture was poured into saturated aqueous NaHCO$_3$ (150 mL) and extracted with methylene chloride (3×50 mL). The combined organics were dried over sodium sulfate. The crude alcohol was purified by flash chromatography on SiO$_2$ eluting with acetone/chloroform (0–5–10% acetone) to give 2.71 g (71% for 2-steps) of intermediate Compound 89B as a clear oil.

C. (2S-trans)-2-[Cyano[(phenylmethyl)amino]methyl]-4-[[(4-methylphenyl)sulfonyl]oxy]-1-pyrrolidinecarboxylic acid, 1,1-dimethylethyl ester (89C)

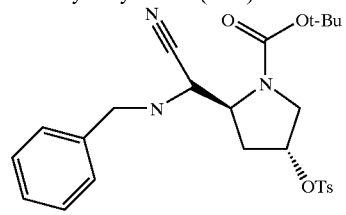

To a solution of oxalyl chloride (2.0 M soln in CH$_2$Cl$_2$, 2.82 mL) in CH$_2$Cl$_2$ (40 mL) at −78° C. was added anhydrous dimethylsulfoxide (0.462 mL, 6.51 mmol). The mixture was allowed to stand for 15 min, after which a solution of Compound 89B (1.61 g, 4.34 mmol) in CH$_2$Cl$_2$ (10 mL) was slowly added. After an additional 30 min, triethylamine (1.81 mL, 13.02 mmol) was added and the reaction was slowly warmed to 0° C. The reaction was then quenched with H$_2$O (25 mL) and diluted with CH$_2$Cl$_2$ (100 mL). The mixture was then washed sequentially with 1 N HCl (1×100 mL), saturated aqueous NaHCO$_3$ (50 mL), and water (2×50 mL). The organics were dried over anhydrous sodium sulfate and the volatile organics removed in vacuo. The crude aldehyde intermediate (1.60 g, 4.34 mmol) was dissolved in THF (25 mL) and diethyl cyanophosphonate (90%, 0.95 mL, 5.64 mmol) was added followed by benzyl amine (1.23 mL, 11.3 mmol). After 2 h, the reaction was complete, as observed by TLC and the volatile organics were removed in vacuo. The crude reaction mixture was purified by flash chromatography on SiO$_2$ eluting with acetone/chloroform (0–2–3% acetone) to give 1.48 g (70%) of intermediate Compound 89C as a white solid. Compound 89C was determined to be a ~1:1 mixture of diastereomers by NMR spectroscopy.

D. (1S-endo)-6-Cyano-5-(phenylmethyl)-2,5-diazabicyclo[2.2.1]heptane-2-carboxylic acid, 1,1-dimethylethyl ester (89Di); (1S-exo)-6-Cyano-5-(phenylmethyl)-2,5-diazabicyclo[2.2.1]heptane-2-carboxylic acid, 1,1-dimethylethyl ester (89Dii)

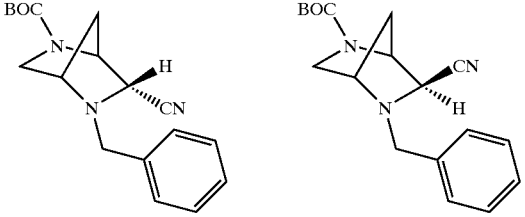

Intermediate Compound 89C (1.48 g, 3.05 mmol) was dissolved in dichloroethane (25 mL) and diisopropyl ethylamine (1.45 mL) was added. The mixture was heated to 100° C. in a sealed tube for 18 h. The volatiles were then removed in vacuo and the resulting crude material was purified by flash chromatography on SiO$_2$ eluting with acetone/chloroform (0–2–3% acetone), to yield a mixture of intermediate Compound 89Di (0.591 g, 62%) and intermediate Compound 89Dii (0.370 g, 38%) as clear oils. Structural assignments for Compounds 89Di and 89Dii were made after NOE, COESY and DEPT NMR experiments.

E. (1S-endo)-5-(Phenylmethyl)-2,5-diazabicyclo[2.2.1]heptane-2,6-dicarboxylic acid, 2-(1,1-dimethylethyl) 6-methyl ester (89E)

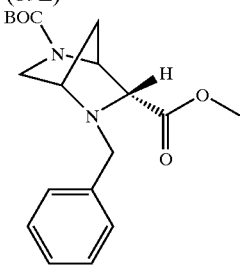

Intermediate Compound 89Di (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous NaHCO$_3$ (50 mL). The mixture was extracted with CH$_2$Cl$_2$ (3×50 mL) and the combined organics were dried over anhydrous sodium sulfate. The crude ester was purified by flash chromatography on SiO$_2$ eluting with chloroform/acetone (0–2–4% acetone) to give 0.320 g (0.92 mmol, 72%) of intermediate Compound 89E as a clear oil.

F. (1S-exo)-5-(Phenylmethyl)-2,5-diazabicyclo[2.2.1]heptane-2,6-dicarboxylic acid, 2-(1,1-dimethylethyl) 6-methyl ester (89F)

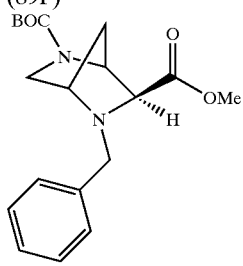

Intermediate Compound 89Dii (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous NaHCO$_3$ (50 mL). The mixture was extracted with CH$_2$Cl$_2$ (3×50 mL) and the combined organics were dried over anhydrous sodium sulfate. The crude ester was purified by flash chromatography on SiO$_2$ eluting with chloroform/acetone (0–2–4% acetone) to give 0.290 g (0.85 mmol, 66%) of intermediate Compound 89F as a clear oil.

G. (1S-endo)-2,5-Diazabicyclo[2.2.1]heptane-2,6-dicarboxylic acid, 2-(1,1-dimethylethyl) 6-methyl ester (89G)

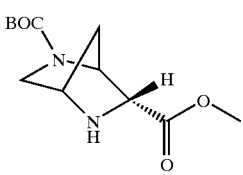

Intermediate Compound 89E (0.280 g, 0.81 mmol) was dissolved in absolute EtOH (10.0 mL) and Pd/C (10% Pd, 0.080 g) was added. An atmosphere of H$_2$ was introduced via a balloon and the reaction was stirred at 25° C. for 20 h. The Pd was removed by filtration through celite followed by rinsing with EtOAc. The volatiles were removed in vacuo to give Compound 89G (0.205 g, 99%) as viscous yellow oil. Compound 89G was taken on directly without purification. MS(ES)=m/z 257.18 [M+H]$^+$. HPLC RT=1.223 min (95%) (YMC S5 ODS column, 4.6×50 mm; 10–90% MeOH/H$_2$O gradient, +0.1% TFA; 4 mL/min, 220 nM detection).

H. (1S-exo)-2,5-Diazabicyclo[2.2.1]heptane-2,6-dicarboxylic acid, 2-(1,1-dimethylethyl) 6-methyl ester (89H)

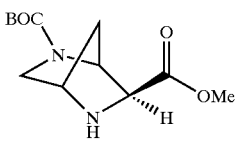

Intermediate Compound 89F (0.310 g, 0.89 mmol) was dissolved in absolute EtOH (10.0 mL) and Pd/C (10% Pd, 0.080 g) was added. An atmosphere of H$_2$ was introduced via a balloon and the reaction was stirred at 25° C. for 20 h. The Pd was removed by filtration through celite, followed by rinsing with EtOAc. The volatiles were removed in vacuo to give Compound 89H (0.210 g, 92%) as a viscous yellow oil. Compound 89H can be taken on directly without purification. MS(ES)=m/z 257.16 [M+H]$^+$ HPLC RT=1.293 min (90%) (YMC S5 ODS column, 4.6×50 mm; 10–90% MeOH/H$_2$O gradient, +0.1% TFA; 4 mL/min, 220 nM detection).

EXAMPLE 90

[5S-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester, (90i)

[5S-(5α,8α,8aβ)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester, (90ii)

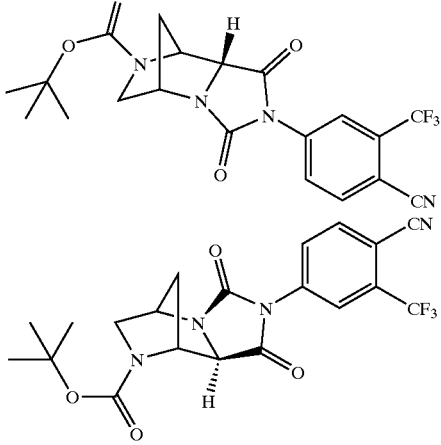

To a solution of 4-isocyanato-2-(trifluoromethyl)-benzonitrile (1.0 mmol) in toluene (4 mL) with activated 4 Å MS (0.300 g) was added Compound 89G (0.220 g, 0.856 mmol) in toluene (6 mL). After 10 h at 25° C., DBU (0.166 mL, 1.11 mmol) was added and the reaction was heated at 81° C. for 2 h. The reaction was then cooled to 25° C. and poured into 1 N HCl (50 mL). The solution was then extracted with methylene chloride (3×30 mL) and the combined organics were dried over anhydrous sodium sulfate. The resulting crude material was purified by flash chromatography on SiO$_2$ eluting with acetone/chloroform (0–2–4–8% acetone) to give Compound 90i (0.155 g, 42%) MS (ES): m/z 437.09 [M+H]$^+$. HPLC RT=3.280 min (100%) (YMC S5 ODS column, 4.6×50 mm; 10–90% MeOH/H$_2$O gradient, +0.1% TFA; 4 mL/min, 220 nM detection) and Compound 90ii (0.061 g, 16%) MS (ES): m/z 437.09 [M+H]$^+$. HPLC RT=3.133 min (100%) (YMC S5 ODS column, 4.6×50 mm; 10–90% MeOH/H$_2$O gradient, +0.1% TFA; 4 mL/min, 220 nM detection); both as white foams.

EXAMPLE 91

5S-(5α,8α,8aα)]-4-(Hexahydro-1,3-dioxo-5,8-methanoimidazo[1,5-a]pyrazin-2(3H)-yl)-2-(trifluoromethyl)benzonitrile (91)

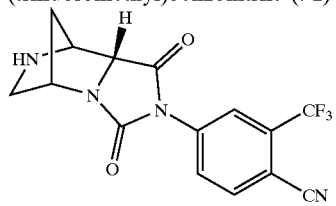

The Compound 90i (0.115 g, 0.264 mmol) was dissolved in anhydrous methylene chloride (3 mL) and anhydrous TFA (1.0 mL) was added at 25° C. After 1 h, the reaction was concentrated in vacuo and the resulting residue was dissolved in methylene chloride and poured into saturated aq NaHCO$_3$. This solution was then extracted with methylene chloride (3×10 mL) and the combined organics dried over anhydrous sodium sulfate. This gave 0.089 g (97%) of free Compound 91 as a yellow solid. MS (ES): m/z 359.09 [M+Na]$^+$. HPLC RT=1.477 min (100%) (YMC S5 ODS column, 4.6×50 mm; 10–90% MeOH/H$_2$O gradient, +0.1% TFA; 4 mL/min, 220 nM detection).

EXAMPLE 92

(1R-endo)-2,5-Diazabicyclo[2.2.1]heptane-2,6-dicarboxylic acid, 2-(1,1-dimethylethyl) 6-methyl ester (92H) & (1R-exo)-2,5-Diazabicyclo[2.2.1]heptane-2,6-dicarboxylic acid, 2-(1,1-dimethylethyl) 6-methyl ester (92I)

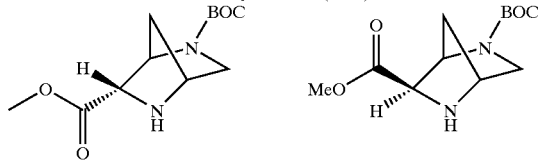

This example illustrates a preferred method for obtaining a compound of formula IIa, which compound is useful as an intermediate in the preparation of compounds of formula I (see, for example, FIG. 2 herein).

A. (2R-cis)-4-Hydroxy-1,2-pyrrolidinedicarboxylic acid, 1-(1,1-dimethylethyl) 2-ethyl ester (92A)

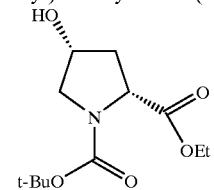

Cis-4-hydroxy-D-proline (10.0 g, 131.1 mmol) was suspended in absolute EtOH (100 mL) and anhydrous HCl (g) was bubbled through the reaction until a homogenous solution resulted. This was left at 25° C. for 1 h and then the volatiles organics were removed in vacuo. The resulting HCl salt was triturated with diethyl ether and filtered to give the crude ethyl ester as a white powder. The ethyl ester salt was used directly in the next reaction.

The salt (~12 g) was suspended in acetone and cooled to 0° C. 10% aq Na$_2$CO$_3$ (6.0 mL) was then added followed by BOC$_2$O (1.37 g, 6.29 mmol) and then the reaction was slowly warmed to 25° C. After 12 h, the reaction mixture was poured into water and extracted with methylene chloride (3×100 mL). The organics were then dried over anhydrous sodium sulfate and concentrated in vacuo to give the crude compound 92A as a white powder. This material was taken on without further purification.

B. (2R-trans)-4-[[(4-Methylphenyl)sulfonyl]oxy]-1,2-pyrrolidinedicarboxylic acid, 1-(1,1-dimethylethyl) 2-ethyl ester (92B)

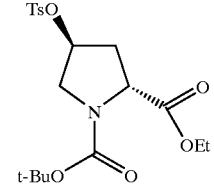

The crude compound 92A (1.41 g, 5.44 mmol) was dissolved in THF (50 mL) and Ph$_3$P (1.86 g, 70.8 mmol) was added. The mixture was cooled to 0° C. and DEAD (1.11 mL, 70.8 mmol) was added. After 15 min, methyl paratoluenesulfonate (1.32 g, 70.8 mmol) was then added and the solution was slowly warmed to 25° C. After 14 h, the reaction was concentrated in vacuo and purified by flash chromatography on silica eluting with acetone in chloroform (0–2–3% acetone) to give 0.845 g of the desired compound 92B as a yellow oil. HPLC RT=3.373 min (95%) (YMC S5 ODS column, 4.6×50 mm; 10–90% MeOH/H$_2$O gradient, +0.1% TFA; 4 mL/min, 220 nM detection). This material was taken on without further purification.

C. (2R-trans)-2-(Hydroxymethyl)-4-[[(4-methylphenyl)sulfonyl]oxy-1-pyrrolidinecarboxylic acid, 1,1-dimethyl ester (92C)

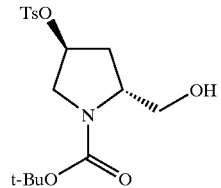

The crude compound 92B (5.50 g, 13.32 mmol) was dissolved in THF (150 mL) and cooled to 0° C. LiBH$_4$ (2.0 M in THF, 16.7 mL, 33.3 mmol) was then slowly added and the reaction was allowed to warm to 25° C. slowly. After 12 h, the mixture was cooled to 0° C. and the reaction was quenched with water (10 mL) and then AcOH (2.0 mL). After 15 min, the solution was poured into sat NaHCO₃ and extracted with methylene chloride (3×50 mL) and the combined organics were dried over anhydrous sodium sulfate. This gave the crude compound 92C (3.91 g) as a yellow oil, which was taken on without purification. HPLC RT=3.043 min (100%) (YMC S5 ODS column, 4.6×50 mm; 10–90% MeOH/H₂O gradient, +0.1% TFA; 4 mL/min, 220 nM detection).

D. (2R-trans)-2-[Cyano[(phenylmethyl)amino]methyl]-4-[[(4-methylphenyl)-sulfonyl]oxy]-1-pyrrolidinecarboxylic acid, 1,1-dimethylethyl ester (92D)

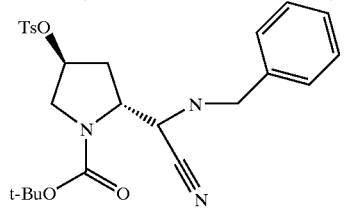

To a solution of oxalyl chloride (2.0 M soln in CH₂Cl₂, 2.82 mL) in CH₂Cl₂ (40 mL) at −78° C. was added anhydrous dimethylsulfoxide (0.462 mL, 6.51 mmol). The mixture was allowed to stand for 15 min, after which a solution of compound 92C (1.61 g, 4.34 mmol) in CH₂Cl₂ (10 mL) was slowly added. After an additional 30 min, triethylamine (1.81 mL, 13.02 mmol) was added and the reaction was slowly warmed to 0° C. The reaction was then quenched with H₂O (25 mL) and diluted with CH₂Cl₂ (100 mL). The mixture was then washed sequentially with 1 N HCl (1×100 mL), saturated aqueous NaHCO₃ (50 mL), and water (2×50 mL). The organics were dried over anhydrous sodium sulfate and the volatile organics removed in Vacuo. The crude aldehyde intermediate (1.60 g, 4.34 mmol) was dissolved in THF (25 mL) and diethyl cyanophosphonate (90%, 0.95 mL, 5.64 mmol) was added followed by benzyl amine (1.23 mL, 11.3 mmol). After 2 h, the reaction was complete, as observed by TLC and the volatile organics were removed in vacuo. The crude reaction mixture was purified by flash chromatography on SiO₂ eluting with acetone/chloroform (0–2–3% acetone) to give 1.48 g (70%) of intermediate Compound 92D as a white solid. Compound 92D was determined to be a ~1:1 mixture of diastereomers by NMR spectroscopy.

E. (1R-endo)-6-Cyano-5-(phenylmethyl)-2,5-diazabicyclo[2.2.1]heptane-2-carboxylic acid, 1,1-dimethylethyl ester (92Ei); (1R-exo)-6-Cyano-5-(phenylmethyl)-2,5-diazabicyclo[2.2.1]heptane-2-carboxylic acid, 1,1-dimethylethyl ester (92Eii)

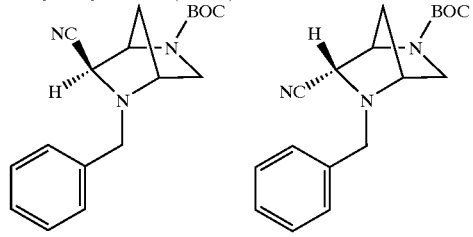

Intermediate compound 92D (1.48 g, 3.05 mmol) was dissolved in dichloroethane (25 mL) and diisopropyl ethylamine (1.45 mL) was added. The mixture was heated to 100° C. in a sealed tube for 18 h. The volatiles were then removed in vacuo and the resulting crude material was purified by flash chromatography on SiO₂ eluting with acetone/chloroform (0–2–3% acetone), to yield a mixture of intermediate compound 92Ei (0.591 g, 62%) and intermediate compound 92Eii (0.370 g, 38%) as clear oils. Structural assignments for Compounds 92Ei and 92Eii were made after NOE, COESY and DEPT NMR experiments.

F. (1R-endo)-5-(Phenylmethyl)-2,5-diazabicyclo[2.2.1]heptane-2,6-dicarboxylic acid, 2-(1,1-dimethylethyl) 6-methyl ester (92F)

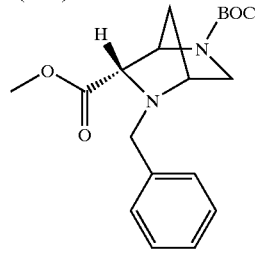

Intermediate Compound 92Ei (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous NaHCO₃ (50 mL). The mixture was extracted with CH₂Cl₂ (3×50 mL) and the combined organics were dried over anhydrous sodium sulfate. The crude ester was purified by flash chromatography on SiO₂ eluting with chloroform/acetone (0–2–4% acetone) to give 0.320 g (0.92 mmol, 72%) of intermediate compound 92F as a clear oil.

G. (1R-exo)-5-(Phenylmethyl)-2,5-diazabicyclo[2.2.1]heptane-2,6-dicarboxylic acid, 2-(1,1-dimethylethyl) 6-methyl ester (92G)

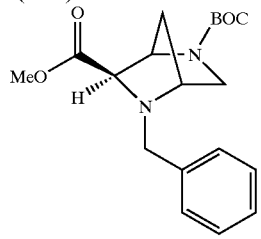

Intermediate compound 92Eii (0.400 g, 1.28 mmol) was dissolved in NaOMe (0.5 M, 12.8 mL) and heated to 60° C. for 5 h. The reaction was cooled to 0° C. and 3 N HCl (4.0 mL) was added slowly. After 2 h at 0° C. the reaction was poured into saturated aqueous NaHCO₃ (50 mL). The mixture was extracted with CH₂Cl₂ (3×50 mL) and the combined organics were dried over anhydrous sodium sulfate. The crude ester was purified by flash chromatography on SiO₂ eluting with chloroform/acetone (0–2–4% acetone) to give 0.290 g (0.85 mmol, 66%) of intermediate compound 92G as a clear oil.

H. (1R-endo)-2,5-Diazabicyclo[2.2.1]heptane-2,6-dicarboxylic acid, 2-(1,1-dimethylethyl) 6-methyl ester (92H)

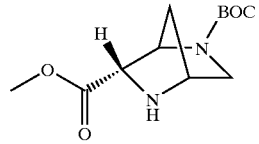

Intermediate compound 92F (0.280 g, 0.81 mmol) was dissolved in absolute EtOH (10.0 mL) and Pd/C (10% Pd, 0.080 g) was added. An atmosphere of H₂ was introduced via a balloon and the reaction was stirred at 25° C. for 20 h. The Pd was removed by filtration through celite followed by rinsing with EtOAc. The volatiles were removed in vacuo to give compound 92H (0.205 g, 99%) as viscous yellow oil. Compound 92H was taken on directly without purification. MS(ES)=m/z 257.18 [M+H]⁺. HPLC RT=1.223 min (95%) (YMC S5 ODS column, 4.6×50 mm; 10–90% MeOH/H₂O gradient, +0.1% TFA; 4 mL/min, 220 nM detection).

I. (1R-exo)-2,5-Diazabicyclo[2.2.1]heptane-2,6-dicarboxylic acid, 2-(1,1-dimethylethyl) 6-methyl ester (92I)

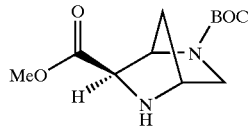

Intermediate compound 92G (0.310 g, 0.89 mmol) was dissolved in absolute EtOH (10.0 mL) and Pd/C (10% Pd, 0.080 g) was added. An atmosphere of H₂ was introduced via a balloon and the reaction was stirred at 25° C. for 20 h. The Pd was removed by filtration through celite, followed by rinsing with EtOAc. The volatiles were removed in vacuo to give compound 92I (0.210 g, 92%) as a viscous yellow oil. Compound 92I can be taken on directly without purification. MS(ES)=m/z 257.16 [M+H]⁺ HPLC RT=1.293 min (90%) (YMC S5 ODS column, 4.6×50 mm; 10–90% MeOH/H₂O gradient, +0.1% TFA; 4 mL/min, 220 nM detection).

EXAMPLE 93

[5R-(5α,8α,8aα)]-4-[Octahydro-7-[(1,1-dimethylethoxy)carbonyl]-1,3-dioxo-5,8-methanoimidazo[1,5-a]pyrazin-2-yl]-2-(trifluoromethyl)benzonitrile (93i)

[5R-(5α,8α,8aβ)]-4-[Octahydro-7-[(1,1-dimethylethoxy)carbonyl]-1,3-dioxo-5,8-methanoimidazo[1,5-a]pyrazin-2-yl]-2-(trifluoromethyl)benzonitrile (93ii)

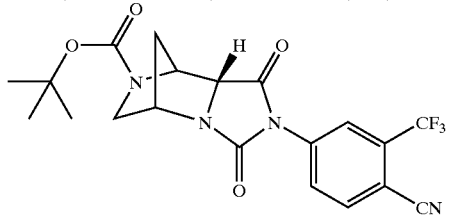

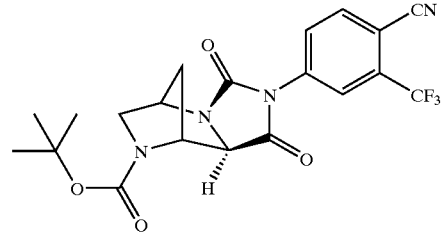

To a solution of 4-isocyanato-2-(trifluoromethyl)-benzonitrile (1.0 mmol) in toluene (4 mL) with activated 4 Å MS (0.300 g) was added Compound 92H or 92I (0.220 g, 0.856 mmol) (compounds epimerize to form same product) in toluene (6 mL). After 10 h at 25° C., DBU (0.166 mL, 1.11 mmol) was added and the reaction was heated at 81° C. for 2 h. The reaction was then cooled to 25° C. and poured into 1 N HCl (50 mL). The solution was then extracted with methylene chloride (3×30 mL) and the combined organics were dried over anhydrous sodium sulfate. The resulting crude material was purified by flash chromatography on SiO₂ eluting with acetone/chloroform (0–2–4–8% acetone) to give Compound 93i (0.155 g, 42%) MS (ES): m/z 437.09 [M+H]⁺. HPLC RT=3.280 min (100%) (YMC S5 ODS column, 4.6×50 mm; 10–90% MeOH/H₂O gradient, +0.1% TFA; 4 mL/min, 220 nM detection) and Compound 93ii (0.061 g, 16%) MS (ES): m/z 437.09 [M+H]⁺. HPLC RT=3.133 min (100%) (YMC S5 ODS column, 4.6×50 mm; 10–90% MeOH/H₂O gradient, +0.1% TFA; 4 mL/min, 220 nM detection); both as white foams.

EXAMPLE 94

[5S-(5α,8α,8aα)]Hexahydro-2-(4-nitro-1-naphthalenyl)-1,3-dioxo-5,8-methanoimidazo[1,5-a]pyrazin-7(8H)-carboxylic acid, 1,1-dimethylethyl ester (94)

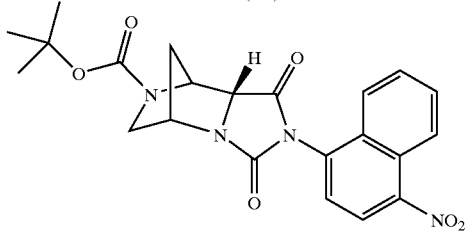

Compound 89G (0.220 g, 0.856 mmol) was added to a suspension of freshly activated 4 Å molecular sieves (0.300 g) in dry toluene (10.0 mL). To this mixture was added 4-nitronaphthal-1-isocyanate (0.214 g, 1.0 mmol). After stirring at 25° C. for 14 h, DBU (0.166 mL, 1.11 mmol) was added and the reaction was heated at 80° C. for 2 h. After 2 h, the reaction was cooled to 25° C. and then poured into 1 N HCl (50 mL). This solution was extracted with methylene chloride (3×30 mL) and the combined organics were dried over anhydrous sodium sulfate. The crude material was purified by flash chromatography on silica eluting with 0–2–6% acetone in chloroform to give 0.211 g of compound 94 as a yellow foam. HPLC: 95% at 3.130 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 439.19 [M+H]⁺.

EXAMPLE 95

[5S-(5α,8α,8aα)]-Tetrahydro-2-(4-nitro-1-naphthalenyl)-5,8 methanoimidazo[1,5-a]pyrazine-1,3(2H,5H)-dione (95)

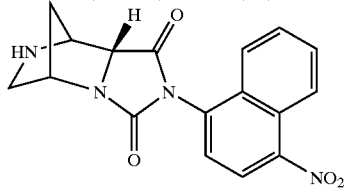

Compound 94 (0.160 g, 0.37 mmol) was dissolved in methylene chloride (5.0 mL) and TFA (1.5 mL) was added at 25° C. After 1.5 h, the reaction was concentrated in vacuo and redissolved in methylene chloride. This solution was washed with sat aq NaHCO₃. The aqueous layer was extracted with methylene chloride (3×25 mL). The combined organics were then dried over anhydrous sodium sulfate. Concentration in vacuo gave 0.115 g of compound 95 as a yellow solid. HPLC: 93% at 1.747 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 369.07 [M+MeOH]⁺.

EXAMPLE 96

[5S-(5α,8α,8aα)]-7-[(4-Fluorophenyl)sulfonyl]
tetrahydro-2-(4-nitro-1-naphthalenyl)-5,8-
methanoimidazo[1,5-a]pyrazine-1,3(2H,5H)-dione
(96)

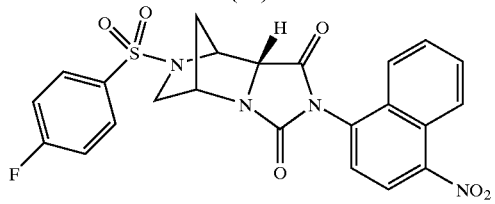

Compound 94 (0.025 g, 0.074 mmol) was dissolved in pyridine (0.5 mL) and then 4-fluorophenylsulfonyl chloride (0.028 g, 0.148 mmol) was added. After 16 h at 25° C., the reaction was concentrated in vacuo. The crude product was purified by flash chromatography on silica eluting with 5% acetone in chloroform to give 0.029 g of compound 96 as a yellow solid. HPLC: 99% at 3.107 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 497.2 [M+H]⁺.

EXAMPLE 97

(5α,8α,8aα)-2-(7-Fluoro-3-benzofuranyl)tetrahydro-
5,8-methanoimidazo[1,5-a]pyridine-1,3(2H,5H)-
dione & (5α,8α,8aβ)-2-(7-Fluoro-3-benzofuranyl)
tetrahydro-5,8-methanoimidazo[1,5-a]pyridine-1,3
(2H,5H)-dione (97Ei & 97Eii, Respectively)

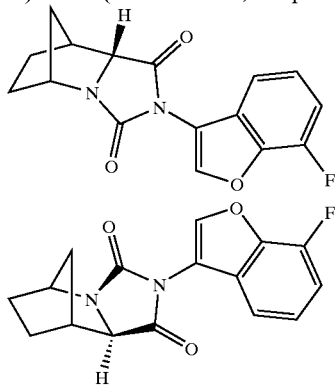

A. 7-Fluoro-2-benzofurancarboxyclic acid (97A)

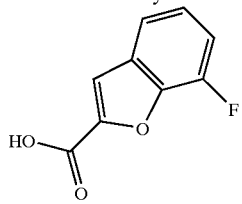

The reagents 3-fluorosalicylaldehyde (1.000 g, 7.14 mmol) and ethyl bromomalonate (1.900 g, 7.29 mmol) were reacted according to the procedure reported by Tanaka (J. Am. Chem. Soc. 1951, 73, 872) to yield 562 mg (44%) of compound 97A.

B. 3-Bromo-7-fluorobenzofuran (97B)

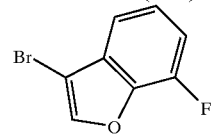

Compound 97A (562 mg, 3.12 mmol) was subjected to decarboxylation under the conditions described by Tanaka (J. Am. Chem. Soc. 1951, 73, 872), followed by bromination and debromination in accordance with the procedures described by Mochida et al. (EP 355827 A2) to afforded 186 mg (28%) of compound 97B.

C. 7-Fluoro-3-benzofurancarboxyclic acid (97C)

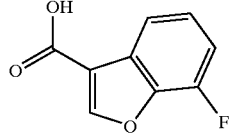

Compound 97B (186 mg, 0.87 mmol) was subjected to lithiation followed by carboxylation, in accordance with the procedures described by Cugnon de Sévricourt et. al., Bull. Soc. Chim. 144 (1977), to yielded 36 mg (23%) of compound 97C.

D. 7-Fluoro-3-benzofurancarboxylic acid azide (97D)

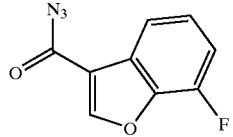

To a solution of compound 97C (36 mg, 0.20 mmol) in THF (2 ml) was added, via syringe at ambient temperature, Et₃N (33 μl, 0.24 mmol) and DPPA (52 μl, 0.24 mmol). The resulting mixture was stirred for 2 h, at which time the reaction was quenched by the addition of H₂O (2 ml). The layers were separated and the aqueous layer was extracted with Et₂O (1×5 ml). The combined organic phases were dried over MgSO₄ and concentrated under reduced pressure to leave a colorless residue which was purified by flash chromatography (silica gel, 0 to 5% EtOAc in hexanes) yielding 36 mg (88%) of compound 97D.

E. (5α,8α,8aα)-2-(7-Fluoro-3-benzofuranyl)tetrahydro-5,8-methanoimidazo[1,5-a]pyridine-1,3(2H,5H)-dione & (5α,8α,8aβ)-2-(7-Fluoro-3-benzofuranyl)tetrahydro-5,8-methanoimidazo[1,5-a]pyridine-1,3(2H,5H)-dione (97Ei & 97Eii, Respectively)

A solution of compound 97D (36 mg, 0.18 mmol) in toluene (1.5 ml) was heated to 95° C. for 2 h. The reaction was cooled before 50 mg of freshly activated 4 Å mol sieves (powdered) and a solution of 2-azabicyclo[2.2.1]heptane-3-carboxylic acid, ethyl ester (32 mg, 0.19 mmol) in toluene (1.5 ml) were added. The resulting mixture was stirred overnight, treated with DBU (30 μl, 0.20 mmol) and heated to 85° C. for 2 h. After cooling the material was filtered through Celite eluting with CH₂Cl₂ (50 ml), washed with 1N HCl solution (2×25 ml) and concentrated under reduced pressure. The remaining residue was purified by flash chromatography (silica gel, 20 to 5% hexanes in CH₂Cl₂) to give 23 mg (44%) of compound 97Ei together with 19 mg (36%) of compound 97Eii as white solids. Compound 97Ei: HPLC: 100% at 2.93 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 301 [M+H]⁺. Compound 97Eii: HPLC: 100% at 3.00 min (retention time) (YMC S5 ODS column 4.6×50 mm eluting with 10–90% aqueous methanol over 4 minutes containing 0.2% phosphoric acid, 4 mL/min, monitoring at 220 nm), MS (ES): m/z 301 [M+H]⁺.

The corresponding compounds where the 7-fluoro-3-benzofuranyl group is replaced with each of the following groups were also prepared: 2-methyl,4,5,6,7-tetrafluoro-3-benzofuranyl, 3-benzofuranyl, 2-benzofuranyl, and 2-methyl-3-benzofuranyl.

EXAMPLE 98

[5S-(5α,8α,8aα)]-2-[4-Cyano-3-(trifluoromethyl) phenyl]hexahydro-8a-methyl-1,3-dioxo-5,8-methanoimidazo[1,5a]pyrazine-7(8H)-carboxylic acid, 1,1-dimethylethyl ester (98)

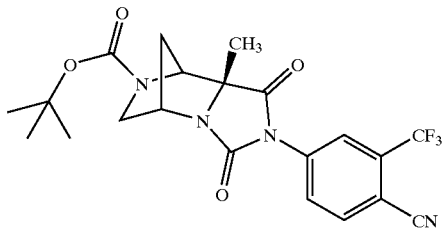

Compound 90i (0.100 g, 0.229 mmol) was added to freshly prepared LDA (0.048 mL diisopropyl amine, 0.186 mL, 1.6M BuLi) in THF (3.0 mL) at −78° C. After 30 min, methyl iodide (0.029 mL, 0.458 mmol) was added and the reaction was slowly warmed to −20° C. over 1 h and then quenched with sat aq ammonium chloride. The mixture was then extracted with methylene chloride (3×30 mL). The organics were dried over anhydrous sodium sulfate and concentrated in vacuo, to give 0.077 g of the crude compound 98 which was taken on without purification. HPLC: 93% at 3.243 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 473.12 [M+NaH]⁺.

EXAMPLE 99

[5S-(5α,8α,8aα)]-4-(Hexahydro-1,3-dioxo-8a-methyl-5,8-methanoimidazo

[1,5-a]pyrazin-2(3H)-yl)-2-(trifluoromethyl) benzonitrile (99)

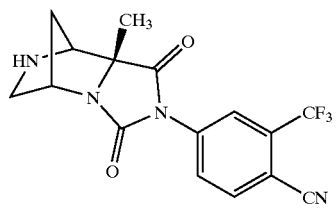

Compound 98 (0.070 g, 0.156 mmol) was dissolved in methylene chloride (2.0 mL) and TFA (0.75 mL) was added at 25° C. After 30 min, the reaction was quenched with sat aq NaHCO₃ and then extracted with methylene chloride (3×30 mL). The organics were then dried over anhydrous sodium sulfate and concentrated in vacuo. The crude material was purified by preparative TLC eluting with 25% acetone in chloroform to give 0.031 g of compound 99 as a white solid. HPLC: 86% at 1.817 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 351.15 [M+H]⁺.

EXAMPLE 100

[5S-(5α,8α,8aα)]-7-Benzoyl-2-[4-cyano-3-(trifluoromethyl)phenyl]tetrahydro-5,8-methanoimidazo[1,5-a]pyrazine-1,3(2H,5H)-dione (100)

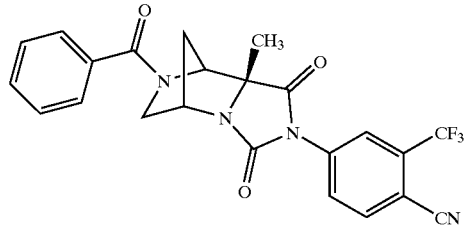

Compound 99 (0.023 g, 0.066 mmol) was dissolved in methylene chloride (2.0 mL) and then TEA (0.018 mL, 0.132 mmol) and 4-DMAP (cat) were added followed by benzoyl chloride (0.011 mL, 0.099 mmol). After 3 h, the reaction was concentrated in vacuo and then purified by preparative TLC on silica eluting with 7% acetone in chloroform to give 0.021 g of compound 100 as a white foam. HPLC: 100% at 2.927 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 455.10 [M+H]⁺.

EXAMPLE 101

[5S-(5α,8α,8aα)]-7-(4-Fluorobenzoyl)tetrahydro-2-(4-nitro-1-naphthalenyl)-5,8-methanoimidazo[1,5-a] pyrazine-1,3(2H,5H)-dione (101)

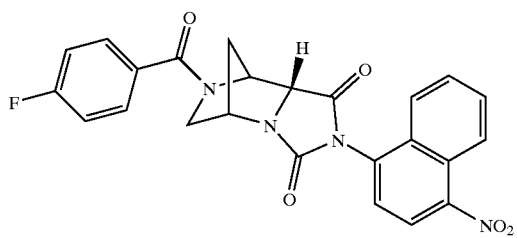

Compound 95 (0.077 g, 0.228 mmol) was dissolved in methylene chloride (2.0 mL) and TEA (0.127 mL, 0.912 mmol) and 4-DMAP (0.001 g) were added. The reaction was cooled to 0° C. and 4-fluorobenzoylchloride (0.040 mL, 0.342 mmol) was added. The reaction was then slowly warmed to 25° C. After 3 h, the reaction was diluted with methylene chloride (50 mL) and then washed successively with 1N HCl and sat aq NaHCO₃ then and dried over anhydrous sodium sulfate. The crude material was purified by preparative TLC on silica eluting with 5% acetone in chloroform to give 0.022 g of compound 101 as a yellow solid. HPLC: 100% at 2.960 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 461.07 [M+H]⁺.

EXAMPLE 102

[5S-(5α,8α,8aα)]-2-(4-Cyano-1-naphthalenyl)tetrahydro-7-(5-isoxazolylcarbonyl)-5,8-methanoimidazo[1,5-a]pyrazine-1,3(2H,5H)-dione (102A), [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, 4-fluorophenyl ester (102B), [5S-(5α,8α,8aα)]-2-(4-Cyano-1-naphthalenyl)tetrahydro-7-[(1-methyl-1H-imidazol-4-yl)sulfonyl]-5,8-methanoimidazo[1,5-a]pyrazine-1,3(2H,5H)-dione (102C) & [5S-(5α,8α,8aα)]-2-(4-Cyano-1-naphthalenyl)-N-(4-fluorophenyl)hexahydro-1,3-dioxo-5,8-methanoimidazo[1,5-a]pyrazine-7(8H)-carboxamide (102D) Solution Phase Library Synthesis The below procedure is a general approach to the synthesis of compounds of formula I in a solution phase library format. A more detailed description of individual compounds made via this combinatorial approach follows.

A series of free amine starting materials, analogous to the structure of [5S-(5α,8α,8aα)]-Tetrahydro-2-(4-nitro-1-naphthalenyl)-5,8 methanoimidazo[1,5-a]pyrazine-1,3(2H,5H)-dione (0.05 mmol, prepared as described in Example 95) were dissolved in dichloromethane (1.5 mL) in a polystyrene tube with a coarse frit. N,N-(Diisopropyl)aminomethyl polystyrene (3.49 mmol/g, 60 mg) was then added to each reaction vessel followed by the addition of the desired acid chloride, isocyanate, chloroformate or sulfonyl chloride (0.10 mmol) in 0.5 mL dichloroethane by automated synthesizer. The reaction vessels were shaken at 25° C. for 24 h and then Tris-(2-Aminoethyl)amine Polystyrene HL (200–400 mesh, 3.3 mmol/g, 75 mg) was added to each reaction vessel and the vessels shaken again for 18 h at 25° C. The liquid from each tube was drained into pretared 2.5 ml STR tubes and the resin was rinsed with dichloromethane (3×0.25 mL). The pretared tubes were then concentrated and analyzed by analytical HPLC and LC-MS. HPLC: (Phenomenex-Prime 5µ C-18 column 4.6×50 mm eluting with 10–90% aqueous methanol over 4 minutes containing 0.1% TFA, 4 mL/min, monitoring at 220 nm).

A. [5S-(5α,8α,8aα)]-2-(4-Cyano-1-naphthalenyl)tetrahydro-7-(5-isoxazolylcarbonyl)-5,8-methanoimidazo[1,5-a]pyrazine-1,3(2H,5H)-dione (102A)

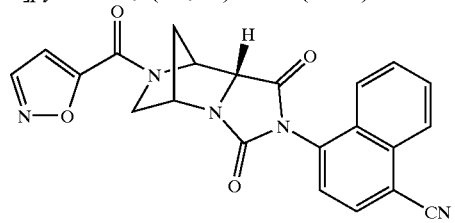

[5S-(5α,8α,8aα)]-4-(Hexahydro-1,3-dioxo-5,8-methanoimidazo[1,5-a]pyrazin-2(3H)-yl)-1-naphthalanecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of isoxazolacid chloride (0.025 g, 0.19, mmol). The tube was shaken at 25° C. for 24 h and then Tris-(2-Aminoethyl)amine Polystyrene HL (200–400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave the crude compound 102A (0.058 g) as a yellow solid. No purification was necessary. HPLC: 100% at 2.237 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 414.11 [M+H]⁺.

B. [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, 4-fluorophenyl ester (102B)

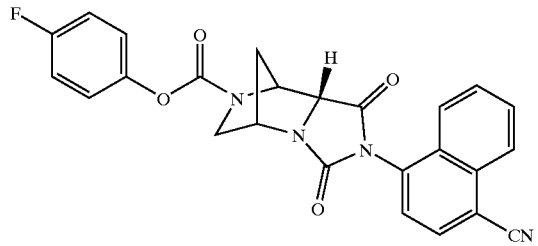

[5S-(5α,8α,8aα)]-4-(Hexahydro-1,3-dioxo-5,8-methanoimidazo[1,5-a]pyrazin-2(3H)-yl)-1-naphthalenecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of 4-fluorophenylchloroformate (0.033 g, 0.19 mmol). The tube was shaken at 25° C. for 24 h and then Tris-(2-Aminoethyl)amine Polystyrene HL (200–400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave crude compound 102B (0.053 g) as a yellow solid. No purification was necessary. HPLC: 93% at 2.987 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 457.07 [M+H]⁺.

C. [5S-(5α,8α,8aα)]-2-(4-Cyano-1-naphthalenyl)tetrahydro-7-[(1-methyl-1H-imidazol-4-yl)sulfonyl]-5,8-methanoimidazo[1,5-a]pyrazine-1,3(2H,5H)-dione (102C)

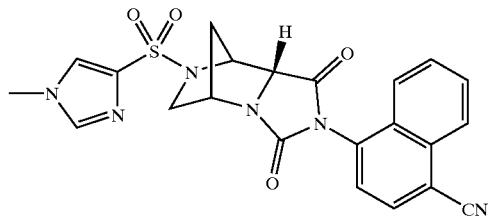

[5S-(5α,8α,8aα)]-4-(Hexahydro-1,3-dioxo-5,8-methanoimidazo[1,5-a]pyrazin-2(3H)-yl)-1-naphthalenecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of imidazolesulfonylchloride (0.034 g, 0.19 mmol). The tube was shaken at 25° C. for 24 h and then Tris-(2-Aminoethyl)amine Polystyrene HL (200–400 mesh, 3.3 mmol/g, 75 mg) was added to the reaction vessel and it was shaken again for 18 h at 25° C. The liquid was drained into pretared 2.5 ml STR tube and the resin was rinsed with dichloromethane (3×0.25 mL). Concentration in vacuo gave the crude compound 102C (0.043 g) as a yellow solid. No purification was necessary. HPLC: 70% at 1.603 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 463.07 [M+H]+.

D. [5S-(5α,8α,8aα)]-2-(4-Cyano-1-naphthalenyl)-N-(4-fluorophenyl)hexahydro-1,3-dioxo-5,8-methanoimidazo[1,5-a]pyrazine-7(8H)-carboxamide (102D)

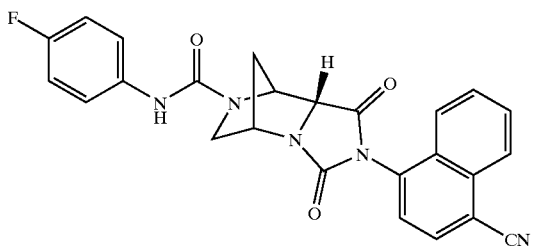

[5S-(5α,8α,8aα)]-4-(Hexahydro-1,3-dioxo-5,8-methanoimidazo[1,5-a]pyrazin-2(3H)-yl)-1-naphthalenecarbonitrile (0.030 g, 0.094 mmol) was dissolved in dichloromethane (2.0 mL) in a polystyrene tube with a coarse frit. N,N-(Diisopropyl)aminomethyl polystyrene (3.49 mmol/g, 65 mg) was then added to each reaction vessel followed by addition of 4-fluorophenylisocyanate (0.026 g, 0.19 mmol). The tube was shaken at 25° C. for 24 h and then Tris-(2-Aminoethyl)amine Polystyrene HL (200–400 mesh, 3.3 mmol/g, 75 mg) was added to the reaction vessel and it was shaken again for 18 h at 25° C. The liquid was drained into a pretared 2.5 ml STR tube and the resin was rinsed with dichloromethane (3×0.25 mL). Concentration in vacuo gave the crude compound 102D (0.058 g) as a yellow solid. No purification was necessary. HPLC: 100% at 2.890 min (retention time) (YMC S5 ODS column 4.6×50 mm, 10–90% aqueous methanol over 4 minutes containing 0.2% phosphoric acid, 4 mL/min, monitoring at 220 nm). MS (ES): m/z 456.4 [M+H]+.

EXAMPLE 103

[5S-(5α,8α,8aβ)]-Tetrahydro-2-(4-nitro-1-naphthalenyl)-7-(phenylmethyl)-5,8-methanoimidazo[1,5-a]pyrazine-1,3(2H,5H)-dione (103)

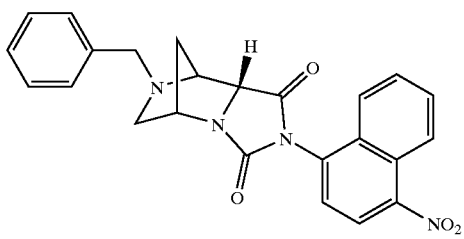

The TFA salt of the compound 95 (0.010 g, 0.022 mmol) was dissolved in DMF (0.5 mL) followed by addition of K₂CO₃ (0.009 g, 0.088 mmol) and benzyl bromide (0.005 mL, 0.044 mmol). After 1 h, the DMF was removed in vacuo and the crude product was purified by flash chromatography on silica eluting with 5% acetone in chloroform. This gave 0.008 g of compound 103 as a yellow solid. Proton NMR showed an intact hydantoin ring system. HPLC: 100% at 2.280 min (retention time) (YMC S5 ODS column 4.6×50 mm, 10–90% aqueous methanol over 4 minutes containing 0.2% phosphoric acid, 4 mL/min, monitoring at 220 nm), MS (ES): m/z 461.12 [M+H+MeOH]+.

EXAMPLES 104 TO 199

Additional compounds of the present invention were prepared by procedures analogous to those described above. The compounds of Examples 104 to 199 have the following structure (L is a bond):

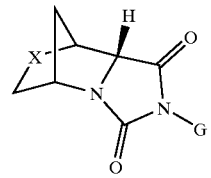

where G, X, the compound name, retention time, molecular mass, and the procedure employed, are set forth in Table 3. The chromatography techniques used to determine the compound retention times of Table 3 are as follows: LCMS= YMC S5 ODS column, 4.6×50 mm eluting with 10–90% MeOH/H₂O over 4 minutes containing 0.1% TFA; 4 mL/min, monitoring at 220 nm. LCMS*=YMC S5 ODS column, 4.6×50 mm eluting with 10–90% MeOH/H₂O over 2 minutes containing 0.1% TFA; 4 mL/min, monitoring at 220 nm. LC=YMC S5 ODS column 4.6×50 mm eluting with 10–90% MeOH/H₂O over 4 minutes containing 0.2% phosphoric acid, 4 mL/min, monitoring at 220 nm. The molecular mass of the compounds listed in Table 3 were determined by MS (ES) by the formula m/z.

TABLE 3

| Ex. No | G | X | Compound Name | Retention Time Min./ Molecular Mass | Procedure of Ex. |
|---|---|---|---|---|---|
| 104 | 4-methyl-2-(trifluoromethyl)-1-cyanophenyl (F₃C, CN substituents) | N-C(=O)-O-C(CH₃)₂CH₃ (Boc) | [5R-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester. | 3.13 LC | 93 |
| 105 | 4-methyl-1-nitronaphthalenyl | N-C(=O)-O-C(CH₃)₂CH₃ (Boc) | [5R-(5α,8α,8aα)]-Hexahydro-2-(4-nitro-1-naphthalenyl)-1,3-dioxo-5,8-methanoimidazo[1,5-a]pyrazine-7(8H)-carboxylic acid, 1,1-dimethylethyl ester. | 3.13 LC | 93, 94 |
| 106 | 4-methyl-1-nitronaphthalenyl | NH | [5R-(5α,8α,8aα)]-Tetrahydro-2-(4-nitro-1-naphthalenyl)-5,8-methanoimidazo[1,5-a]pyrazine-1,3(2H,5H)-dione. | 1.76 LC | 93, 95 |
| 107 | 4-methyl-2-(trifluoromethyl)-1-cyanophenyl | NH | [5R-(5α,8α,8aα)]-4-(Hexahydro-1,3-dioxo-5,8-methanoimidazo[1,5-a]pyrazin-2(3H)-yl)-2-(trifluoromethyl)benzonitrile. | 3.29 LC | 93, 91 |
| 108 | 4-methyl-2-(trifluoromethyl)-1-cyanophenyl | N-C(=O)-C₆H₅ (benzoyl) | [5S-(5α,8α,8aα)]-4-(7-Benzoylhexahydro-1,3-dioxo-5,8-methanoimidazo[1,5-a]pyrazin-2(3H)-yl)-2-(trifluoromethyl)benzonitrile. | 2.98 LC | 100 |
| 109 | 4-methyl-2-(trifluoromethyl)-1-cyanophenyl | N-C(=O)-O-CH₂-C₆H₅ (Cbz) | [5S-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, phenylmethyl ester. | 3.12 LC | 102B |
| 110 | 2-methyl-4-nitrophenyl (H₃C, NO₂) | CH₂ | [5S-(5α,8α,8aα)]-Tetrahydro-2-(2-methyl-4-nitrophenyl)-5,8-methanoimidazo[1,5-a]pyridine-1,3(2H,5H)-dione. | 2.46 LC | 7 |

TABLE 3-continued

| Ex. No | G | X | Compound Name | Retention Time Min./ Molecular Mass | Procedure of Ex. |
|---|---|---|---|---|---|
| 111 | 4-CN-3-CF₃-phenyl-methyl | N—CH₃ | [5S-(5α,8α,8aα)]-4-(Hexahydro-7-methyl-1,3-dioxo-5,8-methanoimidazo[1,5-a]pyrazin-2(3H)-yl)-2-(trifluoromethyl)benzonitrile. | 1.94 LC | 99 |
| 112 | 4-nitro-1-methylnaphthalenyl | N-benzoyl | [5S-(5α,8α,8aα)]-7-Benzoyltetrahydro-2-(4-nitro-1-naphthalenyl)-5,8-methanoimidazo[1,5-a]pyrazine-1,3(2H,5H)-dione. | 2.86 LC | 98A |
| 113 | 4-nitro-1-methylnaphthalenyl | N-C(O)O-CH₂-phenyl | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, phenylmethyl ester. | 3.27 LC | 98B |
| 114 | 3-methyl-4-nitrophenyl | CH₂ | [5S-(5α,8α,8aα)]-Tetrahydro-2-(3-methyl-4-nitrophenyl)-5,8-methanoimidazo[1,5-a]pyridine-1,3(2H,5H)-dione. | 2.66 LC | 7 |
| 115 | 4-nitro-1-methylnaphthalenyl | N—CH₃ | [5S-(5α,8α,8aα)]-Tetrahydro-7-methyl-2-(4-nitro-1-naphthalenyl)-5,8-methanoimidazo[1,5-a]pyridine-1,3(2H,5H)-dione. | 1.79 LC | 103 |
| 116 | 4-nitro-1-methylnaphthalenyl | N-CH₂-CH=CH₂ | [5S-(5α,8α,8aα)]-Tetrahydro-2-(4-nitro-1-naphthalenyl)-7-(2-propenyl)-5,8-methanoimidazo[1,5-a]pyrazine-1,3(2H,5H)-dione. | 3.11 LC | 103 |
| 117 | 4-CN-3-CF₃-phenyl-methyl | N-CH₂-phenyl | [5S-(5α,8α,8aα)]-4-[Hexahydro-1,3-dioxo-7-(phenylmethyl)-5,8-methanoimidazo[1,5-a]pyrazin-2(3H)-yl]-2-(trifluoromethyl)benzonitrile. | 2.81 LC | 103 |

TABLE 3-continued

| Ex. No | G | X | Compound Name | Retention Time Min./ Molecular Mass | Procedure of Ex. |
|---|---|---|---|---|---|
| 118 | 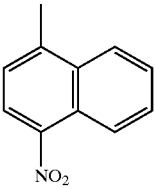 | 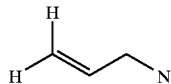 | [5R-(5α,8α,8aα)]-Tetrahydro-2-(4-nitro-1-naphthalenyl)-7-(2-propenyl)-5,8-methanoimidazo[1,5-a]pyrazine-1,3(2H,5H)-dione. | 3.06 LC | 103 |
| 119 | 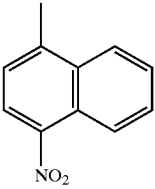 | 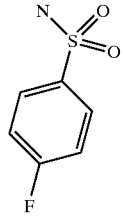 | [5R-(8α,8α,8aα)]-7-[(4-Fluorophenyl)sulfonyl]tetrahydro-2-(4-nitro-1-naphthalenyl)-5,8-methanoimidazo[1,5-a]pyrazine-1,3(2H,5H)-dione. | 3.08 LC | 102C |
| 120 | 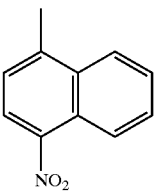 | 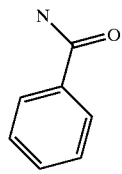 | [5R-(5α,8α,8aα)]-7-Benzoyltetrahydro-2-(4-nitro-1-naphthalenyl)-5,8-methanoimidazo[1,5-a]pyrazine-1,3(2H,5H)-dione. | 2.82 LC | 102A |
| 121 | 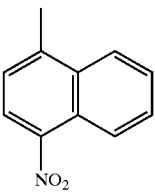 | 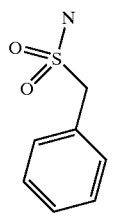 | [5S-(5α,8α,8aα)]-Tetrahydro-2-(4-nitro-1-naphthalenyl)-7-[(phenylmethyl)sulfonyl]-5,8-methanoimidazo[1,5-a]pyrazine-1,3(2H,5H)-dione. | 2.98 LC | 102C |
| 122 | 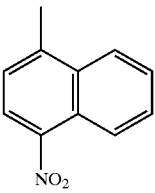 | 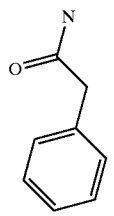 | [5S-(5α,8α,8aα)]-Tetrahydro-2-(4-nitro-1-naphthalenyl)-7-(phenylacetyl)-5,8-methanoimidazo[1,5-a]pyrazine-1,3(2H,5H)-dione. | 3.04 LC | 102A |
| 123 | 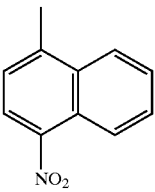 | 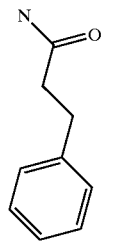 | [5S-(5α,8α,8aα)]-Tetrahydro-2-(4-nitro-1-naphthalenyl)-7-(3-phenyl-1-oxopropyl)-5,8-methanoimidazo[1,5-a]pyrazine-1,3(2H,5H)-dione. | 3.24 LC | 102A |
| 124 | 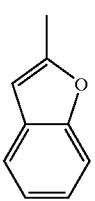 | CH$_2$ | (5α,8α,8aα)-2-(2-Benzofuranyl)tetrahydro-5,8-methanoimidazo[1,5-a]pyridine-1,3(2H,5H)-dione. | 2.80 LC | 7 |

TABLE 3-continued

| Ex. No | G | X | Compound Name | Retention Time Min./ Molecular Mass | Procedure of Ex. |
|---|---|---|---|---|---|
| 125 | (4-methyl-2-methoxyphenyl with 4-oxazolyl) | CH$_2$ | (5α,8α,8aα)-Tetrahydro-2-[3-methoxy-4-(4-oxazolyl)phenyl]-5,8-methanoimidazo[1,5-a]pyridine-1,3(2H,5H)-dione. | 2.52 LC | 7 |
| 126 | (4-methyl-1-cyanonaphthalenyl) | N-C(=O)-O-C(CH$_3$)$_3$ | [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, 1,1-dimethylethyl ester. | 3.00 LC | 94 |
| 127 | (4-methyl-1-cyanonaphthalenyl) | NH | [5S-(5α,8α,8aα)]-4-(Hexahydro-1,3-dioxo-5,8-methanoimidazo[1,5-a]pyrazin-2(3H)-yl)-1-naphthalenecarbonitrile. | 1.65 LC | 95 |
| 128 | (4-methyl-1-cyanonaphthalenyl) | N-C(=O)-CH(CH$_3$)$_2$ | [5S-(5α,8α,8aα)]-4-[Hexahydro-7-(2-methyl-1-oxopropyl)-1,3-dioxo-5,8-methanoimidazo[1,5-a]pyrazin-2(3H)-yl]-1-naphthalenecarbonitrile. | 2.49 LC | 102A |
| 129 | (4-methyl-2-iodo-1-cyanophenyl) | N-C(=O)-O-C(CH$_3$)$_3$ | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 1,1-dimethylethyl ester. | 2.95 LC | 90 |
| 130 | (4-methyl-2-iodo-1-cyanophenyl) | NH | [5S-(5α,8α,8aα)]-4-(Hexahydro-1,3-dioxo-5,8-methanoimidazo[1,5-a]pyrazin-2(3H)-yl)-2-iodobenzonitrile. | 1.34 LC | 91 |
| 131 | (2-methyl-3-methyl-benzofuranyl) | CH$_2$ | (5α,8α,8aα)-Tetrahydro-2-(2-methyl-3-benzofuranyl)-5,8-methanoimidazo[1,5-a]pyridine-1,3(2H,5H)-dione. | 2.80 LC | 7 |

TABLE 3-continued

| Ex. No | G | X | Compound Name | Retention Time Min./ Molecular Mass | Procedure of Ex. |
|---|---|---|---|---|---|
| 132 | 2,2-dimethyl-2H-1-benzopyran-4-yl group | CH$_2$ | (5α,8α,8aα)-2-(2,2-Dimethyl-2H-1-benzopyran-4-yl)tetrahydro-5,8-methanoimidazo[1,5-a]pyridine-1,3(2H,5H)-dione. | 2.87 | 7 |
| 133 | 4-nitro-1-naphthalenyl | N-C(=O)-CH$_3$ (acetyl) | [5S-(5α,8α,8aα)]-7-Acetyltetrahydro-2-(4-nitro-1-naphthalenyl)-5,8-methanoimidazo[1,5-a]pyrazine-1,3(2H,5H)-dione. | 2.76 LC 379.33 [M − H]$^+$ | 98A |
| 134 | 4-nitro-1-naphthalenyl | N-C(=O)-CH(CH$_3$)$_2$ | [5S-(5α,8α,8aα)]-Tetrahydro-7-(2-methyl-1-oxopropyl)-2-(4-nitro-1-naphthalenyl)-5,8-methanoimidazo[1,5-a]pyrazine-1,3(2H,5H)-dione. | 3.16 LC 407.36 [M − H]$^+$ | 102A |
| 135 | 4-nitro-1-naphthalenyl | N-C(=O)-(4-fluoro-3-trifluoromethylphenyl) | [5S-(5α,8α,8aα)]-7-[4-Fluoro-3-(trifluoromethyl)benzoyl]tetrahydro-2-(4-nitro-1-naphthalenyl)-5,8-methanoimidazo[1,5-a]pyrazine-1,3(2H,5H)-dione. | 3.8 LC 529.35 [M + H]$^+$ | 102A |
| 136 | 4-nitro-1-naphthalenyl | N-C(=O)-(4-chloro-3-nitrophenyl) | [5S-(5α,8α,8aα)]-7-(4-Chloro-3-nitrobenzoyl)tetrahydro-2-(4-nitro-1-naphthalenyl)-5,8-methanoimidazo[1,5-a]pyrazine-1,3(2H,5H)-dione. | 3.27 LC 522.33 [M + H]$^+$ | 102A |
| 137 | 4-nitro-1-naphthalenyl | N-C(=O)-(5-isoxazolyl) | [5S-(5α,8α,8aα)]-Tetrahydro-7-(5-isoxazolylcarbonyl)-2-(4-nitro-1-naphthalenyl)-5,8-methanoimidazo[1,5-a]pyrazine-1,3(2H,5H)-dione. | 2.4 LC 434.37 [M + H]$^+$ | 102A |

TABLE 3-continued

| Ex. No | G | X | Compound Name | Retention Time Min./ Molecular Mass | Procedure of Ex. |
|---|---|---|---|---|---|
| 138 | 4-nitro-1-methylnaphthalenyl | 4-butylbenzoyl | [5S-(5α,8α,8aα)]-7-(4-Butylbenzoyl)tetrahydro-2-(4-nitro-1-naphthalenyl)-5,8-methanoimidazo[1,5-a]pyrazine-1,3(2H,5H)-dione. | 3.69 LC 499.45 [M + H]+ | 102A |
| 139 | 4-nitro-1-methylnaphthalenyl | (3-chloro-4-fluorophenyl)urea | [5S-(5α,8α,8aα)]-N-(3-Chloro-4-fluorophenyl)hexahydro-2-(4-nitro-1-naphthalenyl)-1,3-dioxo-5,8-methanoimidazo[1,5-a]pyrazine-7(8H)-carboxamide. | 3.30 LC 510.34 [M + H]+ | 102D |
| 140 | 4-nitro-1-methylnaphthalenyl | 4-(trifluoromethyl)benzoyl | [5S-(5α,8α,8aα)]-Tetrahydro-2-(4-nitro-1-naphthalenyl)-7-[4-(trifluoromethyl)benzoyl]-5,8-methanoimidazo[1,5-a]pyrazine-1,3(2H,5H)-dione. | 3.78 LC 526.38 [M + H]+ | 102D |
| 141 | 4-nitro-1-methylnaphthalenyl | isopropylurea | [5S-(5α,8α,8aα)]-Hexahydro-N-(1-methylethyl)-2-(4-nitro-1-naphthalenyl)-1,3-dioxo-5,8-methanoimidazo[1,5-a]pyrazine-7(8H)-carboxamide. | 3.07 LC 424.43 [M + H]+ | 102D |
| 142 | 4-nitro-1-methylnaphthalenyl | (4-fluorophenyl)urea | [5S-(5α,8α,8aα)]-N-(4-Fluorophenyl)hexahydro-2-(4-nitro-1-naphthalenyl)-1,3-dioxo-5,8-methanoimidazo[1,5-a]pyrazine-7(8H)-carboxamide. | 3.00 LC 476.37 [M + H]+ | 102D |
| 143 | 4-nitro-1-methylnaphthalenyl | (4-fluorophenyl)methylurea | [5S-(5α,8α,8aα)]-N-[(4-Fluorophenyl)methyl]hexahydro-2-(4-nitro-1-naphthalenyl)-1,3-dioxo-5,8-methanoimidazo[1,5-a]pyrazine-7(8H)-carboxamide. | 3.43 LC 490.39 [M + H]+ | 102D |

TABLE 3-continued

| Ex. No | G | X | Compound Name | Retention Time Min./ Molecular Mass | Procedure of Ex. |
|---|---|---|---|---|---|
| 144 | 4-methyl-1-nitronaphthalenyl | 4-nitrophenyl carbamate | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-nitrophenyl ester. | 3.23 LC 536.40 [Me + MeOH]+ | 102B |
| 145 | 4-methyl-1-nitronaphthalenyl | 4-fluorophenyl carbamate | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-fluorophenyl ester. | 3.21 LC 477.38 [M + H]+ | 102B |
| 146 | 4-methyl-1-nitronaphthalenyl | 4-nitrobenzyl carbamate | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, 4-(nitrophenyl)methyl ester | 3.01 LC 518.38 [M + H]+ | 102B |
| 147 | 4-methyl-1-nitronaphthalenyl | butyl carbamate | [5S-(5α,8α,8aα)]-Hexahydro-2-(4-nitro-1-naphthalenyl)-1,3-dioxo-5,8-methanoimidazo[1,5-a]pyrazine-7(8H)-carboxylic acid, butyl ester. | 3.22 LC 439.43 [M + H]+ | 102B |
| 148 | 4-methyl-1-nitronaphthalenyl | 1-methyl-1H-imidazol-4-yl sulfonyl | [5S-(5α,8α,8aα)]-Tetrahydro-7-[(1-methyl-1H-imidazol-4-yl)sulfonyl]-2-(4-nitro-1-naphthalenyl)-5,8-methanoimidazo[1,5-a]pyrazine-1,3(2H,5H)-dione. | 2.45 LC 483.39 [M + H]+ | 102C |
| 149 | 4-methyl-1-nitronaphthalenyl | 4-chloro-3-nitrophenyl sulfonyl | [5S-(5α,8α,8aα)]-7-[(4-Chloro-3-nitrophenyl)sulfonyl]tetrahydro-2-(4-nitro-1-naphthalenyl)-5,8-methanoimidazo[1,5-a]pyrazine-1,3(2H,5H)-dione. | 3.43 LC 556.26 [M − H]+ | 102C |

TABLE 3-continued

| Ex. No | G | X | Compound Name | Retention Time Min./ Molecular Mass | Procedure of Ex. |
|---|---|---|---|---|---|
| 150 | 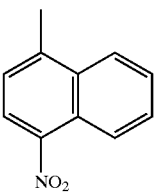 | 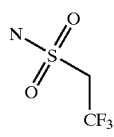 | [5S-(5α,8α,8aα)]-Tetrahydro-2-(4-nitro-1-naphthalenyl)-7-[(2,2,2-trifluoroethyl)sulfonyl]-5,8-methanoimidazo[1,5-a]pyrazine-1,3(2H,5H)-dione. | 2.90 LC 483.17 [M − H]⁺ | 102C |
| 151 | 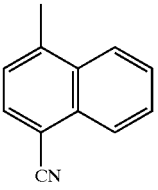 |  | [5S-(5α,8α,8aα)]-7-Acetyl-2-(4-cyano-1-naphthalenyl)tetrahydro-5,8-methanoimidazo[1,5-a]pyrazine-1,3(2H,5H)-dione. | 2.07 LC 359.35 [M − H]⁺ | 102A |
| 152 | 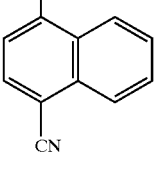 | 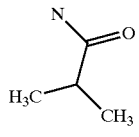 | [5S-(5α,8α,8aα)]-2-(4-Cyano-1-naphthalenyl)tetrahydro-7-(2-methyl-1-oxopropyl)-5,8-methanoimidazo[1,5-a]pyrazine-1,3(2H,5H)-dione. | 2.52 LC 389.44 [M + H]⁺ | 102A |
| 153 | 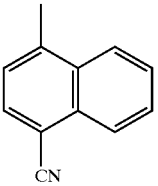 | 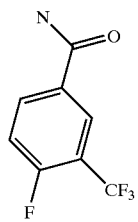 | [5S-(5α,8α,8aα)]-2-(4-Cyano-1-naphthalenyl)-7-[4-fluoro-3-(trifluoromethyl)benzoyl]tetrahydro-5,8-methanoimidazo[1,5-a]pyrazine-1,3(2H,5H)-dione. | 3.24 LC 509.40 [M + H]⁺ | 102A |
| 154 | 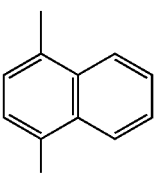 | 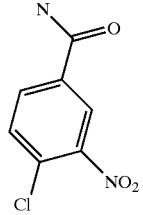 | [5S-(5α,8α,8aα)]-7-(4-Chloro-3-nitrobenzoyl)-2-(4-cyano-1-naphthalenyl)tetrahydro-5,8-methanoimidazo[1,5-a]pyrazine-1,3(2H,5H)-dione. | 3.11 LC 502.33 [M + H]⁺ | 102A |
| 155 | 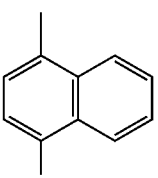 | 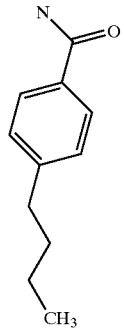 | [5S-(5α,8α,8aα)]-7-(4-Butylbenzoyl)-2-(4-cyano-1-naphthalenyl)tetrahydro-5,8-methanoimidazo[1,5-a]pyrazine-1,3(2H,5H)-dione. | 3.58 LC 479.47 [M + H]⁺ | 102A |

TABLE 3-continued

| Ex. No | G | X | Compound Name | Retention Time Min./ Molecular Mass | Procedure of Ex. |
|---|---|---|---|---|---|
| 156 | 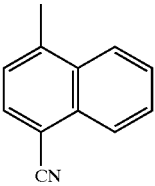 | 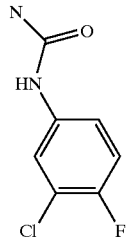 | [5S-(5α,8α,8aα)]-N-(3-Chloro-4-fluorophenyl)-2-(4-cyano-1-naphthalenyl)hexahydro-1,3-dioxo-5,8-methanoimidazo[1,5-a]pyrazine-7(8H)-carboxamide. | 3.20 LC 488.36 [M − H]⁺ | 102D |
| 157 | 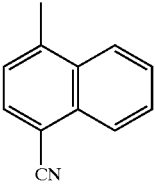 | 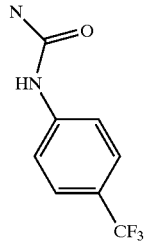 | [5S-(5α,8α,8aα)]-2-(4-Cyano-1-naphthalenyl)hexahydro-1,3-dioxo-N-[4-(trifluoromethyl)phenyl]-5,8-methanoimidazo[1,5-a]pyrazine-7(8H)-carboxamide. | 3.29 LC 504.38 [M − H]⁺ | 102D |
| 158 | 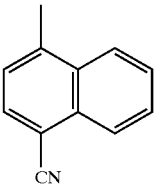 | 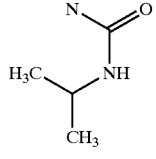 | [5S-(5α,8α,8aα)]-2-(4-Cyano-1-naphthalenyl)hexahydro-N-(1-methylethyl)-1,3-dioxo-5,8-methanoimidazo[1,5-a]pyrazine-7(8H)-carboxamide. | 2.48 LC 404.43 [M − H]⁺ | 102D |
| 159 | 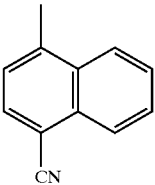 | 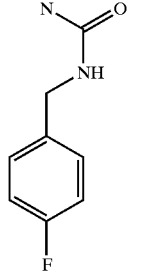 | [5S-(5α,8α,8aα)]-2-(4-Cyano-1-naphthalenyl)-N-[(4-fluorophenyl)methyl]hexahydro-1,3-dioxo-5,8-methanoimidazo[1,5-a]pyrazine-7(8H)-carboxamide. | 2.89 LC 470.41 [M + H]⁺ | 102D |
| 160 | 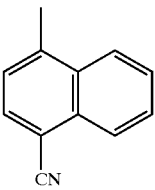 | 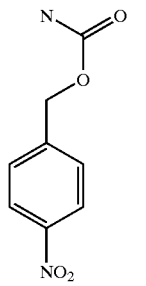 | [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, 4-(nitrophenyl)methyl ester. | 2.88 LC 496.36 [M − H]⁺ | 102B |
| 161 | 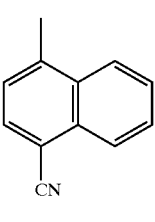 | 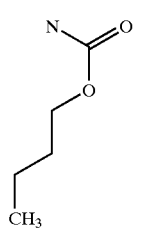 | [5S-(5α,8α,8aα)]-2-(4-Cyano-1-naphthalenyl)hexahydro-1,3-dioxo-5,8-methanoimidazo[1,5-a]pyrazine-7(8H)-carboxylic acid, butyl ester. | 3.09 LC 417.39 [M − H]⁺ | 102B |

TABLE 3-continued

| Ex. No | G | X | Compound Name | Retention Time Min./ Molecular Mass | Procedure of Ex. |
|---|---|---|---|---|---|
| 162 | 4-methyl-1-naphthalenyl-CN | 4-chloro-3-nitrophenylsulfonyl | [5S-(5α,8α,8aα)]-7-[(4-Chloro-3-nitrophenyl)sulfonyl]-2-(4-cyano-1-naphthalenyl)tetrahydro-5,8-methanoimidazo[1,5-a]pyrazine-1,3(2H,5H)-dione. | 3.31 LC 536.28 [M − H]⁺ | 102C |
| 163 | 4-methyl-1-naphthalenyl-CN | (2,2,2-trifluoroethyl)sulfonyl | [5S-(5α,8α,8aα)]-2-(4-Cyano-1-naphthalenyl)tetrahydro-7-[(2,2,2-trifluoroethyl)sulfonyl]-5,8-methanoimidazo[1,5-a]pyrazine-1,3(2H,5H)-dione. | 2.72 LC 463.31 [M − H]⁺ | 102C |
| 164 | 4-cyano-3-(trifluoromethyl)phenyl | acetyl | [5S-(5α,8α,8aα)]-7-Acetyl-2-[4-cyano-3-(trifluoromethyl)phenyl]tetrahydro-5,8-methanoimidazo[1,5-a]pyrazine-1,3(2H,5H)-dione. | 2.26 LC 377.32 [M − H]⁺ | 102A |
| 165 | 4-cyano-3-(trifluoromethyl)phenyl | 2-methyl-1-oxopropyl | [5S-(5α,8α,8aα)]-2-[4-Cyano-3-(trifluoromethyl)phenyl]tetrahydro-7-(2-methyl-1-oxopropyl)-5,8-methanoimidazo[1,5-a]pyrazine-1,3(2H,5H)-dione. | 2.82 LC 405.36 [M − H]⁺ | 102A |
| 166 | 4-cyano-3-(trifluoromethyl)phenyl | 4-fluoro-3-(trifluoromethyl)benzoyl | [5S-(5α,8α,8aα)]-2-[4-Cyano-3-(trifluoromethyl)phenyl]-7-[4-fluoro-3-(trifluoromethyl)benzoyl]tetrahydro-5,8-methanoimidazo[1,5-a]pyrazine-1,3(2H,5H)-dione. | 3.38 LC 525.31 [M − H]⁺ | 102A |
| 167 | 4-cyano-3-(trifluoromethyl)phenyl | 4-chloro-3-nitrobenzoyl | [5S-(5α,8α,8aα)]-7-(4-Chloro-3-nitrobenzoyl)-2-[4-cyano-3-(trifluoromethyl)phenyl]tetrahydro-5,8-methanoimidazo[1,5-a]pyrazine-1,3(2H,5H)-dione. | 3.24 LC 518.30 [M − H]⁺ | 102A |
| 168 | 4-cyano-3-(trifluoromethyl)phenyl | 5-isoxazolylcarbonyl | [5S-(5α,8α,8aα)]-2-[4-Cyano-3-(trifluoromethyl)phenyl]tetrahydro-7-(5-isoxazolylcarbonyl)-5,8-methanoimidazo[1,5-a]pyrazine-1,3(2H,5H)-dione. | 2.40 LC 430.34 [M − H]⁺ | 102A |

TABLE 3-continued

| Ex. No | G | X | Compound Name | Retention Time Min./ Molecular Mass | Procedure of Ex. |
|---|---|---|---|---|---|
| 169 | 4-methyl-2-(trifluoromethyl)benzonitrile group | 4-butylbenzoyl group | [5S-(5α,8α,8aα)]-7-(4-Butylbenzoyl)-2-[4-cyano-3-(trifluoromethyl)phenyl]tetrahydro-5,8-methanoimidazo[1,5-a]pyrazine-1,3(2H,5H)-dione. | 3.65 LC 495.42 [M − H]⁺ | 102A |
| 170 | 4-methyl-2-(trifluoromethyl)benzonitrile group | N-(3-chloro-4-fluorophenyl)carboxamide group | [5S-(5α,8α,8aα)]-N-(3-Chloro-4-fluorophenyl)-2-[4-cyano-3-(trifluoromethyl)phenyl]hexahydro-1,3-dioxo-5,8-methanoimidazo[1,5-a]pyrazine-7(8H)-carboxamide. | 3.24 LC 508.31 [M + H]⁺ | 102D |
| 171 | 4-methyl-2-(trifluoromethyl)benzonitrile group | N-[4-(trifluoromethyl)phenyl]carboxamide group | [5S-(5α,8α,8aα)]-2-[4-Cyano-3-(trifluoromethyl)phenyl]hexahydro-1,3-dioxo-N-[4-(trifluoromethyl)phenyl]-5,8-methanoimidazo[1,5-a]pyrazine-7(8H)-carboxamide. | 3.34 LC 522.33 [M − H]⁺ | 102D |
| 172 | 4-methyl-2-(trifluoromethyl)benzonitrile group | N-(1-methylethyl)carboxamide group | [5S-(5α,8α,8aα)]-2-[4-Cyano-3-(trifluoromethyl)phenyl]hexahydro-N-(1-methylethyl)-1,3-dioxo-5,8-methanoimidazo[1,5-a]pyrazine-7(8H)-carboxamide. | 2.63 LC 422.40 [M + H]⁺ | 102D |
| 173 | 4-methyl-2-(trifluoromethyl)benzonitrile group | N-(4-fluorophenyl)carboxamide group | [5S-(5α,8α,8aα)]-2-[4-Cyano-3-(trifluoromethyl)phenyl]-N-(4-fluorophenyl)hexahydro-1,3-dioxo-5,8-methanoimidazo[1,5-a]pyrazine-7(8H)-carboxamide. | 3.02 LC 472.35 [M − H]⁺ | 102D |

TABLE 3-continued

| Ex. No | G | X | Compound Name | Retention Time Min./ Molecular Mass | Procedure of Ex. |
|---|---|---|---|---|---|
| 174 | 4-CN, 3-CF₃, 1-methyl phenyl | N-[(4-fluorophenyl)methyl] carbamoyl | [5S-(5α,8α,8aα)]-2-[4-Cyano-3-(trifluoromethyl)phenyl]-N-[(4-fluorophenyl)methyl]hexahydro-1,3-dioxo-5,8-methanoimidazo[1,5-a]pyrazine-7(8H)-carboxamide. | 3.09 LC 488.38 [M + H]⁺ | 102D |
| 175 | 4-CN, 3-CF₃, 1-methyl phenyl | 4-nitrophenyl carbonate | [5S-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, 4-nitrophenyl ester. | 3.19 LC 534.37 [M + MeOH]⁺ | 102B |
| 176 | 4-CN, 3-CF₃, 1-methyl phenyl | 4-fluorophenyl carbonate | [5S-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, 4-fluorophenyl ester. | 3.20 LC 507.38 [M + MeOH]⁺ | 102B |
| 177 | 4-CN, 3-CF₃, 1-methyl phenyl | 4-nitrobenzyl carbonate | [5S-(8α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, 4-(nitrophenyl)methyl ester | 3.06 LC 546.34 [M + MeOH]⁺ | 102B |
| 178 | 4-CN, 3-CF₃, 1-methyl phenyl | butyl carbonate | [5S-(5α,8α,8aα)]-2-[4-Cyano-3-(trifluoromethyl)phenyl]hexahydro-1,3-dioxo-5,8-methanoimidazo[1,5-a]pyrazine-7(8H)-carboxylic acid, butyl ester. | 3.22 LC 469.43 [M + MeOH]⁺ | 102B |
| 179 | 4-CN, 3-CF₃, 1-methyl phenyl | (1-methyl-1H-imidazol-4-yl)sulfonyl | [5S-(5α,8α,8aα)]-2-[4-Cyano-3-(trifluoromethyl)phenyl]tetrahydro-7-[(1-methyl-1H-imidazol-4-yl)sulfonyl]-5,8-methanoimidazo[1,5-a]pyrazine-1,3(2H,5H)-dione. | 2.35 LC 481.33 [M + H]⁺ | 102C |

TABLE 3-continued

| Ex. No | G | X | Compound Name | Retention Time Min./ Molecular Mass | Procedure of Ex. |
|---|---|---|---|---|---|
| 180 | 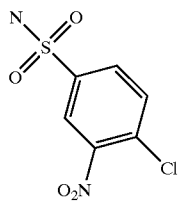 | 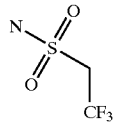 | [5S-(5α,8α,8aα)]-7-[(4-Chloro-3-nitrophenyl)sulfonyl]-2-[4-cyano-3-(trifluoromethyl)phenyl]tetrahydro-5,8-methanoimidazo[1,5-a]pyrazine-1,3(2H,5H)-dione. | 3.29 LC 554.25 [M − H]$^+$ | 102C |
| 181 | 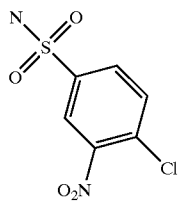 | 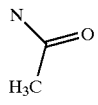 | [5S-(5α,8α,8aα)]-2-[4-Cyano-3-(trifluoromethyl)phenyl]tetrahydro-7-[(2,2,2-trifluoroethyl)sulfonyl]-5,8-methanoimidazo[1,5-a]pyrazine-1,3(2H,5H)-dione. | 4.32 LC 481.29 [M − H]$^+$ | 102C |
| 182 | 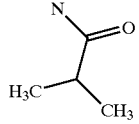 | 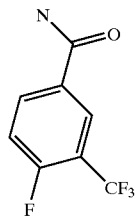 | [5S-(5α,8α,8aα)]-7-Acetyl-2-(4-cyano-3-iodophenyl)tetrahydro-5,8-methanoimidazo[1,5-a]pyrazine-1,3(2H,5H)-dione. | 2.07 LC 435.24 [M − H]$^+$ | 102A |
| 183 | 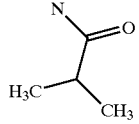 | 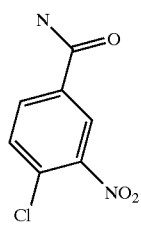 | [5S-(5α,8α,8aα)]-2-(4-Cyano-3-iodophenyl)tetrahydro-7-(2-methyl-1-oxopropyl)-5,8-methanoimidazo[1,5-a]pyrazine-1,3(2H,5H)-dione. | 2.48 LC 463.26 [M − H]$^+$ | 102A |
| 184 | 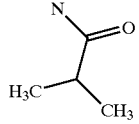 | 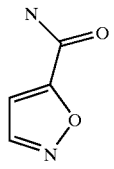 | [5S-(5α,8α,8aα)]-2-(4-Cyano-3-iodophenyl)-7-[4-fluoro-3-(trifluoromethyl)benzoyl]tetrahydro-5,8-methanoimidazo[1,5-a]pyrazine-1,3(2H,5H)-dione. | 3.32 LC 583.21 [M − H]$^+$ | 102A |
| 185 | 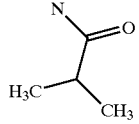 | | [5S-(5α,8α,8aα)]-7-(4-Chloro-3-nitrobenzoyl)-2-(4-cyano-3-iodophenyl)tetrahydro-5,8-methanoimidazo[1,5-a]pyrazine-1,3(2H,5H)-dione. | 3.10 LC 576.18 [M − H]$^+$ | 102A |
| 186 | 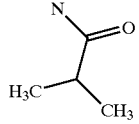 | | [5S-(5α,8α,8aα)]-2-(4-Cyano-3-iodophenyl)tetrahydro-7-(5-isoxazolylcarbonyl)-5,8-methanoimidazo[1,5-a]pyrazine-1,3(2H,5H)-dione. | 2.22 LC 488.24 [M − H]$^+$ | 102A |

TABLE 3-continued

| Ex. No | G | X | Compound Name | Retention Time Min./ Molecular Mass | Procedure of Ex. |
|---|---|---|---|---|---|
| 187 | 4-methyl-2-iodo-benzonitrile | 4-(butyl)benzoyl | [5S-(5α,8α,8aα)]-7-(4-Butylbenzoyl)-2-(4-cyano-3-iodophenyl) tetrahydro-5,8-methanoimidazo[1,5-a]pyrazine-1,3(2H,5H)-dione. | 3.58 LC 553.29 [M − H]+ | 102A |
| 188 | 4-methyl-2-iodo-benzonitrile | 3-chloro-4-fluorophenyl urea | [5S-(5α,8α,8aα)]-N-(3-Chloro-4-fluorophenyl)-2-(4-cyano-3-iodophenyl)hexahydro-1,3-dioxo-5,8-methanoimidazo[1,5-a]pyrazine-7(8H)-carboxamide. | 3.09 LC 566.22 [M + H]+ | 102D |
| 189 | 4-methyl-2-iodo-benzonitrile | 4-(trifluoromethyl)phenyl urea | [5S-(5α,8α,8aα)]-2-(4-Cyano-3-iodophenyl)hexahydro-1,3-dioxo-N-[4-(trifluoromethyl)phenyl]-5,8-methanoimidazo[1,5-a]pyrazine-7(8H)-carboxamide. | 3.21 LC 580.21 [M − H]+ | 102D |
| 190 | 4-methyl-2-iodo-benzonitrile | isopropyl urea | [5S-(5α,8α,8aα)]-2-(4-Cyano-3-iodophenyl)hexahydro-N-(1-methylethyl)-1,3-dioxo-5,8-methanoimidazo[1,5-a]pyrazine-7(8H)-carboxamide. | 2.39 LC 480.31 [M + H]+ | 102D |
| 191 | 4-methyl-2-iodo-benzonitrile | 4-fluorophenyl urea | [5S-(5α,8α,8aα)]-2-(4-Cyano-3-iodophenyl)-N-(4-fluorophenyl)hexahydro-1,3-dioxo-5,8-methanoimidazo[1,5-a]pyrazine-7(8H)-carboxamide. | 2.90 LC 530.23 [M − H]+ | 102D |

TABLE 3-continued

| Ex. No | G | X | Compound Name | Retention Time Min./ Molecular Mass | Procedure of Ex. |
|---|---|---|---|---|---|
| 192 | 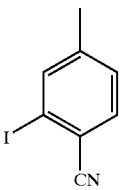 | 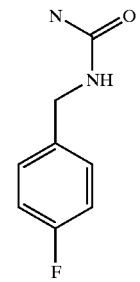 | [5S-(5α,8α,8aα)]-2-(4-Cyano-3-iodophenyl)-N-[(4-fluorophenyl)methyl]hexahydro-1,3-dioxo-5,8-methanoimidazo[1,5-a]pyrazine-7(8H)-carboxamide. | 2.75 LC 544.25 [M − H]+ | 102D |
| 193 | 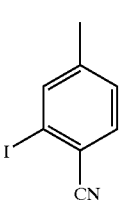 | 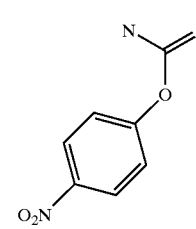 | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 4-nitrophenyl ester. | 2.99 LC 590.25 [M + MeOH]+ | 102B |
| 194 | 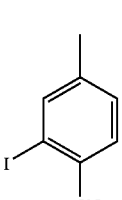 | 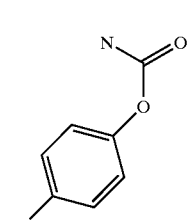 | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, 4-fluorophenyl ester. | 3.02 LC 565.26 [M + MeOH]+ | 102B |
| 195 | 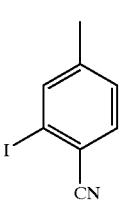 | 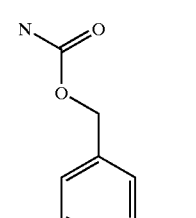 | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, (4-nitrophenyl)methyl ester. | 2.89 LC 572.22 [M − H]+ | 102B |
| 196 | 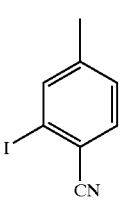 | 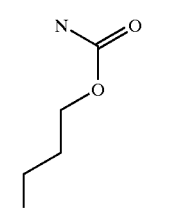 | [5S-(5α,8α,8aα)]-2-(4-Cyano-3-iodophenyl)hexahydro-1,3-dioxo-5,8-methanoimidazo[1,5-a]pyrazine-7(8H)-carboxylic acid, butyl ester. | 3.04 LC 493.28 [M − H]+ | 102B |
| 197 | 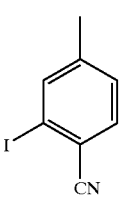 | 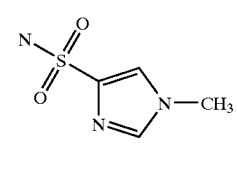 | [5S-(5α,8α,8aα)]-2-(4-Cyano-3-iodophenyl)tetrahydro-7-[(1-methyl-1H-imidazol-4-yl)sulfonyl]-5,8-methanoimidazo[1,5-a]pyrazine-1,3(2H,5H)-dione. | 2.16 LC 539.22 [M + H]+ | 102D |

TABLE 3-continued

| Ex. No | G | X | Compound Name | Retention Time Min./ Molecular Mass | Procedure of Ex. |
|---|---|---|---|---|---|
| 198 | 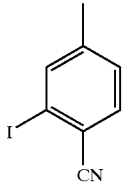 | 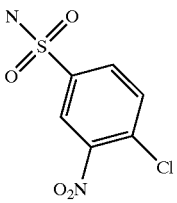 | [5S-(5α,8α,8aα)]-7-[(4-Chloro-3-nitrophenyl)sulfonyl]-2-(4-cyano-3-iodophenyl)tetrahydro-5,8-methanoimidazo[1,5-a]pyrazine-1,3(2H,5H)-dione. | 3.13 LC 612.15 [M − H]⁺ | 102D |
| 199 | 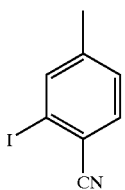 | 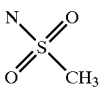 | [5S-(5α,8α,8aα)]-2-(4-Cyano-3-iodophenyl)tetrahydro-7-(methylsulfonyl)-5,8-methanoimidazo[1,5-a]pyrazine-1,3(2H,5H)-dione. | 2.11 LC 471.20 [M − H]⁺ | 102D |

EXAMPLES 200 TO 217

Additional compounds of the present invention were prepared by procedures analogous to those described above. The compounds of Examples 200 to 217 have the following structure (L is a bond):

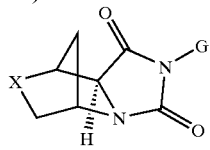

where G, X, the compound name, retention time, molecular mass, and the procedure employed, are set forth in Table 4. The chromatography techniques used to determine the compound retention times of Table 4 are as follows: LCMS= YMC S5 ODS column, 4.6×50 mm eluting with 10–90% MeOH/H₂O over 4 minutes containing 0.1% TFA; 4 mL/min, monitoring at 220 nm. LCMS*=YMC S5 ODS column, 4.6×50 mm eluting with 10–90% MeOH/H₂O over 2 minutes containing 0.1% TFA; 4 mL/min, monitoring at 220 nm. LC=YMC S5 ODS column 4.6×50 mm eluting with 10–90% MeOH/H₂O over 4 minutes containing 0.2% phosphoric acid, 4 mL/min, monitoring at 220 nm. The molecular mass of the compounds listed in Table 4 were determined by MS (ES) by the formula m/z.

TABLE 4

| Ex. No | G | X | Compound Name | Retention Time Min./ Molecular Mass | Procedure of Ex. |
|---|---|---|---|---|---|
| 200 | 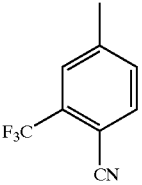 | NH | [5S-(5α,8α,8αβ)]-4-(Hexahydro-1,3-dioxo-5,8-methanoimidazo[1,5-a]pyrazin-2(3H)-yl)-2-(trifluoromethyl)benzonitrile. | 1.46 LC | 91 |
| 201 | 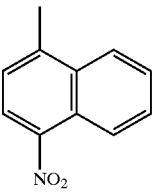 | 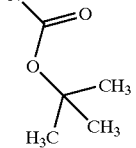 | [5R-(5α,8α,8aβ)]-Hexahydro-2-(4-nitro-1-naphthalenyl)-1,3-dioxo-5,8-methanoimidazo[1,5-a]pyrazine-7(8H)-carboxylic acid, 1,1-dimethylethyl ester. | 3.29 LC | 93 |
| 202 | 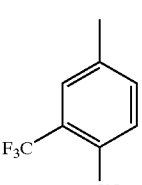 | 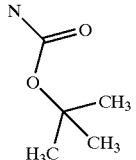 | [5S-(5α,8α,8aβ)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester. | 3.28 LC | 90 |

TABLE 4-continued

| Ex. No | G | X | Compound Name | Retention Time Min./ Molecular Mass | Procedure of Ex. |
|---|---|---|---|---|---|
| 203 | 1-methyl-4-nitronaphthalenyl | NH | [5S-(5α,8α,8aβ)]-Tetrahydro-2-(4-nitro-1-naphthalenyl)-5,8-methanoimidazo[1,5-a]pyrazine-1,3(2H,5H)-dione, trifluoroacetate (1:1). | 1.83 LC | 95 |
| 204 | 4-methyl-2-trifluoromethyl-1-cyanophenyl | N-C(=O)-O-C(CH₃)₂CH₃ (Boc) | [5R-(5α,8α,8aβ)]-2-[4-Cyano-3-(trifluoromethyl)phenyl]hexahydro-1,3-dioxo-5,8-methanoimidazo[1,5-a]pyrazine-7(8H)-carboxylic acid, 1,1-dimethylethyl ester. | 3.29 LC | 93 |
| 205 | 1-methyl-4-nitronaphthalenyl | N-C(=O)-O-C(CH₃)₂CH₃ (Boc) | [5S-(5α,8α,8aβ)]-Hexahydro-2-(4-nitro-1-naphthalenyl)-1,3-dioxo-5,8-methanoimidazo[1,5-a]pyrazine-7(8H)-carboxylic acid, 1,1-dimethylethyl ester. | 3.35 LC | 94 |
| 206 | 4-methyl-2-trifluoromethyl-1-cyanophenyl | NH | [5R-(5α,8α,8aβ)]-4-(Hexahydro-1,3-dioxo-5,8-methanoimidazo[1,5-a]pyrazin-2(1H)-yl)-2-(trifluoromethyl)benzonitrile. | 3.29 LC | 91 |
| 207 | 4-methyl-2-trifluoromethyl-1-cyanophenyl | N-C(=O)-Ph | [5S-(5α,8α,8aβ)]-4-(7-Benzoylhexahydro-1,3-dioxo-5,8-methanoimidazo[1,5-a]pyrazin-2(3H)-yl)-2-(trifluoromethyl)benzonitrile. | 3.09 LC | 102A |
| 208 | 2-methyl-4-nitrophenyl | CH₂ | (5α,8α,8aβ)-Tetrahydro-2-(2-methyl-4-nitrophenyl)-5,8-methanoimidazo[1,5-a]pyridine-1,3(2H,5H)-dione. | 2.61 LC | 7 |
| 209 | 1-methyl-4-nitronaphthalenyl | N-C(=O)-Ph | [5S-(5α,8α,8aβ)]-7-Benzoyltetrahydro-2-(4-nitro-1-naphthalenyl)-5,8-methanoimidazo[1,5-a]pyrazine-1,3(2H,5H)-dione. | 2.97 LC | 102A |

TABLE 4-continued

| Ex. No | G | X | Compound Name | Retention Time Min./ Molecular Mass | Procedure of Ex. |
|---|---|---|---|---|---|
| 210 | (2-methylbenzofuran) | CH₂ | (5α,8α,8aβ)-2-(2-Benzofuranyl) tetrahydro-5,8-methanoimidazo[1,5-a]pyridine-1,3(2H,5H)-dione. | 2.95 LC | 7 |
| 211 | (2,3-dimethyl-4,5,6,7-tetrafluorobenzofuran) | CH₂ | (5α,8α,8aβ)-Tetrahydro-2-(4,5,6,7-tetrafluoro-2-methyl-3-benzofuranyl)-5,8-methanoimidazo[1,5-a]pyridine-1,3(2H,5H)-dione. | 3.52 LC | 7 |
| 212 | (3-methoxy-4-(4-oxazolyl)-methylphenyl) | CH₂ | (5α,8α,8aβ)-Tetrahydro-2-[3-methoxy-4-(4-oxazolyl)phenyl]-5,8-methanoimidazo[1,5-a]pyridine-1,3(2H,5H)-dione. | 2.79 LC | 7 |
| 213 | (4-cyano-1-methylnaphthalenyl) | N-C(=O)-O-C(CH₃)₃ | [5S-(5α,8α,8aβ)]-2-(4-Cyano-1-naphthalenyl)hexahydro-1,3-dioxo-5,8-methanoimidazo[1,5-a]pyrazine-7(8H)-carboxylic acid, 1,1-dimethylethyl ester. | 3.17 LC | 94 |
| 214 | (4-cyano-3-iodo-methylphenyl) | N-C(=O)-O-C(CH₃)₃ | [5S-(5α,8α,8aβ)]-2-(4-Cyano-3-iodophenyl)hexahydro-1,3-dioxo-5,8-methanoimidazo[1,5-a]pyrazine-7(8H)-carboxylic acid, 1,1-dimethylethyl ester. | 3.22 LC | 90 |
| 215 | (2,3-dimethylbenzofuran) | CH₂ | (5α,8α,8aβ)-Tetrahydro-2-(2-methyl-3-benzofuranyl)-5,8-methanoimidazo[1,5-a]pyridine-1,3(2H,5H)-dione. | 2.80 LC | 7 |
| 216 | (3,5-dichloro-methylphenyl) | N-C(=O)-O-C(CH₃)₃ | [5S-(5α,8α,8aβ)]-2-(3,5-Dichlorophenyl)hexahydro-1,3-dioxo-5,8-methanoimidazo[1,5-a]pyrazine-7(8H)-carboxylic acid, 1,1-dimethylethyl ester. | 3.59 LC | 90 |

TABLE 4-continued

| Ex. No | G | X | Compound Name | Retention Time Min./ Molecular Mass | Procedure of Ex. |
|---|---|---|---|---|---|
| 217 | 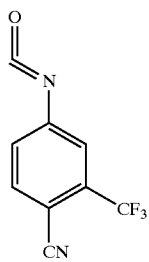 | CH$_2$ | (5α,8α,8aβ)-2-(2,2-Dimethyl-2H-1-benzopyran-4-yl)tetrahydro-5,8-methanoimidazo[1,5-a]pyridine-1,3(2H,5H)-dione. | 3.03 LC | 7 |

EXAMPLE 218

4-Isocyanato-2-trifluoromethyl benzonitrile

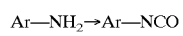

A. General procedure for the conversion of anilines to isocyanates: (218A)

Ar—NH$_2$→Ar—NCO

To a solution of aryl/heteroaryl amine (5 mmol, 1.0 eq) in anhydrous methylene chloride (200 mL) at 0° C. was added sodium bicarbonate (50 mmol, 10.0 eq). To this stirred suspension was added a solution of phosgene (20 mmol, 20% solution in toluene). The reaction mixture was allowed to warm up to rt over 1 h and continued to stir at rt until the reaction was complete. The reaction was monitored by removing aliquots that were filtered and concentrated in vacuo to remove excess phosgene. The residue was reacted with excess piperidine in methylene chloride. The ratio of starting aniline to urea (as determined by LC-MS) indicated the progress of the reaction. When the reaction was complete by (LCMS), the reaction mixture was filtered to get rid of the inorganics and the filtrate was concentrated in vacuo to obtain the crude isocyanate that was used in the next step without further purification.

B. 4-Isocyanato-2-trifluoromethyl benzonitrile (218B)

To a solution of 3-trifluoromethyl-phenylamine (0.372 g, 2 mmol) in anhydrous dichloromethane (50 mL) at 0° C. was added sodium bicarbonate (1.7 g, 20 mmol) followed by a solution of phosgene (4 mL, 20% solution in toluene). The reaction mixture was warmed up to rt over 1 h and stirred for an additional 3 h. The reaction mixture was concentrated in vacuo to generate compound 218B which was used directly in the next step without further purification.

EXAMPLE 219

[5S-(5α,8α,8aα)]-2-[3-(Trifluoromethyl)phenyl]hexahydro-1,3-dioxo-5,8-methanoimidazo[1,5-a]pyrazine-7(8H)-carboxylic acid, 1,1-dimethylethyl ester &

[5S-(5α,8α,8aβ)]-2-[3-(Trifluoromethyl)phenyl]hexahydro-1,3-dioxo-5,8-methanoimidazo[1,5-a]pyrazine-7(8H)-carboxylic acid, 1,1-dimethylethyl ester (219Bi & 219Bii)

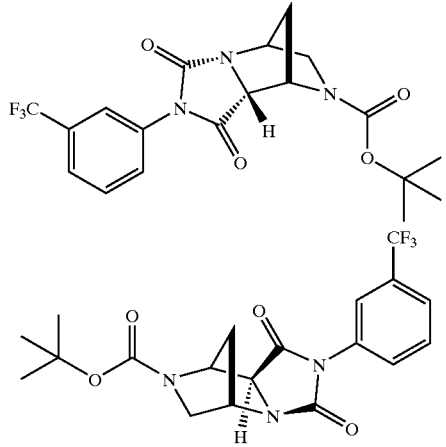

A. General procedure for formation of hydantoin system: (219Aii & 219Aiii)

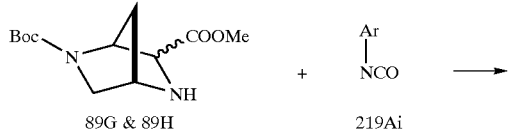

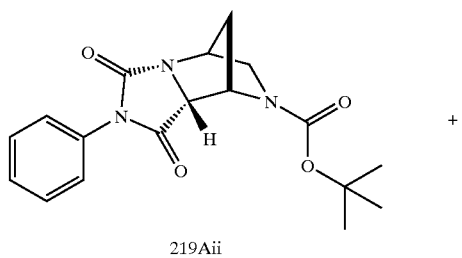

219Aii

169
-continued

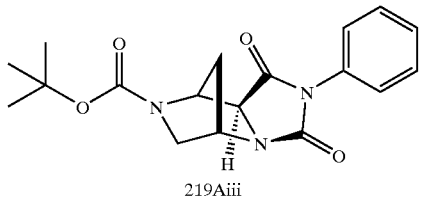

219Aiii

To a solution of a mixture of compounds 89G & 89H (5 mmol, 1.0 eq) in anhydrous chloroform (50 mL) was added molecular sieves (1 g, 4 Å, activated, crushed). To this stirred suspension was added a solution of the aryl/heteroaryl isocyanate, compound 219Ai (5 mmol, 1.0 eq, made as described in example 218) in anhydrous toluene (50 mL). After compounds 89G & 89H were converted to the intermediate urea, as determined by LCMS, 1,5,7-triazabicyclo[4.4.0]dec-5-ene-7-yl polystyrene (2.5 g, 7.5 mmol, Novabiochem Product No. 01-64-0332, Batch# A26683, 2.7 mmol/g) was added. In cases where the reaction was slow, the reaction mixture was heated to 55° C. for 1 h. After the intermediate urea was consumed, (as determined by LC-MS), the reaction mixture was cooled and filtered through celite and washed with EtOAc. The combined filtrate was concentrated in vacuo. Purification by flash chromatography on SiO$_2$ eluting with EtOAc/hexanes gave compounds 219Aii & 219Aiii.

[5S-(5α,8α,8aα)]-2-[3-(Trifluoromethyl)phenyl] hexahydro-1,3-dioxo-5,8-methanoimidazo[1,5-a]pyrazine-7 (8H)-carboxylic acid, 1,1-dimethylethyl ester & [5S-(5α,8α, 8aβ)]-2-[3-(Trifluoromethyl)phenyl]hexahydro-1,3-dioxo-5,8-methanoimidazo[1,5-a]pyrazine-7(8H)-carboxylic acid, 1,1-dimethylethyl ester (219Bi & 219Bii)

To a solution containing a mixture of compounds 89G & 89H (1.28 g, 5 mmol) in anhydrous chloroform (50 mL) was added molecular sieves (1 g, 4 Å, activated). To this stirred suspension was added a solution of 3-trifluoromethylphenyl isocyanate (0.935 g, 5 mmol) in anhydrous toluene (50 mL). After acompounds 89G & 89H were consumed (as determined by LC-MS), 1,5,7-triazabicyclo[4.4.0]dec-5-ene-7-yl polystyrene (2.5 g, 7.5 mmol, Novabiochem Product No. 01-64-0332, Batch# A26683, 2.7 mmol/g) was added and stirred at rt. After the intermediate urea was consumed (as determined by LC-MS), the reaction was filtered through celite and washed with EtOAc. The combined filtrate was concentrated in vacuo. Purification by flash chromatography on SiO$_2$ eluting with 10% to 50% EtOAc/hexanes gave compound 219Bi (0.50 g) and compound 219Bii (0.96 g) adding up to 1.46 g (3.55 mmol, 71% yield). Compound 219Bi: HPLC: 100% at 3.41 min (retention time). Compound 219Bii: 100% at 3.21 min (retention time) (YMC ODS-A column 4.6×50 mm eluting with 10–90% aqueous methanol over 4 minutes containing 0.1% trifluoroacetic acid, 4 mL/min, monitoring at 220 nm). MS (ES): m/z 434.03 [M+Na]+.

170
EXAMPLE 220

[5S-(5α,8α,8aα)]-Tetrahydro-2-(3-(trifluoromethyl) phenyl)-5,8-methanoimidazo[1,5-a]pyrazine-1,3(2H, 5H)-dione & [5S-(5α,8α,8aβ)]-Tetrahydro-2-(3-(trifluoromethyl)phenyl)-5,8-methanoimidazo[1,5-a] pyrazine-1,3(2H,5H)-dione (220Bi & 220Bii)

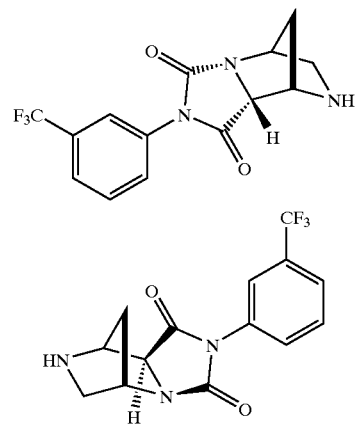

A. General Procedure for the removal of Boc-group: (220A)

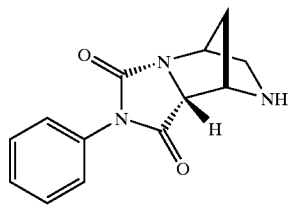

To a dry sample of compound 219Bi (2 mmol, 1.0 eq) was added excess trifluoroacetic acid (25 mL, 20% solution in methylene chloride). After compound 219Bi was consumed, (as determined by LCMS), the reaction mixture was concentrated in vacuo to yield the TFA salt of the free amine. The residue was dissolved in methylene chloride (50 mL) and extracted with saturated aqueous sodium bicarbonate (50 mL). The aqueous layer was extracted with methylene chloride (3×25 mL). The combined organic layers were dried over anhydrous sodium sulfate and concentrated in vacuo to yield the free base of compound 220A, which was used in the next step without further purification.

B. [5S-(5α,8α,8aα)]-Tetrahydro-2-(3-(trifluoromethyl) phenyl)-5,8-methanoimidazo[1,5-a]pyrazine-1,3(2H, 5H)-dione & [5S-(5α,8α,8aβ)]-Tetrahydro-2-(3-(trifluoromethyl)phenyl)-5,8-methanoimidazo[1,5-a] pyrazine-1,3(2H,5H)-dione (220Bi & 220Bii)

Trifluoroacetic acid (20% in methylene chloride, 12 mL) was added to a flask containing compound 219Bi (0.50 g, 1.2 mmol). The reaction mixture was stirred at rt for 1 h. After the starting material was consumed (as determined by LC-MS), the reaction mixture was concentrated in vacuo to yield the TFA salt of compound 220Bi. The residue was dissolved in methylene chloride (50 mL) and extracted with saturated aqueous sodium bicarbonate (50 mL). The aqueous layer was extracted with methylene chloride (3×25 mL). The combined organic layers were dried over anhydrous sodium sulfate and concentrated in vacuo to yield compound 220Bi (0.37 g, 99% yield). HPLC: 100% at 1.94 min (retention times) (YMC ODS-A column 4.6×50 mm eluting with 10–90% aqueous methanol over 4 minutes containing 0.1% trifluoroacetic acid, 4 mL/min, monitoring at 220 nm).

MS (ES): m/z 312.1 [M+H]+. Compound 220Bii was synthesized as described above. MS (ES): m/z 312.1 [M+H]+.

EXAMPLE 221

[5S-(5α,8α,8aα)]-N-1,3-Benzodioxol-5-ylhexahydro-1,3-dioxo-2-[3-(trifluoromethyl)phenyl]-5,8-methanoimidazo[1,5-a]pyrazine-7(1H)-carbothioamide & [5S-(5α,8α,8aα)]-2-(4-Cyano-3-(trifluoromethyl)phenyl)-N-(1,1-dimethylethyl)hexahydro-1,3-dioxo-5,8-methanoimidazo[1,5-a]pyrazine-7(1H)-carboxamide, [5S-(5α,8α,8aα)]-2-[4-Cyano-3-(trifluoromethyl)phenyl]octahydro-1,3-dioxo-7-(1-oxopropyl)-5,8-methanoimidazo[1,5-a]pyrazine, [5S-(5α,8α,8aα)]-2-[4-Cyano-3-(trifluoromethyl)phenyl]hexahydro-1,3-dioxo-5,8-methanoimidazo[1,5-a]pyrazine-7(1H)-carboxylic acid, 1-methyl ester, [5S-(5α,8α,8aα)]-7-[(1-Methylethyl)sulfonyl]tetrahydro-2-[3-(trifluoromethyl)phenyl]-5,8-methanoimidazo[1,5-a]pyrazine-1,3(2H,5H)-dione (221Bi & 221Bii, 221Ci, 221Cii, 221D)

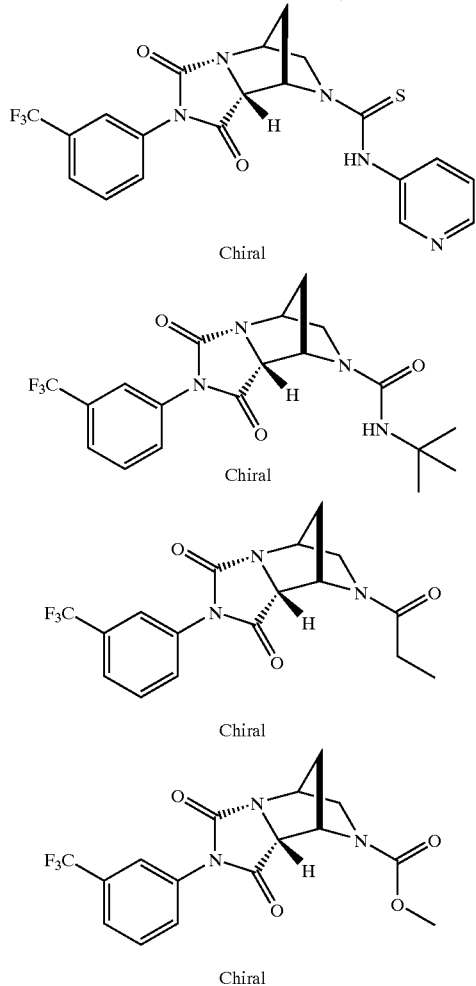

-continued

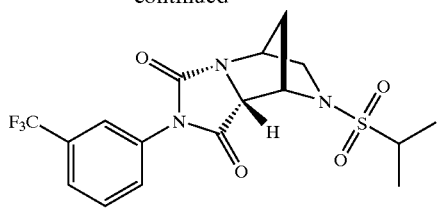

A. General Procedure for the Library Synthesis: (221A)

Stock solutions (0.1 M in anhydrous methylene chloride) of acid chlorides, chloroformates, sulfonyl chlorides, isocyanates, isothiocyanates, anhydrides and carbamoyl chlorides were prepared. A stock solution (0.1 M in anhydrous methylene chloride) of compounds 220Bi was also prepared. All reactions were performed in Bohdan mini blocks. All reactions were agitated on an Innova 2100 shaker at 400 rpm for 24 h. Preparative HPLCs were performed using Shimadzu VP-ODS 20×50 mm column, using 10% to 90% aqueous methanol containing 0.1% TFA as the eluent, at a flow rate of 20 mL per min, using Mass Spec detection. All purified products were weighed and characterized by LS-MS. Proton NMR of random samples were obtained to ensure identity and purity.

Acronyms

PVP=Poly(4-vinylpyridine), 2% crosslinked

STR=Synthesis Tube Rack (2.5 mL capacity, 96 well format).

PS-DMAP=DMAP equivalent, Polymer-bound, 1.5 mmol/g, Argonaut

B. Synthesis of thioureas and urea [5S-(5α,8α,8aα)]-N-1,3-Benzodioxol-5-ylhexahydro-1,3-dioxo-2-[3-(trifluoromethyl)phenyl]-5,8-methanoimidazo[1,5-a]pyrazine-7(1H)-carbothiomide & (221Bi & 221Bii)

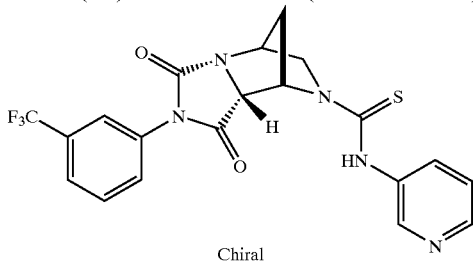

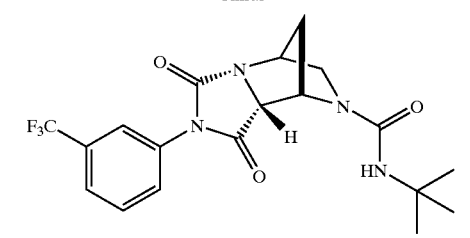

To the wells of a miniblock was added a stock solution of compounds 220Bi (300 uL, 0.1 M, 30 umol) followed by a solution of the isocyanate or isothicyanate (300 uL, 0.1 M, 30 umol). The wells were capped with a teflon lined rubber mat and agitated at rt for 24 h. The reaction mixture was drained into a synthesis tube rack. The wells of the miniblock were washed with methylene chloride (3×300 uL) and drained into the STR. The solvents were evaporated in vacuo. The crude products were purified by preparative HPLC. Compound 221Bi: retention time: 1.10 min. MS (ES): m/z 448.38 [M+H]$^+$. Compound 221Bii: Retention time: 1.45 min. MS (ES): m/z 411.45 [M+H]$^+$. Retention times and MS was determined as shown below.

| Flow inject MS, HPLC-ELS detection | |
|---|---|
| Method: | C:\CLASS-VP\METHODS\Wellere.met |
| Column: | Phenom-PrimeS5 C18 4.6 × 30 mm(2 min grad) |
| Solvents: | 10% MeOH - 90% H20 - 0.1% TFA, |
|  | 90% MeOH - 10% H2O - 0.1% TFA |
| Flow Rate: | 5 ml/min |
| Gradient Time: | 2 min |
| Channel: | B |
| Detector: | ELS |

C. Synthesis of amides and carbamates [5S-(5α,8α,8aα)]-2-[4-Cyano-3-(trifluoromethyl)phenyl]octahydro-1,3-dioxo-7-(1-oxpropyl)-5,8-methanoimidazo[1,5-a]pyrazine & [5S-(5α,8α,8aα)]-2-[4-Cyano-3-(trifluoromethyl)phenyl]hexahydro-1,3-dioxo-5,8-methanoimidazo[1,5-a]pyrazine-7(1H)-carboxylic acid, 1-methyl ester (221Ci & 221Cii)

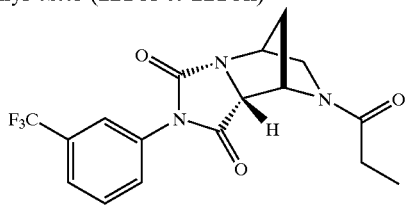

Chiral

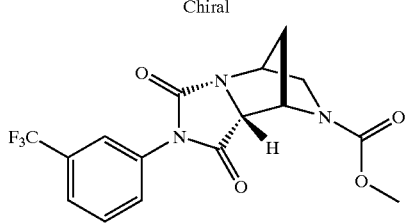

Chiral

To the wells of the miniblock was added PVP (100 mg, 1 mmol), a stock solution of compounds 220Bi (300 uL, 0.1 M, 30 umol) followed by a stock solution of the acid chloride, chloroformate or anhydride (600 uL, 0.1 M, 60 umol). The wells were capped with a teflon lined rubber mat and agitated at rt for 24 h. The reaction mixture was drained into a synthesis tube rack. The resin was washed with methylene chloride (3×300 uL) and drained into the STR. The solvents were evaporated under reduced pressure. The crude products were purified by preparative HPLC. Compound 221Ci: Retention time: 1.22 min. MS (ES): m/z 368.41 [M+H]$^+$. Compound 221Cii: Retention time: 1.23 min. MS (ES): m/z 370.38 [M+H]$^+$. Retention times and MS was determined as shown below.

| Flow inject MS, HPLC-ELS detection | |
|---|---|
| Method: | C:\CLASS-VP\METHODS\Wellere.met |
| Column: | Phenom-PrimeS5 C18 4.6 × 30 mm(2 min grad) |
| Solvents: | 10% MeOH - 90% H20 - 0.1% TFA, |
|  | 90% MeOH - 10% H2O - 0.1% TFA |
| Flow Rate: | 5 ml/min |
| Gradient Time: | 2 min |
| Channel: | B |
| Detector: | ELS |

D. Synthesis of sulfonamides [5S-(5α,8α,8aα)]-7-[(1-Methylethyl)sulfonyl]tetrahydro-2-[3-(trifluoromethyl)phenyl]-5,8-methanoimidazo[1,5-a]pyrazine-1,3(2H,5H)-dione (221D)

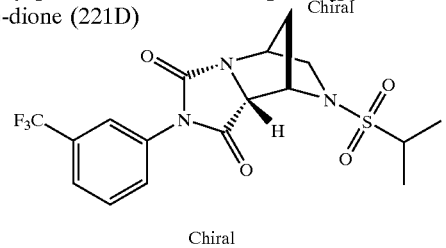

Chiral

To the wells of the miniblock was added PVP (100 mg, 1 mmol), PS-DMAP (25 mg, 37 umol), a stock solution of compounds 220Bi (300 uL, 0.1 M, 30 umol) followed by a solution of the sulfonyl chloride (600 uL, 0.1 M, 60 umol). The wells were capped with a teflon lined rubber mat and agitated at rt for 24 h. The reaction mixture was drained into a synthesis tube rack. The resin was washed with methylene chloride (3×300 uL) and drained into the STR. The solvents were evaporated under reduced pressure. The crude products were purified by preparative HPLC. Compound 221D: Retention time: 1.34 min. MS (ES): m/z 418.40 [M+H]$^+$. Retention times and MS was determined as shown below.

| Flow inject MS, HPLC-ELS detection | |
|---|---|
| Method: | C:\CLASS-VP\METHODS\Wellere.met |
| Column: | Phenom-PrimeS5 C18 4.6 × 30 mm(2 min grad) |
| Solvents: | 10% MeOH - 90% H20 - 0.1% TFA, |
|  | 90% MeOH - 10% H2O - 0.1% TFA |
| Flow Rate: | 5 ml/min |
| Gradient Time: | 2 min |
| Channel: | B |
| Detector: | ELS |

EXAMPLE 222

(5α,6α,8α,8aα)-4-(Octahydro-6-hydroxy-1,3-dioxo-5,8-methanoimidazo[1,5-a]pyridin-2-yl)-2-(trifluoromethyl)benzonitrile & (5α,6β,8α,8aα)-4-(Octahydro-6-hydroxy-1,3-dioxo-5,8-methanoimidazo[1,5-a]pyridin-2-yl)-2-(trifluoromethyl)benzonitrile (222i & 222ii)

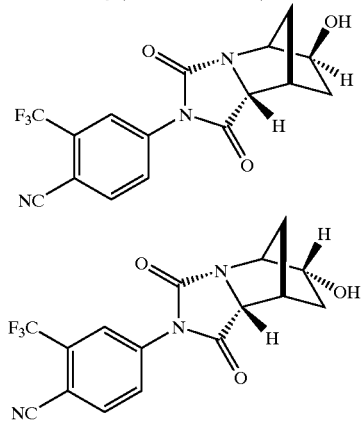

To a solution of compound 61 (0.200g, 0.601 mmol) in THF (4.0 ml) at 0° C. was added BH$_3$.THF (1 M solution in THF, 1.20 ml) dropwise. The reaction mixture was stirred at 0° C. for 1.5 h, then phosphate buffer (pH=7.2, 3.5 ml) was added followed by EtOH (1.5 ml) and 30% $H_2O_2$ in water (2.5 ml). The resulting mixture was stirred at 0° C. for 3 h. EtOAc (50 ml) and water (50 ml) were added and the organic layer was separated, washed with brine, dried over $Na_2SO_4$, and concentrated in vacuo. The resulting solid was purified with silica gel flash chromatography, eluting with EtOAc in hexane from 20% to 50% to give compound 222i (35 mg) as a white solid and compound 222ii (40 mg) as a white solid. Compound 222i: HPLC: 100% at 2.96 min (retention time) (YMC S-5 ODS-A column, 4.6×50 mm, eluting with 10–90% aqueous methanol over 4 min containing 0.2% phosphoric acid, 4 mL/min, monitoring at 220 nm). MS (ESI): m/z 351.99 [M+H]. Compound 222ii: HPLC: 96% at 2.90 min (retention time) (YMC S-5 ODS-A column, 4.6×50 mm, eluting with 10–90% aqueous methanol over 4 min containing 0.2% phosphoric acid, 4 mL/min, monitoring at 220 nm). MS (ESI): m/z 351.97 [M+H].

EXAMPLE 223

(5α,6β,7α,8α,8aα)-4-(Octahydro-6,7-dichloro-1,3-dioxo-5,8-methanoimidazo[1,5-a]pyridin-2-yl)-2-(trifluoromethyl)benzonitrile & (5α,6α,7β,8α,8aα)-4-(Octahydro-6,7-dichloro-1,3-dioxo-5,8-methanoimidazo[1,5-a]pyridin-2-yl)-2-(trifluoromethyl)benzonitrile & (1aα,2β,6aβ,7β,7aα)-4-(Octahydro-4,6-dioxo-2,7-methanoimidazo[1,5-a]oxireno[d]pyridin-5(4H)-yl)-2-(trifluoromethyl)benzonitrile (223i & 223ii & 223iii)

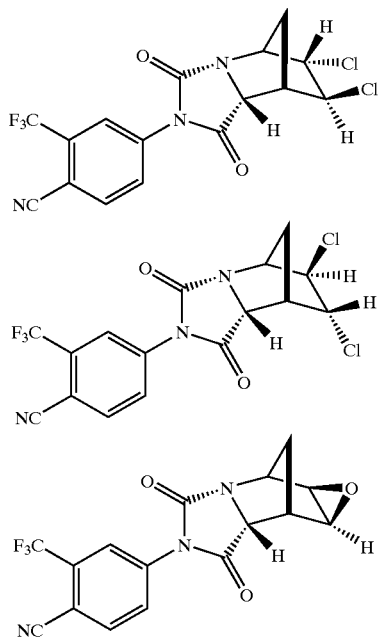

To a solution of compound 61 (0.20 g, 0.60 mmol) in acetone (4.0 ml) and acetic acid (0.8 ml) at 0° C. was added brine (0.8 ml), followed by dropwise addition of bleach (1.6 ml). The reaction mixture was warmed to rt, stirred at rt for 1 h and then concentrated in vacuo. The resulting aqueous phase was extracted with EtOAc (3×30 ml). The combined organic layers were washed with brine, dried over $Na_2SO_4$ and half of the material was purified on an ISCO automated chromatography system (30 g silica-gel column, eluting with 10–100% EtOAc in hexane over 45 mins, 35 ml/min, monitoring at 220 nm) to give compound 223i (9 mg) as white solid, compound 223ii (4 mg) as white solid and compound 223iii (3 mg) as white solid. Compound 223i: HPLC: 100% at 3.817 min (retention time) (YMC S-5 ODS-A column, 4.6×50 mm, eluting with 10–90% aqueous methanol over 4 min containing 0.2% phosphoric acid, 4 mL/min, monitoring at 220 nm). MS (ESI): m/z 402.13 [M−H]. Compound 223ii: HPLC: 90% at 3.75 min (retention time) (YMC S-5 ODS-A column, 4.6×50 mm, eluting with 10–90% aqueous methanol over 4 min containing 0.2% phosphoric acid, 4 mL/min, monitoring at 220 nm). MS (ESI): m/z 402.10 [M−H]. Compound 223iii: 100% at 3.173 min (retention time) (YMC S-5 ODS-A column, 4.6×50 mm, eluting with 10–90% aqueous methanol over 4 min containing 0.2% phosphoric acid, 4 mL/min, monitoring at 220 nm). MS (ESI): m/z 348.14 [M−H].

EXAMPLES 224 TO 491

Additional compounds of the present invention were prepared by procedures analogous to those described above. The compounds of Examples 224 to 491 have the structure, the compound name, retention time, molecular mass, and preparation procedures set forth in Table 5. The absolute configuration for the following compounds was not determined. For simplicity in nomenclature, compound 222i is designated herein as having an "R" configuration and compound 222ii as having an "S" configuration. Enantiomerically pure products derived from compound 222i are designated herein as having an "R" configuration and enantiomerically pure products derived from compound 222ii are designated herein as having an "S" configuration.

The chromatography techniques used to determine the compound retention times of Table 5 are as follows:

| A | Flow inject MS, HPLC-UV detection |
|---|---|
| Method: | C:\CLASS-VP\METHODS\Wellere.met |
| Column: | Phenom-PrimeS5 C18 4.6 × 30 mm(2 min grad) |
| Solvents: | 10% MeOH - 90% H20 - 0.1% TFA, |
| | 90% MeOH - 10% H2O - 0.1% TFA |
| Flow Rate: | 5 ml/min |
| Gradient Time: | 2 min |
| Channel: | A |
| Detector: | UV, 220 nm |
| B | Flow inject MS, HPLC-ELS detection |
| Method: | C:\CLASS-VP\METHODS\Wellere.met |
| Column: | Phenom-PrimeS5 C18 4.6 × 30 mm(2 min grad) |
| Solvents: | 10% MeOH - 90% H20 - 0.1% TFA, |
| | 90% MeOH - 10% H2O - 0.1% TFA |
| Flow Rate: | 5 ml/min |
| Gradient Time: | 2 min |
| Channel: | B |
| Detector: | ELS |
| Detector: | UV, 220 nm |
| C | LC(uv)-MS |
| Instrument: | LVL-L3604 LCMS |
| Source: | MetECN__Data\Data0001\52827-040-01__File0002.LCMS |
| Method: | C:\CLASS-VP\METHODS\WELLER.MET |

-continued

| | |
|---|---|
| Column: | PrimeSphere 5u C18-HC 30 × 4.6(2 min) |
| Solvents: | 10% MeOH - 90% H2O - 0.1% TFA, |
| | 90% MeOH - 10% H2O - 0.1% TFA |
| Flow Rate: | 5 ml/min |
| Gradient Time: | 2 min |
| Detector: | UV, 220 nm |

| | |
|---|---|
| D | MS data from LCMS, HPLC-UV detection |
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, |
| | 90% MeOH - 10% H2O - 0.1% TFA |
| Flow Rate: | 5 ml/min |
| Gradient Time: | 2 min |
| Channel: | A |
| Detector: | UV, 220 nm |

| | |
|---|---|
| E | MS data from LCMS, HPLC-ELS detection |
| Method: | C:\CLASS-VP\METHODS\Wellere.met |
| Column: | Phenom-PrimeS5 C18 4.6 × 30 mm(2 min grad) |
| Solvents: | 10% MeOH - 90% H2O - 0.1% TFA, |
| | 90% MeOH - 10% H2O - 0.1% TFA |
| Flow Rate: | 5 ml/min |
| Gradient Time: | 2 min |
| Channel: | B |
| Detector: | ELS |
| Detector: | UV, 220 nm |

| | |
|---|---|
| F | A. LC(uv)-MS |
| Instrument: | LVL-L3604 LCMS |
| Source: | MetECN__Data\Data0001\52827-040-01__File0002.LCMS |
| Method: | C:\CLASS-VP\METHODS\WELLER.MET |
| Column: | Phenom-PrimeS5 C18 4.6 × 30 mm (2 min. grad) |
| Solvents: | 10% MeOH - 90% H2O - 0.1% TFA, |
| | 90% MeOH - 10% H2O - 0.1% TFA |
| Flow Rate: | 5 ml/min |
| Gradient Time: | 2 min |
| Detector: | UV, 220 nm |

| | |
|---|---|
| G | B. LC(uv)-MS |
| Source: | MetECN__Data\Data0001\52827-040-01__File0002.LCMS |
| Method: | C:\CLASS-VP\METHODS\WELLER.MET |
| Column: | YMC S5 ODS column, 4.6 × 50 mm (4 min. grad) |
| Solvents: | 10% MeOH - 90% H2O - 0.1% TFA, |
| | 90% MeOH - 10% H2O - 0.1% TFA |
| Flow Rate: | 4 ml/min |
| Gradient Time: | 220 min |
| Detector: | UV, 220 nm |

The molecular mass of the compounds listed in Table 5 were determined by MS (ES) by the formula m/z.

TABLE 5

| Ex. No | Structure | Compound Name | Retention Time Min./ Molecular Mass | Proc. of Ex. | LC & MS Con. |
|---|---|---|---|---|---|
| 224 | 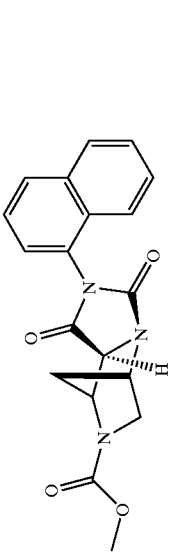 | [5S-(5α,8α,8aβ)]-Hexahydro-2-(1-naphthalenyl)-1,3-dioxo-5,8-methanoimidazo[1,5-a]pyrazine-7(1H)-carboxylic acid, methyl ester. | 1.36 LCMS [M + H]+ = 352.45 | 221Ci | B |
| 225 | 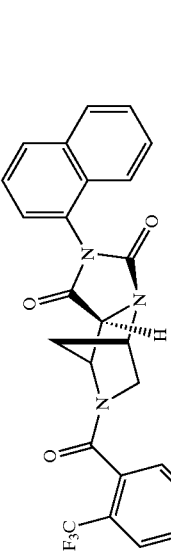 | [5S-(5α,8α,8aβ)]-Tetrahydro-2-(1-naphthalenyl)-7-[2-(trifluoromethyl)benzoyl]-5,8-methanoimidazo[1,5-a]pyrazine-1,3(2H,5H)-dione. | 1.65 LCMS [M + H]+ = 466.40 | 221Ci | B |
| 226 | 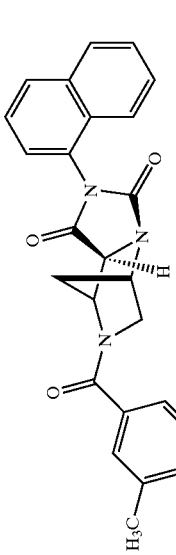 | [5S-(5α,8α,8aβ)]-Tetrahydro-7-(3-methylbenzoyl)-2-(1-naphthalenyl)-5,8-methanoimidazo[1,5-a]pyrazine-1,3(2H,5H)-dione. | 1.65 LCMS [M + H]+ = 412.42 | 221Ci | B |
| 227 | 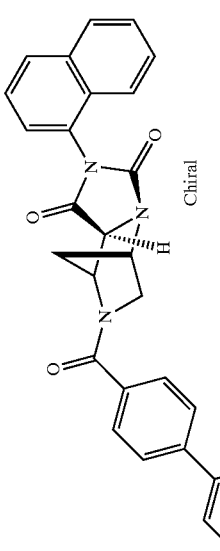 | [5S-(5α,8α,8aβ)]-7-[(1,1'-Biphenyl]-4-ylcarbonyl)tetrahydro-2-(1-naphthalenyl)-5,8-methanoimidazo[1,5-a]pyrazine-1,3(2H,5H)-dione. | 1.87 LCMS [M + H]+ = 474.46 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 228 | 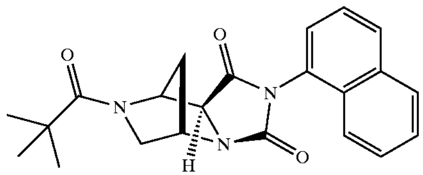 | [5S-(5α,8α,8aβ)]-7-(2,2-Dimethyl-1-oxopropyl) tetrahydro-2-(1-naphthalenyl)-5,8-methanoimidazo[1,5-a]pyrazine-1,3(2H,5H)-dione. | 1.58 LCMS [M + H]$^+$ = 378.48 | 221Ci | B |
| 229 | 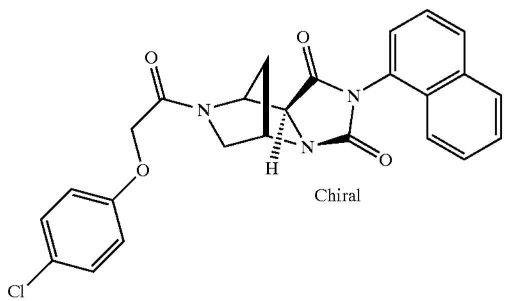 | [5S-(5α,8α,8aβ)]-7-[(4-Chlorophenoxy)acetyl] tetrahydro-2-(1-naphthalenyl)-5,8-methanoimidazo[1,5-a]pyrazine-1,3(2H,5H)-dione. | 1.81 LCMS [M + H]$^+$ = 462.37 | 221Ci | B |
| 230 | 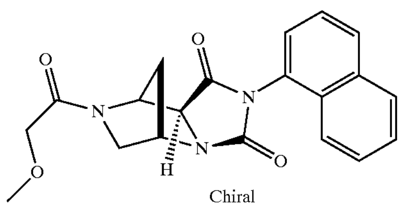 | [5S-(5α,8α,8aβ)]-Tetrahydro-7-(methoxyacetyl)-2-(1-naphthalenyl)-5,8-methanoimidazo[1,5-a]pyrazine-1,3(2H,5H)-dione. | 1.29 LCMS [M + H]$^+$ = 366.44 | 221Ci | B |
| 231 | 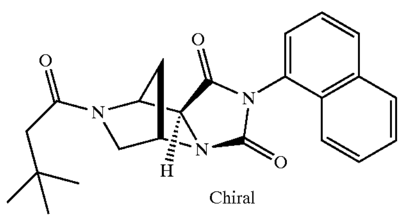 | [5S-(5α,8α,8aβ)]-7-(3,3-Dimethyl-1-oxobutyl) tetrahydro-2-(1-naphthalenyl)-5,8-methanoimidazo[1,5-a]pyrazine-1,3(2H,5H)-dione. | 1.68 LCMS [M + H]$^+$ = 392.48 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 232 | 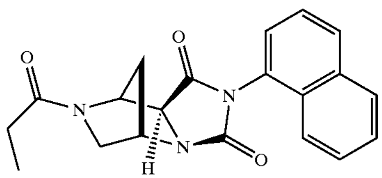 | [5S-(5α,8α,8aβ)]-Tetrahydro-2-(1-naphthalenyl)-7-(1-oxopropyl)-5,8-methanoimidazo[1,5-a]pyrazine-1,3(2H,5H)-dione. | 1.36 LCMS [M + H]⁺ = 350.41 | 221Ci | B |
| 233 | 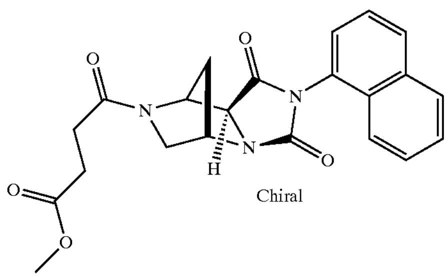 | [5S-(5α,8α,8aβ)]-Hexahydro-2-(1-naphthalenyl)-gamma,1,3-trioxo-5,8-methanoimidazo[1,5-a]pyrazine-7(1H)-butanoic acid, methyl ester. | 1.37 LCMS [M + H]⁺ = 408.42 | 221Ci | B |
| 234 | 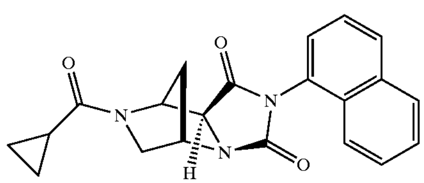 | [5S-(5α,8α,8aβ)]-7-Cyclopropylcarbonyl)tetrahydro-2-(1-naphthalenyl)-5,8-methanoimidazo[1,5-a]pyrazine-1,3(2H,5H)-dione. | 1.41 LCMS [M + H]⁺ = 362.45 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 235 | 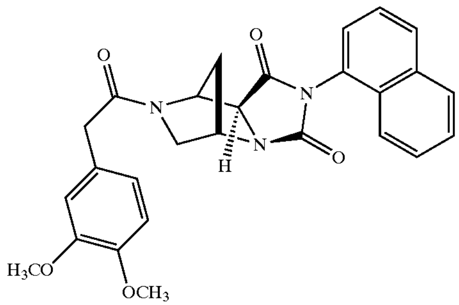 | [5S-(5α,8α,8aβ)]-7-[(3,4-Dimethoxyphenyl)acetyl]tetrahydro-2-(1-naphthalenyl)-5,8-methanoimidazo[1,5-a]pyrazine-1,3(2H,5H)-dione. | 1.51 LCMS [M + H]$^+$ = 472.45 | 221Ci | B |
| 236 | 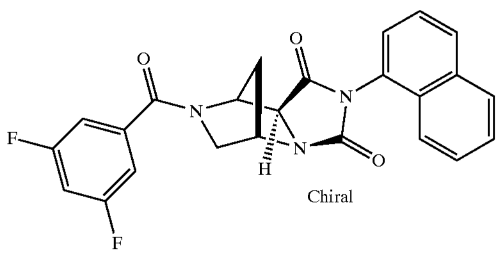 | [5S-(5α,8α,8aβ)]-7-(3,5-Difluorobenzoyl)tetrahydro-2-(1-naphthalenyl)-5,8-methanoimidazo[1,5-a]pyrazine-1,3(2H,5H)-dione. | 1.63 LCMS [M + H]$^+$ = 434.42 | 221Ci | B |
| 237 | 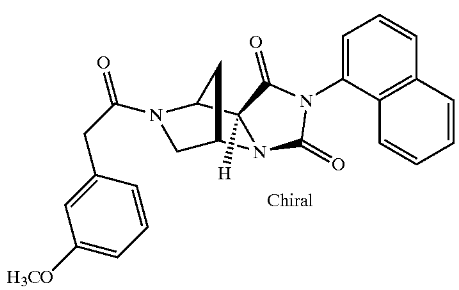 | [5S-(5α,8α,8aβ)]-Tetrahydro-7-[(3-methoxyphenyl)acetyl]-2-(1-naphthalenyl)-5,8-methanoimidazo[1,5-a]pyrazine-1,3(2H,5H)-dione. | 1.64 LCMS [M + H]$^+$ = 442.44 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 238 | 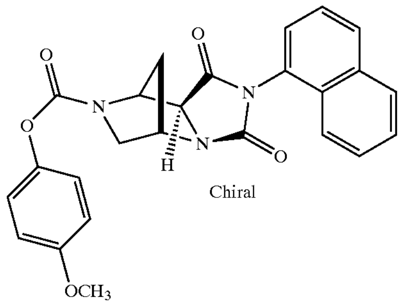 | [5S-(5α,8α,8aβ)]-Hexahydro-2-(1-naphthalenyl)-1,3-dioxo-5,8-methanoimidazo[1,5-a]pyrazine-7(1H)-carboxylic acid, 4-methoxyphenyl ester. | 1.69 LCMS [M + H]+ = 444.42 | 221Cii | B |
| 239 | 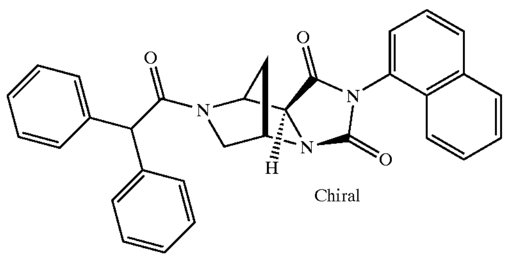 | [5S-(5α,8α,8aβ)]-7-(Diphenylacetyl)tetrahydro-2-(1-naphthalenyl)-5,8-methanoimidazo[1,5-a]pyrazine-1,3(2H,5H)-dione. | 1.85 LCMS [M + H]+ = 488.48 | 221Ci | B |
| 240 | 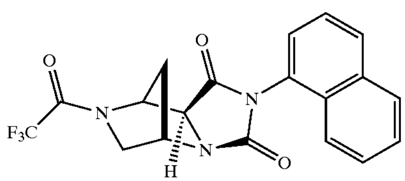 | [5S-(5α,8α,8aβ)]-Tetrahydro-2-(1-naphthalenyl)-7-(trifluoroacetyl)-5,8-methanoimidazo[1,5-a]pyrazine-1,3(2H,5H)-dione. | 1.52 LCMS [M + H]+ = 390.39 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 241 | 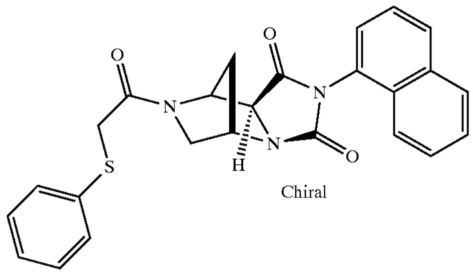 | [5S-(5α,8α,8aβ)]-Tetrahydro-2-(1-naphthalenyl)-7-[(phenylthio)acetyl]-5,8-methanoimidazo[1,5-a]pyrazine-1,3(2H,5H)-dione. | 1.70 LCMS [M + H]⁺ = 444.39 | 221Ci | B |
| 242 | 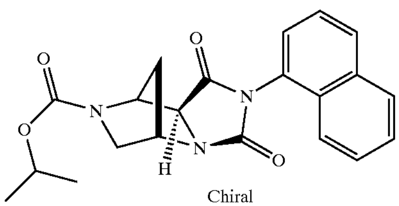 | [5S-(5α,8α,8aβ)]-Hexahydro-2-(1-naphthalenyl)-1,3-dioxo-5,8-methanoimidazo[1,5-a]pyrazine-7(1H)-carboxylic acid, 1-methylethyl ester. | 1.63 LCMS [M + H]⁺ = 402.41 | 221Cii | B |
| 243 | 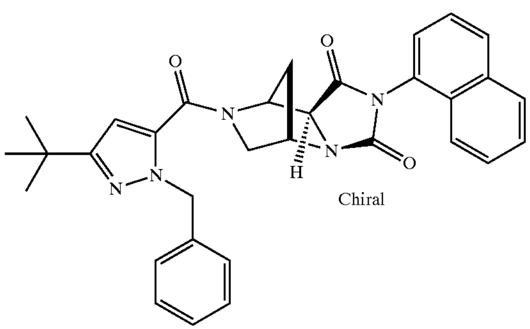 | [5S-(5α,8α,8aβ)]-7-[[3-(1,1-Dimethylethyl)-1-(phenylmethyl)-1H-pyrazol-5-yl]carbonyl]-tetrahydro-2-(1-naphthalenyl)-5,8-methanoimidazo[1,5-a]pyrazine-1,3(2H,5H)-dione. | 1.96 LCMS [M + H]⁺ = 534.50 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 244 | 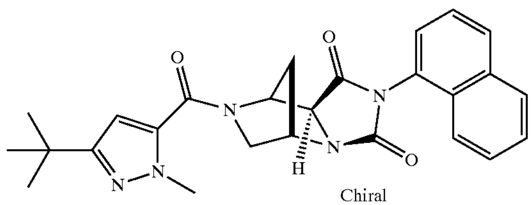 | [5S-(5α,8α,8aβ)]-7-[[3-(1,1-Dimethylethyl)-1-methyl-1H-pyrazol-5-yl]carbonyl][tetrahydro-2-(1-naphthalenyl)-5,8-methanoimidazo[1,5-a]pyrazine-1,3(2H,5H)-dione. | 1.78 LCMS [M + H]+ = 458.50 | 221Ci | B |
| 245 | 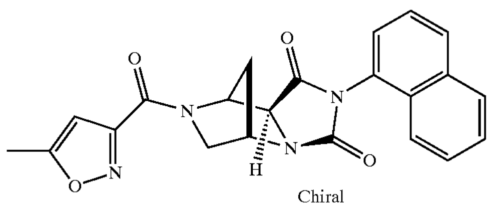 | [5S-(5α,8α,8aβ)]-Tetrahydro-7-[(5-methyl-3-isoxazolyl)carbonyl]-2-(1-naphthalenyl)-5,8-methanoimidazo[1,5-a]pyrazine-1,3(2H,5H)-dione. | 1.53 LCMS [M + H]+ = 403.43 | 221Ci | B |
| 246 | 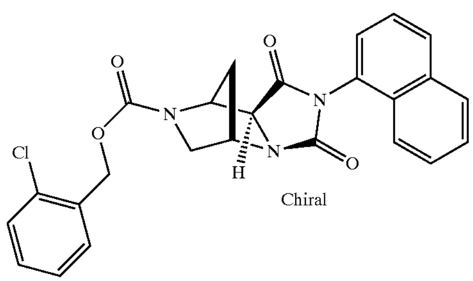 | [5S-(5α,8α,8aβ)]-Hexahydro-2-(1-naphthalenyl)-1,3-dioxo-5,8-methanoimidazo[1,5-a]pyrazine-7(1H)-carboxylic acid, (2-chlorophenyl) methyl ester. | 1.86 LCMS [M + H]+ = 484.37 | 221Cii | B |
| 247 | 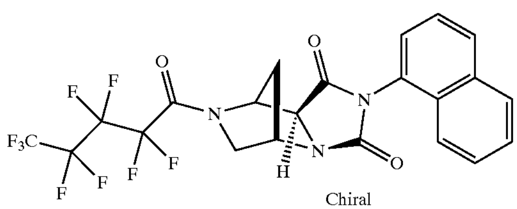 | [5S-(5α,8α,8aβ)]-Tetrahydro-2-(1-naphthalenyl)-7-(2,2,3,3,4,4,5,5,5-nonafluoro-1-oxopentyl)-5,8-methanoimidazo[1,5-a]pyrazine-1,3(2H,5H)-dione. | 1.92 LCMS [M + H]+ = 540.32 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 248 | 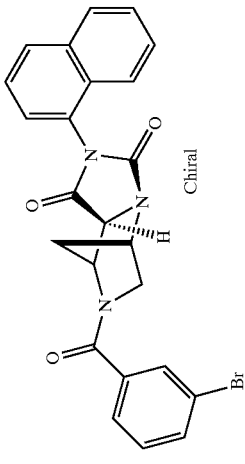 | [5S-(5α,8α,8aβ)]-7-(3-Bromobenzoyl)tetrahydro-2-(1-naphthalenyl)-5,8-methanoimidazo[1,5-a]pyrazine-1,3(2H,5H)-dione. | 1.72 LCMS [M + H]⁺ = 476.34 | 221Ci | B |
| 249 | 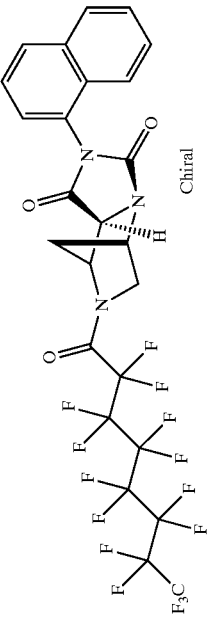 | [5S-(5α,8α,8aβ)]-Tetrahydro-2-(1-naphthalenyl)-7-(2,2,3,3,4,4,5,5,6,6,7,7,8,8,8-pentadecafluoro-1-oxooctyl)-5,8-methanoimidazo[1,5-a]pyrazine-1,3(2H,5H)-dione. | 2.16 LCMS [M + H]⁺ = 690.34 | 221Ci | B |
| 250 | 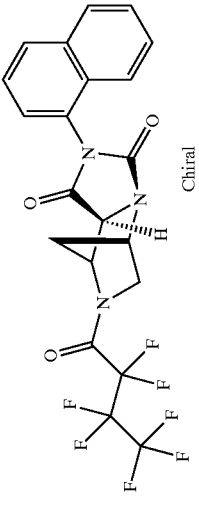 | [5S-(5α,8α,8aβ)]-7-(2,2,3,3,4,4,4-Heptafluoro-1-oxobutyl)tetrahydro-2-(1-naphthalenyl)-5,8-methanoimidazo[1,5-a]pyrazine-1,3(2H,5H)-dione. | 1.82 LCMS [M + H]⁺ = 490.37 | 221Ci | B |
| 251 | 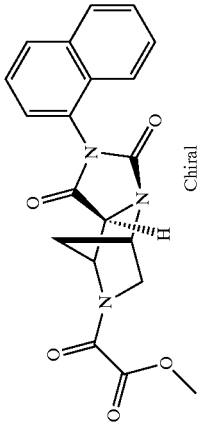 | [5S-(5α,8α,8aβ)]-Hexahydro-2-(1-naphthalenyl)-alpha,1,3-trioxo-5,8-methanoimidazo[1,5-a]pyrazine-7(1H)-acetic acid, methyl ester. | 1.36 LCMS [M + H]⁺ = 380.41 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 252 | 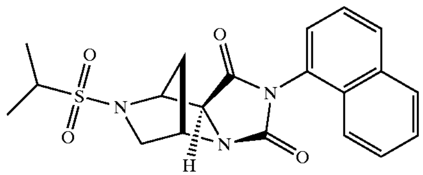 | [5S-(5α,8α,8aβ)]-Tetrahydro-7-[(1-methylethyl)sulfonyl]-2-(1-naphthalenyl)-5,8-methanoimidazo[1,5-a]pyrazine-1,3(2H,5H)-dione. | 1.50 LCMS [M + H]+ = 400.40 | 221D | B |
| 253 | 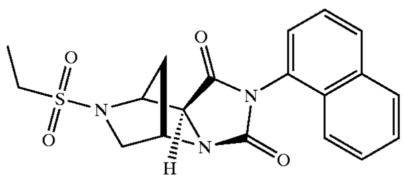 | [5S-(5α,8α,8aβ)]-7-(Ethylsulfonyl)tetrahydro-2-(1-naphthalenyl)-5,8-methanoimidazo[1,5-a]pyrazine-1,3(2H,5H)-dione. | 1.41 LCMS [M + H]+ = 386.40 | 221D | B |
| 254 | 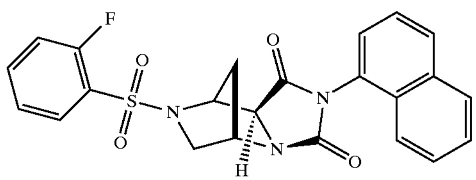 | [5S-(5α,8α,8aβ)]-7-[(2-Fluorophenyl)sulfonyl]tetrahydro-2-(1-naphthalenyl)-5,8-methanoimidazo[1,5-a]pyrazine-1,3(2H,5H)-dione. | 1.63 LCMS [M + H]+ = 474.36 | 221D | B |
| 255 | 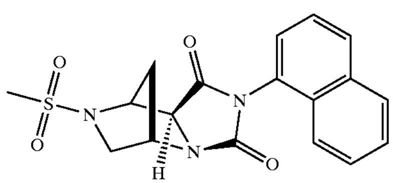 | [5S-(5α,8α,8aβ)]-Tetrahydro-7-(methylsulfonyl)-2-(1-naphthalenyl)-5,8-methanoimidazo[1,5-a]pyrazine-1,3(2H,5H)-dione. | 1.34 LCMS [M + H]+ = 394.37 | 221D | B |

TABLE 5-continued

| Ex. No | Structure | Compound Name | Retention Time Min./ Molecular Mass | Proc. of Ex. | LC & MS Con. |
|---|---|---|---|---|---|
| 256 | 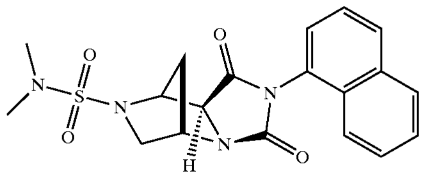 | [5S-(5α,8α,8aβ)]-Hexahydro-N,N-dimethyl-2-(1-naphthalenyl)-1,3-dioxo-5,8-methanoimidazo[1,5-a]pyrazine-7(1H)-sulfonamide. | 1.48 LCMS [M + H]+ = 423.38 | 221D | B |
| 257 | 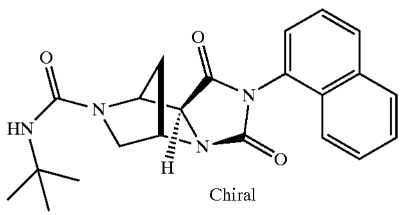 | [5S-(5α,8α,8aβ)]-N-(1,1-Dimethylethyl)hexahydro-2-(1-naphthalenyl)-1,3-dioxo-5,8-methanoimidazo[1,5-a]pyrazine-7(1H)-carboxamide. | 1.62 LCMS [M + H]+ = 393.47 | 221Bii | B |
| 258 | 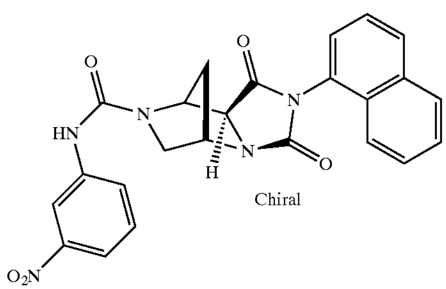 | [5S-(5α,8α,8aβ)]-Hexahydro-2-(1-naphthalenyl)-N-(3-nitrophenyl)-1,3-dioxo-5,8-methanoimidazo[1,5-a]pyrazine-7(1H)-carboxamide. | 1.69 LCMS [M + H]+ = 458.42 | 221Bii | B |

TABLE 5-continued

| Ex. No | Structure | Compound Name | Retention Time Min./ Molecular Mass | Proc. of Ex. | LC & MS Con. |
|---|---|---|---|---|---|
| 259 | 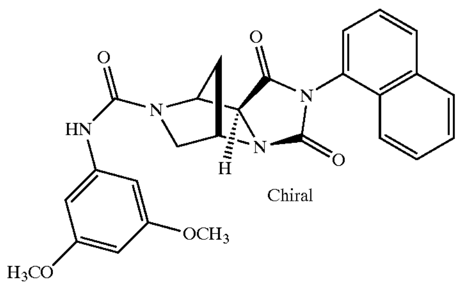 | [5S-(5α,8α,8aβ)]-N-(3,5-Dimethoxyphenyl) hexahydro-2-(1-naphthalenyl)-1,3-dioxo-5,8-methanoimidazo[1,5-a]pyrazine-7(1H)-carboxamide. | 1.68 LCMS [M + H]+ = 473.46 | 221Bii | B |
| 260 | 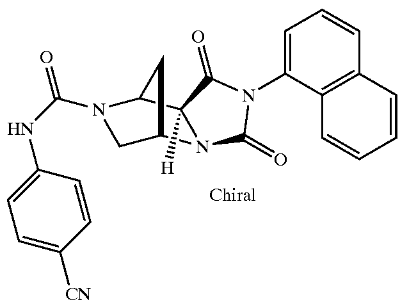 | [5S-(5α,8α,8aβ)]-N-(4-Cyanophenyl)hexahydro-2-(1-naphthalenyl)-1,3-dioxo-5,8-methanoimidazo[1,5-a]pyrazine-7(1H)-carboxamide. | 1.60 LCMS [M + H]+ = 438.40 | 221Bii | B |
| 261 | 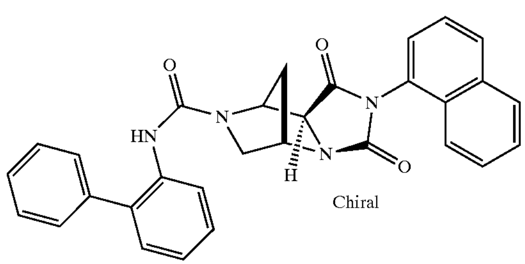 | [5S-(5α,8α,8aβ)]-N-[1,1′-Biphenyl]-2-ylhexahydro-2-(1-naphthalenyl)-1,3-dioxo-5,8-methanoimidazo[1,5-a]pyrazine-7(1H)-carboxamide. | 1.83 LCMS [M + H]+ = 489.45 | 221Bii | B |

TABLE 5-continued

| Ex. No | Structure | Compound Name | Retention Time Min./ Molecular Mass | Proc. of Ex. | LC & MS Con. |
|---|---|---|---|---|---|
| 262 | 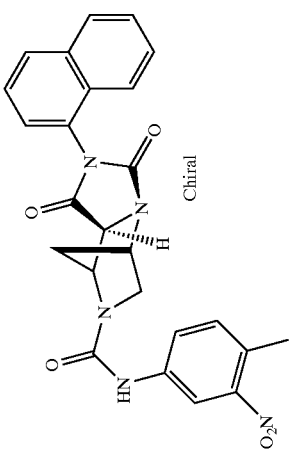 | [5S-(5α,8α,8aβ)]-Hexahydro-N-(4-methyl-3-nitrophenyl)-2-(1-naphthalenyl)-1,3-dioxo-5,8-methanoimidazo[1,5-a]pyrazine-7(1H)-carboxamide. | 1.75 LCMS [M + H]+ = 472.43 | 221Bii | B |
| 263 | 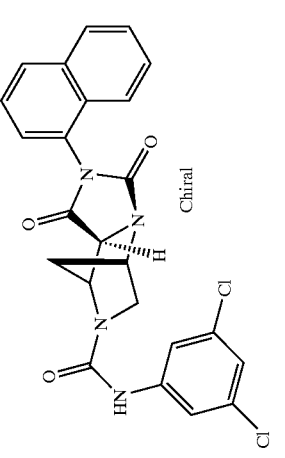 | [5S-(5α,8α,8aβ)]-N-(3,5-Dichlorophenyl)hexahydro-2-(1-naphthalenyl)-1,3-dioxo-5,8-methanoimidazo[1,5-a]pyrazine-7(1H)-carboxamide. | 1.98 LCMS [M + H]+ = 481.36 | 221Bii | B |
| 264 | 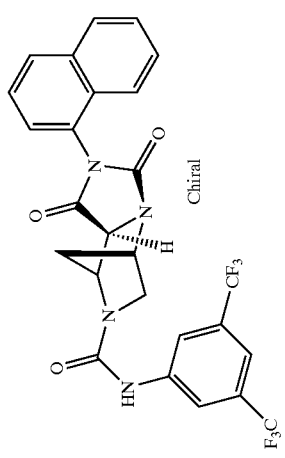 | [5S-(5α,8α,8aβ)]-N-[3,5-Bis(trifluoromethyl)phenyl]hexahydro-2-(1-naphthalenyl)-1,3-dioxo-5,8-methanoimidazo[1,5-a]pyrazine-7(1H)-carboxamide. | 2.03 LCMS [M + H]+ = 549.39 | 221Bii | B |

TABLE 5-continued

| Ex. No | Structure | Compound Name | Retention Time Min./ Molecular Mass | Proc. of Ex. | LC & MS Con. |
|---|---|---|---|---|---|
| 265 | 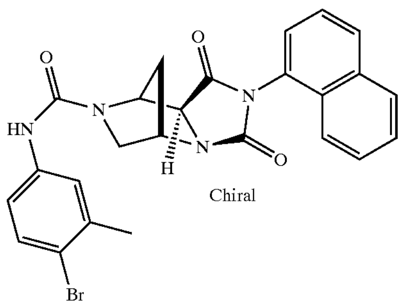 | [5S-(5α,8α,8aβ)]-N-(4-Bromo-3-methylphenyl) hexahydro-2-(1-naphthalenyl)-1,3-dioxo-5,8-methanoimidazo[1,5-a]pyrazine-7(1H)-carboxamide. | 1.91 LCMS [M + H]$^+$ = 505.35 | 221Bii | B |
| 266 | 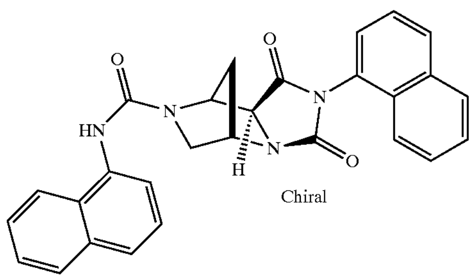 | [5S-(5α,8α,8aβ)]-Hexahydro-N,2-di-1-naphthalenyl-1,3-dioxo-5,8-methanoimidazo[1,5-a]pyrazine-7(1H)-carboxamide. | 1.71 LCMS [M + H]$^+$ = 463.45 | 221Bii | B |
| 267 | 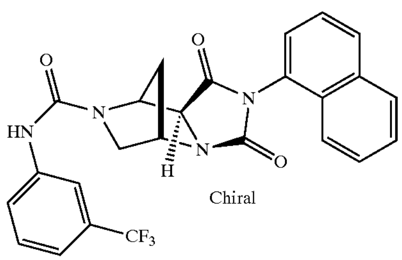 | [5S-(5α,8α,8aβ)]-Hexahydro-2-(1-naphthalenyl)-1,3-dioxo-N-[3-(trifluoromethyl)phenyl]-5,8-methanoimidazo[1,5-a]pyrazine-7(1H)-carboxamide. | 1.84 LCMS [M + H]$^+$ = 481.43 | 221Bii | B |

TABLE 5-continued

| Ex. No | Structure | Compound Name | Retention Time Min./ Molecular Mass | Proc. of Ex. | LC & MS Con. |
|---|---|---|---|---|---|
| 268 | 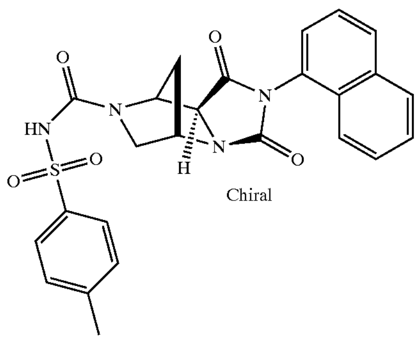 | [5S-(5α,8α,8aβ)]-Hexahydro-N-[(4-methylphenyl)sulfonyl]-2-(1-naphthalenyl)-1,3-dioxo-5,8-methanoimidazo[1,5-a]pyrazine-7(1H)-carboxamide. | 1.57 LCMS [M + H]+ = 491.41 | 221Bii | B |
| 269 | 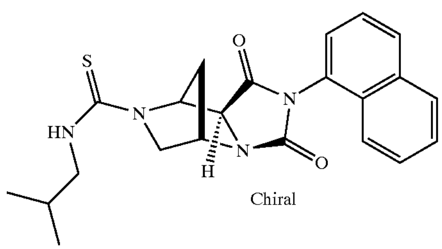 | [5S-(5α,8α,8aβ)]-Hexahydro-N-(2-methylpropyl)-2-(1-naphthalenyl)-1,3-dioxo-5,8-methanoimidazo[1,5-a]pyrazine-7(1H)-carbothioamide. | 1.72 LCMS [M + H]+ = 409.45 | 221Bi | B |
| 270 | 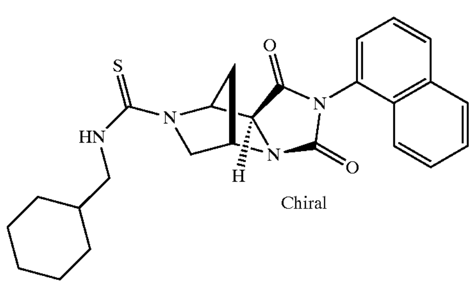 | [5S-(5α,8α,8aβ)]-N-(Cyclohexylmethyl)hexahydro-2-(1-naphthalenyl)-1,3-dioxo-5,8-methanoimidazo[1,5-a]pyrazine-7(1H)-carbothioamide. | 1.93 LCMS [M + H]+ = 449.49 | 221Bi | B |

TABLE 5-continued

| Ex. No | Structure | Compound Name | Retention Time Min./ Molecular Mass | Proc. of Ex. | LC & MS Con. |
|---|---|---|---|---|---|
| 271 | 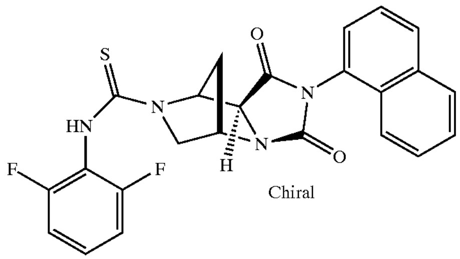 | [5S-(5α,8α,8aβ)]-N-(2,6-Difluorophenyl)hexahydro-2-(1-naphthalenyl)-1,3-dioxo-5,8-methanoimidazo[1,5-a]pyrazine-7(1H)-carbothioamide. | 1.61 LCMS [M + H]+ = 465.39 | 221Bi | B |
| 272 | 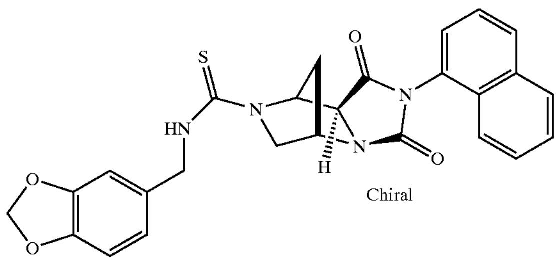 | [5S-(5α,8α,8aβ)]-N-(1,3-Benzodioxol-5-ylmethyl)hexahydro-2-(1-naphthalenyl)-1,3-dioxo-5,8-methanoimidazo[1,5-a]pyrazine-7(1H)-carbothioamide. | 1.73 LCMS [M + H]+ = 487.41 | 221Bi | B |
| 273 | 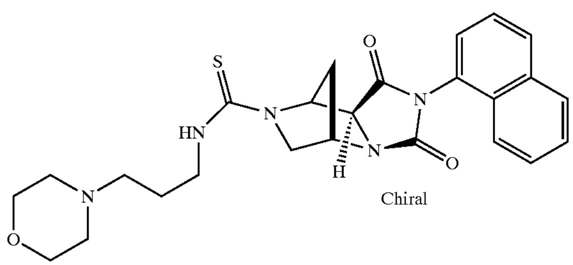 | [5S-(5α,8α,8aβ)]-Hexahydro-N-[3-(4-morpholinyl)propyl]-2-(1-naphthalenyl)-1,3-dioxo-5,8-methanoimidazo[1,5-a]pyrazine-7(1H)-carbothioamide. | 1.31 LCMS [M + H]+ = 480.50 | 221Bi | B |

TABLE 5-continued

| Ex. No | Structure | Compound Name | Retention Time Min./ Molecular Mass | Proc. of Ex. | LC & MS Con. |
|---|---|---|---|---|---|
| 274 | 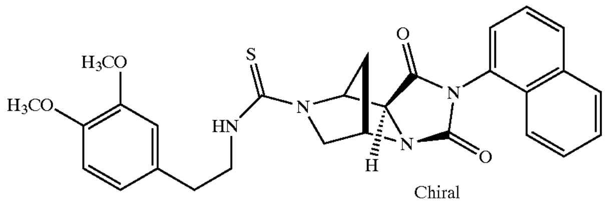 | [5S-(5α,8α,8aβ)]-N-[2-(3,4-Dimethoxyphenyl)ethyl]hexahydro-2-(1-naphthalenyl)-1,3-dioxo-5,8-methanoimidazo[1,5-a]pyrazine-7(1H)-carbothioamide. | 1.72 LCMS [M + H]⁺ = 517.47 | 221Bi | B |
| 275 | 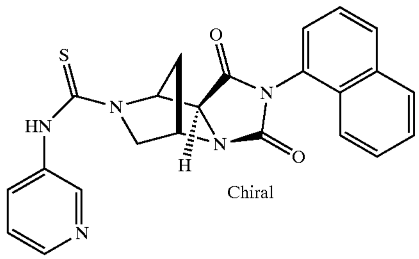 | [5S-(5α,8α,8aβ)]-Hexahydro-2-(1-naphthalenyl)-1,3-dioxo-N-3-pyridinyl-5,8-methanoimidazo[1,5-a]pyrazine-7(1H)-carbothioamide. | 1.32 LCMS [M + H]⁺ = 430.40 | 221Bi | B |
| 276 | 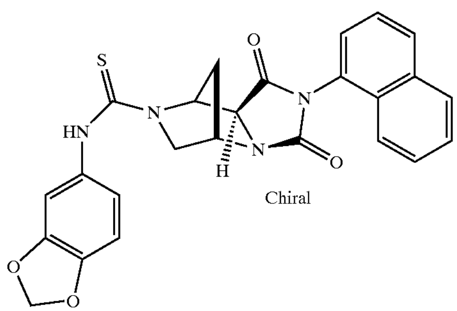 | [5S-(5α,8α,8aβ)]-N-1,3-Benzodioxol-5-ylhexahydro-2-(1-naphthalenyl)-1,3-dioxo-5,8-methanoimidazo[1,5-a]pyrazine-7(1H)-carbothioamide. | 1.61 LCMS [M + H]⁺ = 473.39 | 221Bi | B |

TABLE 5-continued

| Ex. No | Structure | Compound Name | Retention Time Min./ Molecular Mass | Proc. of Ex. | LC & MS Con. |
|---|---|---|---|---|---|
| 277 | 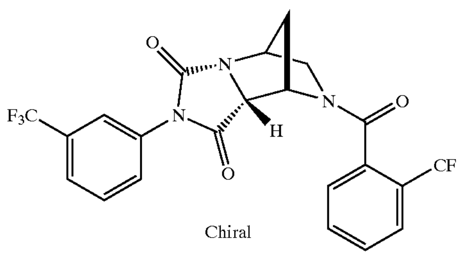 | [5S-(5α,8α,8aα)]-Tetrahydro-7-[2-(trifluoromethyl)benzoyl]-2-[3-(trifluoromethyl)phenyl]-5,8-methanoimidazo[1,5-a]pyrazine-1,3(2H,5H)-dione. | 1.47 LCMS [M + H]+ = 484.37 | 221Ci | B |
| 278 | 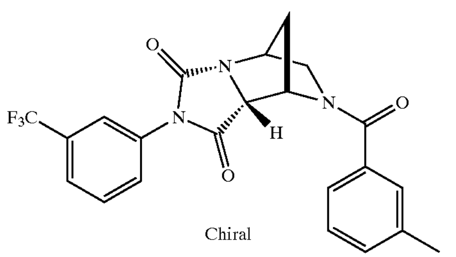 | [5S-(5α,8α,8aα)]-Tetrahydro-7-(3-methylbenzoyl)-2-[3-(trifluoromethyl)phenyl]-5,8-methanoimidazo[1,5-a]pyrazine-1,3(2H,5H)-dione. | 1.53 LCMS [M + H]+ = 430.41 | 221Ci | B |
| 279 | 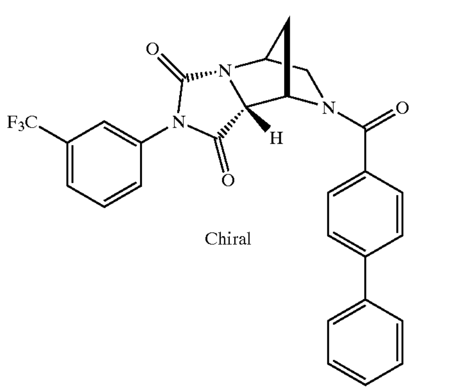 | [5S-(5α,8α,8aα)]-7-([1,1'-Biphenyl]-4-ylcarbonyl)tetrahydro-2-[3-(trifluoromethyl)phenyl]-5,8-methanoimidazo[1,5-a]pyrazine-1,3(2H,5H)-dione. | 1.77 LCMS [M + H]+ = 492.41 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 280 | 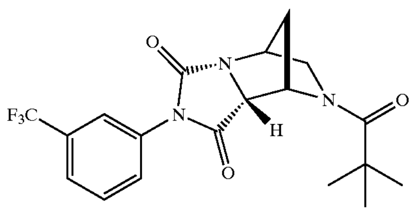 | [5S-(5α,8α,8aα)]-7-(2,2-Dimethyl-1-oxopropyl) tetrahydro-2-[3-(trifluoromethyl)phenyl]-5,8-methanoimidazo[1,5-a]pyrazine-1,3(2H,5H)-dione. | 1.46 LCMS $[M+H]^+$ = 396.41 | 221Ci | B |
| 281 | 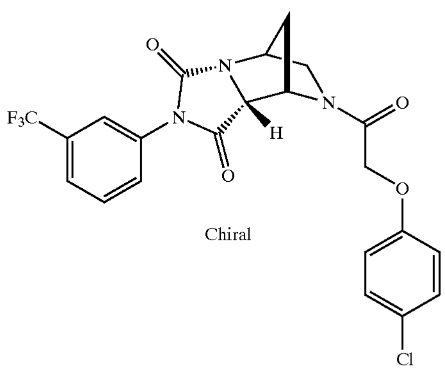 | [5S-(5α,8α,8aα)]-7-[(4-Chlorophenoxy)acetyl] tetrahydro-2-[3-trifluoromethyl)phenyl]-5,8-methanoimidazo[1,5-a]pyrazine-1,3(2H,5H)-dione. | 1.66 LCMS $[M+H]^+$ = 480.36 | 221Ci | B |
| 282 | 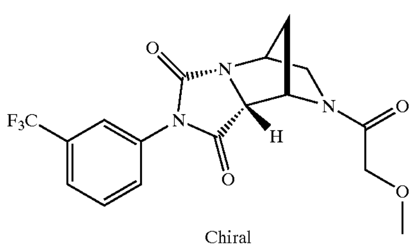 | [5S-(5α,8α,8aα)]-Tetrahydro-7-methoxyacetyl)-2-[3-(trifluoromethyl)phenyl]-5,8-methanoimidazo[1,5-a]pyrazine-1,3(2H,5H)-dione. | 1.12 LCMS $[M+H]^+$ = 384.40 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 283 | 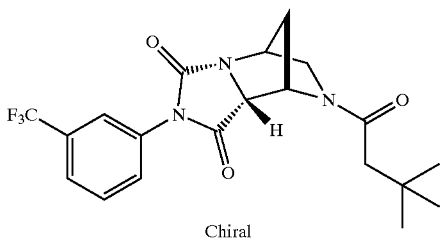 | [5S-(5α,8α,8aα)]-7-(3,3-Dimethyl-1-oxobutyl) tetrahydro-2-[3-(trifluoromethyl) phenyl]-5,8-methanoimidazo[1,5-a]pyrazine-1,3(2H,5H)-dione. | 1.57 LCMS [M + H]⁺ = 410.44 | 221Ci | B |
| 284 | 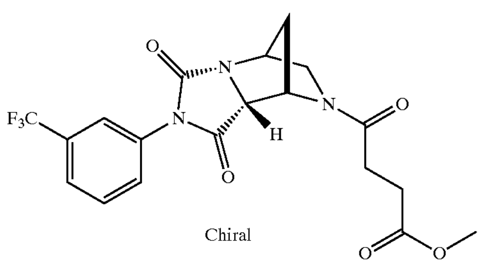 | [5S-(5α,8α,8aα)]-Hexahydro-gamma,1,3-trioxo-2-[3-(trifluoromethyl)phenyl]-5,8-methanoimidazo[1,5-a]pyrazine-7(1H)-butanoic acid, methyl ester. | 1.25 LCMS [M + H]⁺ = 426.40 | 221Ci | B |
| 285 | 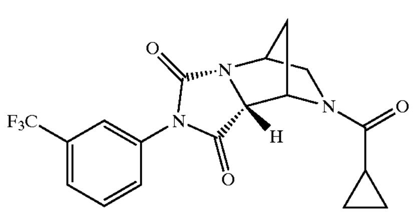 | [5S-(5α,8α,8aα)]-7-(Cyclopropylcarbonyl) tetrahydro-2-[3-(trifluoromethyl)phenyl]-5,8-methanoimidazo[1,5-a]pyrazine-1,3(2H,5H)-dione. | 1.24 LCMS [M + H]⁺ = 380.42 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 286 | 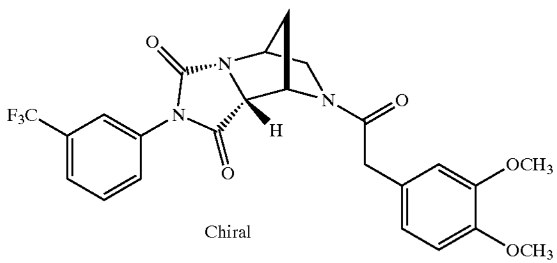 | [5S-(5α,8α,8aα)]-7-[(3,4-Dimethoxyphenyl) acetyl]tetrahydro-2-[3-(trifluoro-methyl)phenyl]-5,8-methanoimidazo[1,5-a]pyrazine-1,3(2H,5H)-dione. | 1.35 LCMS [M + H]$^+$ = 490.41 | 221Ci | B |
| 287 | 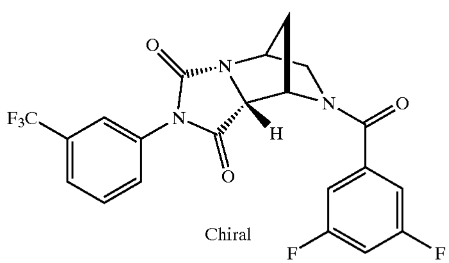 | [5S-(5α,8α,8aα)]-7-(3,5-Difluorobenzyl) tetrahydro-2-[3-trifluoromethyl) phenyl]-5,8-methanoimidazo[1,5-a]pyrazine-1,3(2H,5H)-dione. | 1.52 LCMS [M + H]$^+$ = 452.36 | 221Ci | B |
| 288 | 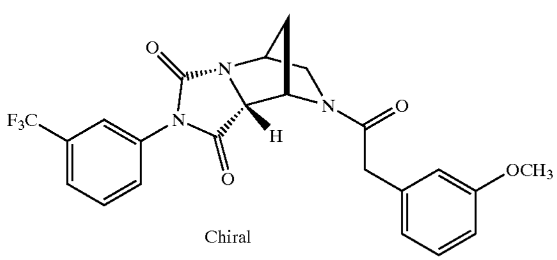 | [5S-(5α,8α,8aα)]-Tetrahydro-7-[(3-methoxyphenyl)acetyl]-2-[3-(trifluoromethyl)phenyl]-5,8-methanoimidazo[1,5-a]pyrazine-1,3(2H,5H)-dione. | 1.49 LCMS [M + H]$^+$ = 460.41 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 289 | 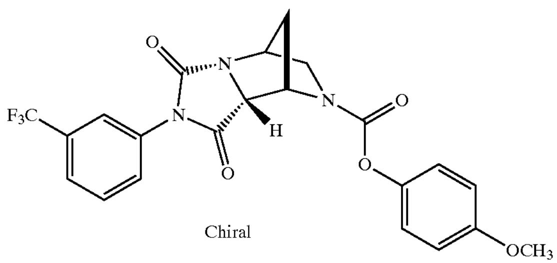 | [5S-(5α,8α,8aα)]-Hexahydro-1,3-dioxo-2-[3-(trifluoromethyl)phenyl]-5,8-methanoimidazo[1,5-a]pyrazine-7(1H)-carboxylic acid, 4-methoxyphenyl ester. | 1.51 LCMS [M + H]⁺ = 462.41 | 221Cii | B |
| 290 | 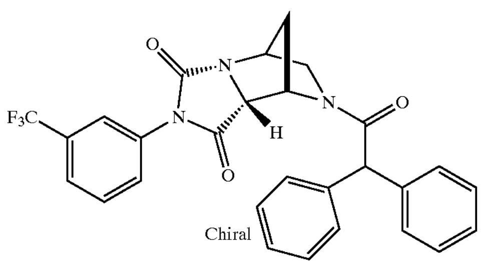 | [5S-(5α,8α,8aα)]-7-(Diphenylacetyl)tetrahydro-2-[3-(trifluoromethyl)phenyl]-5,8-methanoimidazo[1,5-a]pyrazine-1,3(2H,5H)-dione. | 1.72 LCMS [M + H]⁺ = 506.43 | 221Ci | B |
| 291 | 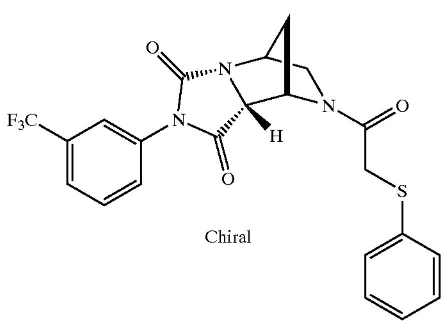 | [5S-(5α,8α,8aα)]-Tetrahydro-7-[(phenylthio)acetyl]-2-[3-(trifluoromethyl)phenyl]-5,8-methanoimidazo[1,5-a]pyrazine-1,3(2H,5H)-dione. | 1.55 LCMS [M + H]⁺ = 462.39 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 292 | 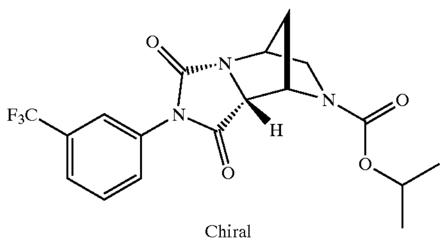 | [5S-(5α,8α,8aα)]-Hexahydro-1,3-dioxo-2-[3-(trifluoromethyl)phenyl]-5,8-methanoimidazo[1,5-a]pyrazine-7(1H)-carboxylic acid, 1-methylethyl ester. | 1.44 LCMS [M + H]⁺ = 420.41 | 221Cii | B |
| 293 | 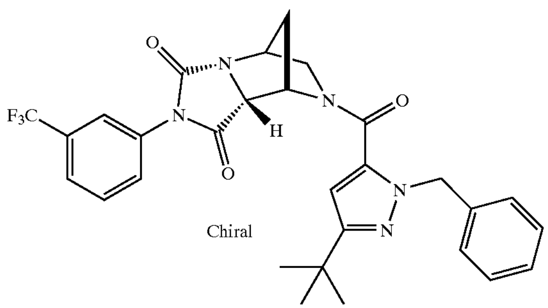 | [5S-(5α,8α,8aα)]-7-[[3-(1,1-Dimethylethyl)-1-(phenylmethyl)-1H-pyrazol-5-yl]carbonyl]tetrahydro-2-[3-(trifluoromethyl)phenyl]-5,8-methanoimidazo[1,5-a]pyrazine-1,3(2H,5H)-dione. | 1.87 LCMS [M + H]⁺ = 552.45 | 221Ci | B |
| 294 | 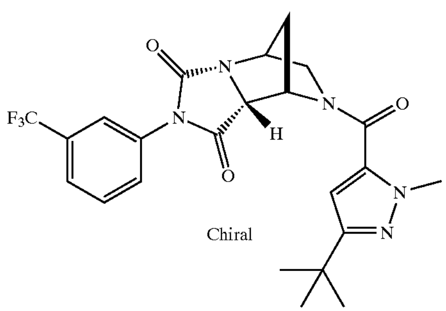 | [5S-(5α,8α,8aα)]-7-[[3-(1,1-Dimethylethyl)-1-methyl-1H-pyrazol-5-yl]carbonyl]tetrahydro-2-[3-(trifluoromethyl)phenyl]-5,8-methanoimidazo[1,5-a]pyrazine-1,3(2H,5H)-dione. | 1.65 LCMS [M + H]⁺ = 476.45 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 295 | 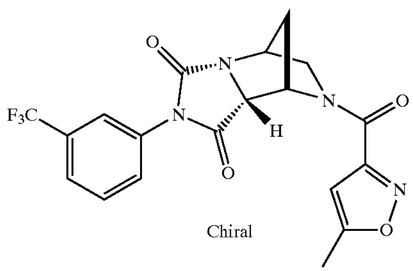 | [5S-(5α,8α,8aα)]-Tetrahydro-7-[(5-methyl-3-isoxazolyl)carbonyl]-2-[3-(trifluoromethyl)phenyl]-5,8-methanoimidazo[1,5-a]pyrazine-1,3(2H,5H)-dione. | 1.29 LCMS [M + H]⁺ = 421.37 | 221Ci | A |
| 296 | 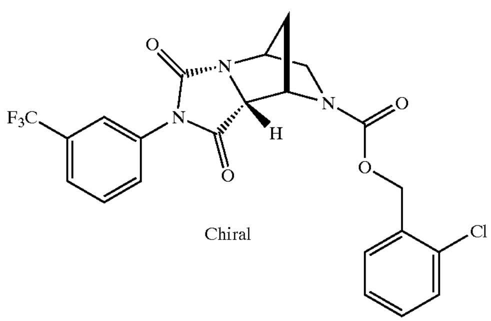 | [5S-(5α,8α,8aα)]-Hexahydro-1,3-dioxo-2-[3-(trifluoromethyl)phenyl]-5,8-methanoimidazo[1,5-a]pyrazine-7(1H)-carboxylic acid, (2-chlorophenyl) methyl ester. | 1.69 LCMS [M + H]⁺ = 502.33 | 221Cii | B |
| 297 | 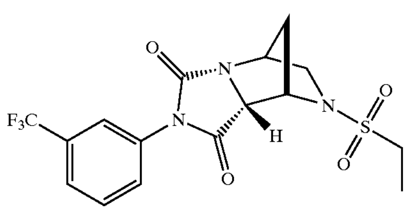 | [5S-(5α,8α,8aα)]-7-(Ethylsulfonyl)tetrahydro-2-[3-(trifluoromethyl)phenyl]-5,8-methanoimidazo[1,5-a]pyrazine-1,3(2H,5H)-dione. | 1.22 LCMS [M + H]⁺ = 404.35 | 221D | B |

TABLE 5-continued

| Ex. No | Structure | Compound Name | Retention Time Min./ Molecular Mass | Proc. of Ex. | LC & MS Con. |
|---|---|---|---|---|---|
| 298 | 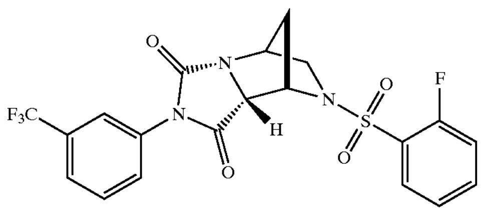 | [5S-(5α,8α,8aα)]-7-[(2-Fluorophenyl)sulfonyl] tetrahydro-2-[3-(trifluoromethyl) phenyl]-5,8-methanoimidazo[1,5-a]pyrazine-1,3(2H,5H)-dione. | 1.41 LCMS [M + H]⁺ = 470.35 | 221D | A |
| 299 | 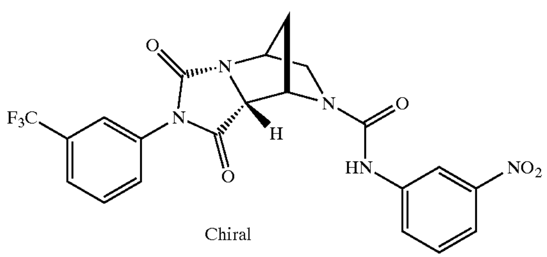 | [5S-(5α,8α,8aα)]-Hexahydro-N-(3-nitrophenyl)-1,3-dioxo-2-[3-(trifluoromethyl)phenyl]-5,8-methanoimidazo[1,5-a]pyrazine-7(1H)-carboxamide. | 1.46 LCMS [M + H]⁺ = 476.36 | 221Bii | B |
| 300 | 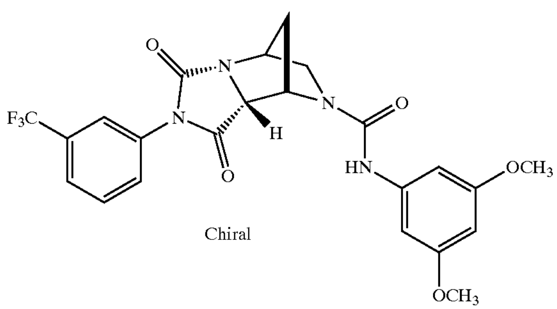 | [5S-(5α,8α,8aα)]-N-(3,5-Dimethoxyphenyl) hexahydro-1,3-dioxo-2-[3-(trifluoromethyl)phenyl]-5,8-methanoimidazo[1,5-a]pyrazine-7(1H)-carboxamide. | 1.45 LCMS [M + H]⁺ = 491.42 | 221Bii | B |

TABLE 5-continued

| Ex. No | Structure | Compound Name | Retention Time Min./ Molecular Mass | Proc. of Ex. | LC & MS Con. |
|---|---|---|---|---|---|
| 301 | 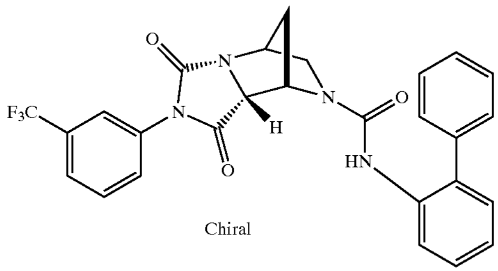 | [5S-(5α,8α,8aα)]-N-[1,1'-Biphenyl]-2-ylhexahydro-1,3-dioxo-2-[3-(trifluoromethyl)phenyl]-5,8-methanoimidazo[1,5-a]pyrazine-7(1H)-carboxamide. | 1.69 LCMS [M + H]+ = 507.43 | 221Bii | B |
| 302 | 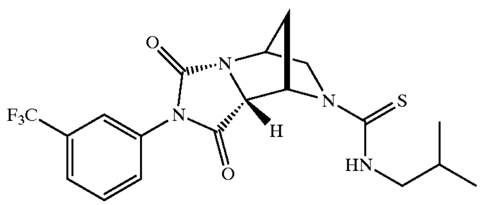 | [5S-(5α,8α,8aα)]-Hexahydro-N-(2-methylpropyl)-1,3-dioxo-2-[3-(trifluoromethyl)phenyl]-5,8-methanoimidazo[1,5-a]pyrazine-7(1H)-carbothioamide. | 1.52 LCMS [M + H]+ = 427.42 | 221Bi | B |
| 303 | 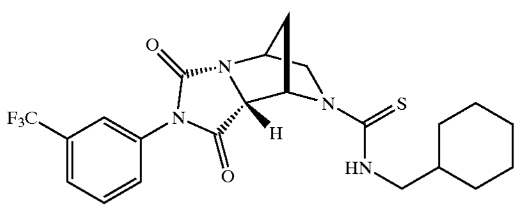 | [5S-(5α,8α,8aα)]-N-(Cyclohexylmethyl)hexahydro-1,3-dioxo-2-[3-(trifluoromethyl)phenyl]-5,8-methanoimidazo[1,5-a]pyrazine-7(1H)-carbothioamide. | 1.75 LCMS [M + H]+ = 467.44 | 221Bi | B |

TABLE 5-continued

| Ex. No | Structure | Compound Name | Retention Time Min./ Molecular Mass | Proc. of Ex. | LC & MS Con. |
|---|---|---|---|---|---|
| 304 | 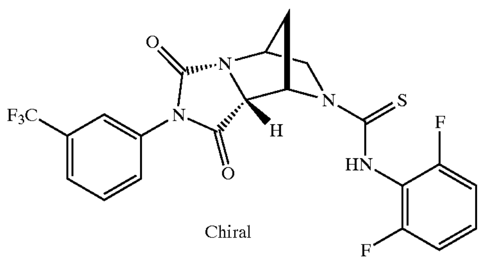 | [5S-(5α,8α,8aα)]-N-(2,6-(Difluorophenyl)hexahydro-1,3-dioxo-2-[3-(trifluoromethyl)phenyl]-5,8-methanoimidazo[1,5-a]pyrazine-7(1H)-carbothioamide. | 1.34 LCMS [M + H]$^+$ = 483.34 | 221Bi | B |
| 305 | 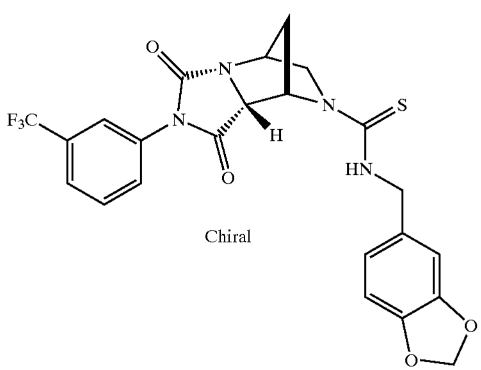 | [5S-(5α,8α,8aα)]-N-(1,3-Benzodioxol-5-ylmethyl)hexahydro-1,3-dioxo-2-[3-(trifluoromethyl)phenyl]-5,8-methanoimidazo[1,5-a]pyrazine-7(1H)-carbothioamide. | 1.52 LCMS [M + H]$^+$ = 505.40 | 221Bi | B |

TABLE 5-continued

| Ex. No | Structure | Compound Name | Retention Time Min./ Molecular Mass | Proc. of Ex. | LC & MS Con. |
|---|---|---|---|---|---|
| 306 | 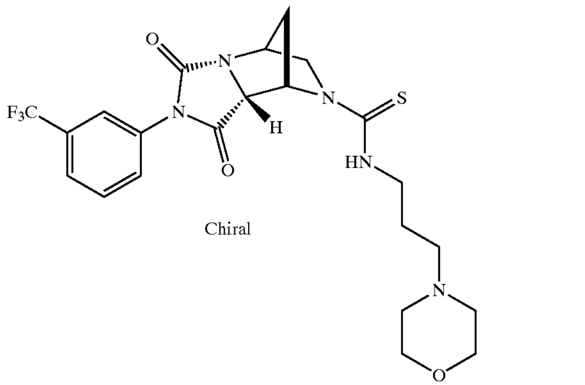 | [5S-(5α,8α,8aα)]-Hexahydro-N-[3-(4-morpholinyl)propyl]-1,3-dioxo-2-[3-(trifluoromethyl)phenyl]-5,8-methanoimidazo[1,5-a]pyrazine-7(1H)-carbothioamide. | 1.02 LCMS $[M+H]^+$ = 498.45 | 221Bi | B |
| 307 | 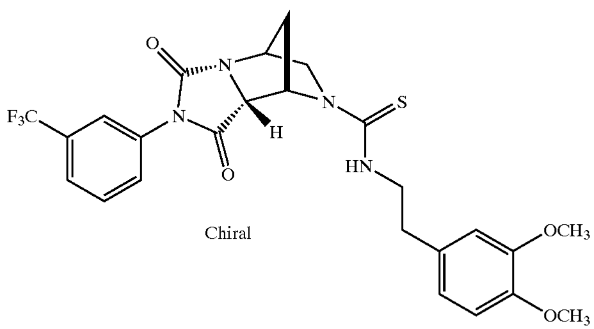 | [5S-(5α,8α,8aα)]-N-[2-(3,4-Dimethoxyphenyl)ethyl]hexahydro-1,3-dioxo-2-[3-(trifluoromethyl)phenyl]-5,8-methanoimidazo[1,5-a]pyrazine-7(1H)-carbothioamide. | 1.48 LCMS $[M+H]^+$ = 535.41 | 221Bi | B |
| 308 | 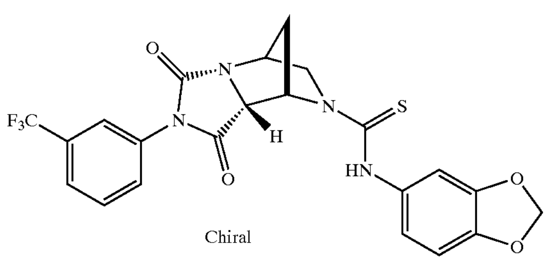 | [5S-(5α,8α,8aα)]-N-1,3-Benzodioxol-5-ylhexahydro-1,3-dioxo-2-[3-(trifluoromethyl)phenyl]-5,8-methanoimidazo[1,5-a]pyrazine-7(1H)-carbothioamide. | 1.37 LCMS $[M+H]^+$ = 491.38 | 221Bi | B |

TABLE 5-continued

| Ex. No | Structure | Compound Name | Retention Time Min./ Molecular Mass | Proc. of Ex. | LC & MS Con. |
|---|---|---|---|---|---|
| 309 | 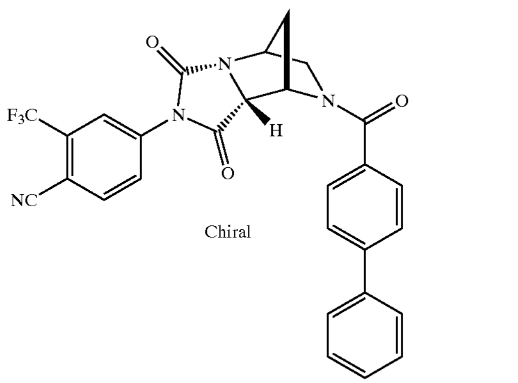 | [5S-(5α,8α,8aα)]-7-[(1,1′-Biphenyl]-4-ylcarbonyl)-2-[4-cyano-3-(trifluoromethyl)phenyl]octahydro-1,3-dioxo-5,8-methanoimidazo[1,5-a]pyrazine. | 1.93 LCMS [M + H]⁺ = 517.43 | 221Ci | B |
| 310 | 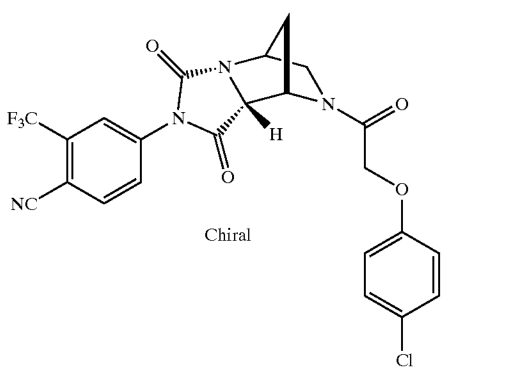 | [5S-(5α,8α,8aα)]-7-[(4-Chlorophenoxy)acetyl]-2-[4-cyano-3-(trifluoromethyl)phenyl]octahydro-1,3-dioxo-5,8-methanoimidazo[1,5-a]pyrazine. | 1.89 LCMS [M + H]⁺ = 505.35 | 221Ci | B |
| 311 | 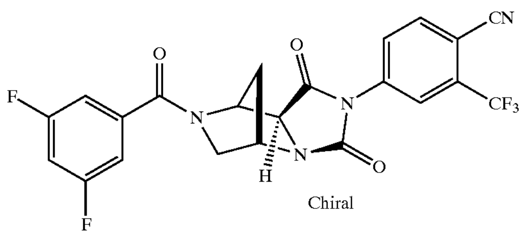 | [5S-(5α,8α,8aβ)]-2-[4-Cyano-3-(trifluoromethyl)phenyl]-7-(3,5-difluorobenzoyl)octahydro-1,3-dioxo-5,8-methanoimidazo[1,5-a]pyrazine. | 1.68 LCMS [M + H]⁺ = 477.41 | 221Ci | B |

| Ex. No | Compound Name | Retention Time Min./ Molecular Mass | Proc. of Ex. | LC & MS Con. |
|---|---|---|---|---|
| 312 | [5S-(5α,8α,8aβ)]-2-[4-Cyano-3-(trifluoromethyl)phenyl]hexahydro-1,3-dioxo-5,8-methanoimidazo[1,5-a]pyrazine-7(1H)-carboxylic acid, (2-chlorophenyl) methyl ester. | 1.85 LCMS [M + H]$^+$ = 505.37 | 221Cii | B |
| 313 | [5S-(5α,8α,8aβ)]-2-[4-Cyano-3-(trifluoromethyl)phenyl]octahydro-7-(2,2,3,3,4,4,5,5,5-nonafluoro-1-oxopentyl)-1,3-dioxo-5,8-methanoimidazo[1,5-a]pyrazine. | 1.92 LCMS [M + H]$^+$ = 581.22 | 221Ci | B |
| 314 | [5S-(5α,8α,8aβ)]-2-[4-Cyano-3-(trifluoromethyl)phenyl]octahydro-1,3-dioxo-7-(2,2,3,3,4,4,5,5,6,6,7,7,8,8,8-pentadecafluoro-1-oxooctyl)-5,8-methanoimidazo[1,5-a]pyrazine. | 2.12 LCMS [M + H]$^+$ = 731.31 | 221Ci | B |
| 315 | [5S-(5α,8α,8aβ)]-2-[4-Cyano-3-(trifluoromethyl)phenyl]-7-(2,2,3,3,4,4,4-heptafluoro-1-oxobutyl)octahydro-1,3-dioxo-5,8-methanoimidazo[1,5-a]pyrazine. | 1.82 LCMS [M + H]$^+$ = 531.25 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 316 | 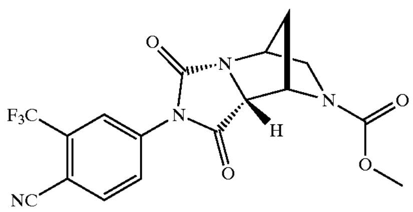 | [5S-(5α,8α,8aα)]-2-[4-Cyano-3-(trifluoromethyl)phneyl]hexahydro-1,3-dioxo-5,8-methanoimidazo[1,5-a]pyrazine-7(1H)-carboxylic acid, methyl ester. | 1.45 LCMS [M + H]$^+$ = 393.31 | 221Cii | B |
| 317 | 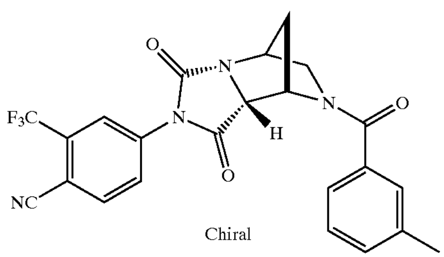 | [5S-(5α,8α,8aα)]-2-[4-Cyano-3-(trifluoromethyl)phenyl]octahydro-7-(3-methylbenzoyl)-1,3-dioxo-5,8-methanoimidazo[1,5-a]pyrazine. | 1.74 LCMS [M + H]$^+$ = 455.43 | 221Ci | B |
| 318 | 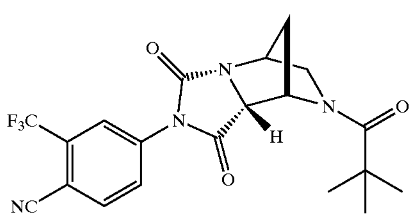 | [5S-(5α,8α,8aα)]-2-[4-Cyano-3-(trifluoromethyl)phenyl]-7-(2,2-dimethyl-1-oxopropyl)octahydro-1,3-dioxo-5,8-methanoimidazo[1,5-a]pyrazine. | 1.66 LCMS [M + H]$^+$ = 421.43 | 221Ci | B |
| 319 | 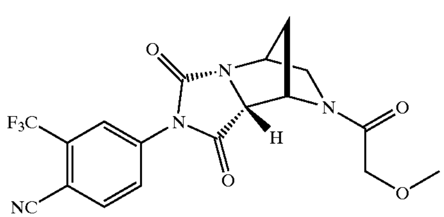 | [5S-(5α,8α,8aα)]-2-[4-Cyano-3-(trifluoromethyl)phenyl]octahydro-7-(methoxyacetyl)-1,3-dioxo-5,8-methanoimidazo[1,5-a]pyrazine. | 1.38 LCMS [M + H]$^+$ = 409.40 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 320 | 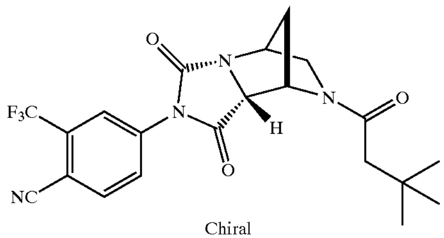 | [5S-(5α,8α,8aα)]-2-[4-Cyano-3-(trifluoromethyl)phenyl]-7-(3,3-dimethyl-1-oxobutyl)octahydro-1,3-dioxo-5,8-methanoimidazo[1,5-a]pyrazine. | 1.74 LCMS [M + H]⁺ = 435.44 | 221Ci | |
| 321 | 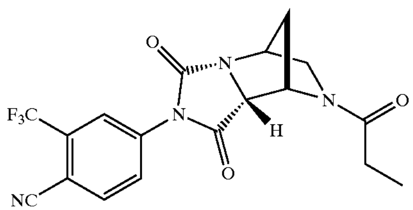 | [5S-(5α,8α,8aα)]-2-[4-Cyano-3-(trifluoromethyl)phenyl]octahydro-1,3-dioxo-7-(1-oxopropyl)-5,8-methanoimidazo[1,5-a]pyrazine. | 1.45 LCMS [M + H]⁺ = 393.41 | 221Ci | B |
| 322 | 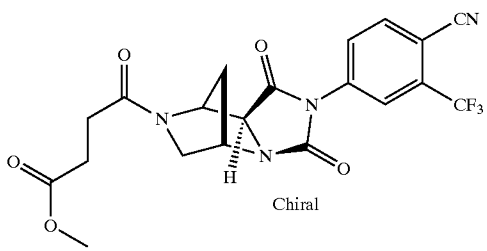 | [5S-(5α,8α,8aβ)]-2-[4-Cyano-3-(trifluoromethyl)phenyl]hexahydro-gamma,1,3-trioxo-5,8-methanoimidazo[1,5-a]pyrazine-7(1H)-butanoic acid, methyl ester. | 1.42 LCMS [M + H]⁺ = 451.41 | 221Ci | B |
| 323 | 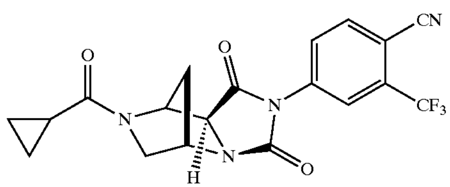 | [5S-(5α,8α,8aβ)]-2-[4-Cyano-3-(trifluoromethyl)phenyl]-7-(cyclopropylcarbonyl)octahydro-1,3-dioxo-5,8-methanoimidazo[1,5-a]pyrazine. | 1.41 LCMS [M + H]⁺ = 405.38 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 324 | 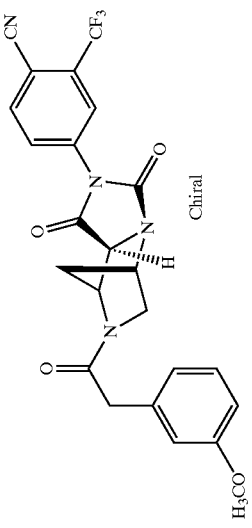 | [5S-(5α,8α,8aβ)]-2-[4-Cyano-3-(trifluoromethyl)phenyl]octahydro-7-[(3-methoxyphenyl)acetyl]-1,3-dioxo-5,8-methanoimidazo[1,5-a]pyrazine. | 1.61 LCMS [M + H]+ = 485.44 | 221Ci | B |
| 325 | 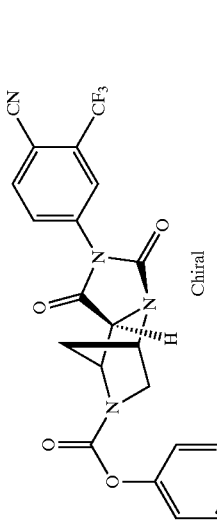 | [5S-(5α,8α,8aβ)]-2-[4-Cyano-3-(trifluoromethyl)phenyl]hexahydro-1,3-dioxo-5,8-methanoimidazo[1,5-a]pyrazine-7(1H)-carboxylic acid, 4-methoxyphenyl ester. | 1.68 LCMS [M + H]+ = 487.41 | 221Cii | B |
| 326 | 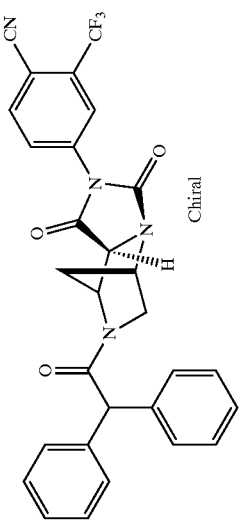 | [5S-(5α,8α,8aβ)]-2-[4-Cyano-3-(trifluoromethyl)phenyl]-7-(diphenylacetyl)octahydro-1,3-dioxo-5,8-methanoimidazo[1,5-a]pyrazine. | 1.87 LCMS [M + H]+ = 531.44 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 327 | 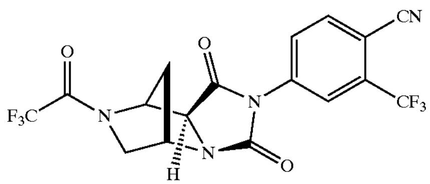 | [5S-(5α,8α,8aβ)]-2-[4-Cyano-3-(trifluoromethyl)phenyl]octahydro-1,3-dioxo-7-(trifluoroacetyl)-5,8-methanoimidazo[1,5-a]pyrazine. | 1.54 LCMS [M + H]+ = 431.27 | 221Ci | B |
| 328 | 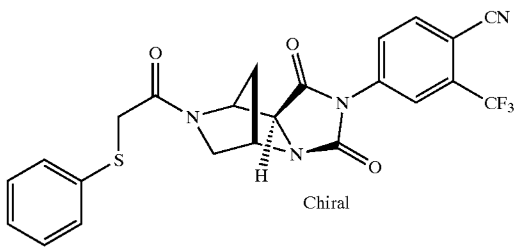 | [5S-(5α,8α,8aβ)]-2-[4-Cyano-3-(trifluoromethyl)phenyl]octahydro-1,3-dioxo-7-[(phenylthio)acetyl]-5,8-methanoimidazo[1,5-a]pyrazine. | 1.71 LCMS [M + H]+ = 487.38 | 221Ci | B |
| 329 | 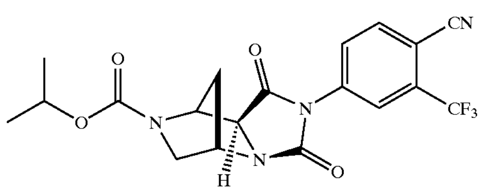 | [5S-(5α,8α,8aβ)]-2-[4-Cyano-3-(trifluoromethyl)phenyl]hexahydro-1,3-dioxo-5,8-methanoimidazo[1,5-a]pyrazine-7(1H)-carboxylic acid, 1-methylethyl ester. | 1.64 LCMS [M + H]+ = 421.34 | 221Cii | B |

TABLE 5-continued

| Ex. No | Structure | Compound Name | Retention Time Min./ Molecular Mass | Proc. of Ex. | LC & MS Con. |
|---|---|---|---|---|---|
| 330 | 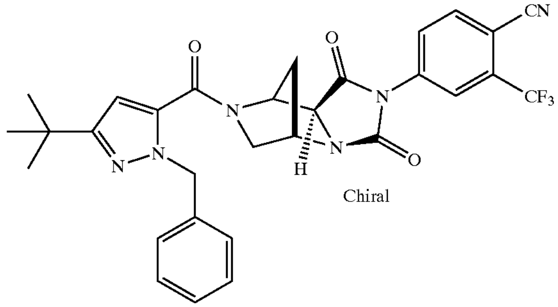 | [5S-(5α,8α,8aβ)]-2-[4-Cyano-3-(trifluoromethyl)phenyl]-7-[[3-(1,1-dimethylethyl)-1-(phenylmethyl)-1H-pyrazol-5-yl]carbonyl]octahydro-1,3-dioxo-5,8methanoimidazo[1,5-a]pyrazine. | 1.98 LCMS [M + H]$^+$ = 577.48 | 221Ci | B |
| 331 | 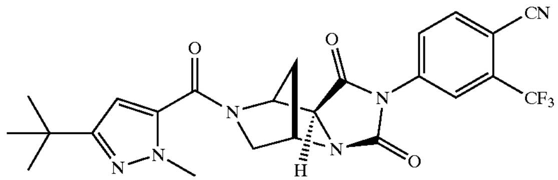 | [5S-(5α,8α,8aβ)]-2-[4-Cyano-3-(trifluoromethyl)phenyl]-7-[[3-(1,1-dimethylethyl)-1-methyl-1H-pyrazol-5-yl]carbonyl]octahydro-1,3-dioxo-5,8-methanoimidazo[1,5-a]pyrazine. | 1.79 LCMS [M + H]$^+$ = 501.48 | 221Ci | B |
| 332 | 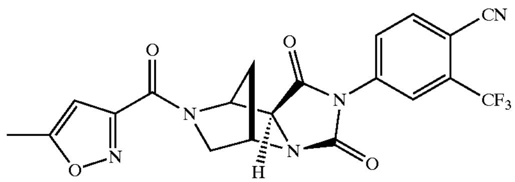 | [5S-(5α,8α,8aβ)]-2-[4-Cyano-3-(trifluoromethyl)phenyl]octahydro-7-[(5-methyl-3-isoxazolyl)carbonyl]-1,3-dioxo-5,8-methanoimidazo[1,5-a]pyrazine. | 1.48 LCMS [M + H]$^+$ = 446.41 | 221Ci | B |
| 333 | 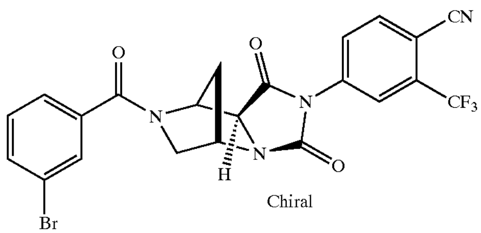 | [5S-(5α,8α,8aβ)]-7-(3-Bromobenzoyl)-2-[4-cyano-3-(trifluoromethyl)phenyl]octahydro-1,3-dioxo-5,8-methanoimidazo[1,5-a]pyrazine. | 1.75 LCMS [M + H]$^+$ = 519.31 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 334 | 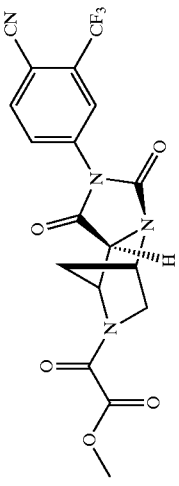 | [5S-(5α,8α,8aβ)]-2-[4-Cyano-3-(trifluoromethyl)phenyl]hexahydro-alpha,1,3-trioxo-5,8-methanoimidazo[1,5-a]pyrazine-7(1H)-acetic acid, methyl ester. | 1.31 LCMS $[M+H]^+ = 423.38$ | 221Ci | B |
| 335 | 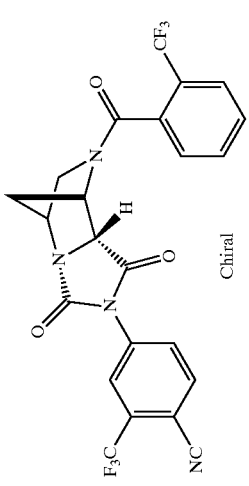 | [5S-(5α,8α,8aα)]-2-[4-Cyano-3-(trifluoromethyl)phenyl]octahydro-7-[2-(trifluoromethyl)benzoyl]-5,8-methanoimidazo[1,5-a]pyrazine. | 1.75 LCMS $[M+H]^+ = 509.38$ | 221Ci | B |
| 336 | 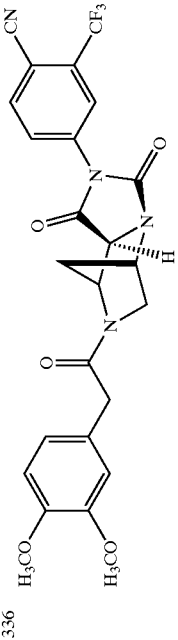 | [5S-(5α,8α,8aβ)]-2-[4-Cyano-3-(trifluoromethyl)phenyl]-7-[(3,4-dimethoxyphenyl)acetyl]octahydro-1,3-dioxo-5,8-methanoimidazo[1,5-a]pyrazine. | 1.48 LCMS $[M+H]^+ = 515.43$ | 221Ci | B |
| 337 | 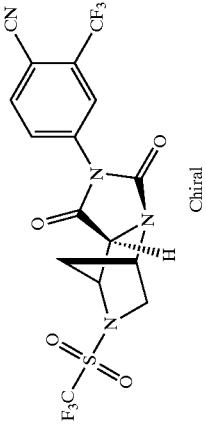 | [5S-(5α,8α,8aβ)]-2-[4-Cyano-3-(trifluoromethyl)phenyl]-1,3-dioxo-7-[(trifluoromethyl)sulfonyl]-5,8-methanoimidazo[1,5-a]pyrazine. | 1.72 LCMS $[M+H]^+ = 467.26$ | 221D | B |

TABLE 5-continued

| Ex. No | Structure | Compound Name | Retention Time Min./ Molecular Mass | Proc. of Ex. | LC & MS Con. |
|---|---|---|---|---|---|
| 338 | 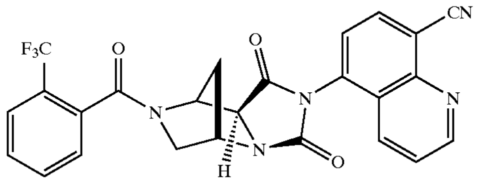 | [5S-(5α,8α,8aβ)]-2-(8-Cyano-5-quinolinyl)octahydro-1,3-dioxo-7-[2-(trifluoromethyl)benzoyl]-5,8-methanoimidazo[1,5-a]pyrazine. | 1.33 LCMS [M + H]$^+$ = 492.39 | 221Ci | B |
| 339 | 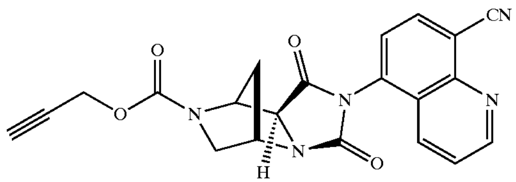 | [5S-(5α,8α,8aβ)]-2-(8-Cyano-5-quinolinyl)hexahydro-1,3-dioxo-5,8-methanoimidazo[1,5-a]pyrazine-7(1H)-carboxylic acid, 2-propynyl ester. | 1.04 LCMS [M + H]$^+$ = 402.38 | 221Cii | B |
| 340 | 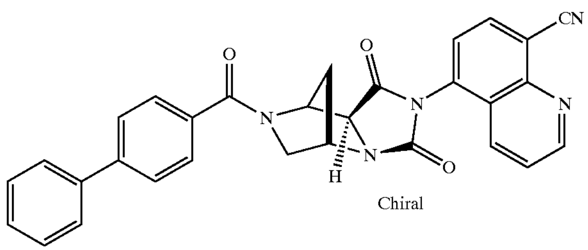 | [5S-(5α,8α,8aβ)]-7-{[1,1'-Biphenyl]-4-ylcarbonyl)-2-(8-cyano-5-quinolinyl)octahydro-1,3-dioxo-5,8-methanoimidazo[1,5-a]pyrazine. | 1.67 LCMS [M + H]$^+$ = 500.43 | 221Ci | B |
| 341 | 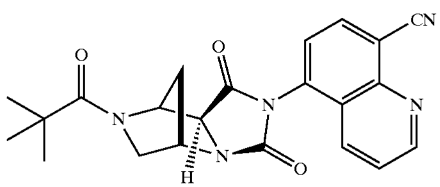 | [5S-(5α,8α,8aβ)]-2-(8-Cyano-5-quinolinyl)-7-(2,2-dimethyl-1-oxopropyl)octahydro-1,3-dioxo-5,8-methanoimidazo[1,5-a]pyrazine. | 1.24 LCMS [M + H]$^+$ = 404.44 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 342 | 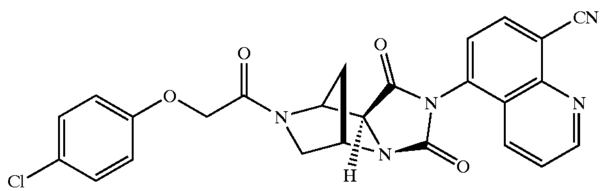 | [5S-(5α,8α,8aβ)]-7-[(4-Chlorophenoxy) acetyl]-2-(8-cyano-5-quinolinyl) octahydro-1,3-dioxo-5,8-methanoimidazo[1,5-a]pyrazine. | 1.49 LCMS [M + H]$^+$ = 488.38 | 221Ci | B |
| 343 | 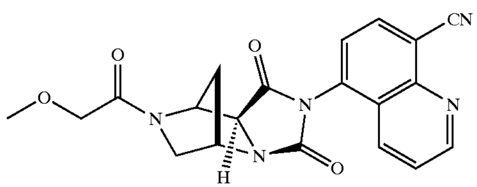 | [5S-(5α,8α,8aβ)]-2-(8-Cyano-5-quinolinyl)-octahydro-7-(methoxyacetyl)-1,3-dioxo-5,8-methanoimidazo[1,5-a]pyrazine. | 0.85 LCMS [M + H]$^+$ = 392.42 | 221Ci | B |
| 344 | 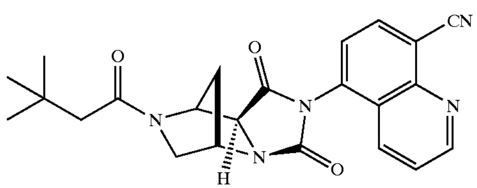 | [5S-(5α,8α,8aβ)]-2-(8-Cyano-5-quinolinyl)-7-(3,3-dimethyl-1-oxobutyl)octahydro-1,3-dioxo-5,8-methanoimidazo[1,5-a]pyrazine. | 1.40 LCMS [M + H]$^+$ = 418.45 | 221Ci | B |
| 345 | 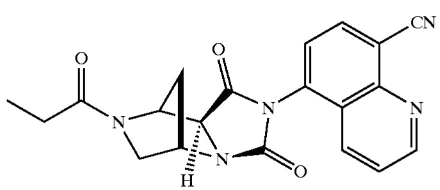 | [5S-(5α,8α,8aβ)]-2-(8-Cyano-5-quinolinyl) octahydro-1,3-dioxo-7-(1-oxopropyl)-5,8-methanoimidazol[1,5-a]pyrazine. | 0.96 LCMS [M + H]$^+$ = 376.43 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 346 | 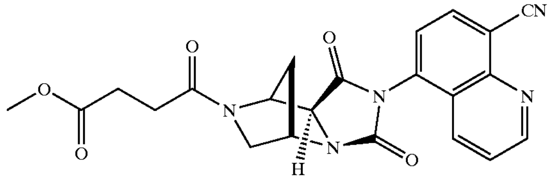 | [5S-(5α,8α,8aβ)]-2-(8-Cyano-5-quinolinyl) hexahydro-gamma,1,3-trioxo-5,8-methanoimidazo[1,5-a]pyrazine-7(1H)-butanoic acid, methyl ester. | 0.98 LCMS [M + H]$^+$ = 434.42 | 221Ci | B |
| 347 | 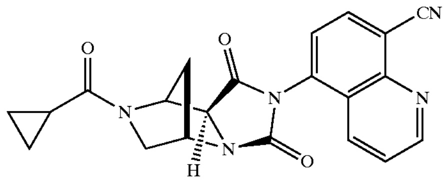 | [5S-(5α,8α,8aβ)]-2-(8-Cyano-5-quinolinyl)-7-(cyclopropylcarbonyl)octahydro-1,3-dioxo-5,8-methanoimidazo[1,5-a]pyrazine. | 0.98 LCMS [M + H]$^+$ = 388.44 | 221Ci | B |
| 348 | 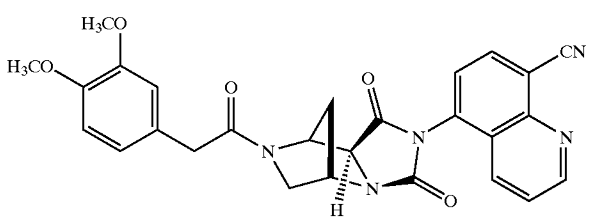 | [5S-(5α,8α,8aβ)]-2-(8-Cyano-5-quinolinyl)-7-[(3,4-dimethoxyphenyl)acetyl]octahydro-1,3-dioxo-5,8-methanoimidazo[1,5-a]pyrazine. | 1.17 LCMS [M + H]$^+$ = 498.44 | 221Ci | B |
| 349 | 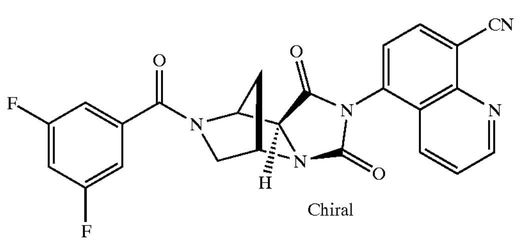 | [5S-(5α,8α,8aβ)]-2-(8-Cyano-5-quinolinyl)-7-(3,5-difluorobenzoyl)octahydro-1,3-dioxo-5,8-methanoimidazo[1,5-a]pyrazine. | 1.35 LCMS [M + H]$^+$ = 460.41 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 350 | H3CO-phenyl-CH2-C(O)-N-[methanoimidazopyrazine bicycle]-N-quinoline-CN (Chiral) | [5S-(5α,8α,8aβ)]-2-(8-Cyano-5-quinolinyl) octahydro-7-[(3-methoxyphenyl)acetyl]-1,3-dioxo-5,8-methanoimidazo[1,5-a]pyrazine. | 1.31 LCMS [M + H]+ = 468.43 | 221Ci | B |
| 351 | H3CO-phenyl-O-C(O)-N-[methanoimidazopyrazine bicycle]-N-quinoline-CN (Chiral) | [5S-(5α,8α,8aβ)]-2-(8-Cyano-5-quinolinyl) hexahydro-1,3-dioxo-5,8-methanoimidazo[1,5-a]pyrazine-7(1H)-carboxylic acid, 4-methoxyphenyl ester. | 1.38 LCMS [M + H]+ = 470.41 | 221Cii | B |
| 352 | (C6H5)2CH-C(O)-N-[methanoimidazopyrazine bicycle]-N-quinoline-CN (Chiral) | [5S-(5α,8α,8aβ)]-2-(8-Cyano-5-quinolinyl)-7-(diphenylacetyl)octahydro-1,3-dioxo-5,8-methanoimidazo[1,5-a]pyrazine. | 1.66 LCMS [M + H]+ = 514.46 | 221Ci | B |
| 353 | F3C-C(O)-N-[methanoimidazopyrazine bicycle]-N-quinoline-CN (Chiral) | [5S-(5α,8α,8aβ)]-2-(8-Cyano-5-quinolinyl) octahydro-1,3-dioxo-7-(trifluoroacetyl)-5,8-methanoimidazo[1,5-a]pyrazine. | 1.15 LCMS [M + H]+ = 416.36 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 354 | 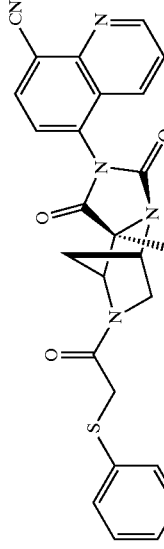 | [5S-(5α,8α,8aβ)]-2-(8-Cyano-5-quinolinyl) octahydro-1,3-dioxo-7-[(phenylthio)acetyl]-5,8-methanoimidazo[1,5-a]pyrazine. | 1.40 LCMS [M + H]$^+$ = 470.38 | 221Ci | B |
| 355 | 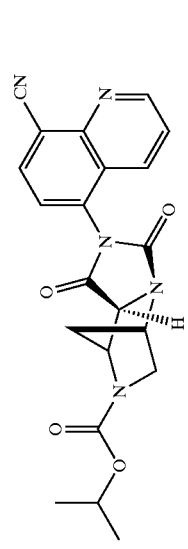 | [5S-(5α,8α,8aβ)]-2-(8-Cyano-5-quinolinyl) hexahydro-1,3-dioxo-5,8-methanoimidazo[1,5-a]pyrazine-7(1H)-carboxylic acid, 1-methylethyl ester. | 1.24 LCMS [M + H]$^+$ = 406.41 | 221Cii | B |
| 356 | 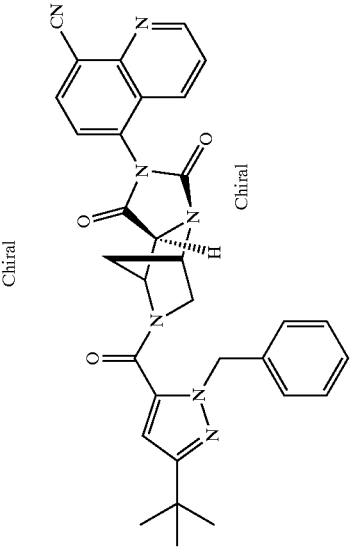 | [5S-(5α, 8α,8aβ)]-2-(8-Cyano-5-quinolinyl)-7-[[3-(1,1-dimethylethyl)1-(phenylmethyl)-1H-pyrazol-5-yl]carbonyl] octahydro-1,3-dioxo-5,8-methanoimidazo[1,5-a]pyrazine. | 1.79 LCMS [M + H]$^+$ = 560.47 | 221Ci | B |
| 357 | 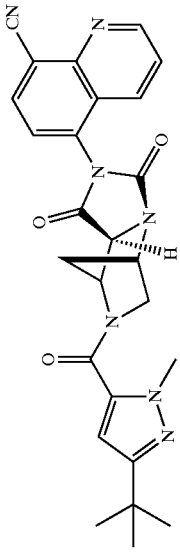 | [5S-(5α,8α,8aβ)]-2-(8-Cyano-5-quinolinyl)-7-[[3-(1,1-dimethylethyl)-1-methyl-1H-pyrazol-5-yl]carbonyl]octahydro-1,3-dioxo-5,8-methanoimidazo[1,5-a]pyrazine. | 1.50 LCMS [M + H]$^+$ = 484.48 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 358 | 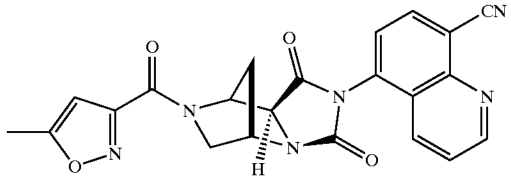 | [5S-(5α,8α,8aβ)]-2-(8-Cyano-5-quinolinyl) octahydro-7-[(5-methyl-3-isoxazolyl)carbonyl]-1,3-dioxo-5,8-methanoimidazo[1,5-a]pyrazine. | 1.13 LCMS [M + H]⁺ = 429.40 | 221Ci | B |
| 359 | 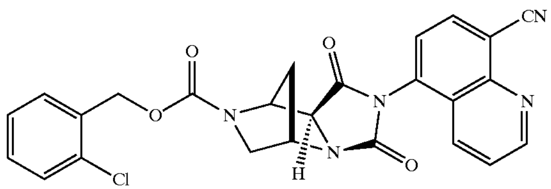 | [5S-(5α,8α,8aβ)]-2-(8-Cyano-5-quinolinyl) hexahydro-1,3-dioxo-5,8-methanoimidazo[1,5-a]pyrazine-7(1H)-carboxylic acid, (2-chlorophenyl) methyl ester. | 1.57 LCMS [M + H]⁺ = 488.39 | 221Cii | B |
| 360 | 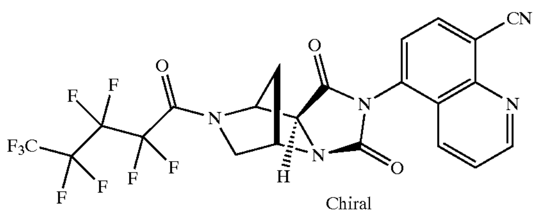 | [5S-(5α,8α,8aβ)]-2-(8-Cyano-5-quinolinyl) octahydro-7-(2,2,3,3,4,4,5,5,5-nonafluoro-1-oxopentyl)-1,3-dioxo-5,8-methanoimidazo[1,5-a]pyrazine. | 1.72 LCMS [M + H]⁺ = 566.33 | 221Ci | B |
| 361 | 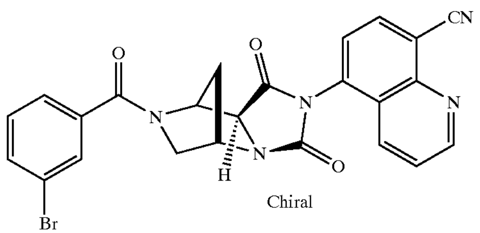 | [5S-(5α,8α,8aβ)]-7-(3-Bromobenzoyl)-2-(8-cyano-5-quinolinyl)octahydro-1,3-dioxo-5,8-methanoimidazo[1,5-a]pyrazine. | 1.43 LCMS [M + H]⁺ = 502.31 | 221Ci | B |

TABLE 5-continued

| Ex. No | Structure | Compound Name | Retention Time Min./ Molecular Mass | Proc. of Ex. | LC & MS Con. |
|---|---|---|---|---|---|
| 362 | 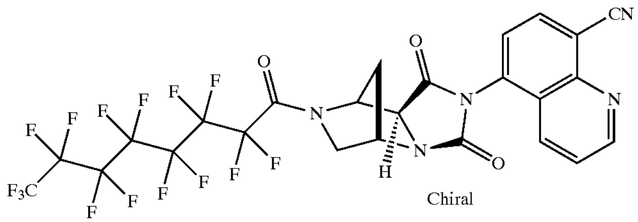 | [5S-(5α,8α,8aβ)]-2-(8-Cyano-5-quinolinyl) octahydro-1,3-dioxo-7-(2,2,3,3,4,4,5,5,6,6,7,7,8,8,8-pentadecafluoro-1-oxooctyl)-5,8-methanoimidazo[1,5-a]pyrazine. | 2.03 LCMS [M + H]⁺ = 716.32 | 221Ci | B |
| 363 | 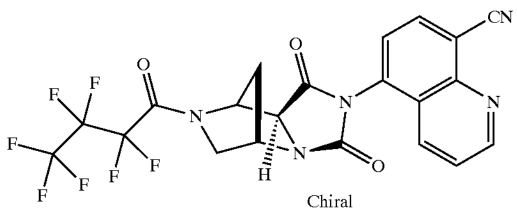 | [5S-(5α,8α,8aβ)]-2-(8-Cyano-5-quinolinyl)-7-(2,2,3,3,4,4,4-heptafluoro-1-oxobutyl)octahydro-1,3-dioxo-5,8-methanoimidazo[1,5-a]pyrazine. | 1.58 LCMS [M + H]⁺ = 516.35 | 221Ci | B |
| 364 | 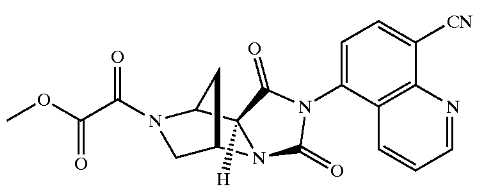 | [5S-(5α,8α,8aβ)]-2-(8-Cyano-5-quinolinyl)-hexahydro-alpha,1,3-trioxo-5,8-methanoimidazo[1,5-a]pyrazine-7(1H)-acetic acid, methyl ester. | 0.91 LCMS [M + H]⁺ = 406.39 | 221Ci | B |
| 365 | 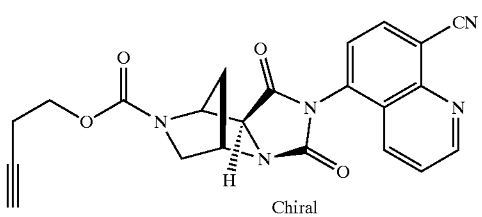 | [5S-(5α,8α,8aβ)]-2-(8-Cyano-5-quinolinyl)-hexahydro-1,3-dioxo-5,8-methanoimidazo[1,5-a]pyrazine-7(1H)-carboxylic acid, 3-butynyl ester. | 1.10 LCMS [M + H]⁺ = 416.41 | 221Cii | A |

TABLE 5-continued

| Ex. No | Structure | Compound Name | Retention Time Min./ Molecular Mass | Proc. of Ex. | LC & MS Con. |
|---|---|---|---|---|---|
| 366 | 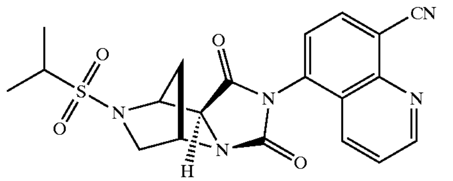 | [5S-(5α,8α,8aβ)]-2-(8-Cyano-5-quinolinyl)-octahydro-7-[(1-methylethyl)sulfonyl]-1,3-dioxo-5,8-methanoimidazo[1,5-a]pyrazine. | 2.25 LCMS [M + H]+ = 426.40 | 221D | A |
| 367 | 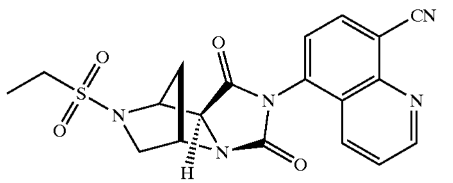 | [5S-(5α,8α,8aβ)]-2-(8-Cyano-5-quinolinyl)-7-(ethylsulfonyl)octahydro-1,3-dioxo-5,8-methanoimidazo[1,5-a]pyrazine. | 0.97 LCMS [M + H]+ = 412.39 | 221D | B |
| 368 | 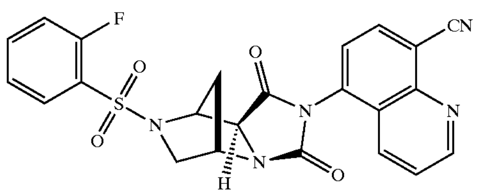 | [5S-(5α,8α,8aβ)]-2-(8-Cyano-5-quinolinyl)-7-[(2-fluorophenyl)sulfonyl]octahydro-1,3-dioxo-5,8-methanoimidazo[1,5-a]pyrazine. | 1.32 LCMS [M + H]+ = 478.38 | 221D | B |
| 369 | 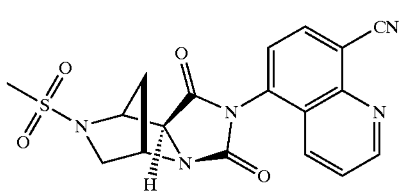 | [5S-(5α,8α,8aβ)]-2-(8-Cyano-5-quinolinyl)-octahydro-7-(methylsulfonyl)-1,3-dioxo-5,8-methanoimidazo[1,5-a]pyrazine. | 0.85 LCMS [M + H]+ = 398.38 | 221D | B |

TABLE 5-continued

| Ex. No | Structure | Compound Name | Retention Time Min./ Molecular Mass | Proc. of Ex. | LC & MS Con. |
|---|---|---|---|---|---|
| 370 | 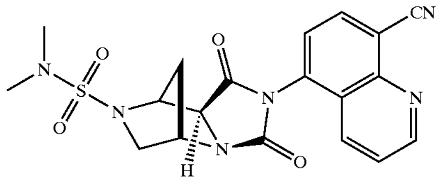 | [5S-(5α,8α,8aβ)]-2-(8-Cyano-5-quinolinyl)-hexahydro-N,N-dimethyl-1,3-dioxo-5,8-methanoimidazo[1,5-a]pyrazine-7(1H)-sulfonamide. | 1.08 LCMS [M + H]⁺ = 427.38 | 221D | B |
| 371 | 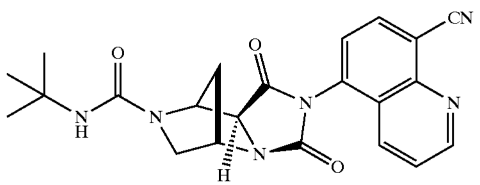 | [5S-(5α,8α,8aβ)]-2-(8-Cyano-5-quinolinyl)-N-(1,1-dimethylethyl)hexahydro-1,3-dioxo-5,8-methanoimidazo[1,5-a]pyrazine-7(1H)-carboxamide. | 1.23 LCMS [M + H]⁺ = 419.46 | 221Bii | B |
| 372 | 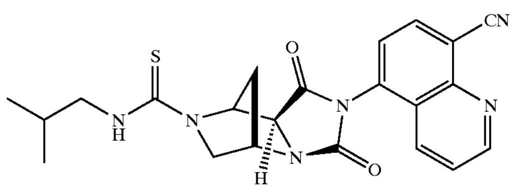 | [5S-(5α,8α,8aβ)]-2-(8-Cyano-5-quinolinyl)-hexahydro-N-(2-methylpropyl)-1,3-dioxo-5,8-methanoimidazo[1,5-a]pyrazine-7(1H)-carbothioamide. | 1.39 LCMS [M + H]⁺ = 435.43 | 221Bi | B |
| 373 | 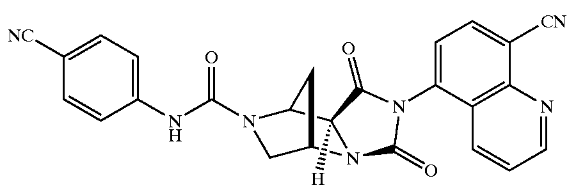 | [5S-(5α,8α,8aβ)]-N-(4-Cyanophenyl)-2-(8-cyano-5-quinolinyl)hexahydro-1,3-dioxo-5,8-methanoimidazo[1,5-a]pyrazine-7(1H)-carboxamide. | 1.15 LCMS [M + H]⁺ = 464.45 | 221Bii | B |

TABLE 5-continued

| Ex. No | Structure | Compound Name | Retention Time Min./ Molecular Mass | Proc. of Ex. | LC & MS Con. |
|---|---|---|---|---|---|
| 374 | 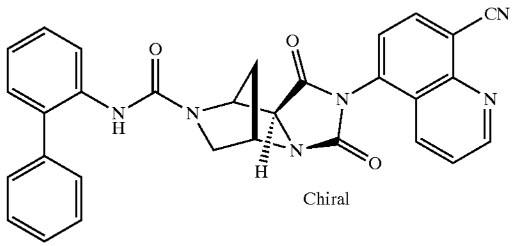 | [5S-(5α,8α,8aβ)]-N-[1,1'-Biphenyl]-2-yl-2-(8-cyano-5-quinolinyl)hexahydro-1,3-dioxo-5,8-methanoimidazo[1,5-a]pyrazine-7(1H)-carboxamide. | 1.62 LCMS [M + H]⁺ = 515.45 | 221Bii | B |
| 375 | 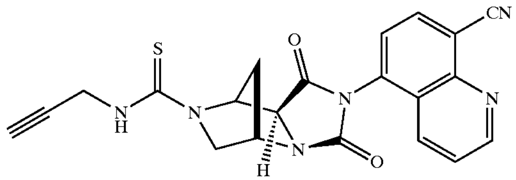 | [5S-(5α,8α,8aβ)]-2-(8-Cyano-5-quinolinyl)-hexahydro-1,3-dioxo-N-2-propynyl-5,8-methanoimidazo[1,5-a]pyrazine-7(1H)-carbothioamide. | 0.77 LCMS [M + H]⁺ = 417.37 | 221Bi | A |
| 376 | 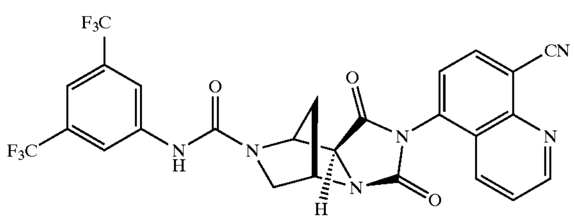 | [5S-(5α,8α,8aβ)]-N-[3,5-Bis(trifluoromethyl)phenyl]-2-(8-cyano-5-quinolinyl)hexahydro-1,3-dioxo-5,8-methanoimidazo[1,5-a]pyrazine-7(1H)-carboxamide. | 1.90 LCMS [M + H]⁺ = 575.39 | 221Bii | B |
| 377 | 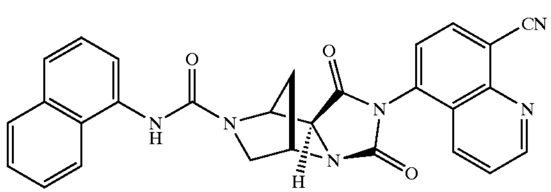 | [5S-(5α,8α,8aβ)]-2-(8-Cyano-5-quinolinyl)-hexahydro-N-1-naphthalenyl-1,3-dioxo-5,8-methanoimidazo[1,5-a]pyrazine-7(1H)-carboxamide. | 1.41 LCMS [M + H]⁺ = 489.45 | 221Bii | A |

TABLE 5-continued

| Ex. No | Structure | Compound Name | Retention Time Min./ Molecular Mass | Proc. of Ex. | LC & MS Con. |
|---|---|---|---|---|---|
| 378 | 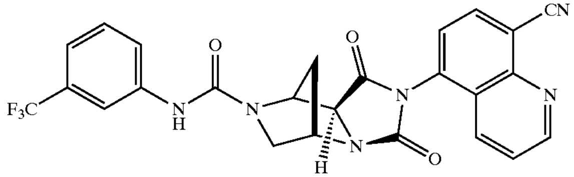 | [5S-(5α,8α,8aβ)]-2-(8-Cyano-5-quinolinyl)-hexahydro-1,3-dioxo-N-[3-(trifluoromethyl)phenyl]-5,8-methanoimidazo[1,5-a]pyrazine-7(1H)-carboxamide. | 1.52 LCMS [M + H]⁺ = 507.41 | 221Bii | B |
| 379 | 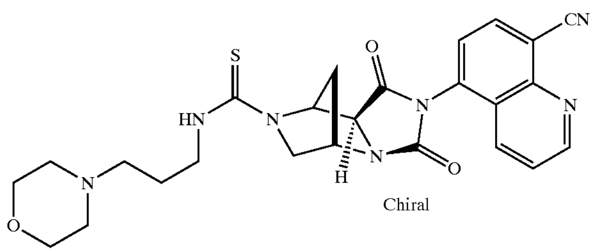 | [5S-(5α,8α,8aβ)]-2-(8-Cyano-5-quinolinyl)-hexahydro-N-[3-(4-morpholinyl)propyl]-1,3-dioxo-5,8-methanoimidazo[1,5-a]pyrazine-7(1H)-carbothioamide. | 0.94 LCMS [M + H]⁺ = 506.47 | 221Bi | B |
| 380 | 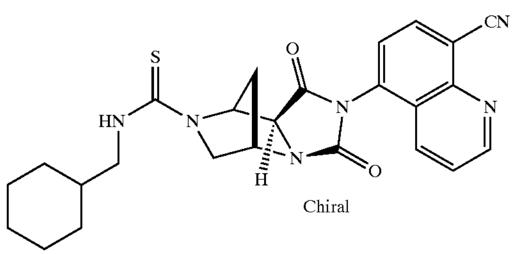 | [5S-(5α,8α,8aβ)]-2-(8-Cyano-5-quinolinyl)-N-(cyclohexylmethyl)hexahydro-1,3-dioxo-5,8-methanoimidazo[1,5-a]pyrazine-7(1H)-carbothioamide. | 1.76 LCMS [M + H]⁺ = 475.47 | 221Bi | B |
| 381 | 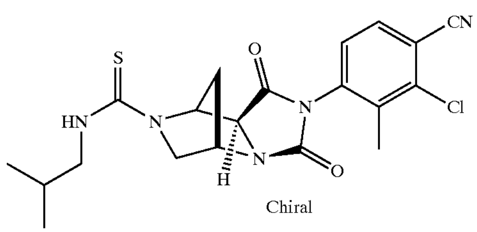 | [5S-(5α,8α,8aβ)]-2-(3-Chloro-4-cyano-2-methylphenyl)hexahydro-N-(2-methylpropyl)-1,3-dioxo-5,8-methanoimidazo[1,5-a]pyrazine-7(1H)-carbothioamide. | 1.69 LCMS [M + H]⁺ = 432.17 | 221Bi | E |

TABLE 5-continued

| Ex. No | Structure | Compound Name | Retention Time Min./ Molecular Mass | Proc. of Ex. | LC & MS Con. |
|---|---|---|---|---|---|
| 382 | 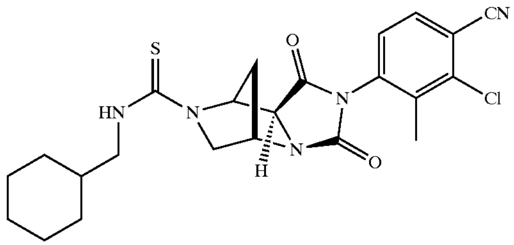 | [5S-(5α,8α,8aβ)]-2-(3-Chloro-4-cyano-2-methylphenyl)-N-hexahydro-1,3-dioxo-5,8-methanoimidazo[1,5-a]pyrazine-7(1H)-carbothioamide. | 1.91 LCMS [M + H]$^+$ = 472.16 | 221Bi | E |
| 383 | 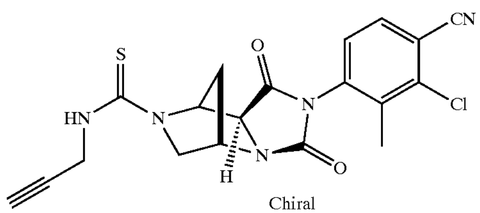 | [5S-(5α,8α,8aβ)]-2-(3-Chloro-4-cyano-2-methylphenyl)hexahydro-1,3-dioxo-N-2-propynyl-5,8-methanoimidazo[1,5-a]pyrazine-7(1H)-carbothioamide. | 1.11 LCMS [M + H]$^+$ = 414.14 | 221Bi | F |
| 384 | 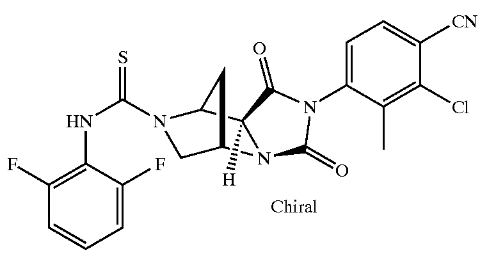 | [5S-(5α,8α,8aβ)]-2-(3-Chloro-4-cyano-2-methylphenyl)-N-(2,6-difluorophenyl)-hexahydro-1,3-dioxo-5,8-methanoimidazo[1,5-a]pyrazine-7(1H)-carbothioamide. | 1.49 LCMS [M + H]$^+$ = 488.10 | 221Bi | F |

TABLE 5-continued

| Ex. No | Structure | Compound Name | Retention Time Min./ Molecular Mass | Proc. of Ex. | LC & MS Con. |
|---|---|---|---|---|---|
| 385 | 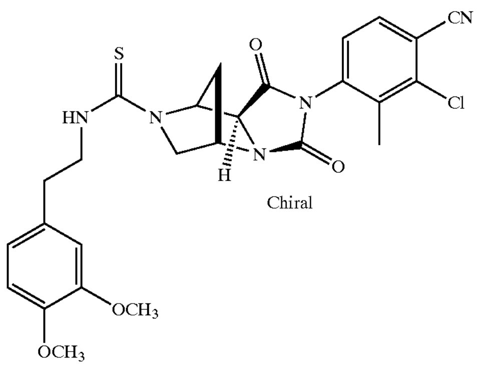 | [5S-(5α,8α,8aβ)]-2-(3-Chloro-4-cyano-2-methylphenyl)-N-[2-(3,4-dimethoxyphenyl)-ethyl]hexahydro-1,3-dioxo-5,8-methanoimidazo[1,5-a]pyrazine-7(1H)-carbothioamide. | 1.63 LCMS $[M + H]^+$ = 538.15 | 221Bi | F |
| 386 | 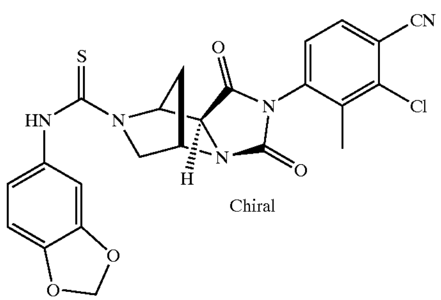 | [5S-(5α,8α,8aβ)]-N-1,3-Benzodioxol-5-yl-2-(3-chloro-4-cyano-2-methylphenyl)-hexahydro-1,3-dioxo-5,8-methanoimidazo[1,5-a]pyrazine-7(1H)-carbothioamide. | 1.51 LCMS $[M + H]^+$ = 496.10 | 221Bi | F |
| 387 | 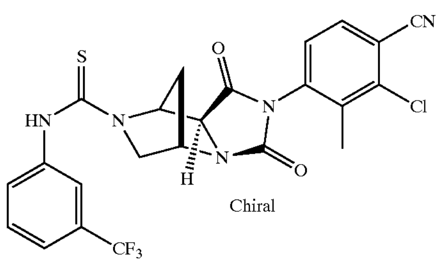 | [5S-(5α,8α,8aβ)]-2-(3-Chloro-4-cyano-2-methylphenyl)hexahydro-1,3-dioxo-N-[3-(trifluoromethyl)phenyl]-5,8-methanoimidazo[1,5-a]pyrazine-7(1H)-carboxamide. | 1.75 LCMS $[M + H]^+$ = 504.13 | 221Bii | F |

TABLE 5-continued

| Ex. No | Structure | Compound Name | Retention Time Min./ Molecular Mass | Proc. of Ex. | LC & MS Con. |
|---|---|---|---|---|---|
| 388 | 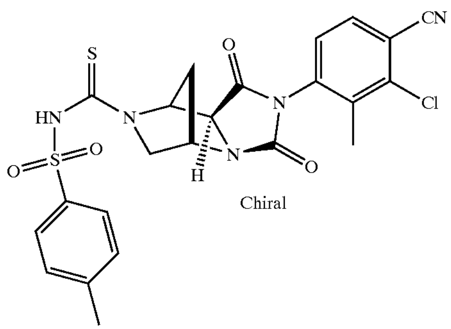 | [5S-(5α,8α,8aβ)]-2-(3-Chloro-4-cyano-2-methylphenyl)hexahydro-N-[(4-methylphenyl)-sulfonyl]-1,3-dioxo-5,8-methanoimidazo[1,5-a]pyrazine-7(1H)-carboxamide. | 1.53 LCMS [M + H]$^+$ = 514.10 | 221Bii | F |
| 389 | 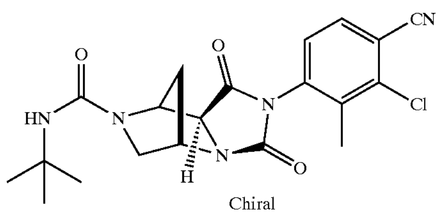 | [5S-(5α,8α,8aβ)]-2-(3-Chloro-4-cyano-2-methylphenyl)-N-(1,1-dimethylethyl)-hexahydro-1,3-dioxo-5,8-methanoimidazo[1,5-a]pyrazine-7(1H)-carboxamide. | 1.55 LCMS [M + H]$^+$ = 416.20 | 221Bii | F |
| 390 | 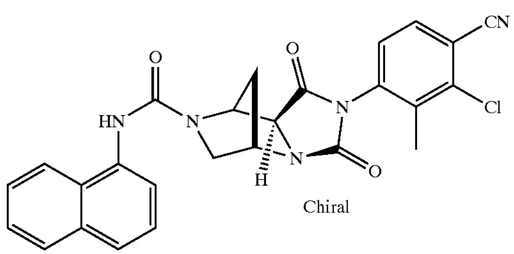 | [5S-(5α,8α,8aβ)]-2-(3-Chloro-4-cyano-2-methylphenyl)hexahydro-N-1-naphthalenyl-1,3-dioxo-5,8-methanoimidazo[1,5-a]pyrazine-7(1H)-carboxamide. | 1.63 LCMS [M + H]$^+$ = 486.16 | 221Bii | F |

TABLE 5-continued

| Ex. No | Structure | Compound Name | Retention Time Min./ Molecular Mass | Proc. of Ex. | LC & MS Con. |
|---|---|---|---|---|---|
| 391 | 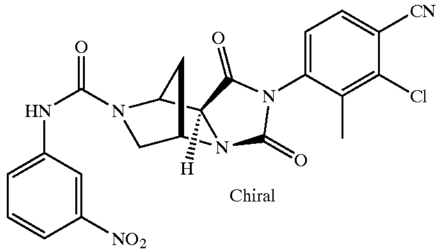 | [5S-(5α,8α,8aβ)]-2-(3-Chloro-4-cyano-2-methylphenyl)hexahydro-N-(3-nitrophenyl)-1,3-dioxo-5,8-methanoimidazo[1,5-a]pyrazine-7(1H)-carboxamide. | 1.55 LCMS [M + H]+ = 481.12 | 221Bii | F |
| 392 | 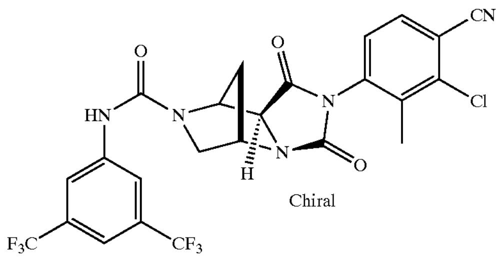 | [5S-(5α,8α,8aβ)]-N-[3,5-Bis(trifluoromethyl)-phenyl]-2-(3-chloro-4-cyano-2-methylphenyl)hexahydro-1,3-dioxo-5,8-methanoimidazo[1,5-a]pyrazine-7(1H)-carboxamide. | 2.01 LCMS [M + H]+ = 572.11 | 221Bii | E |
| 393 | 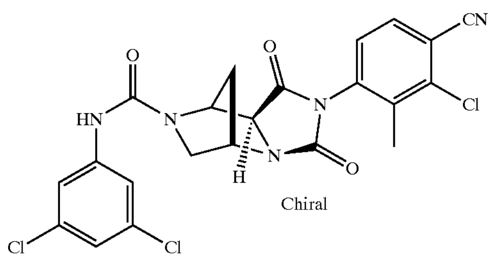 | [5S-(5α,8α,8aβ)]-2-(3-Chloro-4-cyano-2-methylphenyl)-N-(3,5-dichlorophenyl)-hexahydro-1,3-dioxo-5,8-methanoimidazo[1,5-a]pyrazine-7(1H)-carboxamide. | 1.92 LCMS [M + H]+ = 504.04 | 221Bii | F |

TABLE 5-continued

| Ex. No | Structure | Compound Name | Retention Time Min./ Molecular Mass | Proc. of Ex. | LC & MS Con. |
|---|---|---|---|---|---|
| 394 | 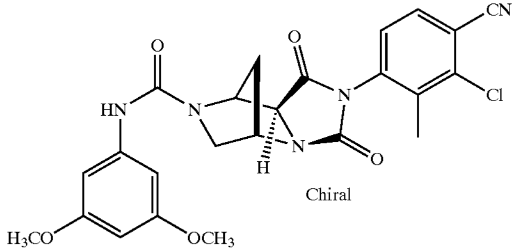 | [5S-(5α,8α,8aβ)]-2-(3-Chloro-4-cyano-2-methylphenyl)-N-(3,5-dimethoxyphenyl)-hexahydro-1,3-dioxo-5,8-methanoimidazo[1,5-a]pyrazine-7(1H)-carboxamide. | 1.57 LCMS [M + H]+ = 496.14 | 221Bii | E |
| 395 | 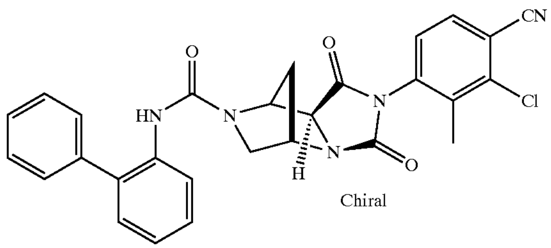 | [5S-(5α,8α,8aβ)]-N-[1,1'-Biphenyl]-2-yl-2-(3-chloro-4-cyano-2-methylphenyl)hexahydro-1,3-dioxo-5,8-methanoimidazo[1,5-a]pyrazine-7(1H)-carboxamide. | 1.79 LCMS [M + H]+ = 512.18 | 221Bii | E |
| 396 | 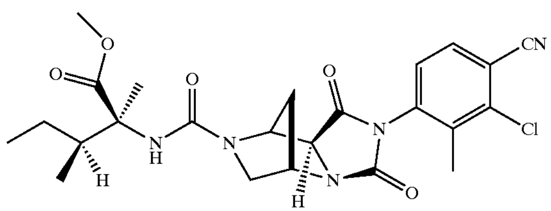 | [5S-(5α,8α,8aβ)]-N-[[2-(3-Chloro-4-cyano-2-methylphenyl)hexahydro-1,3-dioxo-5,8-methanoimidazo[1,5-a]pyrazin-7(1H)-yl]carbonyl]isoleucine, methyl ester. | 1.66 LCMS [M + H]+ = 488.23 | 221Bii | E |
| 397 | 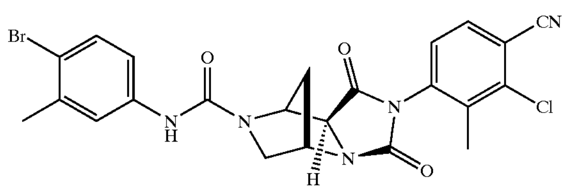 | [5S-(5α,8α,8aβ)]-N-(4-Bromo-3-methylphenyl)-2-(3-chloro-4-cyano-2-methylphenyl)-hexahydro-1,3-dioxo-5,8-methanoimidazo[1,5-a]pyrazine-7(1H)-carboxamide. | 1.86 LCMS [M + H]+ = 530.06 | 221Bii | E |

TABLE 5-continued

| Ex. No | Structure | Compound Name | Retention Time Min./ Molecular Mass | Proc. of Ex. | LC & MS Con. |
|---|---|---|---|---|---|
| 398 | 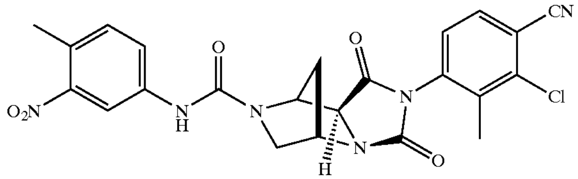 | [5S-(5α,8α,8aβ)]-2-(3-Chloro-4-cyano-2-methylphenyl)hexahydro-N-(4-methyl-3-nitrophenyl)-1,3-dioxo-5,8-methanoimidazo[1,5-a]pyrazine-7(1H)-carboxamide. | 1.68 LCMS [M + H]⁺ = 495.14 | 221Bii | E |
| 399 | 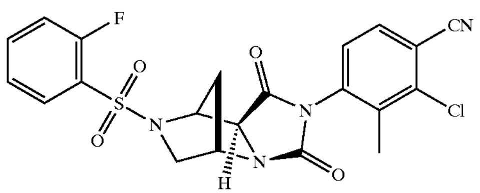 | [5S-(5α,8α,8aβ)]-2-(3-Chloro-4-cyano-2-methylphenyl)-7-[(2-fluorophenyl)-sulfonyl] octahydro-1,3-dioxo-5,8-methanoimidazo[1,5-a]pyrazine. | 1.62 LCMS [M + H]⁺ = 473.19 | 221D | E |
| 400 | 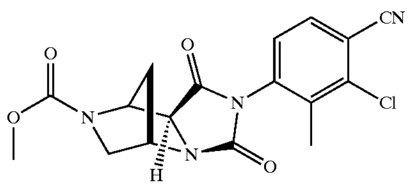 | [5S-(5α,8α,8aβ)]-2-(3-Chloro-4-cyano-2-methylphenyl)hexahydro-1,3-dioxo-5,8-methanoimidazo[1,5-a]pyrazine-7(1H)-carboxylic acid, methyl ester. | 1.30 LCMS [M + H]⁺ = 375.16 | 221Cii | F |
| 401 | 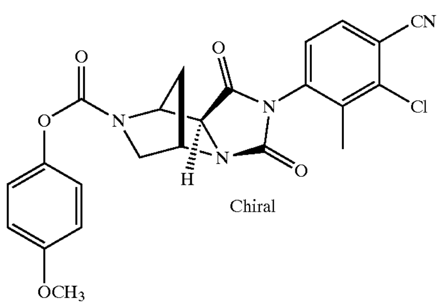 | [5S-(5α,8α,8aβ)]-2-(3-Chloro-4-cyano-2-methylphenyl)hexahydro-1,3-dioxo-5,8-methanoimidazo[1,5-a]pyrazine-7(1H)-carboxylic acid, 4-methoxyphenyl ester. | 1.62 LCMS [M + H]⁺ = 467.14 | 221Cii | F |

TABLE 5-continued

| Ex. No | Structure | Compound Name | Retention Time Min./ Molecular Mass | Proc. of Ex. | LC & MS Con. |
|---|---|---|---|---|---|
| 402 | 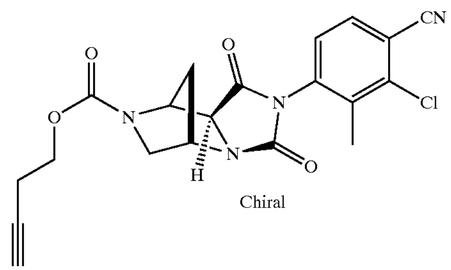 | [5S-(5α,8α,8aβ)]-2-(3-Chloro-4-cyano-2-methylphenyl)hexahydroimidazo[1,5-a]pyrazine-5,8-methanoimidazo[1,5-a]pyrazine-7(1H)-carboxylic acid, 3-butynyl ester. | 1.45 LCMS [M + H]+ = 413.16 | 221Cii | F |
| 403 | 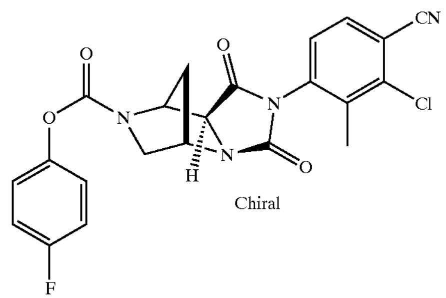 | [5S-(5α,8α,8aβ)]-2-(3-Chloro-4-cyano-2-methylphenyl)hexahydroimidazo[1,5-a]pyrazine-5,8-methanoimidazo[1,5-a]pyrazine-7(1H)-carboxylic acid, 4-fluorophenyl ester. | 1.67 [M + H]+ = 455.13 | 221Cii | F |
| 404 | 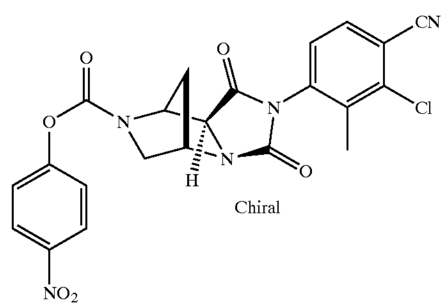 | [5S-(5α,8α,8aβ)]-2-(3-Chloro-4-cyano-2-methylphenyl)hexahydroimidazo[1,5-a]pyrazine-5,8-methanoimidazo[1,5-a]pyrazine-7(1H)-carboxylic acid, 4-nitrophenyl ester. | 1.65 LCMS [M + H]+ = 482.09 | 221Cii | F |

TABLE 5-continued

| Ex. No | Structure | Compound Name | Retention Time Min./ Molecular Mass | Proc. of Ex. | LC & MS Con. |
|---|---|---|---|---|---|
| 405 | 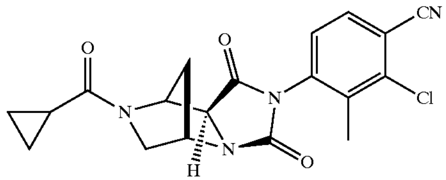 | [5S-(5α,8α,8aβ)]-2-(3-Chloro-4-cyano-2-methylphenyl)-7-(cyclopropylcarbonyl)-octahydro-1,3-dioxo-5,8-methanoimidazo[1,5-a]pyrazine. | 1.35 LCMS [M + H]+ = 385.18 | 221Ci | E |
| 406 | 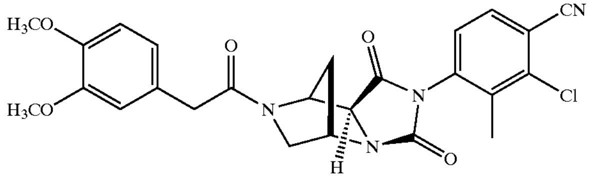 | [5S-(5α,8α,8aβ)]-2-(3-Chloro-4-cyano-2-methylphenyl)-7-[(3,4-dimethoxyphenyl)-acetyl]octahydro-1,3-dioxo-5,8-methanoimidazo[1,5-a]pyrazine. | 1.46 LCMS [M + H]+ = 495.15 | 221Ci | E |
| 407 | 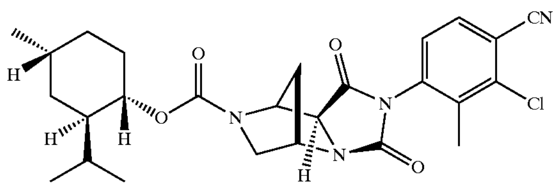 | [5S-(5α,8α,8aβ)]-2-(3-Chloro-4-cyano-2-methylphenyl)hexahydro-1,3-dioxo-5,8-methanoimidazo[1,5-a]pyrazine-7(1H)-carboxylic acid, (1S,2R,5S)-5-methyl-2-(1-methyethyl)-cyclohexylester. | 2.12 LCMS [M + H]+ = 497.37 | 221Cii | D |
| 408 | 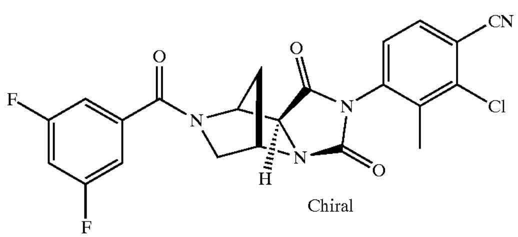 | [5S-(5α,8α,8aβ)]-2-(3-Chloro-4-cyano-2-methylphenyl)-7-(3,5-difluorobenzoyl)-octahydro-1,3-dioxo-5,8-methanoimidazo[1,5-a]pyrazine. | 1.63 LCMS [M + H]+ = 457.13 | 221Ci | F |

TABLE 5-continued

| Ex. No | Structure | Compound Name | Retention Time Min./ Molecular Mass | Proc. of Ex. | LC & MS Con. |
|---|---|---|---|---|---|
| 409 | 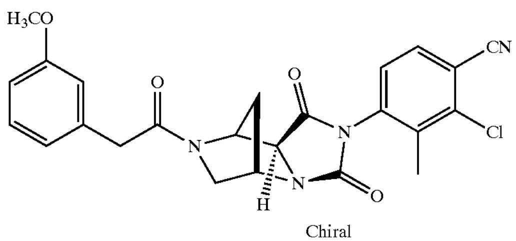 | [5S-(5α,8α,8aβ)]-2-(3-Chloro-4-cyano-2-methylphenyl)octahydro-7-[(3-methoxyphenyl)acetyl]-1,3-dioxo-5,8-methanoimidazo[1,5-a]pyrazine. | 1.58 LCMS [M + H]$^+$ = 465.19 | 221Ci | F |
| 410 | 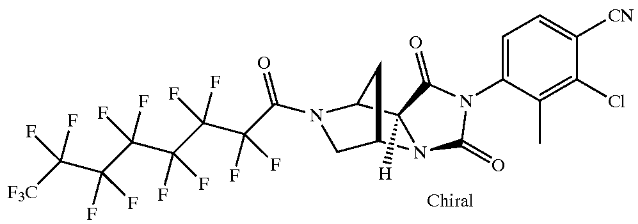 | [5S-(5α,8α,8aβ)]-2-(3-Chloro-4-cyano-2-methylphenyl)octahydro-1,3-dioxo-7-(2,2,3,3,4,4,5,5,6,6,7,7,8,8,8-pentadecafluoro-1-oxooctyl)-5,8methanoimidazo[1,5-a]pyrazine. | 2.18 LCMS [M + H]$^+$ = 734.97 | 221Ci | E |
| 411 | 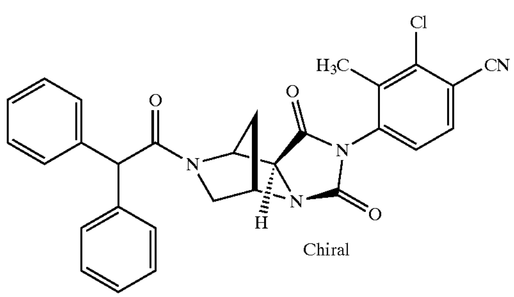 | [5S-(5α,8α,8aβ)]-2-(3-Chloro-4-cyano-2-methylphenyl)-7-(diphenylacetyl)-octahydro-1,3-dioxo-5,8-methanoimidazo[1,5-a]pyrazine. | 1.83 LCMS [M + H]$^+$ = 511.18 | 221Ci | F |

TABLE 5-continued

| Ex. No | Structure | Compound Name | Retention Time Min./ Molecular Mass | Proc. of Ex. | LC & MS Con. |
|---|---|---|---|---|---|
| 412 | 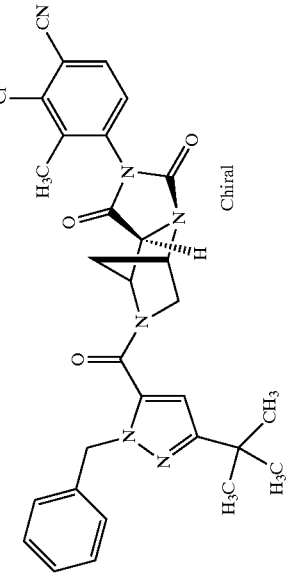 | [5S-(5α,8α,8aβ)]-2-(3-Chloro-4-cyano-2-methylphenyl)-7-[[3-(1,1-dimethylethyl)-1-(phenylmethyl)-1H-pyrazol-5-yl]carbonyl]-octahydro-1,3-dioxo-5,8-methanoimidazo[1,5-a]pyrazine. | 2.00 LCMS [M + H]⁺ = 557.26 | 221Ci | E |
| 413 | 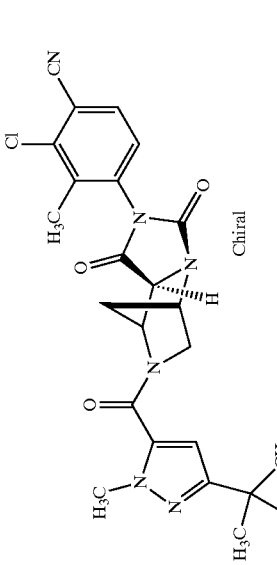 | [5S-(5α,8α,8aβ)]-2-(3-Chloro-4-cyano-2-methylphenyl)-7-[[3-(1,1-dimethylethyl)-1-methyl-1H-pyrazol-5-yl]carbonyl]-octahydro-1,3-dioxo-5,8-methanoimidazo[1,5-a]pyrazine. | 1.76 LCMS [M + H]⁺ = 481.25 | 221Ci | F |
| 414 | 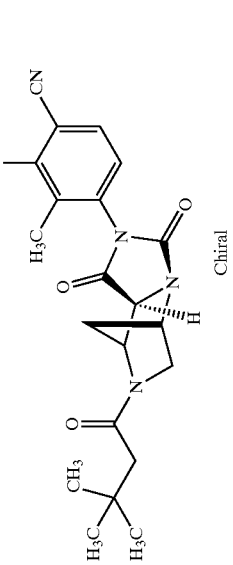 | [5S-(5α,8α,8aβ)]-2-(3-Chloro-4-cyano-2-methylphenyl)-7-(3,3-dimethyl-1-oxobutyl)-octahydro-1,3-dioxo-5,8-methanoimidazo[1,5-a]pyrazine. | 1.67 LCMS [M + H]⁺ = 415.23 | 221Ci | E |

TABLE 5-continued

| Ex. No | Structure | Compound Name | Retention Time Min./ Molecular Mass | Proc. of Ex. | LC & MS Con. |
|---|---|---|---|---|---|
| 415 | 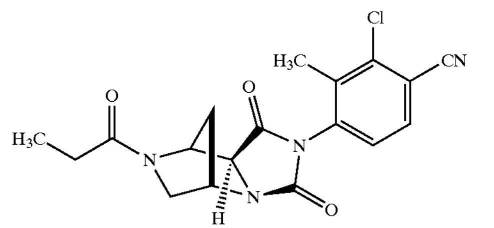 | [5S-(5α,8α,8aβ)]-2-(3-Chloro-4-cyano-2-methylphenyl)octahydro-7-(1-oxopropyl)-5,8-methanoimidazo[1,5-a]pyrazine. | 1.28 LCMS [M + H]⁺ = 373.15 | 221Ci | F |
| 416 | 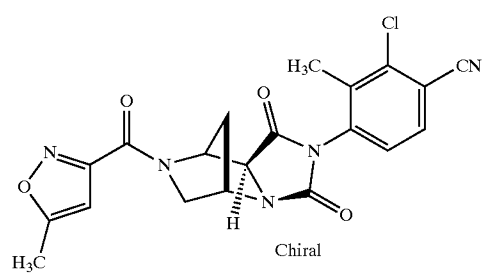 | [5S-(5α,8α,8aβ)]-2-(3-Chloro-4-cyano-2-methylphenyl)octahydro-7-[(5-methyl-3-isoxazolyl)carbonyl]-1,3-dioxo-5,8-methanoimidazo[1,5-a]pyrazine. | 1.43 LCMS [M + H]⁺ = 426.12 | 221Ci | F |
| 417 | 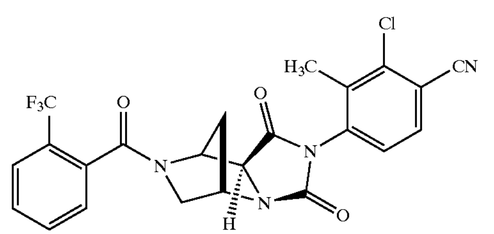 | [5S-(5α,8α,8aβ)]-2-(3-Chloro-4-cyano-2-methylphenyl)octahydro-1,3-dioxo-7-[2-(trifluoromethyl)benzoyl]-5,8-methanoimidazo[1,5-a]pyrazine. | 1.60 LCMS [M + H]⁺ = 489.19 | 221Ci | E |

TABLE 5-continued

| Ex. No | Structure | Compound Name | Retention Time Min./ Molecular Mass | Proc. of Ex. | LC & MS Con. |
|---|---|---|---|---|---|
| 418 | 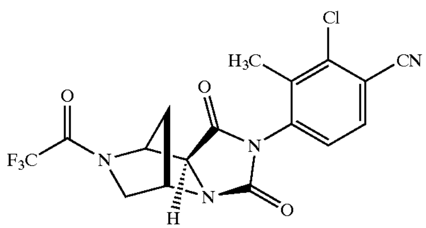 | [5S-(5α,8α,8aβ)]-2-(3-Chloro-4-cyano-2-methylphenyl)octahydro-1,3-dioxo-7-(trifluoroacetyl)-5,8-methanoimidazo[1,5-a]pyrazine | 1.55 LCMS [M + H]$^+$ = 413.31 | 221Ci | F |
| 419 | 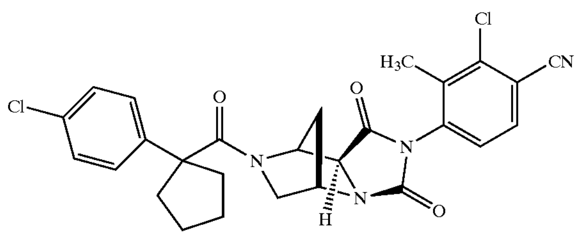 | [5S-(5α,8α,8aβ)]-2-(3-Chloro-4-cyano-2-methylphenyl)-7[[1-(4-chlorophenyl)cyclopentyl]carbonyl]octahydro-1,3-dioxo-5,8-methanoimidazo[1,5-a]pyrazine. | 2.00 LCMS [M + H]$^+$ = 523.14 | 221Ci | E |
| 420 | 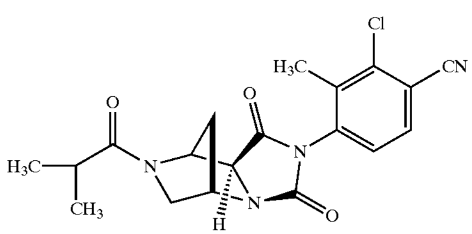 | [5S-(5α,8α,8aβ)]-2-(3-Chloro-4-cyano-2-methylphenyl)octahydro-7-(2-methyl-1-oxopropyl)-1,3-dioxo-5,8-methanoimidazo[1,5-a]pyrazine. | 1.40 LCMS [M + H]$^+$ = 387.20 | 221Ci | F |

TABLE 5-continued

| Ex. No | Structure | Compound Name | Retention Time Min./ Molecular Mass | Proc. of Ex. | LC & MS Con. |
|---|---|---|---|---|---|
| 421 | 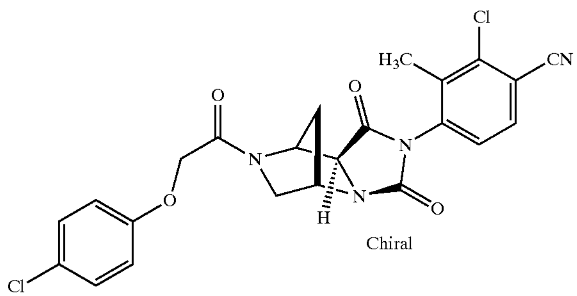 | [5S-(5α,8α,8aβ)]-2-(3-Chloro-4-cyano-2-methylphenyl)-7-[(4-chlorophenoxy)acetyl]-octahydro-1,3-dioxo-5,8-methanoimidazo[1,5-a]pyrazine. | 1.75 LCMS [M + H]+ = 485.11 | 221Ci | F |
| 422 | 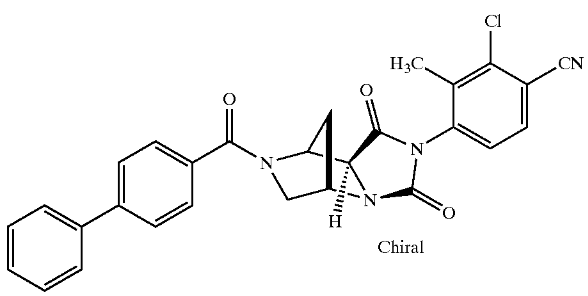 | [5S-(5α,8α,8aβ)]-7-[(1,1'-Biphenyl-4-ylcarbonyl)-2-(3-chloro-4-cyano-2-methylphenyl)octahydro-1,3-dioxo-5,8-methanoimidazo[1,5-a]pyrazine. | 1.87 LCMS [M + H]+ = 497.16 | 221Ci | E |
| 423 | 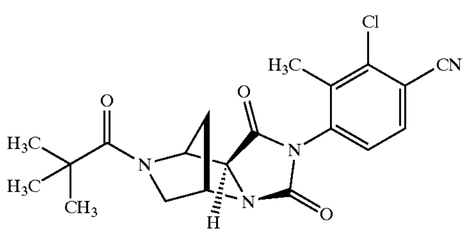 | [5S-(5α,8α,8aβ)]-2-(3-Chloro-4-cyano-2-methylphenyl)-7-(2,2-dimethyl-1-oxopropyl)-octahydro-1,3-dioxo-5,8-methanoimidazo[1,5-a]pyrazine. | 1.56 LCMS [M + H]+ = 401.22 | 221Ci | E |

TABLE 5-continued

| Ex. No | Structure | Compound Name | Retention Time Min./ Molecular Mass | Proc. of Ex. | LC & MS Con. |
|---|---|---|---|---|---|
| 424 | 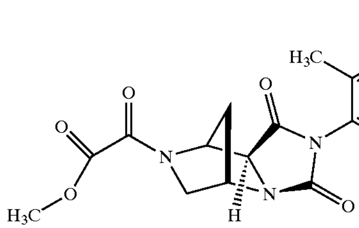 | [5S-(5α,8α,8aβ)]-2-(3-Chloro-4-cyano-2-methylphenyl)hexahydro-alpha,1,3-trioxo-5,8-methanoimidazo[1,5-a]pyrazine-7(1H)-acetic acid, methyl ester. | 1.32 LCMS [M + H]+ = 403.15 | 221Ci | E |
| 425 | 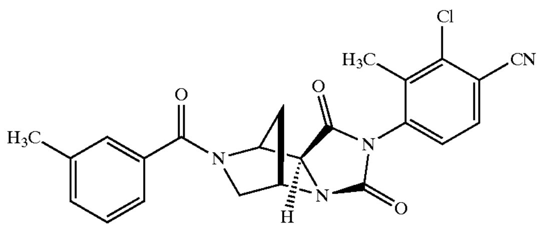 | [5S-(5α,8α,8aβ)]-2-(3-Chloro-4-cyano-2-methylphenyl)octahydro-7-(3-methylbenzoyl)-1,3-dioxo-5,8-methanoimidazo[1,5-a]pyrazine. | 1.65 LCMS [M + H]+ = 435.16 | 221Ci | E |
| 426 | 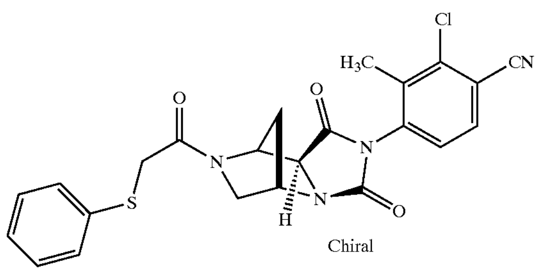 | [5S-(5α,8α,8aβ)]-2-(3-Chloro-4-cyano-2-methylphenyl)octahydro-1,3-dioxo-7-[(phenylthio)acetyl]-5,8-methanoimidazo[1,5-a]pyrazine. | 1.66 LCMS [M + H]+ = 467.10 | 221Ci | F |

TABLE 5-continued

| Ex. No | Structure | Compound Name | Retention Time Min./ Molecular Mass | Proc. of Ex. | LC & MS Con. |
|---|---|---|---|---|---|
| 427 | 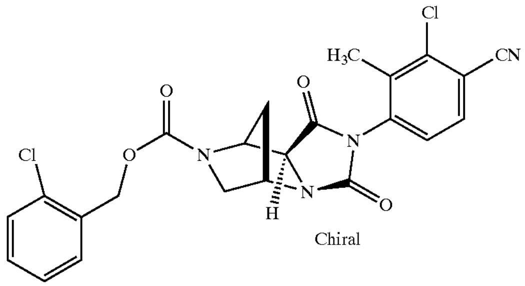 | [5S-(5α,8α,8aβ)]-2-(3-Chloro-4-cyano-2-methylphenyl)hexahydro-1,3-dioxo-5,8-methanoimidazo[1,5-a]pyrazine-7(1H)-carboxylic acid, (2-chlorophenyl) methyl ester. | 1.82 LCMS [M + H]+ = 485.06 | 221Cii | E |
| 428 | 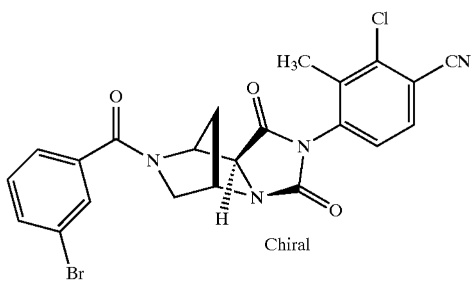 | [5S-(5α,8α,8aβ)]-7-(3-Bromobenzoyl)-2-(3-chloro-4-cyano-2-methylphenyl)octahydro-1,3-dioxo-5,8-methanoimidazo[1,5-a]pyrazine. | 1.72 LCMS [M + H]+ = 501.01 | 221Ci | E |
| 429 | 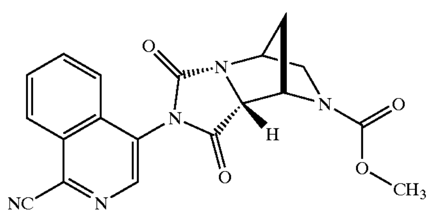 | [5S-(5α,8α,8aα)]-2-(1-Cyano-4-isoquinolinyl)hexahydro-1,3-dioxo-5,8-methanoimidazo[1,5-a]pyrazine-7(1H)-carboxylic acid, methyl ester. | 1.21 LCMS [M + H]+ = 378.19 | 221Cii | C |

TABLE 5-continued

| Ex. No | Structure | Compound Name | Retention Time Min./ Molecular Mass | Proc. of Ex. | LC & MS Con. |
|---|---|---|---|---|---|
| 430 | 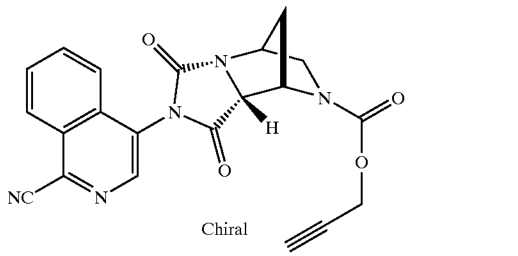 | [5S-(5α,8α,8aα)]-2-(1-Cyano-4-isoquinolinyl)hexahydro-1,3-dioxo-5,8-methanoimidazo[1,5-a]pyrazine-7(1H)-carboxylic acid, 2-propynyl ester. | 1.23 LCMS $[M + H]^+$ = 402.18 | 221Cii | C |
| 431 | 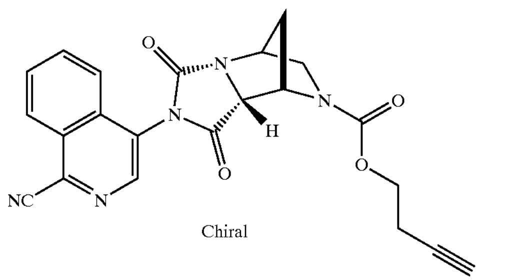 | [5S-(5α,8α,8aα)]-2-(1-Cyano-4-isoquinolinyl)hexahydro-1,3-dioxo-5,8-methanoimidazo[1,5-a]pyrazine-7(1H)-carboxylic acid, 3-butynyl ester. | 1.35 LCMS $[M + H]^+$ = 416.18 | 221Cii | C |
| 432 | 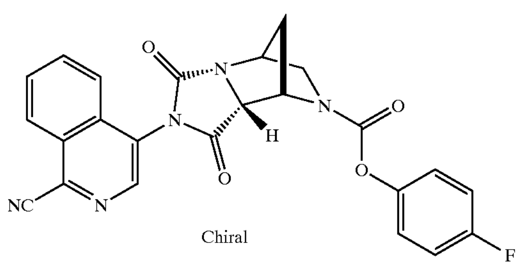 | [5S-(5α,8α,8aα)]-2-(1-Cyano-4-isoquinolinyl)hexahydro-1,3-dioxo-5,8-methanoimidazo[1,5-a]pyrazine-7(1H)-carboxylic acid, 4-fluorophenyl ester. | 1.59 LCMS $[M + H]^+$ = 458.23 | 221Cii | C |

TABLE 5-continued

| Ex. No | Structure | Compound Name | Retention Time Min./ Molecular Mass | Proc. of Ex. | LC & MS Con. |
|---|---|---|---|---|---|
| 433 | 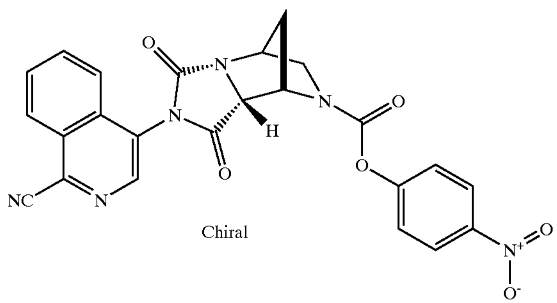 | [5S-(5α,8α,8aα)]-2-(1-Cyano-4-isoquinolinyl)hexahydro-1,3-dioxo-5,8-methanoimidazo[1,5-a]pyrazine-7(1H)-carboxylic acid, 4-nitrophenyl ester. | 1.57 LCMS $[M + H]^+$ = 485.23 | 221Cii | C |
| 434 | 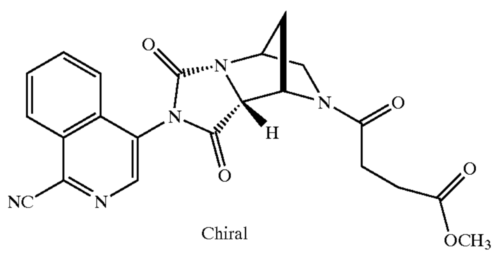 | [5S-(5α,8α,8aα)]-2-(1-Cyano-4-isoquinolinyl)hexahydro-gamma, 1,3-trioxo-5,8-methanoimidazo[1,5-a]pyrazine-7(1H)butanoic acid, methyl ester. | 1.20 LCMS $[M + H]^+$ = 434.20 | 221Ci | C |
| 435 | 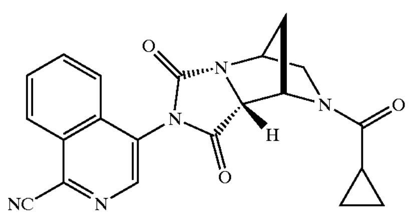 | [5S-(5α,8α,8aα)]-2-(1-Cyano-4-isoquinolinyl)-7-(cyclopropylcarbonyl)octahydro-1,3-dioxo-5,8-methanoimidazo[1,5-a]pyrazine. | 1.21 LCMS $[M + H]^+$ = 388.21 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 436 | 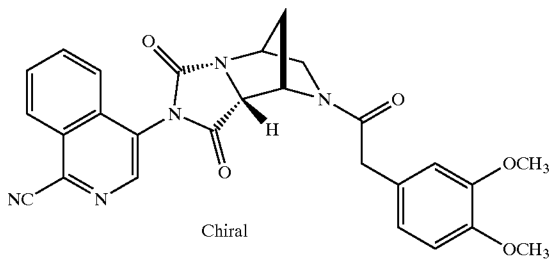 | [5S-(5α,8α,8aα)]-2-(1-Cyano-4-isoquinolinyl)-7-[(3,4-dimethoxyphenyl)acetyl]-octahydro-5,8-dioxo-5,8-methanoimidazo[1,5-a]pyrazine. | 1.37 LCMS [M + H]⁺ = 498.25 | 221Ci | C |
| 437 | 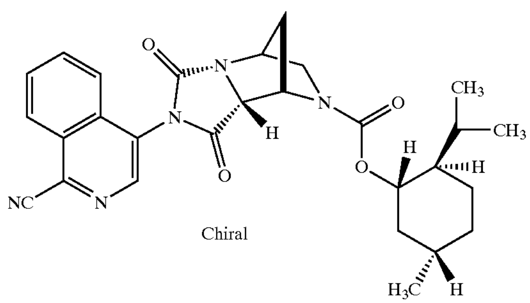 | [5S-(5α,8α,8aα)]-2-(1-Cyano-4-isoquinolinyl) hexahydro-1,3-dioxo-5,8-methanoimidazo[1,5-a]pyrazine-7(1H)-carboxylic acid, (1S,2R,5S)-5-methyl-2-(1-methylethyl)-cyclohexyl ester. | 2.03 LCMS [M + H]⁺ = 502.32 | 221Cii | D |
| 438 | 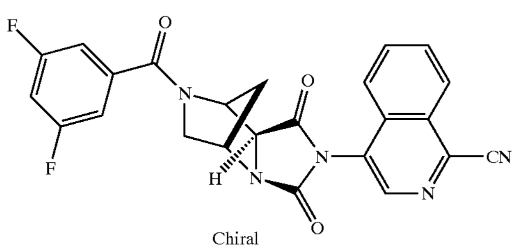 | [5S-(5α,8α,8aβ)]-2-(1-Cyano-4-isoquinolinyl)-7-(3,5-difluorobenzoyl)octahydro-1,3-dioxo-5,8-methanoimidazo[1,5-a]pyrazine. | 1.54 LCMS [M + H]⁺ = 460.22 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 439 | 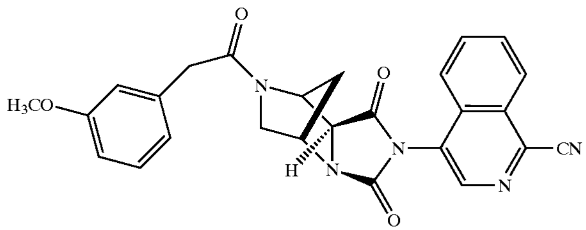 | [5S-(5α,8α,8aβ)]-2-(1-Cyano-4-isoquinolinyl) octahydro-7-[(3-methoxyphenyl)acetyl]-1,3-dioxo-5,8-methanoimidazo[1,5-a]pyrazine. | 1.51 LCMS [M + H]+ = 468.28 | 221Ci | C |
| 440 | 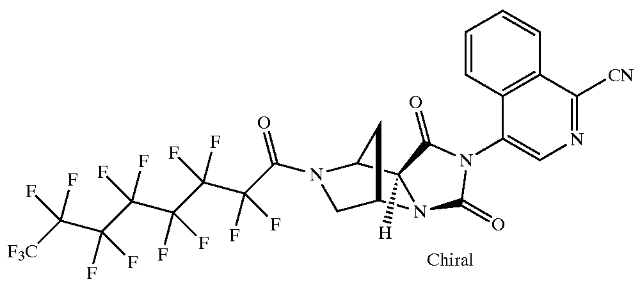 | [5S-(5α,8α,8aβ)]-2-(1-Cyano-4-isoquinolinyl) octahydro-7-(2,2,3,3,4,4,5,5,6,6,7,7,8,8,8-pentadecafluoro-1-oxooctyl)-5,8-methanoimidazo[1,5-a]pyrazine. | 2.06 LCMS [M + H]+ = 716.14 | 221Ci | C |
| 441 | 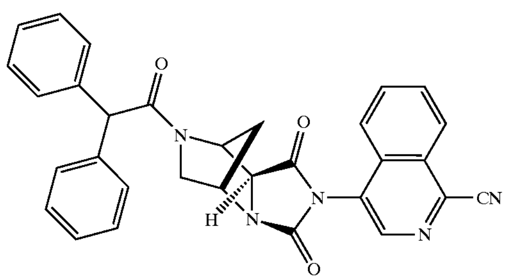 | [5S-(5α,8α,8aβ)]-2-(1-Cyano-4-isoquinolinyl)-7-(diphenylacetyl)octahydro-1,3-dioxo-5,8-methanoimidazo[1,5-a]pyrazine. | 1.79 LCMS [M + H]+ = 514.21 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 442 | 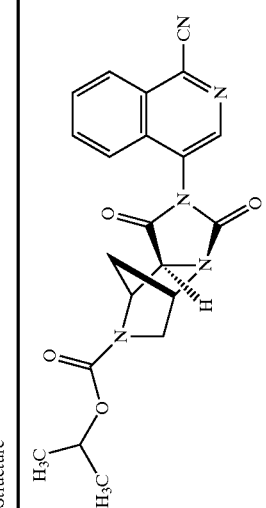 | [5S-(5α,8α,8aβ)]-2-(1-Cyano-4-isoquinolinyl) hexahydro-1,3-dioxo-5,8-methanoimidazo[1,5-a]pyrazine-7(1H)-carboxylic acid, 1-methylethyl ester. | 1.43 LCMS [M + H]⁺ = 406.20 | 221Cii | C |
| 443 | 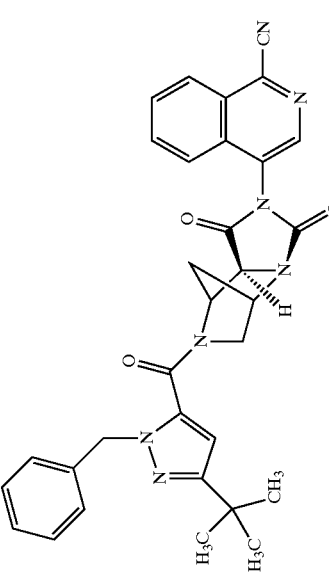 | [5S-(5α,8α,8aβ)]-2-(1-Cyano-4-isoquinolinyl)-7-[[3-(1,1-dimethylethyl)-1-(phenylmethyl)-1H-pyrazol-5-yl]carbonyl]octahydro-5,8-methanoimidazo[1,5-a]pyrazine-1,3-dioxo. | 1.93 LCMS [M + H]⁺ = 560.35 | 221Ci | C |
| 444 | 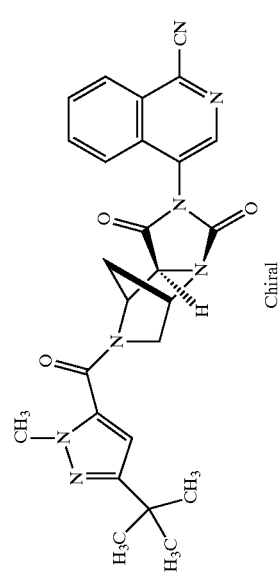 | [5S-(5α,8α,8aβ)]-2-(1-Cyano-4-isoquinolinyl)-7-[[3-(1,1-dimethylethyl)-1-methyl-1H-pyrazol-5-yl]carbonyl]octahydro-1,3-dioxo-5,8-methanoimidazo[1,5-a]pyrazine. | 1.69 LCMS [M + H]⁺ = 484.28 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 445 | 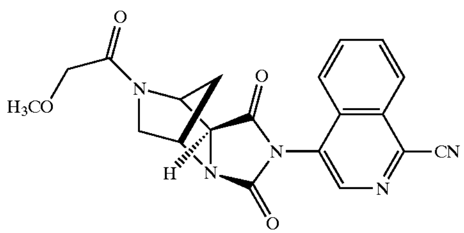 | [5S-(5α,8α,8aβ)]-2-(1-Cyano-4-isoquinolinyl) octahydro-7-(methoxyacetyl)-1,3-dioxo-5,8-methanoimidazo[1,5-a]pyrazine. | 1.07 LCMS [M + H]$^+$ = 392.19 | 221Ci | C |
| 446 | 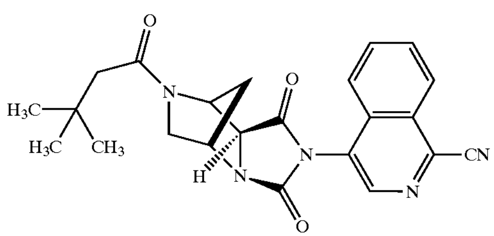 | [5S-(5α,8α,8aβ)]-2-(1-Cyano-4-isoquinolinyl)-7-(3,3-dimethyl-1-oxobutyl)octahydro-1,3-dioxo-5,8-methanoimidazo[1,5-a]pyrazine. | 1.58 LCMS [M + H]$^+$ = 418.21 | 221Ci | C |
| 447 | 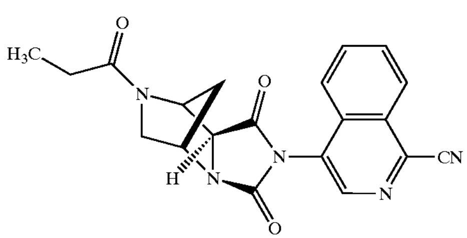 | [5S-(5α,8α,8aβ)]-2-(1-Cyano-4-isoquinolinyl) octahydro-1,3-dioxo-7-(1-oxopropyl)-5,8-methanoimidazo[1,5-a]pyrazine. | 1.20 LCMS [M + H]$^+$ = 376.22 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 448 | 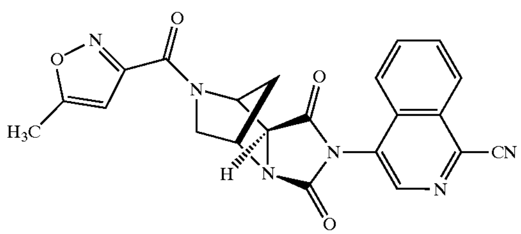 | [5S-(5α,8α,8aβ)]-2-(1-Cyano-4-isoquinolinyl) octahydro-7-[(5-methyl-3-isoxazolyl)-carbonyl]-1,3-dioxo-5,8-methanoimidazo[1,5-a]pyrazine. | 1.32 LCMS [M + H]+ = 429.17 | 221Ci | C |
| 449 | 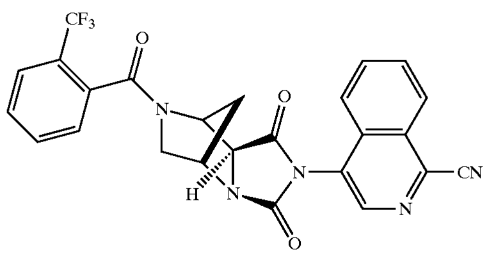 | [5S-(5α,8α,8aβ)]-2-(1-Cyano-4-isoquinolinyl) octahydro-7-[2-(trifluoromethyl)-benzoyl]-5,8-methanoimidazo[1,5-a]pyrazine. | 1.50 LCMS [M + H]+ = 492.19 | 221Ci | C |
| 450 | 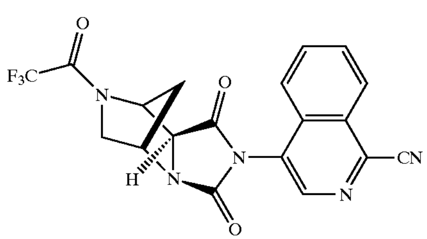 | [5S-(5α,8α,8aβ)]-2-(1-Cyano-4-isoquinolinyl) octahydro-1,3-dioxo-7-(trifluoroacetyl)-5,8-methanoimidazo[1,5-a]pyrazine. | 1.36 LCMS [M + H]+ = 416.13 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 451 | 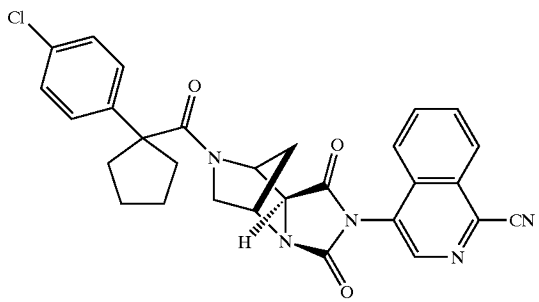 | [5S-(5α,8α,8aβ)]-7-[[1-(4-Chlorophenyl)-cyclopentyl]carbonyl]-2-(1-cyano-4-isoquinolinyl)octahydro-1,3-dioxo-5,8-methanoimidazo[1,5-a]pyrazine. | 1.89 LCMS [M + H]+ = 526.20 | 221Ci | C |
| 452 | 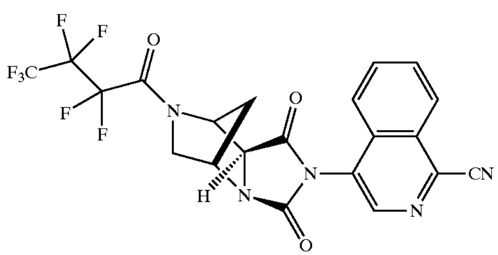 | [5S-(5α,8α,8aβ)]-2-(1-Cyano-4-isoquinolinyl)-7-(2,2,3,3,4,4,4-heptafluoro-1-oxobutyl)octahydro-1,3-dioxo-5,8-methanoimidazo[1,5-a]pyrazine. | 1.74 LCMS [M + H]+ = 516.12 | 221Ci | C |
| 453 | 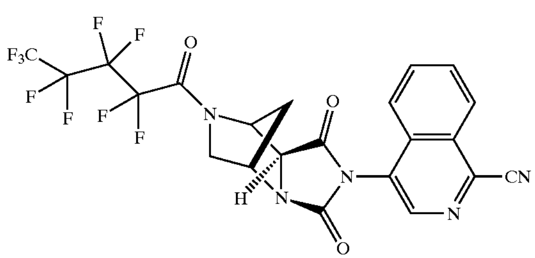 | [5S-(5α,8α,8aβ)]-2-(1-Cyano-4-isoquinolinyl)octahydro-7-(2,2,3,3,4,4,5,5,5-nonafluoro-1-oxopentyl)-1,3-dioxo-5,8-methanoimidazo[1,5-a]pyrazine. | 1.85 LCMS [M + H]+ = 566.20 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 454 | 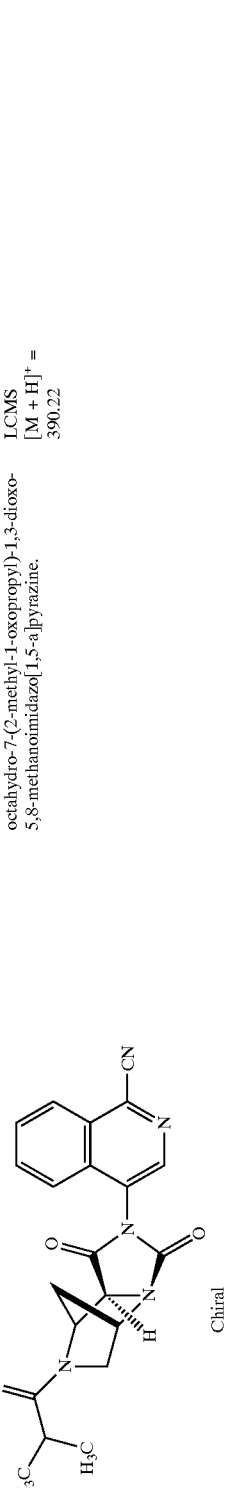 Chiral | [5S-(5α,8α,8aβ)]-2-(1-Cyano-4-isoquinolinyl) octahydro-7-(2-methyl-1-oxopropyl)-1,3-dioxo-5,8-methanoimidazo[1,5-a]pyrazine. | 1.32 LCMS [M + H]⁺ = 390.22 | 221Ci | C |
| 455 | 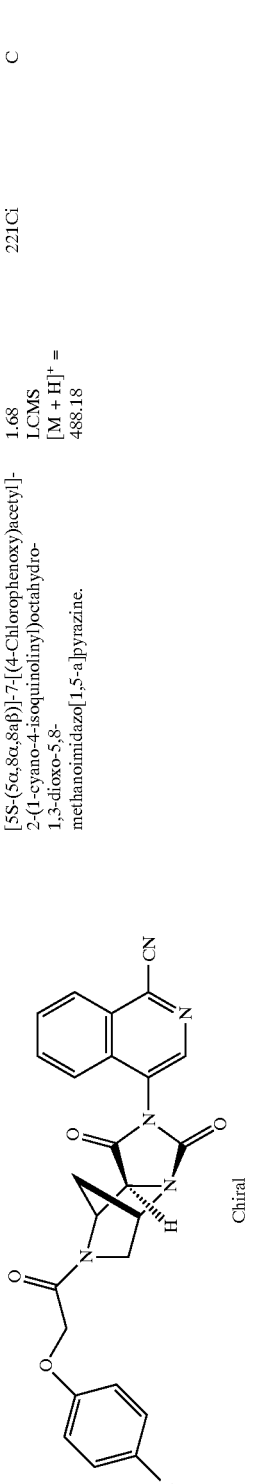 Chiral | [5S-(5α,8α,8aβ)]-7-[(4-Chlorophenoxy)acetyl]-2-(1-cyano-4-isoquinolinyl)octahydro-1,3-dioxo-5,8-methanoimidazo[1,5-a]pyrazine. | 1.68 LCMS [M + H]⁺ = 488.18 | 221Ci | C |
| 456 | 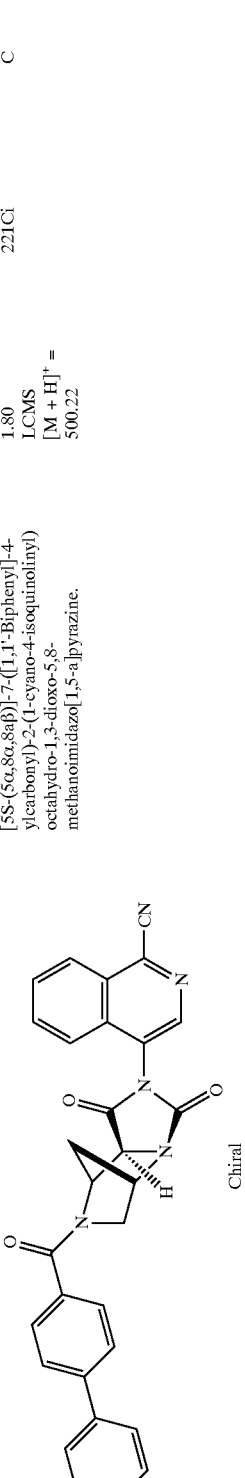 Chiral | [5S-(5α,8α,8aβ)]-7-[(1,1'-Biphenyl]-4-ylcarbonyl)-2-(1-cyano-4-isoquinolinyl) octahydro-1,3-dioxo-5,8-methanoimidazo[1,5-a]pyrazine. | 1.80 LCMS [M + H]⁺ = 500.22 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 457 | 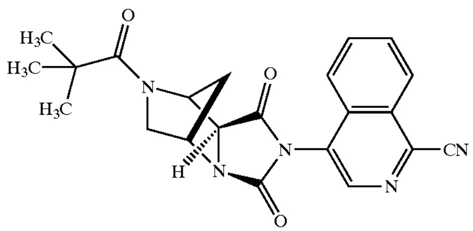 | [5S-(5α,8α,8aβ)]-2-(1-Cyano-4-isoquinolinyl)-7-(2,2-dimethyl-1-oxopropyl)octahydro-1,3-dioxo-5,8-methanoimidazo[1,5-a]pyrazine. | 1.43 LCMS [M + H]$^+$ = 404.22 | 221Ci | C |
| 458 | 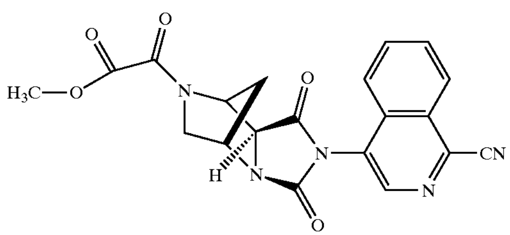 | [5S-(5α,8α,8aβ)]-2-(1-Cyano-4-isoquinolinyl)hexahydro-alpha,1,3-trioxo-5,8-methanoimidazo[1,5-a]pyrazine-7(1H)-acetic acid, methyl ester. | 1.12 LCMS [M + H]$^+$ = 406.15 | 221Ci | C |
| 459 | 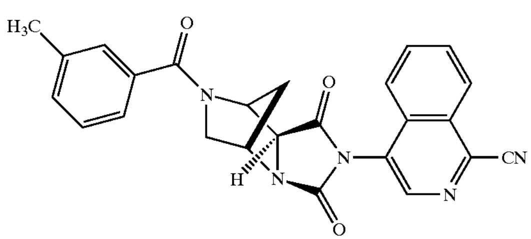 | [5S-(5α,8α,8aβ)]-2-(1-Cyano-4-isoquinolinyl)octahydro-7-(3-methylbenzoyl)-1,3-dioxo-5,8-methanoimidazo[1,5-a]pyrazine. | 1.53 LCMS [M + H]$^+$ = 438.19 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 460 | 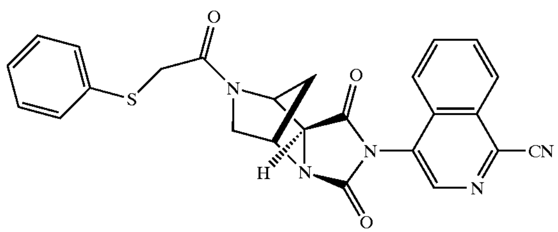 | [5S-(5α,8α,8aβ)]-2-(1-Cyano-4-isoquinolinyl) octahydro-1,3-dioxo-7-[(phenylthio)acetyl]-5,8-methanoimidazo[1,5-a]pyrazine. | 1.55 LCMS $[M + H]^+$ = 470.22 | 221Ci | C |
| 461 | 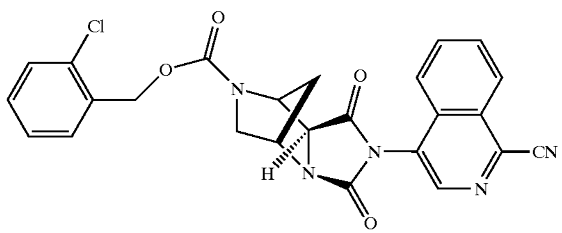 | [5S-(5α,8α,8aβ)]-2-(1-Cyano-4-isoquinolinyl) hexahydro-1,3-dioxo-5,8-methanoimidazo[1,5-a]pyrazine-7(1H)-carboxylic acid, (2-chlorophenyl) methyl ester. | 1.80 LCMS $[M + H]^+$ = 488.18 | 221Cii | C |
| 462 | 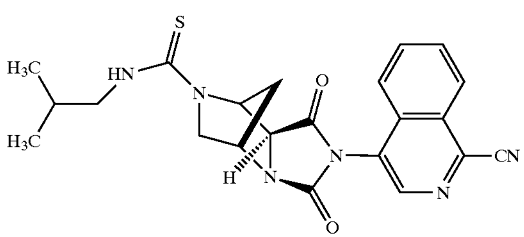 | [5S-(5α,8α,8aβ)]-2-(1-Cyano-4-isoquinolinyl) hexahydro-N-(2-methylpropyl)-1,3-dioxo-5,8-methanoimidazo[1,5-a]pyrazine-7(1H)-carbothioamide. | 1.57 LCMS $[M + H]^+$ = 435.21 | 221Bi | C |

TABLE 5-continued

| Ex. No | Structure | Compound Name | Retention Time Min./ Molecular Mass | Proc. of Ex. | LC & MS Con. |
|---|---|---|---|---|---|
| 463 | 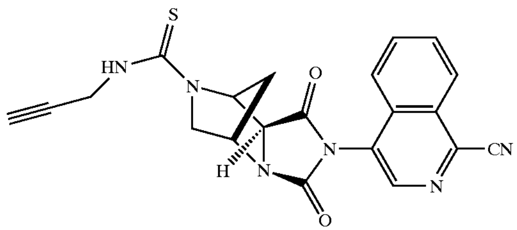 | [5S-(5α,8α,8aβ)]-2-(1-Cyano-4-isoquinolinyl) hexahydro-1,3-dioxo-N-2-propynyl-5,8-methanoimidazo[1,5-a]pyrazine-7(1H)-carbothioamide. | 1.11 LCMS [M + H]$^+$ = 417.13 | 221Bi | C |
| 464 | 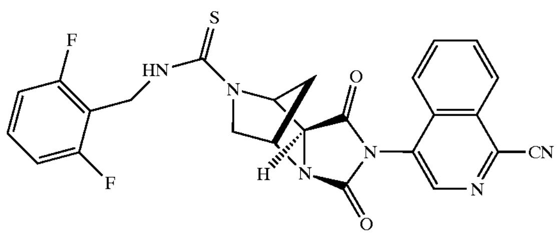 | [5S-(5α,8α,8aβ)]-2-(1-Cyano-4-isoquinolinyl)-N-(2,6-difluorophenyl)hexahydro-1,3-dioxo-5,8-methanoimidazo[1,5-a]pyrazine-7(1H)-carbothioamide. | 1.51 LCMS [M + H]$^+$ = 491.17 | 221Bi | C |
| 465 | 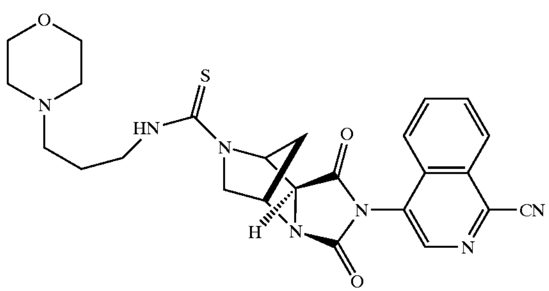 | [5S-(5α,8α,8aβ)]-2-(1-Cyano-4-isoquinolinyl) hexahydro-N-[3-(4-morpholinyl) propyl]-1,3-dioxo-5,8-methanoimidazo[1,5-a]pyrazine-7(1H)-carbothioamide. | 1.18 LCMS [M + H]$^+$ = 506.25 | 221Bi | C |

TABLE 5-continued

| Ex. No | Structure | Compound Name | Retention Time Min./ Molecular Mass | Proc. of Ex. | LC & MS Con. |
|---|---|---|---|---|---|
| 466 | H₃CO, OCH₃ structure | [5S-(5α,8α,8aβ)]-2-(1-Cyano-4-isoquinolinyl)-N-[2-(3,4-dimethoxyphenyl)ethyl]hexahydro-1,3-dioxo-5,8-methanoimidazo[1,5-a]pyrazine-7(1H)-carbothioamide. | 1.70 LCMS [M + H]⁺ = 543.26 | 221Bi | C |
| 467 | structure | [5S-(5α,8α,8aβ)]-N-1,3-Benzodioxol-5-yl-2-(1-cyano-4-isoquinolinyl)hexahydro-1,3-dioxo-5,8-methanoimidazo-[1,5-a]pyrazine-7(1H)-carbothioamide. | 1.47 LCMS [M + H]⁺ = 499.17 | 221Bi | C |
| 468 | structure | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, methyl ester. | 1.01 LCMS [M + H]⁺ = 342.15 | 221Cii | C |

TABLE 5-continued

| Ex. No | Structure | Compound Name | Retention Time Min./ Molecular Mass | Proc. of Ex. | LC & MS Con. |
|---|---|---|---|---|---|
| 469 | 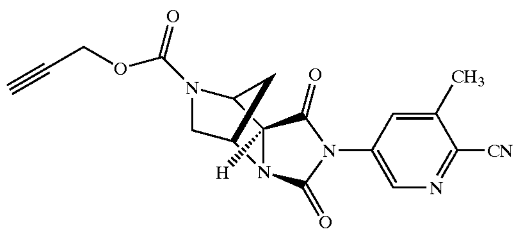 | [5S-(5α,8α,8aβ)]-2-(6-Cyano-5-methyl-3-pyridinyl)hexahydroimidazo[1,5-a]pyrazine-7(1H)-methanoimidazo[1,5-a]pyrazine-7(1H)-carboxylic acid, 2-propynyl ester. | 1.07 LCMS [M + H]+ = 366.20 | 221Cii | C |
| 470 | 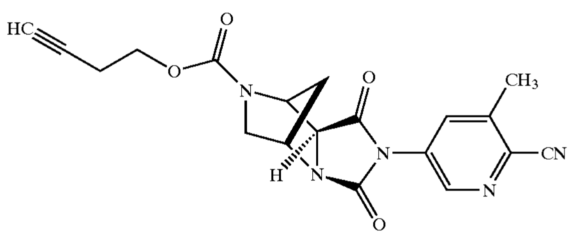 | [5S-(5α,8α,8aβ)]-2-(6-Cyano-5-methyl-3-pyridinyl)hexahydroimidazo[1,5-a]pyrazine-7(1H)-methanoimidazo[1,5-a]pyrazine-7(1H)-carboxylic acid, 3-butynyl ester. | 1.17 LCMS [M + H]+ = 380.21 | 221Cii | C |
| 471 | 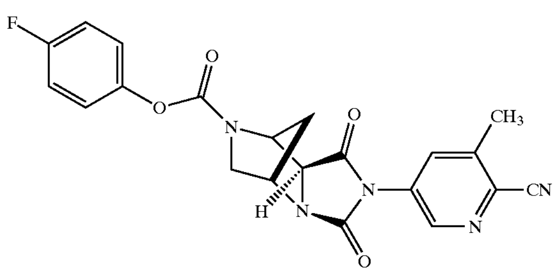 | [5S-(5α,8α,8aβ)]-2-(6-Cyano-5-methyl-3-pyridinyl)hexahydroimidazo[1,5-a]pyrazine-7(1H)-methanoimidazo[1,5-a]pyrazine-7(1H)-carboxylic acid, 4-fluorophenyl ester. | 1.45 LCMS [M + H]+ = 422.13 | 221Cii | C |

TABLE 5-continued

| Ex. No | Structure | Compound Name | Retention Time Min./ Molecular Mass | Proc. of Ex. | LC & MS Con. |
|---|---|---|---|---|---|
| 472 | 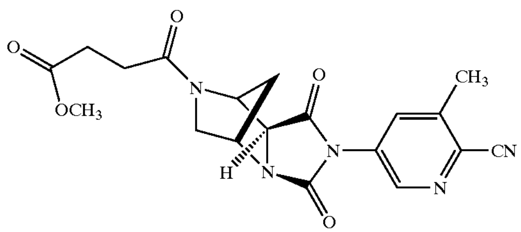 | [5S-(5α,8α,8aβ)]-2-(6-Cyano-5-methyl-3-pyridinyl)hexahydro-gamma, 1,3-trioxo-5,8-methanoimidazo[1,5-a]pyrazine-7(1H)-butanoic acid, methyl ester. | 1.02 LCMS $[M + H]^+ =$ 398.20 | 221Ci | C |
| 473 | 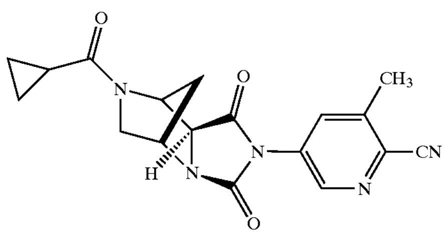 | [5S-(5α,8α,8aβ)]-2-(6-Cyano-5-methyl-3-pyridinyl)-7-(cyclopropylcarbonyl)octahydro-1,3-dioxo-5,8-methanoimidazo[1,5-a]pyrazine. | 1.00 LCMS $[M + H]^+ =$ 352.19 | 221Ci | C |
| 474 | 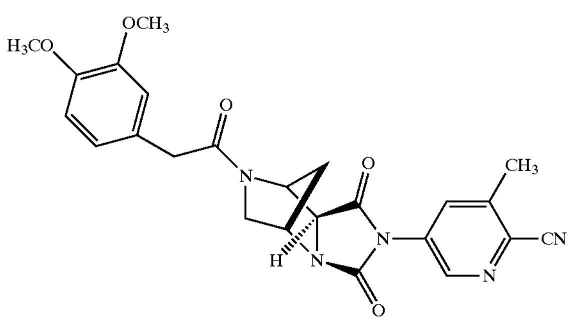 | [5S-(5α,8α,8aβ)]-2-(6-Cyano-5-methyl-3-pyridinyl)-7-[(3,4-dimethoxyphenyl)acetyl]-octahydro-1,3-dioxo-5,8-methanoimidazo[1,5-a]pyrazine. | 1.16 LCMS $[M + H]^+ =$ 462.26 | 221Ci | |

TABLE 5-continued

| Ex. No | Structure | Compound Name | Retention Time Min./ Molecular Mass | Proc. of Ex. | LC & MS Con. |
|---|---|---|---|---|---|
| 475 | 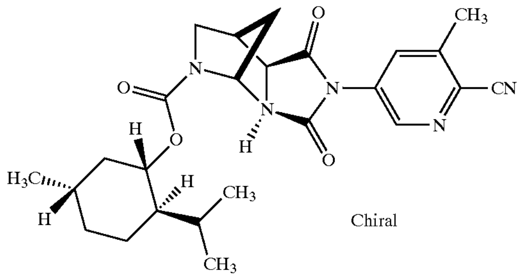 | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, (1S,2R,5S)-5-methyl-2-(1-methylethyl)-cyclohexyl ester. | 1.96 LCMS [M + H]$^+$ = 466.34 | 221Cii | D |
| 476 | 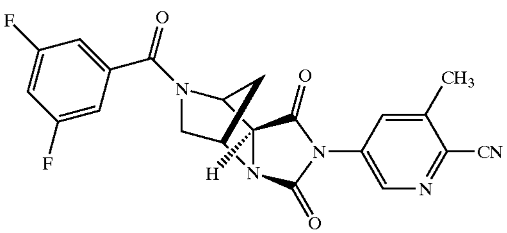 | [5S-(5α,8α,8aβ)]-2-(6-Cyano-5-methyl-3-pyridinyl)-7-(3,5-difluorobenzoyl)-octahydro-1,3-dioxo-5,8-methanoimidazo[1,5-a]pyrazine. | 1.39 LCMS [M + H]$^+$ = 424.14 | 221Ci | C |
| 477 | 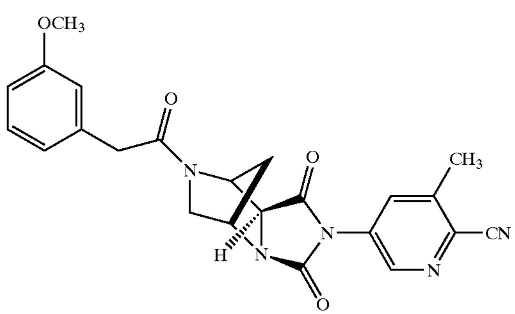 | [5S-(5α,8α,8aβ)]-2-(6-Cyano-5-methyl-3-pyridinyl)octahydro-7-[(3-methoxyphenyl)-acetyl]-1,3-dioxo-5,8-methanoimidazo[1,5-a]pyrazine. | 1.31 LCMS [M + H]$^+$ = 432.20 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 478 | 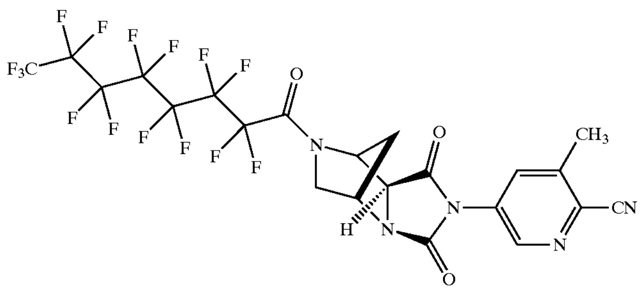 | [5S-(5α,8α,8aβ)]-2-(6-Cyano-5-methyl-3-pyridinyl)octahydro-1,3-dioxo-7-(2,2,3,3,4,4,5,5,6,6,7,7,8,8,8-pentadecafluoro-1-oxooctyl)-5,8-methanoimidazo[1,5-a]pyrazine. | 2.01 LCMS [M + H]$^+$ = 680.15 | 221Ci | C |
| 479 | 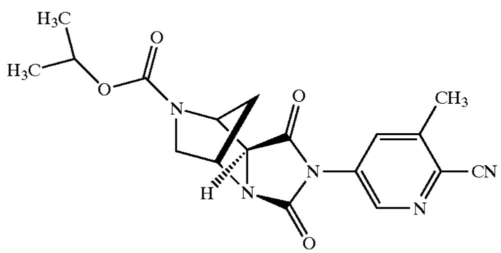 | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, 1-methylethyl ester. | 1.30 LCMS [M + H]$^+$ = 370.22 | 221Cii | C |
| 480 | 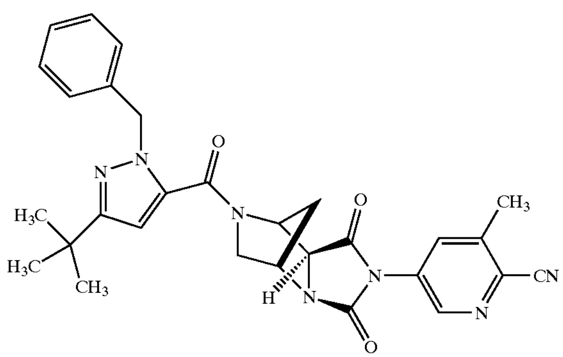 | [5S-(5α,8α,8aβ)]-2-(6-Cyano-5-methyl-3-pyridinyl)-7-[[3-(1,1-dimethylethyl)-1-(phenylmethyl)-1H-pyrazol-5-yl]carbonyl]-octahydro-1,3-dioxo-5,8-methanoimidazo[1,5-a]pyrazine. | 1.82 LCMS [M + H]$^+$ = 524.27 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 481 | 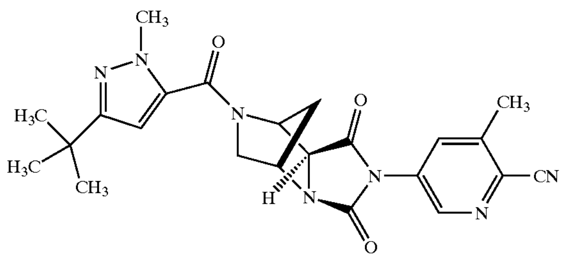 | [5S-(5α,8α,8aβ)]-2-(6-Cyano-5-methyl-3-pyridinyl)-7-[[3-(1,1-dimethylethyl)-1-methyl-1H-pyrazol-5-yl]carbonyl]octahydro-1,3-dioxo-5,8-methanoimidazo[1,5-a]pyrazine. | 1.57 LCMS [M + H]$^+$ = 448.26 | 221Ci | C |
| 482 | 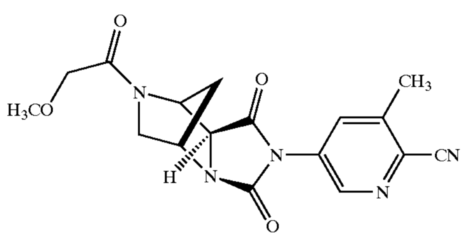 | [5S-(5α,8α,8aβ)]-2-(6-Cyano-5-methyl-3-pyridinyl)octahydro-7-(methoxyacetyl)-1,3-dioxo-5,8-methanoimidazo[1,5-a]pyrazine. | 0.89 LCMS [M + H]$^+$ = 356.20 | 221Ci | C |
| 483 | 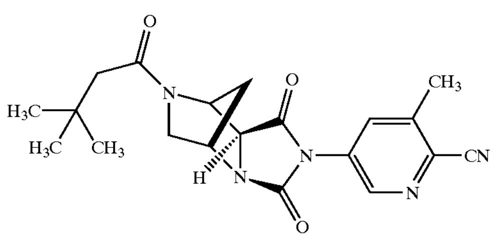 | [5S-(5α,8α,8aβ)]-2-(6-Cyano-5-methyl-3-pyridinyl)-7-(3,3-dimethyl-1-oxobutyl)-octahydro-1,3-dioxo-5,8-methanoimidazo[1,5-a]pyrazine. | 1.41 LCMS [M + H]$^+$ = 382.26 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 484 |  Chiral | [5S-(5α,8α,8aβ)]-2-(6-Cyano-5-methyl-3-pyridinyl)octahydro-7-(1-oxopropyl)-5,8-methanoimidazo[1,5-a]pyrazine. | 0.97 LCMS [M + H]+ = 340.17 | 221Ci | C |
| 485 |  Chiral | [5S-(5α,8α,8aβ)]-2-(6-Cyano-5-methyl-3-pyridinyl)octahydro-7-[(5-methyl-3-isoxazolyl)carbonyl]-1,3-dioxo-5,8-methanoimidazo[1,5-a]pyrazine. | 1.12 LCMS [M + H]+ = 393.19 | 221Ci | D |
| 486 |  Chiral | [5S-(5α,8α,8aβ)]-2-(6-Cyano-5-methyl-3-pyridinyl)octahydro-7-[2-(trifluoromethyl)benzoyl]-5,8-methanoimidazo[1,5-a]pyrazine. | 1.46 LCMS [M + H]+ = 456.20 | 221Ci | C |

TABLE 5-continued

| Ex. No | Structure | Compound Name | Retention Time Min./ Molecular Mass | Proc. of Ex. | LC & MS Con. |
|---|---|---|---|---|---|
| 487 | 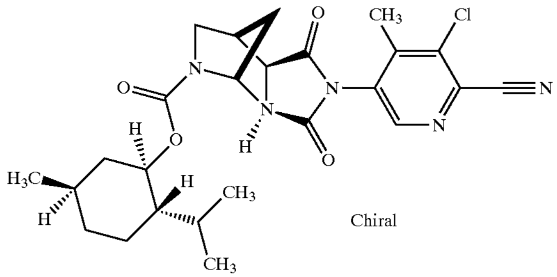 | [5S-(5α,8α,8aβ)]-2-(3-Chloro-4-cyano-2-methylphenyl)hexahydro-1,3-dioxo-5,8-methanoimidazo[1,5-a]pyrazine-7(1H)-carboxylic acid, 5-methyl-2-(1-methylethyl)cyclohexyl ester. | 2.13 LCMS [M + H]+ = 521.21 | 221Cii | E |
| 488 | 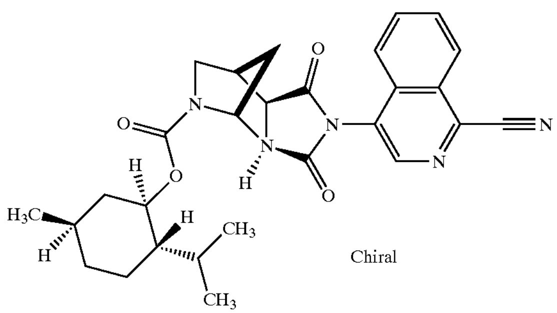 | [5S-(5α,8α,8aβ)]-2-(1-Cyano-4-isoquinolinyl)hexahydro-1,3-dioxo-5,8-methanoimidazo[1,5-a]pyrazine-7(1H)-carboxylic acid, 5-methyl-2-(1-methylethyl)cyclohexyl ester. | 2.05 LCMS [M + H]+ = 502.30 | 221Cii | C |
| 489 | 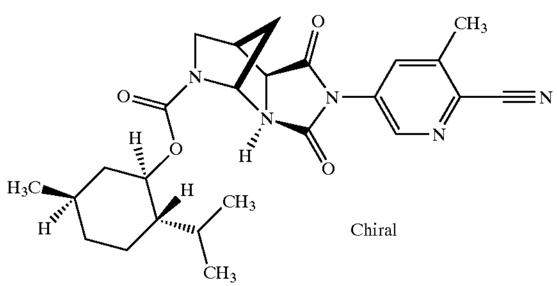 | [5S-(5α,8α,8aβ)]-2-(6-Cyano-5-methyl-3-pyridinyl)hexahydro-1,3-dioxo-5,8-methanoimidazo[1,5-a]pyrazine-7(1H)-carboxylic acid, (1R,2S,5R)-5-methyl-2-(1-methylethyl)cyclohexyl ester. | 1.94 LCMS [M + H]+ = 466.33 | 221Cii | D |

TABLE 5-continued

| Ex. No | Structure | Compound Name | Retention Time Min./ Molecular Mass | Proc. of Ex. | LC & MS Con. |
|---|---|---|---|---|---|
| 490 | 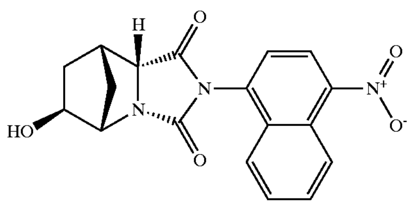 | (5α,6α,8α,8aα)-Tetrahydro-6-hydroxy-2-(4-nitro-1-naphthalenyl)-5,8-methanoimidazo[1,5-a]pyridine-1,3(2H,5H)-dione | LCMS [M + H]⁺ = | 222i | G |
| 491 | 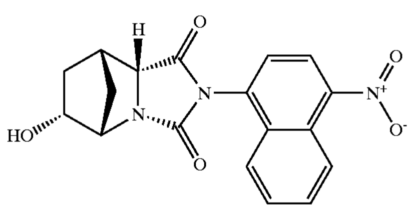 | (5α,6β,8α,8aα)-Tetrahydro-6-hydroxy-2-(4-nitro-1-naphthalenyl)-5,8-methanoimidazo[1,5-a]pyridine-1,3(2H,5H)-dione | LCMS [M + H]⁺ = | 222ii | G |

We claim:
1. A compound selected from the group consisting of: (5α,8α,8aα)-8,8a-Dihydro-2-[3-(trifluoromethyl)phenyl]-5,8-methanoimidazo[1,5-a]pyridine-1,3(2H,5H)-dione; (5α,8α,8aα)-2,3,8,8a-Tetrahydro-2-[3-(trifluoromethyl)phenyl]-3-thioxo-5,8-methanoimidazo[1,5-a]pyrid-1(5H)-one; (5α,8α,8aα)-8,8a-Dihydro-8a-methyl-2-[3-(trifluoromethyl)phenyl]-5,8-methanoimidazo[1,5-a]pyridine-1,3(2H,5H)-dione; (5α,8α,8aα)-2,3,8,8a-Tetrahydro-8a-methyl-3-thioxo-2-[3-(trifluoromethyl)phenyl]-5,8-methanoimidazol[1,5-a]pyridin-1(5H)-one; (5α,8α,8aα)-2,3,8,8a-Tetrahydro-2-(1-naphthalenyl)-3-thioxo-5,8-methanoimidazo[1,5-a]pyridin-1(5H)-one; (5α,8α,8aα)-Hexahydro-2-[3-(trifluoromethyl)phenyl]-5,8-methanoimidazo[1,5-a]pyridine-1(5H)-one; (5α,8α,8aα)-2-[3,5-Bis(trifluoromethyl)phenyl]-8,8a-dihydro-5,8-methanoimidazo[1,5-a]pyridin-1,3(2H,5H)-one; (5α,8α,8aα)-8,8a-Dihydro-2-(2-naphthalenyl)-5,8-methanoimidazo[1,5-a]pyridine-1,3(2H,5H)-dione; (5α,8α,8aα)-8,8a-Dihydro-2-(1-naphthalenyl)-5,8-methanoimidazo[1,5-a]pyridine-1,3(2H,5H)-dione; (5α,8α,8aα)-2-(3,5-Dichlorophenyl)-8,8a-dihydro-5,8-methanoimidazo[1,5-a]pyridine-1,3(2H,5H)-dione; [5S-(5α,8α,8aβ)]-Tetrahydro-2-[3-(trifluoromethyl)phenyl]-5,8-methanoimidazo[1,5-a]pyridine-1,3(2H,5H)-dione; [5R-(5α,8α,8aβ)]-Tetrahydro-2-[3-(trifluoromethyl)phenyl]-5,8-methanoimidazo[1,5-a]pyridine-1,3(2H,5H)-dione; Tetrahydro-2-(1-naphthalenyl)-5,8-ethanoimidazo[1,5-a]pyridine-1,3(2H,5H)-dione; Tetrahydro-2-[3-(trifluoromethyl)phenyl]-5,8-ethanoimidazo[1,5-a]pyridine-1,3(2H,5H)-dione; (5α,8α,8aα)-2-(4-Bromo-1-naphthalenyl)-8,8a-dihydro-5,8-methanoimidazo[1,5-a]pyridine-1,3(2H,5H)-dione; [5S-(5α,8α,8aβ)]-2-(3,5-Dichlorophenyl)tetrahydro-5,8-methanoimidazo[1,5-a]pyridine-1,3(2H,5H)-dione; [5S-(5α,8α,8aβ)]-2-(4-Bromo-1-naphthalenyl)tetrahydro-5,8-methanoimidazo[1,5-a]pyridine-1,3(2H,5H)-dione; [5R-(5α,8α,8aβ)]-2-(4-Bromo-1-naphthalenyl)tetrahydro-5,8-methanoimidazo[1,5-a]pyridine-1,3(2H,5H)-dione; [5R-(5α,8α,8aβ)]-2-(3,5-Dichlorophenyl)tetrahydro-5,8-methanoimidazo[1,5-a]pyridine-1,3(2H,5H)-dione; (5α,8α,8aβ)-Tetrahydro-2-(4-nitro-1-naphthalenyl)-5,8-methanoimidazo[1,5-a]pyridine-1,3(2H,5H)-dione; (5α,8α,8aβ)-Hexahydro-2-(1-naphthaleny)-3-thioxo-5,8-methanoimidazo[1,5-a]pyridine-1(5H)-one; (5α,8α,8aβ)-Hexahydro-3-thioxo-2-[3-(trifluoromethyl)phenyl]-5,8-methanoimidazo[1,5-a]pyridine-1(5H)-one; (5α,8α,8aα)-2-(3,5-Dichlorophenyl)tetrahydro-5,8-methanoimidazo[1,5-a]pyridine-1,3(2H,5H)-dione; (5α,8α,8aβ)-Tetrahydro-2-[3-(trifluoromethyl)phenyl]-5,8-methanoimidazo[1,5-a]pyridine-1,3(2H,5H)-dione; (5α,8α,8aα)-Tetrahydro-2-[3-(trifluoromethyl)phenyl]-5,8-methanoimidazo[1,5-a]pyridine-1,3(2H,5H)-dione; (5α,8α,8aα)-Tetrahydro-2-(4-nitro-1-naphthalenyl)-5,8-methanoimidazo[1,5-a]pyridine-1,3(2H,5H)-dione; (5α,8α,8aα)-Hexahydro-3-thioxo-2-[3-(trifluoromethyl)phenyl]-5,8-methanoimidazo[1,5-a]pyridine-1(5H)-one; [5S-(5α,8α,8aα)]-Tetrahydro-2-[3-(trifluoromethyl)phenyl]-5,8-methanoimidazo[1,5-a]pyridine-1,3(2H,5H)-dione; (5α,8α,8aβ)-Tetrahydro-2-(2-naphthalenyl)-5,8-methanoimidazo[1,5-a]pyridine-1,3(2H,5H)-dione; (5α,8α,8aα)-Tetrahydro-2-(2-naphthalenyl)-5,8-methanoimidazo[1,5-a]pyridine-1,3(2H,5H)-dione; (5α,8α,8aα)-Tetrahydro-8a-methyl-2-(4-nitro-1-naphthalenyl)-5,8-methanoimidazo[1,5-a]pyridine-1,3(2H,5H)-dione; (5α,8α,8aα)-8,8a-Dihydro-2-(4-nitro-1-naphthalenyl)-5,8-methanoimidazo[1,5-a]pyridine-1,3(2H,5H)-dione; (5α,8α,8aβ)-8,8a-Dihydro-2-(4-nitro-1-naphthalenyl)-5,8-methanoimidazo[1,5-a]pyridine-1,3(2H,5H)-dione; (5α,8α,8aα)-Tetrahydro-8a-(2-propenyl)-2-[3-(trifluoromethyl)phenyl]-5,8-methanoimidazo[1,5-a]pyridine-1,3(2H,5H)-dione; (5α,8α,8aα)-Tetrahydro-8a-(phenylmethyl)-2-[3-(trifluoromethyl)phenyl]-5,8-methanoimidazo[1,5-a]pyridine-1,3(2H,5H)-dione; [(Octahydro-1-oxo-2-phenyl-5,8-methanoimidazo[1,5-a]pyridin-3-ylidene)amino]carbonitrile; (5α,8α,8aβ)-[[2-(3-Chloro-4-fluorophenyl)octahydro-1-oxo-5,8-methanoimidazo[1,5-a]pyridin-3-ylidene]amino]carbonitrile; (5α,8α,8aα)-[[2-(3-Chloro-4-fluorophenyl)octahydro-1-oxo-5,8-methanoimidazo[1,5-a]pyridin-3-ylidene]amino]carbonitrile; (5α,8α,8aβ)-2-(3-Chlorophenyl)tetrahydro-5,8-methanoimidazo[1,5-a]pyridine-1,3(2H,5H)-dione; (5α,8α,8aα)-2-(3-Chlorophenyl)tetrahydro-5,8-methanoimidazo[1,5-a]pyridine-1,3(2H,5H)-dione; (5α,8α,8aβ)-[[2-(3-Chlorophenyl)octahydro-1-oxo-5,8-methanoimidazo[1,5-a]pyridin-3-ylidene]amino]carbonitrile; (5α,8α,8aα)-[[2-(3-Chlorophenyl)octahydro-1-oxo-5,8-methanoimidazo[1,5-a]pyridin-3-ylidene]amino]carbonitrile; (5α,8α,8aαβ)-[[2-(3,5-Dichlorophenyl)octahydro-1-oxo-5,8-methanoimidazo[1,5-a]pyridin-3-ylidene]amino]carbonitrile; (5α,8α,8aα)-[[2-(3,5-Dichlorophenyl)octahydro-1-oxo-5,8-methanoimidazo[1,5-a]pyridin-3-ylidene]amino]carbonitrile; (5α,8α,8aα)-2-(3-Chloro-4-fluorophenyl)tetrahydro-5,8-methanoimidazo[1,5-a]pyridine-1,3(2H,5H)-dione; (5α,8α,8aβ)-2-(3-Chloro-4-fluorophenyl)tetrahydro-5,8-methanoimidazo[1,5-a]pyridine-1,3(2H,5H)-dione; (5α,8α,8aβ)-[[2-(3,4-Dichlorophenyl)octahydro-1-oxo-5,8-methanoimidazo[1,5-a]pyridin-3-ylidene]amino]carbonitrile; (5α,8α,8aα)-[[2-(3,4-Dichlorophenyl)octahydro-1-oxo-5,8-methanoimidazo[1,5-a]pyridin-3-ylidene]amino]carbonitrile; (5α,8α,8aβ)-Tetrahydro-2-[4-nitro-3-(trifluoromethyl)phenyl]-5,8-methanoimidazo[1,5-a]pyridine-1,3(2H,5H)-dione; (5α,8α,8aα)-Tetrahydro-2-[4-nitro-3-(trifluoromethyl)phenyl]-5,8-methanoimidazo[1,5-a]pyridine-1,3(2H,5H)-dione; (5α,8α,8aβ)-2-(3-Chloro-4-fluorophenyl)-8,8a-dihydro-5,8-methanoimidazo[1,5-a]pyridine-1,3(2H,5H)-dione; (5α,8α,8aα)-2-(3-Chloro-4-fluorophenyl)-8,8a-dihydro-5,8-methanoimidazo[1,5-a]pyridine-1,3(2H,5H)-dione; (5α,8α,8aα)-8,8a-Dihydro-8a-methyl-2-[4-nitro-3-(trifluoromethyl)phenyl]-5,8-methanoimidazol[1,5-a]pyridine-1,3(2H,5H)-dione; (5α,8α,8aβ)-4-(Octahydro-1,3-dioxo-5,8-methanoimidazo[1,5-a]pyridin-2-yl)-2-(trifluoromethyl)benzonitrile; (5α,8α,8aα)-4-(Octahydro-1,3-dioxo-5,8-methanoimidazo[1,5-a]pyridin-2-yl)-2-(trifluoromethyl)benzonitrile; (5α,8α,8aα)-4-(1,2,3,5,8,8a-Hexahydro-1,3-dioxo-5,8-methanoimidazo[1,5-a]pyridin-2-yl)-2-(trifluoromethyl)benzonitrile; (5α,8α,8aα)-Hexahydro-2-(2-naphthaleny)-3-(phenylimino)-5,8-methanoimidazo[1,5-a]pyridin-1(5H)-one; (5α,8α,8aβ)-2-Methoxy-4-(octahydro-1,3-dioxo-5,8-methanoimidazo[1,5-a]pyridin-2-yl)-1-naphthalenecarbonitrile; (5α,8α,8aα)-2-Methoxy-4-(octahydro-1,3-dioxo-5,8-methanoimidazo[1,5-a]pyridin-2-yl)-1-naphthalenecarbonitrile; (5α,8α,8aα)-8a-[(4-Bromophenyl)methyl]-2-(3,5-dichlorophenyl)tetrahydro-5,8-methanoimidazo[1,5-a]pyridine-1,3(2H,5H)-dione; [5S-(5α,8α,8aβ)]-Tetrahydro-2-(4-nitro-1-naphthalenyl)-5,8-methanoimidazo[1,5-a]pyridine-1,3(2H,5H)-dione; [5S-(5α,8α,8aα)]-Tetrahydro-2-(4-nitro-1-naphthalenyl)-5,8-methanoimidazo[1,5-a]pyridine-1,3(2H,5H)-dione; [5R-(5α,8α,8aα)]-Tetrahydro-2-(4-nitro-1-naphthalenyl)-5,8-methanoimidazo[1,5-a]pyridine-1,3(2H,5H)-dione; [5R-(5α,8α,8aα)]-4-(Octahydro-1,3-dioxo-5,8-methanoimidazo[1,5-a]pyridin-2-yl)-2-(trifluoromethyl)benzonitrile; [5S-(5α,8α,8aβ)]-Tetrahydro-2-[4-nitro-3-(trifluoromethyl)phenyl]-5,8-methanoimidazo[1,5-a]

pyridine-1,3(2H,5H)-dione; [5S-(5α,8α,8aα)]-Tetrahydro-2-[4-nitro-3-(trifluoromethyl)phenyl]-5,8-methanoimidazo[1,5-a]pyridine-1,3(2H,5H)-dione; [5S-(5α,8α,8aβ)]-4-(Octahydro-1,3-dioxo-5,8-methanoimidazo[1,5-a]pyridin-2-yl)-2-(trifluoromethyl)benzonitrile; [5S-(5α,8α,8aα)]-4-(Octahydro-1,3-dioxo-5,8-methanoimidazo[1,5-a]pyridin-2-yl)-2-(trifluoromethyl)benzonitrile; (5α,8α,8aα)-2-(Benzo[b]thiophen-3-yl)-8,8a-dihydro-5,8-methanoimidazo[1,5-a]pyridine-1,3(2H,5H)-dione; [5R-(5α,8α,8aβ)]-4-(Octahydro-1,3-dioxo-5,8-methano-imidazo[1,5-a]pyridin-2-yl)-2-(trifluoromethyl)benzonitrile; [5R-(5α,8α,aα)]-Tetrahydro-2-[4-nitro-3-(trifluoromethyl)phenyl]-5,8-methanoimidazo[1,5-a]pyridine-1,3(2H,5H)-dione; [5R-(5α,8α,8aβ)]-Tetrahydro-2-[4-nitro-3-(trifluoromethyl)phenyl]-5,8-methanoimidazo[1,5-a]pyridine-1,3(2H,5H)-dione; [5R-(5α,8α,8aβ)]-Tetrahydro-2-(4-nitro-1-naphthalenyl)-5,8-methanoimidazo[1,5-a]pyridine-1,3(2H,5H)-dione; (5α,8α,8aα)-8,8a-Dihydro-2-(1H-indol-3-yl)-5,8-methanoimidazo[1,5-a]pyridine-1,3(2H,5H)-dione; (5α,8α,8aα)-2-(3-Chlorophenyl)-8,8a-dihydro-5,8-methano-imidazo[1,5-a]pyridine-1,3(2H,5H)-dione; (5α,8α,8aβ)-8,8a-Dihydro-2-(1H-indol-3-yl)-5,8-methanoimidazo[1,5-a]pyridine-1,3(2H,5H)-dione; (5α,8α,8aα)-2-(Benzo[b]thiophene-3-yl)-8,8a-dihydro-5,8-methanoimidazo[1,5-a]pyridine-1,3(2H,5H)-dione; (5α,8α,8aα) & (5α,8α,8aβ)-2-(1,2-Benzisoxazol-3-yl)tetrahydro-5,8-methanoimidazo[1,5-a]pyridine-1,3(2H,5H)-dione; (5α,8α,8aα)-4-(Octahydro-1,3-dioxo-5,8-methanoimidazo[1,5-a]pyridin-2-yl)-1-naphthalenecarbonitrile; (5α,8α,8aβ)-4-(Octahydro-1,3-dioxo-5,8-methanoimidazo[1,5-a]pyridin-2-yl)-1-naphthalenecarbonitrile; (5α,8α,8aβ)-Tetrahydro-2-(1-naphthalenyl)-5,8-methanoimidazo[1,5-a]pyridine-1,3(2H,5H)-dione; (5α,8α,8aα)-Tetrahydro-2-(1-naphthalenyl)-5,8-methanoimidazo[1,5-a]pyridine-1,3(2H,5H)-dione; (5α,8α,8aα)-2-(4-Fluoro-1-naphthalenyl)tetrahydro-5,8-methanoimidazo[1,5-a]pyridine-1,3(2H,5H)-dione; (5α,8α,8aβ)-2-(4-Fluoro-1-naphthalenyl)tetrahydro-5,8-methanoimidazo[1,5-a]pyridine-1,3(2H,5H)-dione; (5α,8α,8aβ)-2-(4-Chloro-1-naphthalenyl)tetrahydro-5,8-methanoimidazo[1,5-a]pyridine-1,3(2H,5H)-dione; (5α,8α,8aα)-2-(4-Chloro-1-naphthalenyl)tetrahydro-5,8-methanoimidazo[1,5-a]pyridine-1,3(2H,5H)-dione; (5α,8α,8aα)-8,8a-Dihydro-2-(1-oxidobenzo[b]thiophen-3-yl)-5,8-methanoimidazo[1,5-a]pyridine-1,3(2H,5H)-dione; (5α,8α,8aα)-4-(1,2,3,5,8,8a-Hexahydro-1,3-dioxo-5,8-methanoimidazo[1,5-a]pyridin-2-yl)-1-naphthalenecarbonitrile; (5α,8α,8aα)-Tetrahydro-2-[4-(1H-tetrazol-5-yl)-1-naphthalenyl]-5,8-methanoimidazo[1,5-a]pyridine-1,3(2H,5H)-dione; (5α,8α,8aα)-2-(7-Fluoro-3-benzofuranyl)tetrahydro-5,8-methanoimidazo[1,5-a]pyridine-1,3(2H,5H)-dione; (5α,8α,8aβ)-2-(7-Fluoro-3-benzofuranyl)tetrahydro-5,8-methanoimidazo[1,5-a]pyridine-1,3(2H,5H)-dione; [5S-(5α,8α,8aα)]-Tetrahydro-2-(2-methyl-4-nitrophenyl)-5,8-methanoimidazo[1,5-a]pyridine-1,3(2H,5H)-dione; [5S-(5α,8α,8aα)]-Tetrahydro-2-(3-methyl-4-nitrophenyl)-5,8-methanoimidazo[1,5-a]pyridine-1,3(2H,5H)-dione; [5S-(5α,8α,8aα)]-Tetrahydro-7-methyl-2-(4-nitro-1-naphthalenyl)-5,8-methanoimidazo[1,5-a]pyridine-1,3(2H,5H)-dione; (5α,8α,8aα)-2-(2-Benzofuranyl)tetrahydro-5,8-methanoimidazo[1,5-a]pyridine-1,3(2H,5H)-dione; (5α,8α,8aα)-Tetrahydro-2-[3-methoxy-4-(4-oxazolyl)phenyl]-5,8-methanoimidazo[1,5-a]pyridine-1,3(2H,5H)-dione; (5α,8α,8aα)-Tetrahydro-2-(2-methyl-3-benzofuranyl)-5,8-methanoimidazo[1,5-a]pyridine-1,3(2H,5H)-dione; (5α,8α,8aα)-2-(2,2-Dimethyl-2H-1-benzopyran-4-yl)tetrahydro-5,8-methanoimidazo[1,5-a]pyridine-1,3(2H,5H)-dione; (5α,8α,8aβ)-Tetrahydro-2-(2-methyl-4-nitrophenyl)-5,8-methanoimidazo[1,5-a]pyridine-1,3(2H,5H)-dione; (5α,8α,8aβ)-2-(2-Benzofuranyl)tetrahydro-5,8-methanoimidazo[1,5-a]pyridine-1,3(2H,5H)-dione; (5α,8α,8aβ)-Tetrahydro-2-(4,5,6,7-tetrafluoro-2-methyl-3-benzofuranyl)-5,8-methanoimidazo[1,5-a]pyridine-1,3(2H,5H)-dione; (5α,8α,8aβ)-Tetrahydro-2-[3-methoxy-4-(4-oxazolyl)phenyl]-5,8-methanoimidazo[1,5-a]pyridine-1,3(2H,5H)-dione; (5α,8α,8aβ)-Tetrahydro-2-(2-methyl-3-benzofuranyl)-5,8-methanoimidazo[1,5-a]pyridine-1,3(2H,5H)-dione; and (5α,8α,8aβ)-2-(2,2-Dimethyl-2H-1-benzopyran-4-yl)tetrahydro-5,8-methanoimidazo[1,5-a]pyridine-1,3(2H,5H)-dione; or a pharmaceutically acceptable salt, solvate, prodrug or stereoisomer thereof.

2. A compound of the following formula (Ia) or (Ib):

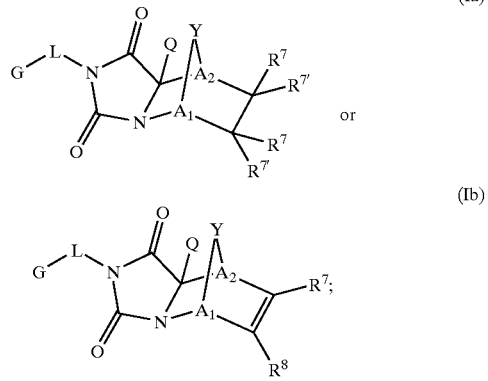

or a pharmaceutically acceptable salt, solvate, prodrug or stereoisomer thereof;

wherein the symbols have the following meanings and are, for each occurrence, independently selected:

G is an aryl or heterocyclo group, where said group is mono- or polycyclic and is optionally substituted at one or more positions;

$A_1$ is $CR^7$;

$A_2$ is $CR^7$;

Y is $(CR^7R^{7'})_n$ and n=1 or 2;

Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo or substituted heterocyclo, halo, CN, —(C=O)OR$^1$, —C(=O)R$^4$, —C(=O)NR$^5$R$^6$, —C(R$^7$R$^{7'}$)—OH, nitro, —(C$_2$)OR$^1$, —OR$^1$, —C(=O)SR$^1$, —SO$_2$R$^1$, —NH$_2$, or —NR$^4$R$^5$;

L is a bond, $(CR^7R^{7'})_n$, NH, NR$^5$ or N$(CR^7R^{7'})_n$, where n=0–2;

$R^1$ and $R^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, provided, however, that R$^1$ and R$^{1'}$ are not hydrogen when attached to —SO$_2$O— or —SO$_2$—;

$R^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)$R^1$, —C(=O)O$R^1$, —C(=O)NH$R^1$, —SO$_2$O$R^1$, —SO$_2$$R^1$ or —SO$_2$N$R^1$$R^{1'}$;

$R^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)$R^1$, —C(=O)NH$R^1$, —SO$_2$O$R^1$, —SO$_2$$R^1$ or —SO$_2$N$R^1$$R^{1'}$;

$R^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, —O$R^1$, —C(=O)$R^1$, —C(=O)NH$R^1$, —SO$_2$$R^1$, —SO$_2$O$R^1$ or —SO$_2$N$R^1$$R^{1'}$;

$R^7$ and $R^{7'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, O$R^1$, nitro, hydroxylamine, hydroxylamide, NH$R^4$, —N$R^2$$R^5$, —NHO$R^1$, thiol, alkylthio or substituted alkylthio, —C(=O)$R^1$, —OC(=O)$R^1$, —C(=O)O$R^1$, —PO$_3$$R^1$$R^{1'}$, —C(=O)N$R^1$$R^1$, —C(=O)S$R^1$, —C(=O)NHSO$_2$$R^1$, —SO$R^1$, —SO$_2$$R^1$, —SO$_2$O$R^1$ or —SO$_2$N$R^1$$R^{1'}$;

or two groups $R^7$ and $R^{7'}$ attached to the same carbon atom may be joined to form a spiro ring, or groups $R^7$ and $R^{7'}$ attached to two adjacent carbon atoms may be joined to form a fused, optionally-substituted monocyclic or bicyclic heterocyclic or carbocyclic ring;

$R^8$ and $R^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, halo, CN, O$R^1$, nitro, NH$R^4$, —N$R^2$$R^5$, —NHO$R^1$, alkylthio or substituted alkylthio, —C(=O)$R^1$, —OC(=O)$R^1$, —C(=O)O$R^1$, —PO$_3$$R^1$$R^{1'}$, —C(=O)N$R^1$$R^1$, —C(=O)S$R^1$, —C(=O)NHSO$_2$$R^1$, —SO$R^1$, —SO$_2$$R^1$, —SO$_2$O$R^1$ or —SO$_2$N$R^1$$R^{1'}$; and or, groups $R^8$ and $R^{8'}$ may be joined to form a fused, optionally-substituted monocyclic or bicyclic heterocyclic or carbocyclic ring;

with the provisos that:
(a) when $A_1$ and $A_2$ are both CH, Q is H, CH$_3$, or —CO$_2$CH$_3$, and $R^7$, $R^{7'}$, $R^8$ and $R^{8'}$ are at each occurrence hydrogen, then G—L considered together are not unsubstituted phenyl, 4-chlorophenyl, 4-methoxyphenyl, or benzyl; (b) when $A_1$ and $A_2$ are both CH, Q is H, and either or both of (i) $R^7$ and $R^{7'}$ of the group Y, and (ii) $R^8$ and $R^{8'}$, are taken together to form phenyl, then G—L is not 4-chlorophenyl or benzyl; and (c) when Q is H, Y is —CH$_2$—CH$_2$—, $R^7$, $R^{7'}$, $R^8$ and $R^{8'}$ are at each other occurrence hydrogen, then G—L— is not 4-chlorophenyl when (i) $A_1$ and $A_2$ are both C—CH$_3$; and (ii) when $A_1$ is C-isopropyl and $A_2$ is C—CH$_3$.

3. A compound according to claim 2, or a pharmaceutically acceptable salt, solvate, prodrug or stereoisomer thereof, wherein, G is an aryl or heterocyclo group, where said group is mono- or polycyclic and is optionally substituted at one or more positions;

Y is (CH$_2$)$_n$ and n=1 or 2;

Q is H, alkyl or substituted alkyl;

L is a bond;

$R^1$ and $R^{1'}$ are each independently selected from H, alkyl or substituted alkyl, alkenyl or substituted alkenyl, cycloalkyl or substituted cycloalkyl, heterocyclo or substituted heterocyclo, and aryl or substituted aryl;

$R^2$ is alkyl or substituted alkyl, alkenyl or substituted alkenyl, cycloalkyl or substituted cycloalkyl, heterocyclo or substituted heterocyclo, or aryl or substituted aryl;

$R^4$ is H, alkyl or substituted alkyl, alkenyl or substituted alkenyl, cycloalkylalkyl or substituted cycloalkylalkyl, arylalkyl or substituted arylalkyl, —C(=O)$R^1$, —C(=O)O$R^1$, —C(=O)NH$R^1$, —SO$_2$$R^1$ or —SO$_2$N$R^1$$R^{1'}$;

$R^5$ is alkyl or substituted alkyl, cycloalkyl or substituted cycloalkyl, heterocyclo or substituted heterocyclo, aryl or substituted aryl, —C(=O)$R^1$, —SO$_2$$R^1$, or —SO$_2$N$R^1$$R^{1'}$;

$R^6$ is alkyl or substituted alkyl, alkenyl or substituted alkenyl, cycloalkyl or substituted cycloalkyl, heterocyclo or substituted heterocyclo, aryl or substituted aryl, or CN;

$R^7$ and $R^{7'}$ are independently at each occurrence selected from H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, O$R^4$, —NH$R^4$, —N$R^2$$R^5$, —C(=O)$R^1$, —OC(=O)$R^1$, —C(=O)O$R^1$, —C(=O)N$R^1$$R^{1'}$, —SO$_2$$R^1$, and —SO$_2$N$R^1$$R^{1'}$; and $R^8$ and $R^{8'}$ are independently at each occurrence selected from H, alkyl or substituted alkyl, alkenyl or substituted alkenyl, cycloalkyl or substituted cycloalkyl, heterocyclo or substituted heterocyclo, aryl or substituted aryl, halo, CN, O$R^1$, nitro, NH$R^4$, —N$R^2$$R^5$, alkylthio or substituted alkylthio, —C(=O)$R^1$, —OC(=O)$R^1$, —C(=O)O$R^1$, —C(=O)N$R^1$$R^{1'}$, SO$_2$$R^1$, and —SO$_2$N$R^1$$R^{1'}$.

4. A compound according to claim 2, or a pharmaceutically acceptable salt, solvate, prodrug or stereoisomer thereof, having the formula (Ia), wherein, G is a di-substituted or tri-substituted phenyl or napthyl group;

Q is H, alkyl or substituted alkyl;

L is a bond;

$R^1$ and $R^{1'}$ are each independently selected from H, alkyl or substituted alkyl, alkenyl or substituted alkenyl, cycloalkyl or substituted cycloalkyl, heterocyclo or substituted heterocyclo, and aryl or substituted aryl;

$R^2$ is alkyl or substituted alkyl, alkenyl or substituted alkenyl, cycloalkyl or substituted cycloalkyl, heterocyclo or substituted heterocyclo, or aryl or substituted aryl;

$R^4$ is H, alkyl or substituted alkyl, alkenyl or substituted alkenyl, cycloalkylalkyl or substituted cycloalkylalkyl, arylalkyl or substituted arylalkyl, —C(=O)$R^1$, —C(=O)O$R^1$, —C(=O)NH$R^1$, —SO$_2$$R^1$ or —SO$_2$N$R^1$$R^{1'}$;

$R^5$ is alkyl or substituted alkyl, cycloalkyl or substituted cycloalkyl, heterocyclo or substituted heterocyclo, aryl or substituted aryl, —C(=O)$R^1$, —SO$_2$$R^1$, or —SO$_2$N$R^1$$R^{1'}$;

$R^6$ is alkyl or substituted alkyl, alkenyl or substituted alkenyl, cycloalkyl or substituted cycloalkyl, heterocyclo or substituted heterocyclo, aryl or substituted aryl, or CN;

$R^7$ and $R^{7'}$ are independently at each occurrence selected from H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, O$R^4$, —NH$R^4$, —N$R^2$$R^5$, —C(=O)$R^1$, —OC(=O)$R^1$, —C(=O)O$R^1$, —C(=O)N$R^1$$R^{1'}$, —SO$_2$$R^1$, and —SO$_2$N$R^1$$R^{1'}$;and $R^8$ and $R^{8'}$ are independently at each occurrence selected from H, alkyl or substituted alkyl, alkenyl or substituted alkenyl, cycloalkyl or substituted cycloalkyl, heterocyclo or substituted heterocyclo, aryl or substituted aryl, halo, CN, O$R^1$, nitro, NH$R^4$, —N$R^2$$R^5$, alkylthio or substituted alkylthio, —C(=O)$R^1$, —OC(=O)$R^1$, —C(=O)O$R^1$, —C(=O)N$R^1$$R^{1'}$, SO$_2$$R^1$, and —SO$_2$N$R^1$$R^{1'}$.

5. A compound according to claim 2, or a pharmaceutically acceptable salt, solvate, prodrug or stereoisomer thereof, having the formula (Ib), wherein, G is a di-substituted or tri-substituted phenyl or napthyl group;

Q is H, alkyl or substituted alkyl;

L is a bond;

$R^1$ and $R^{1'}$ are each independently selected from H, alkyl or substituted alkyl, alkenyl or substituted alkenyl, cycloalkyl or substituted cycloalkyl, heterocyclo or substituted heterocyclo, and aryl or substituted aryl;

$R^2$ is alkyl or substituted alkyl, alkenyl or substituted alkenyl, cycloalkyl or substituted cycloalkyl, heterocyclo or substituted heterocyclo, or aryl or substituted aryl;

$R^4$ is H, alkyl or substituted alkyl, alkenyl or substituted alkenyl, cycloalkylalkyl or substituted cycloalkylalkyl, arylalkyl or substituted arylalkyl, —C(=O)$R^1$, —C(=O)O$R^1$, —C(=O)NH$R^1$, —SO$_2$$R^1$ or —SO$_2$N$R^1$$R^{1'}$;

$R^5$ is alkyl or substituted alkyl, cycloalkyl or substituted cycloalkyl, heterocyclo or substituted heterocyclo, aryl or substituted aryl, —C(=O)$R^1$, —SO$_2$$R^1$, or —SO$_2$N$R^1$$R^{1'}$;

$R^6$ is alkyl or substituted alkyl, alkenyl or substituted alkenyl, cycloalkyl or substituted cycloalkyl, heterocyclo or substituted heterocyclo, aryl or substituted aryl, or CN;

$R^7$ and $R^{7'}$ are at each occurrence independently selected from H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, O$R^4$, —NH$R^4$, —N$R^2$$R^1$, —C(=O)$R^5$, —OC(=O)$R^1$, —C(=O)O$R^1$, —C(=O)N$R^1$$R^{1'}$, —SO$_2$$R^1$, and —SO$_2$N$R^1$$R^{1'}$;

$R^8$ and $R^{8'}$ are at each occurrence independently selected from H, alkyl or substituted alkyl, alkenyl or substituted alkenyl, cycloalkyl or substituted cycloalkyl, heterocyclo or substituted heterocyclo, aryl or substituted aryl, halo, CN, O$R^1$, nitro, NH$R^4$, —N$R^2$$R^5$, alkylthio or substituted alkylthio, —C(=O)$R^1$, —OC(=O)$R^1$, —C(=O)O$R^1$, —C(=O)N$R^1$$R^{1'}$, SO$_2$$R^1$, and —SO$_2$N$R^1$$R^{1'}$.

6. A compound according to claim 2, or a pharmaceutically acceptable salt, solvate, prodrug or stereoisomer thereof, wherein, at least one of $A_1$ and $A_2$ is C(alkyl) or C(substituted alkyl); and Y is $(CR^7R^{7'})_n$ wherein n=1.

7. A compound according to claim 2, or a pharmaceutically acceptable salt, solvate, prodrug or stereoisomer thereof, wherein, at least one of $A_1$ and $A_2$ is C(alkyl) or C(substituted alkyl);

Y is $(CR^7R^{7'})_n$ wherein n=2; and at least one of $R^7$, $R^{7'}$, $R^8$ and $R^{8'}$ is other than hydrogen.

8. A compound according to claim 2, or a pharmaceutically acceptable salt, solvate, prodrug or stereoisomer thereof, having the formula,

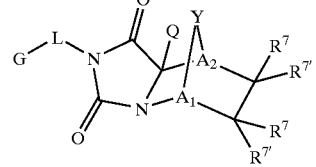

wherein n is 1 or 2.

9. A compound according to claim 8, or a pharmaceutically acceptable salt, solvate, prodrug or stereoisomer thereof, wherein, G is

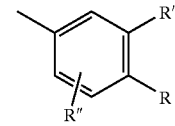

wherein R, R' and R" are selected from hydrogen, trifluoromethyl, methyl, halogen, cyano, nitro, OH, O(alkyl), alkyl, substituted alkyl, and cycloalkyl.

10. A compound according to claim 9, or a pharmaceutically acceptable salt, solvate, prodrug or stereoisomer thereof, wherein, at least one of $A_1$ and $A_2$ is C(alkyl) or C(substituted alkyl);

Q is H; and

R⁷ and R⁷' are independently at each occurrence selected from H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, OR⁴, —NHR⁴, —NR²R⁵, —C(=O)R¹, —OC(=O)R¹, —C(=O)OR¹, —C(=O)NR¹R¹', —SO₂R¹, and —SO₂NR¹R¹'.

11. A compound according to claim 2, or a pharmaceutically acceptable salt, solvate, prodrug or stereoisomer thereof, having the formula,

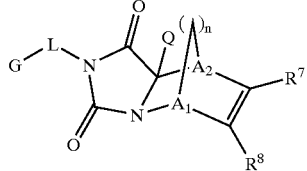

wherein n is 1 or 2.

12. A compound according to claim 11, or a pharmaceutically acceptable salt, solvate, prodrug or stereoisomer thereof, wherein, G is

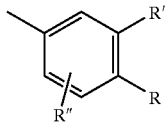

wherein R, R' and R" are selected from hydrogen, trifluoromethyl, methyl, halogen, cyano, nitro, OH, O(alkyl), alkyl, substituted alkyl, and cycloalkyl.

13. A compound according to claim 12, or a pharmaceutically acceptable salt, solvate, prodrug or stereoisomer thereof, wherein, at least one of A₁ and A₂ is C(alkyl) or C(substituted alkyl);

Q is H; and

R⁸ and R⁸' are independently at each occurrence selected from H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, OR⁴, —NHR⁴, —NR²R⁵, —C(=O)R¹, —OC(=O)R¹, —C(=O)OR¹, —C(=O)NR¹R¹', —SO₂R¹, and —SO₂NR¹R¹'.

14. A compound having the formula (Ia*) or (Ib*),

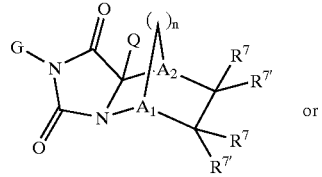

or

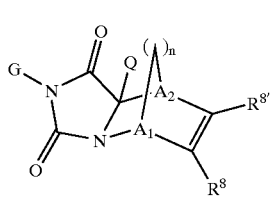

or a pharmaceutically acceptable salt, solvate, prodrug or stereoisomer thereof;

wherein the symbols have the following meanings and are, for each occurrence, independently selected:

G is an aryl or heterocyclo group, where said group is mono- or polycyclic and is optionally substituted at one or more positions, provided that G is not 4-chlorophenyl;

A₁ is CR⁷;

A₂ is CR⁷;

R¹ and R¹' are each independently selected from H, alkyl or substituted alkyl, alkenyl or substituted alkenyl, cycloalkyl or substituted cycloalkyl, heterocyclo or substituted heterocyclo, and aryl or substituted aryl;

R² is alkyl or substituted alkyl, alkenyl or substituted alkenyl, cycloalkyl or substituted cycloalkyl, heterocyclo or substituted heterocyclo, or aryl or substituted aryl;

R⁴ is H, alkyl or substituted alkyl, alkenyl or substituted alkenyl, cycloalkylalkyl or substituted cycloalkylalkyl, arylalkyl or substituted arylalkyl, —C(=O)R¹, —C(=O)OR¹, —C(=O)NHR¹, —SO₂R¹ or —SO₂NR¹R¹';

R⁵ is alkyl or substituted alkyl, cycloalkyl or substituted cycloalkyl, heterocyclo or substituted heterocyclo, aryl or substituted aryl, —C(=O)R¹, —SO₂R¹, or —SO₂NR¹R¹';

R⁶ is alkyl or substituted alkyl, alkenyl or substituted alkenyl, cycloalkyl or substituted cycloalkyl, heterocyclo or substituted heterocyclo, aryl or substituted aryl, or CN;

R⁷ and R⁷' are independently at each occurrence selected from H, alkyl or substituted alkyl, alkenyl or substituted alkenyl, heterocycloalkyl or substituted heterocycloalkyl, cycloalkyl or substituted cycloalkyl, heterocyclo or substituted heterocyclo, aryl or substituted aryl, halo, cyano, OR⁴, —NHR⁴, —NR²R⁵, —C(=O)R¹, —OC(=O)R¹, —C(=O)OR¹, —C(=O)NR¹R¹40, —SO₂R¹, and —SO₂NR¹R¹', provided, however, that every group R⁷, R⁷' is not simultaneously hydrogen;

R⁸ and R⁸' are independently at each occurrence selected from H, alkyl or substituted alkyl, alkenyl or substituted alkenyl, cycloalkyl or substituted cycloalkyl, heterocyclo or substituted heterocyclo, aryl or substituted aryl, halo, CN, OR¹, nitro, NHR⁴, —NR²R⁵, alkylthio or substituted alkylthio, —C(=O)R¹, —OC(=O)R¹, —C(=O)OR¹, —C(=O)NR¹R¹, SO₂R¹, and —SO₂NR¹R¹'; and n=1 or 2.

15. A pharmaceutical composition comprising a compound according to claim 2, and a pharmaceutically-acceptable carrier.

16. A pharmaceutical composition of claim 15 further comprising another anti-cancer agent.

17. A method of modulating the function of the androgen receptor in a mammal which comprises administering to the mammal in need thereof an effective androgen receptor modulating amount of a compound of the following formula (Ia) or (Ib):

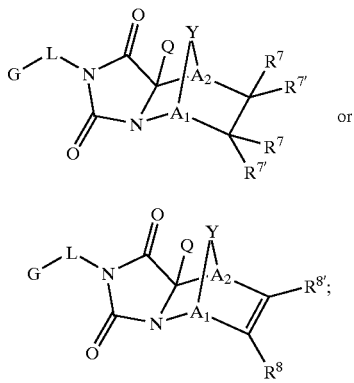

(Ia)

(Ib)

or a pharmaceutically acceptable salt, solvate, prodrug or stereoisomer thereof;
wherein the symbols have the following meanings and are, for each occurrence, independently selected:

G is an aryl or heterocyclo group, where said group is mono- or polycyclic and is optionally substituted at one or more positions;

$A_1$ is $CR^7$;

$A_2$ is $CR^7$;

Y is $(CR^7R^{1'})_n$ and n=1 or 2;

Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo or substituted heterocyclo, halo, CN, —(C=O)OR$^1$, —C(=O)R$^4$, —C(=O)NR$^5$R$^6$, —C(R$^7$R$^{7'}$)—OH, nitro, —(CH$_2$)OR$^1$, —OR$^1$, —C(=O)SR$^1$, —SO$_2$R$^1$, —NH$_2$, or —NR$^4$R$^5$;

L is a bond, $(CR^7R^{7'})_n$, NH, NR$^5$ or N(CR$^7$R$^{7'})_n$, where n=0–2;

R$^1$ and R$^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, provided, however, that R$^1$ and R$^{1'}$ are not hydrogen when attached to —SO$_2$O— or —SO$_2$—;

R$^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

R$^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)R$^1$, —C(=O)OR$^1$, —C(=O)NHR$^1$, —SO$_2$OR$^1$, —S$_2$R$^1$ or —SO$_2$NR$^1$R$^{1'}$;

R$^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)R$^1$, —C(=O)NHR$^1$, —SO$_2$OR$^1$, —SO$_2$R$^1$ or —SO$_2$NR$^1$R$^{1'}$;

R$^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, —OR$^1$, —C(=O)R$^1$, —C(=O)NHR$^1$, —SO$_2$R$^1$, —SO$_2$OR$^1$ or —SO$_2$NR$^1$R$^{1'}$, R$^7$ and R$^{7'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, OR$^1$, nitro, hydroxylamine, hydroxylamide, NHR$^4$, —NR$^2$R$^5$, —NHOR$^1$, thiol, alkylthio or substituted alkylthio, —C(=O)R$^1$, —OC(=O)R$^1$, —C(=O)OR$^1$, —PO$_3$R$^1$R$^{1'}$, —C(=O)NR$^1$R$^1$, —C(=O)SR$^1$, —C(=O)NHSO$_2$R$^1$, —SOR$^1$, —SO$_2$R$^1$, —SO$_2$OR$^1$ or —SO$_2$NR$^1$R$^{1'}$;

or two groups R$^7$ and R$^{7'}$ attached to the same carbon atom may be joined to form a spiro ring, or groups R$^7$ and R$^{7'}$ attached to two adjacent carbon atoms may be joined to form a fused, optionally-substituted monocyclic or bicyclic heterocyclic or carbocyclic ring;

R$^8$ and R$^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, halo, CN, OR$^1$, nitro, NHR$^4$, —NR$^2$R$^5$, —NHOR$^1$, alkylthio or substituted alkylthio, —C(=O)R$^1$, —OC(=O)R$^1$, —C(=O)OR$^1$, —PO$_3$R$^1$R$^{1'}$, —C(=O)NR$^1$R$^1$, —C(=O)SR$^1$, —C(=O)NHSO$_2$R$^1$, —SOR$^1$, —SO$_2$R$^1$, —SO$_2$OR$^1$ or —SO$_2$NR$^1$R$^{1'}$;

or, groups R$^8$ and R$^{8'}$ may be joined to form a fused, optionally-substituted monocyclic or bicyclic heterocyclic or carbocyclic ring.

18. The method of claim 17 wherein said nuclear hormone receptor is the androgen receptor.

19. The method of claim 17 wherein said nuclear hormone receptor is selected from the estrogen receptor, the progesterone receptor, the glucocorticoid receptor, the mineralocorticoid receptor, the aldosterone receptor, the RORbeta receptor, and the COUP-TF2 receptor.

20. A method for treating a condition or disorder comprising administering to a mammalian species in need thereof a therapeutically effective amount of a compound of the following formula (Ia) or (Ib):

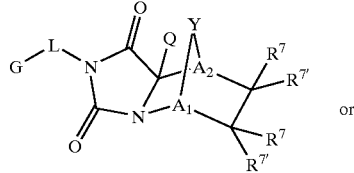
(Ia)

or

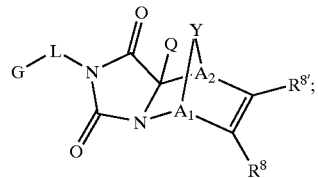
(Ib)

or a pharmaceutically acceptable salt, solvate, prodrug or stereoisomer thereof;
wherein the symbols have the following meanings and are, for each occurrence, independently selected:

G is an aryl or heterocyclo group, where said group is mono- or polycyclic and is optionally substituted at one or more positions;

$A_1$ is $CR^7$;

$A_2$ is $CR^7$;

Y is $(CR^7R^{7'})_n$ and n=1 or 2;

Q is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo or substituted heterocyclo, halo, CN, —(C=O)OR$^1$, —C(=O)R$^4$, —C(=O)NR$^5$R$^6$, —C(R$^7$R$^{7'}$)—OH, nitro, —(CH$_2$)OR$^1$, —OR$^1$, —C(=O)SR$^1$, —SO$_2$R$^1$, —NH$_2$, or —NR$^4$R$^5$;

L is a bond, $(CR^7R^{7'})_n$, NH, NR$^5$ or N(CR$^7$R$^{7'}$)$_n$, where n=0–2;

R$^1$ and R$^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, provided, however, that R$^1$ and R$^{1'}$ are not hydrogen when attached to —SO$_2$O— or —SO$_2$—;

R$^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

R$^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)R$^1$, —C(=O)OR$^1$, —C(=O)NHR$^1$, —SO$_2$OR$^1$, —SO$_2$R$^1$ or —SO$_2$NR$^1$R$^{1'}$;

R$^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, —C(=O)R$^1$, —C(=O)NHR$^1$, —SO$_2$OR$^1$, —SO$_2$R$^1$ or —SO$_2$NR$^1$R$^{1'}$;

R$^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, —OR$^1$, —C(=O)R$^1$, —C(=O)NHR$^1$, —SO$_2$R$^1$, —SO$_2$OR$^1$ or —SO$_2$NR$^1$R$^{1'}$;

R$^7$ and R$^{7'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, OR$^1$, nitro, hydroxylamine, hydroxylamide, NHR$^4$, —NR$^2$R$^5$, —NHOR$^1$, thiol, alkylthio or substituted alkylthio, —C(=O)R$^1$, —OC(=O)R$^1$, —C(=O)OR$^1$, —PO$_3$R$^1$R$^{1'}$, —C(=O)NR$^1$R$^1$, —C(=O)SR$^1$, —C(=O)NHSO$_2$R$^1$, —SOR$^1$, —SO$_2$R$^1$, —SO$_2$OR$^1$ or —SO$_2$NR$^1$R$^{1'}$;

or two groups R$^7$ and R$^{7'}$ attached to the same carbon atom may be joined to form a spiro ring, or groups R$^7$ and R$^{7'}$ attached to two adjacent carbon atoms may be joined to form a fused, optionally-substituted monocyclic or bicyclic heterocyclic or carbocyclic ring;

R$^8$ and R$^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, halo, CN, OR$^1$, nitro, NHR$^4$, —NR$^2$R$^5$, —NHOR$^4$, alkylthio or substituted alkylthio, —C(=O)R$^1$, —OC(=O)R$^1$, —C(=O)OR$^1$, —PO$_3$R$^1$R$^{1'}$, —C(=O)NR$^1$R$^1$, —C(=O)SR$^1$, —C(=O)NHSO$_2$R$^1$, —SOR$^1$, —SO$_2$R$^1$, —SO$_2$OR$^1$ or —SO$_2$NR$^1$R$^{1'}$;

or, groups R$^8$ and R$^{8'}$ may be joined to form a fused, optionally-substituted monocyclic or bicyclic heterocyclic or carbocyclic ring;

wherein said condition or disorder is selected from the group consisting of benign prostate hypertrophia, hirsutism, ance, hyperpilosity, seborrhea, endometriosis, polycystic ovary syndrome, androgenic alopecia, hypogonadism, osteoporosis, suppressing spermatogenesis, libido, cachexia, anorexia, androgen supplementation for age related decreased testosterone levels in men, prostate cancer, breast cancer, endometrial cancer, and hot flashes.

21. The method of claim 20, wherein said compound has the formula,

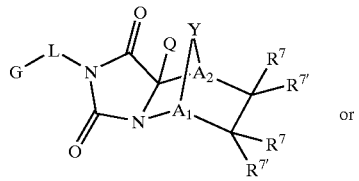

(Ia)

or

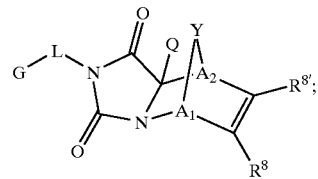

(Ib)

and said condition or disorder is prostate cancer.

* * * * *

UNITED STATES PATENT AND TRADEMARK OFFICE
CERTIFICATE OF CORRECTION

| | | |
|---|---|---|
| PATENT NO. | : 7,001,911 B2 | Page 1 of 11 |
| APPLICATION NO. | : 10/322306 | |
| DATED | : February 21, 2006 | |
| INVENTOR(S) | : Mark E. Salvati et al. | |

It is certified that error appears in the above-identified patent and that said Letters Patent is hereby corrected as shown below:

Column 1, lines 5-16
"This application claims priority from and is a continuation-in-part of U.S. application Ser. No. 10/025,233 filed Dec. 19, 2001 now abandoned and from U.S. Application Ser. No. 60/214,392, filed Jun. 28, 2000, from U.S. Application Ser. No. 60/284,617, filed Apr. 18, 2001, and from U.S. application Ser. No. 60/284,438, filed Apr. 18, 2001, which provisional applications are incorporated herein by reference in their entirety, and further claims priority from and is a continuation-in-part of U.S. application Ser. No. 09/885,798, filed Jun. 20, 2001, and U.S. application Ser. No. 09/885,827, filed Jun. 20, 2001, which applications are incorporated herein by reference in their entirety."
should read
--This application is a continuation-in-part of U.S. Application Serial No. 10/025,233 filed December 19, 2001, abandoned, which is a continuation-in-part of U.S. Application Serial No. 09/855,798, filed June 20, 2001, abandoned, which claims priority from U.S. Application Serial No. 60/214,392, filed June 28, 2000, from U.S. Application Serial No. 60/284,617, filed April 18, 2001, and from U.S. Application Serial No. 60/284,438, filed April 18, 2001; and a continuation-in-part of U.S. Application Serial No. 09/885,827, filed June 20, 2001, issued as U.S. Patent No. 6,960,474 B2, which claims priority from U.S. Application Serial No. 60/284,438, filed April 18, 2001, which applications are incorporated herein by reference in their entirety.--

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Column 23, lines 26-57

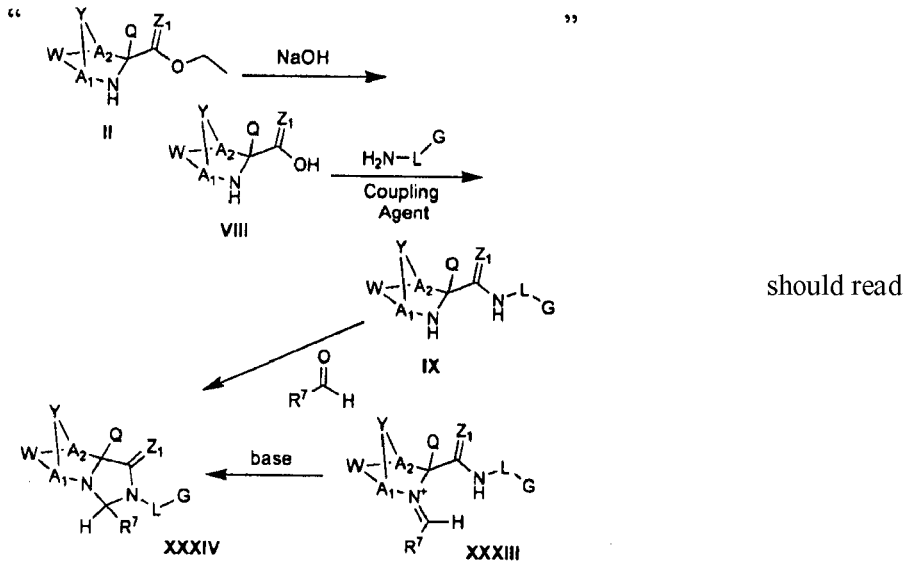

should read

UNITED STATES PATENT AND TRADEMARK OFFICE
CERTIFICATE OF CORRECTION

PATENT NO. : 7,001,911 B2  
APPLICATION NO. : 10/322306  
DATED : February 21, 2006  
INVENTOR(S) : Mark E. Salvati et al.

It is certified that error appears in the above-identified patent and that said Letters Patent is hereby corrected as shown below:

Column 25, lines 2-7

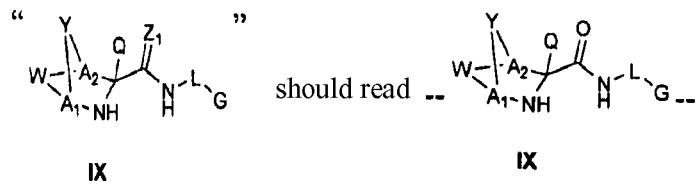

Column 26, lines 12-25

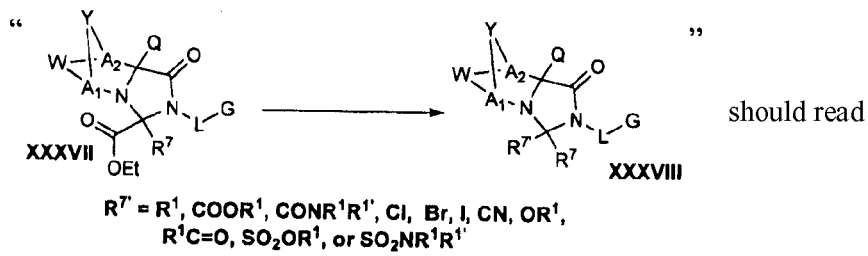

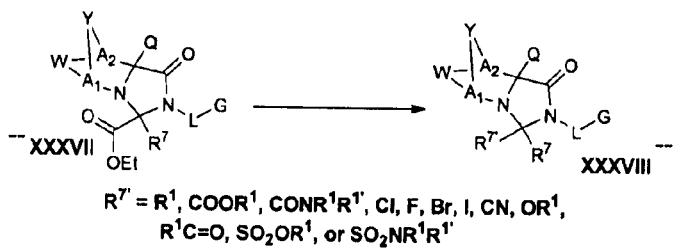

Column 32, lines 27-32

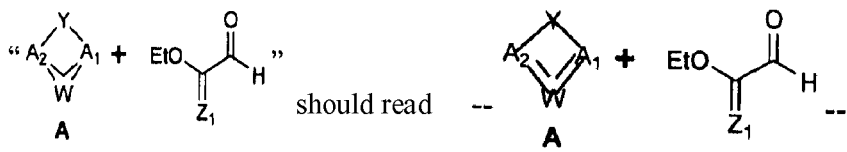

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Columns 37-38, lines 2-24
Compound M and Compound A

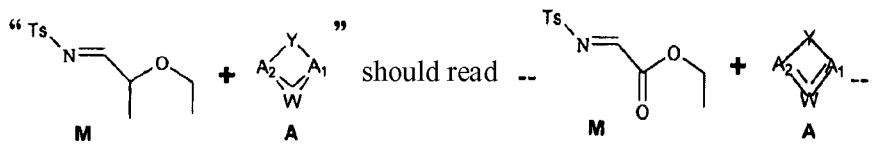

Columns 37-38, lines 2-24
Compound T

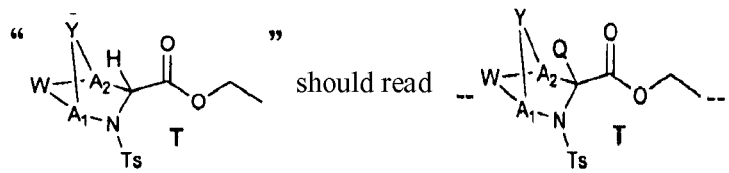

Column 42, lines 38-44

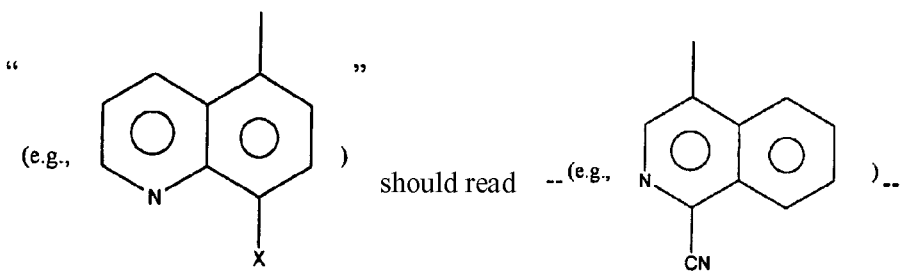

Column 77, lines 7-13

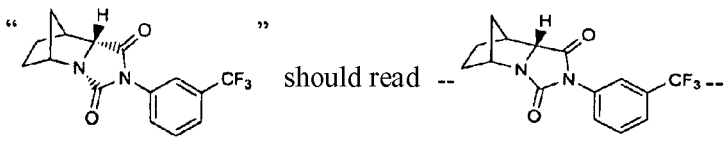

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Ex. No. 224

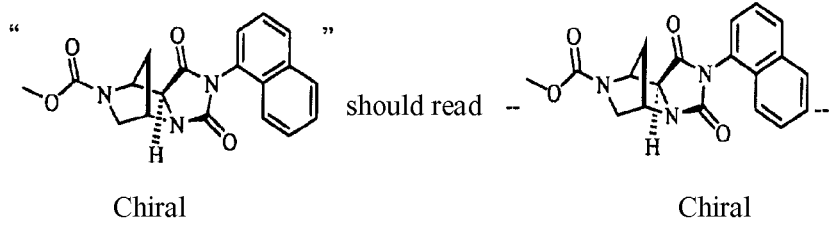

Ex. No. 225

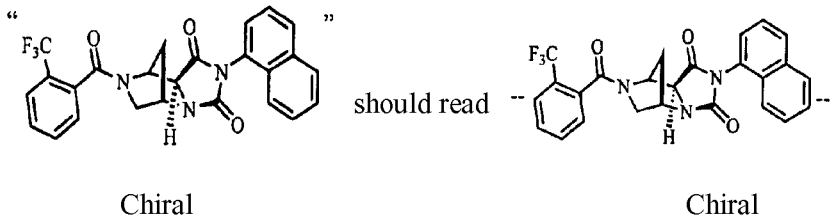

Ex. No. 226

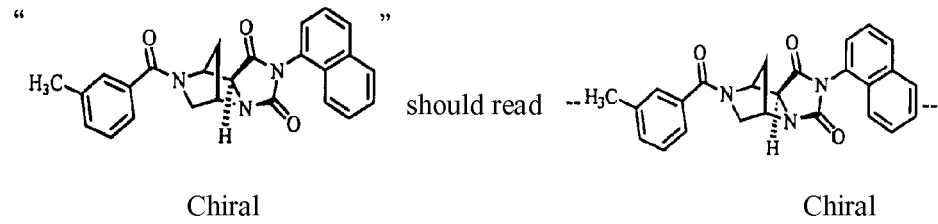

Ex. No. 227

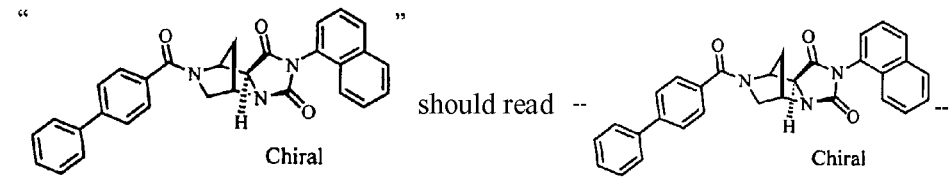

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Ex. No. 228

" 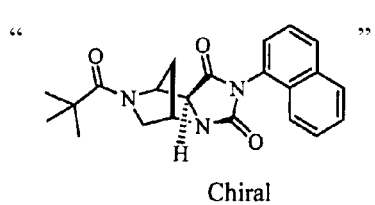 "   should read --  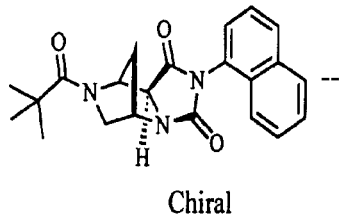  --

Chiral                                    Chiral

Ex. No. 229

" 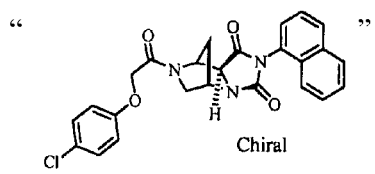 "   should read --  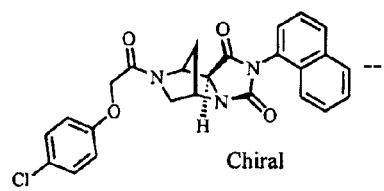  --

Chiral                                    Chiral

Ex. No. 230

" 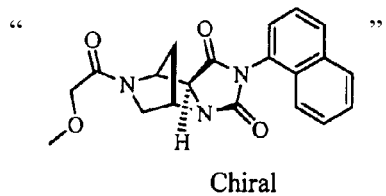 "   should read --  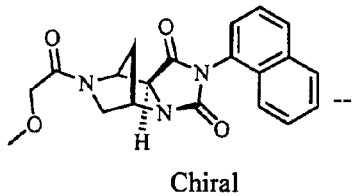  --

Chiral                                    Chiral

Ex. No. 231

" 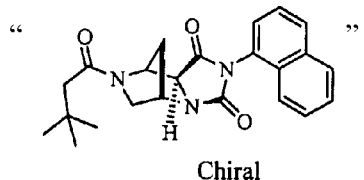 "   should read --  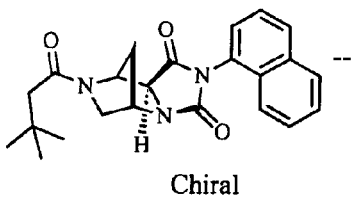  --

Chiral                                    Chiral

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Ex. No. 232

" 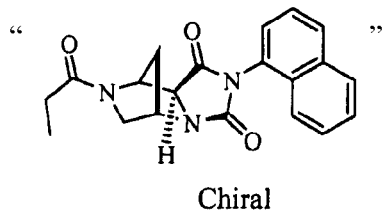 "  should read -- 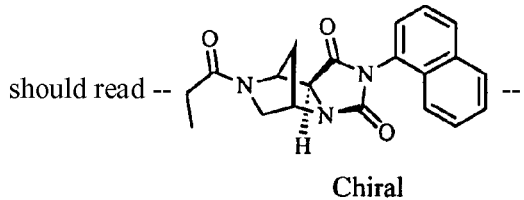 --

Ex. No. 233

" 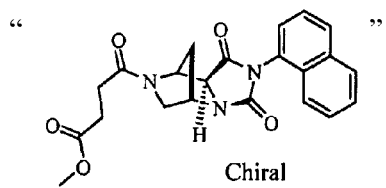 "  should read -- 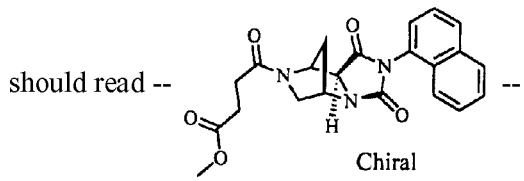 --

Ex. No. 234

" 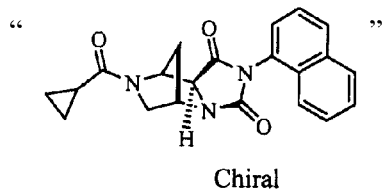 "  should read -- 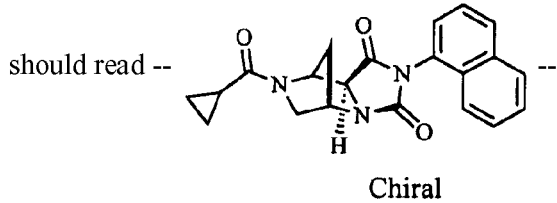 --

Ex. No. 235

" 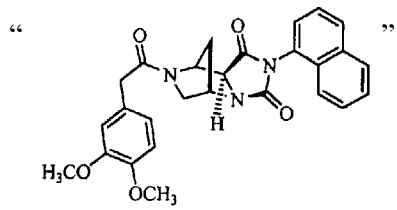 "  should read -- 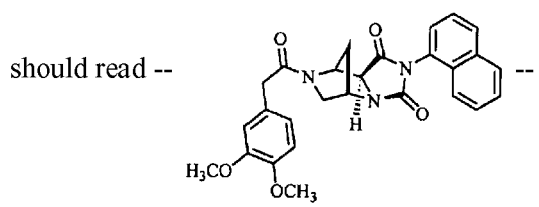 --

UNITED STATES PATENT AND TRADEMARK OFFICE
CERTIFICATE OF CORRECTION

PATENT NO. : 7,001,911 B2  
APPLICATION NO. : 10/322306  
DATED : February 21, 2006  
INVENTOR(S) : Mark E. Salvati et al.

Page 8 of 11

It is certified that error appears in the above-identified patent and that said Letters Patent is hereby corrected as shown below:

Ex. No. 236

" 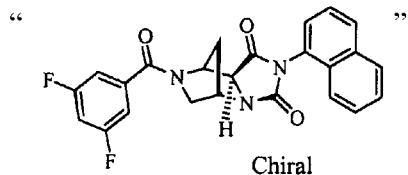 " should read -- 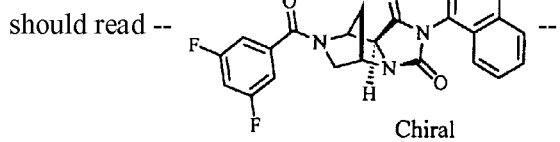 --

Ex. No. 237

" 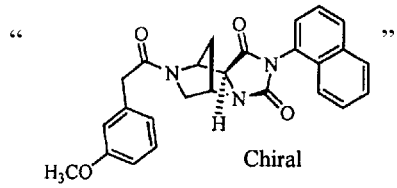 " should read -- 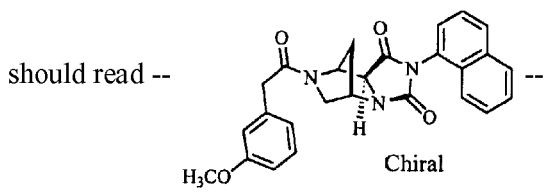 --

Ex. No. 238

" 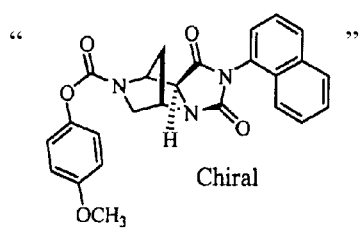 " should read -- 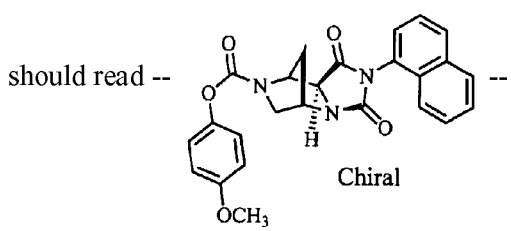 --

Ex. No. 239

" 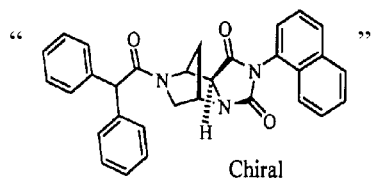 " should read -- 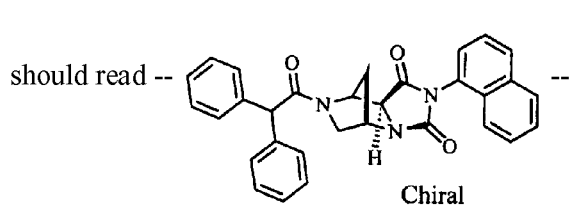 --

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Ex. No. 240

" 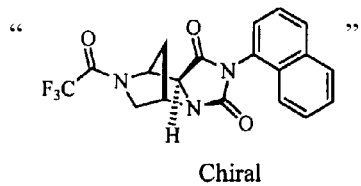 "  should read -- 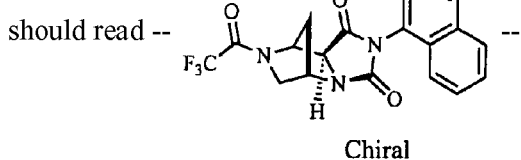 --

Ex. No. 241

" 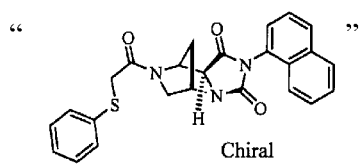 "  should read -- 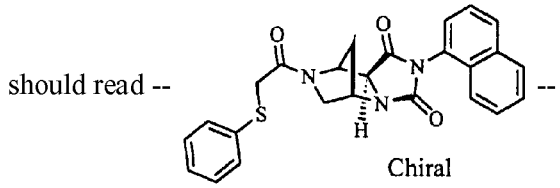 --

Ex. No. 242

" 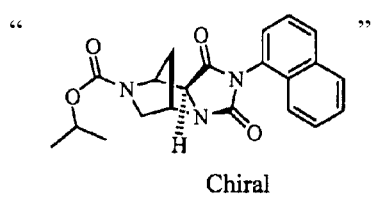 "  should read -- 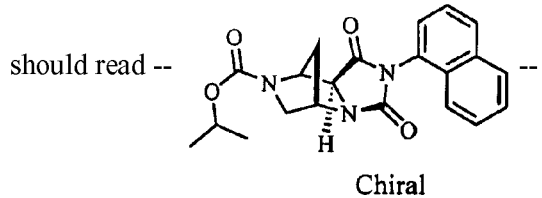 --

Ex. No. 243

" 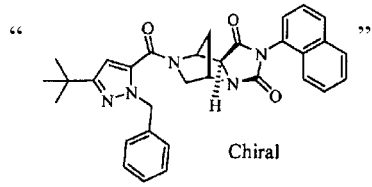 "  should read -- 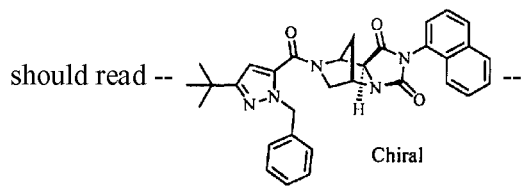 --

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Ex. No. 244

" 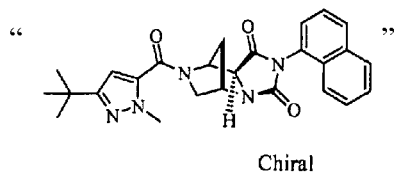 "   should read -- 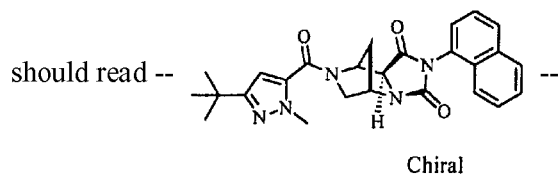 --

Chiral                                      Chiral

Ex. No. 245

" 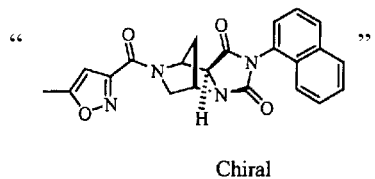 "   should read -- 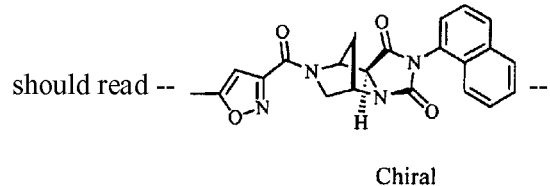 --

Chiral                                      Chiral

Ex. No. 246

" 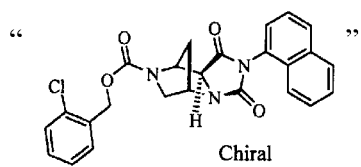 "   should read -- 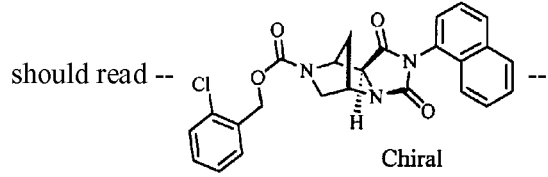 --

Chiral                                      Chiral

UNITED STATES PATENT AND TRADEMARK OFFICE
CERTIFICATE OF CORRECTION

PATENT NO. : 7,001,911 B2
APPLICATION NO. : 10/322306
DATED : February 21, 2006
INVENTOR(S) : Mark E. Salvati et al.

It is certified that error appears in the above-identified patent and that said Letters Patent is hereby corrected as shown below:

Ex. No. 247

" 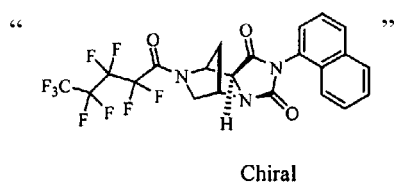 " should read -- 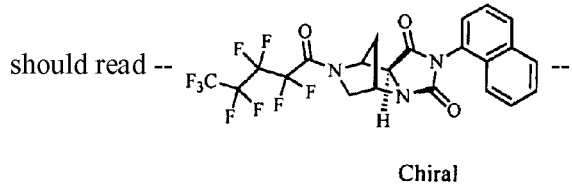 --

Signed and Sealed this

Nineteenth Day of February, 2008

JON W. DUDAS
*Director of the United States Patent and Trademark Office*